US008431770B2

(12) United States Patent
Harvey

(10) Patent No.: US 8,431,770 B2
(45) Date of Patent: Apr. 30, 2013

(54) METHOD OF PRODUCING SIALYTRANSFERASE-MODIFIED PROTEINS

(75) Inventor: Alex J. Harvey, Athens, GA (US)

(73) Assignee: Synageva BioPharma Corp., Lexington, MA (US)

( * ) Notice: Subject to any disclaimer, the term of this patent is extended or adjusted under 35 U.S.C. 154(b) by 0 days.

(21) Appl. No.: 12/319,396

(22) Filed: Jan. 7, 2009

(65) Prior Publication Data

US 2009/0178147 A1 Jul. 9, 2009

Related U.S. Application Data

(60) Provisional application No. 61/010,207, filed on Jan. 7, 2008.

(51) Int. Cl.
*C12P 21/00* (2006.01)
*A01K 67/027* (2006.01)

(52) U.S. Cl.
USPC .................................................. 800/19; 800/4

(58) Field of Classification Search .................... 800/19, 800/3, 4, 21
See application file for complete search history.

(56) References Cited

U.S. PATENT DOCUMENTS

| 6,825,396 | B2 * | 11/2004 | MacArthur | 800/19 |
|---|---|---|---|---|
| 7,129,390 | B2 | 10/2006 | Ivarie et al. | |
| 7,276,475 | B2 | 10/2007 | Defrees et al. | |
| 2002/0155998 | A1 | 10/2002 | Young et al. | |
| 2005/0188430 | A1 | 8/2005 | Ivaarie et al. | |
| 2006/0015960 | A1 | 1/2006 | Ivarie et al. | |
| 2006/0130170 | A1 | 6/2006 | Leavitt et al. | |
| 2006/0143725 | A1 | 6/2006 | Iijima et al. | |
| 2006/0171921 | A1 | 8/2006 | Ivarie et al. | |
| 2007/0077650 | A1 | 4/2007 | Harvey | |
| 2007/0113299 | A1 | 5/2007 | Harvey et al. | |
| 2007/0124829 | A1 | 5/2007 | Rapp et al. | |
| 2007/0180546 | A1 | 8/2007 | Rapp et al. | |
| 2007/0243165 | A1 | 10/2007 | Ivarie et al. | |
| 2008/0064862 | A1 | 3/2008 | Harvey et al. | |

OTHER PUBLICATIONS table of Bird Classification/Families of the Eastern US Birds, 2009.*
Proudman, 2001, "The quest for transgenic poultry: birds are not mice with feathers" Biotechnology in Animal Husbandry, vol. 5, Kluwer Academic Publishers, p. 283-299.*
Mizuarai (Biochemical and Biophysical Res. Comm. Aug. 24, 2001, vol. 286, p. 456-463).*
Shaper (J. Biological Chem., Dec. 12, 1997, vol. 272, No. 50, p. 31389-31399).*
Andacht, T., W. Hu, et al. (2004). "Rapid and improved method for windowing eggs accessing the stage X chicken embryo." *Mol Reprod Dev* 69(1): 31-4.
Ashwell, G. and A. G. Morell (1974). "The role of surface carbohydrates in the hepatic recognition and transport of circulating glycoproteins." *Adv Enzymol Relat Areas Mol Biol* 41(0): 99-128.

Cosset et al., (1991). "Improvement of Avian Leukosis Virus (ALV)-Based Retrovirus Vectors by Using Different cis-Acting Sequences from ALVs." *Journal of Virology* 65:p.3388-3394.
Deguchi, K., H. Ito, et al. (2006). "Complementary structural information of positive-and negative-ion MSn spectra of glycopeptides with neutral and sialylated N-glycans." *Rapid Commun Mass Spectrom* 20(5): 741-6.
de Lavoir et al., (2006). "Germline transmission of genetically modified primordial germ cells." *Nature* 441p766-769.
Feeney, R. E., J. S. Anderson, et al. (1960). "The comparative biochemistry of avian egg white proteins." *J Biol Chem* 235: 2307-11.
Feeney, R. E., M. B. Rhodes, et al. (1960). "The distribution and role of sialic acid in chicken egg white." *J Biol Chem* 235: 2633-7.
Fukuta, K., R. Abe, et al. (2001). "The widespread effect of beta 1,4-galactosyltransferase on N-glycan processing." Arch Biochem Biophys 392(1): 79-86.
Fukuta, K., R. Abe, et al. (2000). "Control of bisecting GlcNAc addition to N-linked sugar chains." *J Biol Chem* 275(31): 23456-61.
Ghattas, I. R., J. R. Sanes, et al. (1991). "The encephalomyocarditis virus internal ribosome entry site allows efficient coexpression of two genes from a recombinant provirus in cultured cells and in embryos." *Mol Cell Biol* 11(12): 5848-59.
Guo, S., T. Sato, et al. (2001). "Galactosylation of N-linked oligosaccharides by human beta-1,4-galactosyltransferases I, II, III, IV, V, and VI expressed in Sf-9 cells." *Glycobiology* 11(10): 813-20.
Harduin-Lepers, A., V. Vallejo-Ruiz, et al. (2001). "The human sialyltransferase family." *Biochimie* 83(8): 727-37.
Harvey, A. J., G. Speksnijder, et al. (2002). "Consistent Production of Transgenic Chickens using Replication Deficient Retroviral Vectors and High-throughput Screening Procedures." *Poultry Science* 81(2): 202-12.
Harvey, A. J., G. Speksnijder, et al. (2002). "Expression of exogenous protein in the egg white of transgenic chickens." *Nat Biotechnol* 20(4): 396-9.
Harvey, D. J., D. R. Wing, et al. (2000). "Composition of N-linked carbohydrates from ovalbumin and co-purified glycoproteins." *J Am Soc Mass Spectrom* 11(6): 564-71.
Hennet, T. (2002). "The galactosyltransferase family." *Cell Mol Life Sci* 59(7): 1081-95.
Huang, L., S. Biolsi, et al. (2006). "Impact of variable domain glycosylation on antibody clearance: an LC/MS characterization." *Anal Biochem* 349(2): 197-207.
Ito, H., Y. Takegawa, et al. (2006). "Direct structural assignment of neutral and sialylated N-glycans of glycopeptides using collision-induced dissociation MSn spectral matching." *Rapid Commun Mass Spectrom* 20(23): 3557-65.
Jang, S. K., H. G. Krausslich, et al. (1988). "A segment of the 5' nontranslated region of encephalomyocarditis virus RNA directs internal entry of ribosomes during in vitro translation." *J Virol* 62(8): 2636-43.
Kotani, N., M. Asano, et al. (2004). "Polylactosamine synthesis and branch formation of N-glycans in beta1,4-galactosyltransferase-1-deficient mice." *Arch Biochem Biophys* 426(2): 258-65.
Kurosawa, N., T. Hamamoto, et al. (1995). "Molecular cloning and expression of chick Gal beta 1,3GalNAc alpha 2,3-sialyltransferase." *Biochim Biophys Acta* 1244(1): 216-22.

(Continued)

*Primary Examiner* — Michael C. Wilson
(74) *Attorney, Agent, or Firm* — Hak J. Chang; Eugene J. Kim

(57) ABSTRACT

Transgenic avians which produce proteins in their oviduct tissue having modified oligosaccharide structures and methods of making such avians are disclosed herein. The invention also includes the modified proteins produced in the transgenic birds.

9 Claims, 39 Drawing Sheets

OTHER PUBLICATIONS

Lattova, E., H. Perreault, et al. (2004). "Matrix-assisted laser desorption/ionization tandem mass spectrometry and post-source decay fragmentation study of phenylhydrazones of N-linked oligosaccharides from ovalbumin." *J Am Soc Mass Spectrom* 15(5): 725-35.

Lee, E. U., J. Roth, et al. (1989). "Alteration of terminal glycosylation sequences on N-linked oligosaccharides of Chinese hamster ovary cells by expression of beta-galactoside alpha 2,6-sialyltransferase." *J Biol Chem* 264(23): 13848-55.

Lee, J., S. Sundaram, et al. (2001). "Chinese hamster ovary (CHO) cells may express six beta 4-galactosyltransferases (beta 4GalTs). Consequences of the loss of functional beta 4GalT-1, beta 4GalT-6, or both in CHO glycosylation mutants." *J Biol Chem* 276(17): 13924-34.

Patel, T. B., E. Pequignot, et al. (2007). "Transgenic avian-derived recombinant human interferon-alpha2b (AVI-005) in healthy subjects: an open-label, single-dose, controlled study." *Int J Clin Pharmacol Ther* 45(3): 161-8.

Raju, T. S., J. B. Briggs, et al. (2000). "Species-specific variation in glycosylation of IgG: evidence for the species-specific sialylation and branch-specific galactosylation and importance for engineering recombinant glycoprotein therapeutics." *Glycobiology* 10(5): 477-86.

Rapp, J. C., A. J. Harvey, et al. (2003). "Biologically active human interferon alpha-2b produced in the egg white of transgenic hens." *Transgenic Res* 12(5): 569-75.

Robinson, D. S. and J. B. Monsey (1975). "The composition and proposed subunit structure of egg-white beta-ovomucin. The isolation of an unreduced soluble ovomucin." *Biochem J* 147(1): 55-62.

Sasaki, H., B. Bothner, et al. (1987). "Carbohydrate structure of erythropoietin expressed in Chinese hamster ovary cells by a human erythropoietin cDNA." *J Biol Chem* 262(25): 12059-76.

Schlesinger, P. H., J. S. Rodman, et al. (1980). "The role of extra-hepatic tissues in the receptor-mediated plasma clearance of glycoproteins terminated by mannose or N-acetylglucosamine." *Biochem J* 192(2): 597-606.

Shaper, N. L., J. A. Meurer, et al. (1997). "The chicken genome contains two functional nonallelic beta1,4-galactosyltransferase genes. Chromosomal assignment to syntenic regions tracks fate of the two gene lineages in the human genome." *J Biol Chem* 272(50): 31389-99.

Shields, R. L., J. Lai, et al. (2002). "Lack of fucose on human IgG1 N-linked oligosaccharide improves binding to human Fcgamma RIII and antibody-dependent cellular toxicity." *J Biol Chem* 277(30): 26733-40.

Shinkawa, T., K. Nakamura, et al. (2003). "The absence of fucose but not the presence of galactose or bisecting N-acetylglucosamine of human IgG1 complex-type oligosaccharides shows the critical role of enhancing antibody-dependent cellular cytotoxicity." *J Biol Chem* 278(5): 3466-73.

Soriano, P., G. Friedrich, et al. (1991). "Promoter interactions in retrovirus vectors introduced into fibroblasts and embryonic stem cells." *J Virol* 65(5): 2314-9.

Weikert, S., D. Papac, et al. (1999). "Engineering Chinese hamster ovary cells to maximize sialic acid content of recombinant glycoproteins." *Nat Biotechnol* 17(11):1116-21.

Yamashita, K., J. P. Kamerling, et al. (1982). "Structural study of the carbohydrate moiety of hen ovomucoid. Occurrence of a series of pentaantennary complex-type asparagine-linked sugar chains." *J Biol Chem* 257(21): 12809-14.

Yamashita, K., Y. Tachibana, et al. (1984). "Sialic acid-containing sugar chains of hen ovalbumin and ovomucoid." *Carbohydr Res* 130: 271-88.

Yu, S. F., T. von Ruden, et al. (1986). "Self-inactivating retroviral vectors designed for transfer of whole genes into mammalian cells." *Proc Natl Acad Sci U S A* 83(10): 3194-8.

Zhu, L., M. C. van de Lavoir, et al. (2005). "Production of human monoclonal antibody in eggs of chimeric chickens." *Nat Biotechnol* 23(9): 1159-69.

\* cited by examiner

■ GlcNac
○ Mannose
● Galactose
◆ Sialic acid

```
   1 cgaggaatat aaaaaaatta caggaggctt ataagcagcc cgaaagaaga gcgtaggcga
  61 gttcttgtat tccgtgtgat agctggttgg attggtaatt gatcggctgg cacgcggaat
 121 ataggaggtc gctgaatagt aaacttgtag acttggctac agcatagagt atcttctgta
 181 gctctgatga ctgctaggaa ataatgctac ggataatgtg gggagggcaa ggcttgcgaa
 241 tcgggttgta acgggcaagg cttgactgag gggacaatag catgtttagg cgaaaagcgg
 301 ggcttcggtt gtacgcggtt aggagtcccc tcaggatata gtagtttcgc ttttgcatag
 361 ggaggggggac ggattggacg aaccactgaa ttccgcattg cagagatatt gtatttaagt
 421 gcctagctcg atacaataaa cgccatttga ccattcacca cattggtgtg cacctgggtt
 481 gatggccgga ccgttgattc cctgrcgact acgagcacat gcatgaagca gaaggcttca
 541 tttggtgacc ccgacgtgat cgttagggaa tacgcgctca ctggccgtcg ttttacaacg
 601 tcgtgactgg gaaaaccctg gcgttaccca acttaatcgc cttgcagcac atccccttt
 661 cgccagctgg cgtaatagcg aagaggcccg caccgatcgc ccttcccaac agttgcgcag
 721 cctgaatggc gaatggaaat tgtaagcgtt aatattttgt taaaattcgc gttaaatttt
 781 tgttaaatca gctcattttt taaccaatag gccgaaatcg gcaaaatccc ttataaatca
 841 aagaataga ccgagatagg gttgagtgtt gttccagttt ggaacaagag tccactatta
 901 aagaacgtgg actccaacgt caaagggcga aaaccgtct atcagggcga tggcccacta
 961 cgtgaaccat cacccctaatc aagtttttg gggtcgaggt gccgtaaagc actaaatcgg
1021 aaccctaaag ggagccccccg atttagagct tgacggggaa agccggcgaa cgtggcgaga
1081 aaggaaggga agaaagcgaa aggagcgggc gctagggcgc tggcaagtgt agcggtcacg
1141 ctgcgcgtaa ccaccacacc cgccgcgctt aatgcgccgc tacagggcgc gtcaggtggc
1201 acttttcggg gaaatgtgcg cggaacccct atttgtttat ttttctaaat acattcaaat
1261 atgtatccgc tcatgagaca ataaccctga taaatgcttc aataatattg aaaaaggaag
1321 agtatgagta ttcaacattt ccgtgtcgcc cttattccct tttttgcggc attttgcctt
1381 cctgtttttg ctcacccaga aacgctggtg aaagtaaaag atgctgaaga tcagttgggt
1441 gcacgagtgg gttacatcga actggatctc aacagcggta agatccttga gagttttcgc
1501 cccgaagaac gttttccaat gatgagcact tttaaagttc tgctatgtgg cgcggtatta
1561 tcccgtattg acgccgggca agagcaactc ggtcgccgca tacactattc tcagaatgac
1621 ttggttgagt actcaccagt cacagaaaag catcttacgg atggcatgac agtaagagaa
1681 ttatgcagtg ctgccataac catgagtgat aacactgcgg ccaacttact tctgacaacg
1741 atcggaggac cgaaggagct aaccgctttt ttgcacaaca tgggggatca tgtaactcgc
1801 cttgatcgtt gggaaccgga gctgaatgaa gccataccaa acgacgagcg tgacaccacg
1861 atgcctgtag caatggcaac aacgttgcgc aaactattaa ctggcgaact acttactcta
1921 gcttcccggc aacaattaat agactggatg gagcggata agttgcagg accacttctg
1981 cgctcggccc ttccggctgg ctggtttatt gctgataaat ctggagccgg tgagcgtggg
2041 tctcgcggta tcattgcagc actggggcca gatggtaagc cctcccgtat cgtagttatc
2101 tacacgacgg ggagtcaggc aactatggat gaacgaaata gacagatcgc tgagataggt
2161 gcctcactga ttaagcattg gtaactgtca gaccaagttt actcatatat actttagatt
2221 gatttaaaac ttcattttta atttaaaagg atctaggtga agatcctttt tgataatctc
2281 atgaccaaaa tcccttaacg tgagttttcg ttccactgag cgtcagaccc cgtagaaaag
2341 atcaaaggat cttcttgaga tcctttttt ctgcgcgtaa tctgctgctt gcaaacaaaa
2401 aaaccaccgc taccagcggt ggtttgtttg ccggatcaag agctaccaac tctttttccg
2461 aaggtaactg gcttcagcag agcgcagata ccaaatactg tccttctagt gtagccgtag
2521 ttaggccacc acttcaagaa ctctgtagca ccgcctacat acctcgctct gctaatcctg
2581 ttaccagtgg ctgctgccag tggcgataag tcgtgtctta ccgggttgga ctcaagacga
2641 tagttaccgg ataaggcgca gcggtcgggc tgaacggggg gttcgtgcac acagcccagc
2701 ttggagcgaa cgacctacac cgaactgaga tacctacagc gtgagctatg agaaagcgcc
2761 acgcttcccg aagggagaaa ggcggacagg tatccggtaa gcggcagggt cggaacagga
2821 gagcgcacga gggagcttcc agggggaaac gcctggtatc tttatagtcc tgtcgggttt
2881 cgccacctct gacttgagcg tcgatttttg tgatgctcgt caggggggcg gagcctatgg
2941 aaaaacgcca gcaacgcggc ctttttacgg ttcctggcct tttgctggcc ttttgctcac
3001 atgttctttc ctgcgttatc ccctgattct gtggataacc gtattaccgc ctttgagtga
3061 gctgataccg ctcgccgcag ccgaacgacc gagcgcagcg agtcagtgag cgaggaagcg
3121 gaagagcgcc caatacgcaa accgcctctc cccgcgcgtt ggccgattca ttaatgcagc
3181 tggcacgaca ggtttcccga ctggaaagcg ggcagtgagc gcaacgcaat taatgtgagt
```

Fig. 9A

```
3241 tagctcactc attaggcacc ccaggcttta cactttatgc ttccggctcg tatgttgtgt
3301 ggaattgtga gcggataaca atttcacaca ggaaacagct atgaccatga ttacgccaag
3361 cgcgcattgg taattgatcg gctggcacgc ggaatatagg aggtcgctga atagtaaact
3421 tgtagacttg gctacagcat agagtatctt ctgtagctct gatgactgct aggaaataat
3481 gctacggata atgtggggag ggcaaggctt gcgaatcggg ttgtaacggg caaggcttga
3541 ctgaggggac aatagcatgt ttaggcgaaa agcggggctt cggttgtacg cggttaggag
3601 tcccctcagg atatagtagt ttcgcttttg cataggagg gggaaatgta gtcttatgca
3661 atactcttgt agtcttgcaa catgcttatg taacgatgag ttagcaacat gccttataag
3721 gagagaaaaa gcaccgtgca tgccgattgg tgggagtaag gtggtatgat cgtggtatga
3781 tcgtgccttg ttaggaaggc aacagacggg tctaacacgg attggacgaa ccactgaatt
3841 ccgcattgca gagatattgt atttaagtgc ctagctcgat acaataaacg ccatttgacc
3901 attcaccaca ttggtgtgca cctgggttga tggccggacc gttgattccc tgrcgactac
3961 gagcacatgc atgaagcaga aggcttcatt tggtgacccc gacgtgatcg ttagggaata
4021 gtggtcggcc acaggcggcg tgcgatcct gtcctcatcc gtctcgctta ttcggggagc
4081 ggacgatgac cctagtagag ggggctgcgg cttaggaggg cagaagctga gtggcgtcgg
4141 agggagccct actgcagggg gccaacatac cctaccgaga actcagagag tcgttggaag
4201 acgggaagga agcccgacga ctgagcggtc caccccaggc gtgattccgg ttgctctgcg
4261 tgattccggt cgcccggtgg atcaagcatg gaagccgtca taaaggtgat ttcgtccgcg
4321 tgtaagacct attgcgggaa aacctctcct tctaagaagg aaataggggc tatgttgtcc
4381 ctgttacaaa aggaagggtt gcttacgtcc ccctcagact tatattcccc ggggtcctgg
4441 gatctctgcc cttgtgctga ctcctgcaca caagagcatt tccctgtagc caaacagcga
4501 ttagccataa gctgcacctg actttgagga ttaagagttt gcaattaagt ggattgcagc
4561 aggagatcag tggcagggtt gcagatgaaa tccttttcta ggggtagcta agggctgagc
4621 aacctgtcct acagcacaag ccaaaccagc caagggtttt cctgtgctgt tcacagaggc
4681 agggccagct ggagctggag gaggttgtgc tgggacccct ctccctgtgc tgagaatgga
4741 gtgatttctg ggtgctgttc ctgtggcttg cactgagcag ctcaagggag atcggtgctc
4801 ctcatgcagt gccaaaactc gtgtttgatg cagaaagatg gatgtgcacc tccctcctgc
4861 taatgcagcc gtgagcttat gaaggcaatg agccctcagt gcagcaggag ctgtagtgca
4921 ctcctgtagg tgctagggaa aatctctggt tcccagggat gcattcataa gggcaatata
4981 tcttgaggct gcgccaaatc tttctgaaat attcatgcgt gttcccttaa tttatagaaa
5041 caaacacagc agaataatta ttccaatgcc tcccctcgaa ggaaacccat atttccatgt
5101 agaaatgtaa cctatataca cacagccatg ctgcatcctt cagaacgtgc cagtgctcat
5161 ctcccatggc aaaatactac aggtattctc actatgttgg acctgtgaaa ggaaccatgg
5221 taagaaactt cggttaaagg tatggctgca aaactactca taccaaaaca gcagagctcc
5281 agacctcctc ttaggaaaga gccacttgga gagggatggt gtgaaggctg gaggtgagag
5341 acagagcctg tcccagtttt cctgtctcta ttttctgaaa cgtttgcagg aggaaaggac
5401 aactgtactt tcaggcatag ctggtgccct cacgtaaata agttccccga acttctgtgt
5461 catttgttct taagatgctt tggcagaaca ctttgagtca attcgcttaa ctgtgactag
5521 gtctgtaaat aagtgctccc tgctgataag gttcaagtga catttttagt ggtatttgac
5581 agcatttacc ttgctttcaa gtcttctacc aagctcttct atacttaagc agtgaaaccg
5641 ccaagaaacc cttcctttta tcaagctagt gctaaatacc attaacttca taggttagat
5701 acggtgctgc cagcttcacc tggcagtggt tggtcagttc tgctggtgac aaagcctccc
5761 tggcctgtgc ttttacctag aggtgaatat ccaagaatgc agaactgcat ggaaagcaga
5821 gctgcaggca cgatggtgct gagccttagc tgcttcctgc tgggagatgt ggatgcagag
5881 acgaatgaag gacctgtccc ttactcccct cagcattctg tgctatttag ggttctacca
5941 gagtccttaa gaggttttt ttttttttgg tccaaaagtc tgtttgtttg gttttgacca
6001 ctgagagcat gtgacacttg tctcaagcta ttaaccaagt gtccagccaa aatcaattgc
6061 ctgggagacg cagaccatta cctggaggtc aggacctcaa taaatattac cagcctcatt
6121 gtgccgctga cagattcagc tggctgctcc gtgttccagt ccaacagttc ggacgccacg
6181 tttgtatata tttgcaggca gcctcggggg gaccatctca ggagcagagc accggcagcc
6241 gcctgcagag ccgggcagta cctcaacatg aaagaacctg cacttcctgg tacttcactg
6301 caaagagcat gtagactgct ggtagcattt tgcgccctgc acctgagcgc aaccctgctc
6361 tactacctgg ctggatccag cctgactcca ccccgctctc cagaacctcc cctcggagg
6421 ccgcctccag ccaacctctc cctgccaccc tcccggcctc ctcctccccc tgcggctcgc
6481 ccccgcccag gacctgtttc tgcacaaccc cggaacctgc cagattctgc accatctgga
6541 ctgtgccccg atccaagtcc actgctcgtt ggtcctctgc gggtggagtt tagtcagcca
```

Fig. 9B

```
6601 gtgaacctgg aggaagtggc ttctaccaat ccggaggtca gggaaggagg gagattcgcc
6661 ccaaaggact gcaaagcgct ccagaaggtg gctattatta tccccttcag gaacagagag
6721 gagcacctga agtattggct gtactacatg cacccgattc ttcagagaca gcaattggac
6781 tatggggtct atgtgattaa tcaagacggc gatgaagaat ttaacagagc taaactgctt
6841 aatgtcggtt tcactgaggc actcaaggaa tacgattatg attgctttgt gttttccgat
6901 gtggatctga ttcctatgga cgaccgtaac acatataagt gctatagtca accacgtcac
6961 ctgagtgtgt caatggacaa gtttggcttt aggctgccgt ataaccagta tttcggagga
7021 gtttcagcat tgagtaaaga acagtttaca aaaatcaacg ggttcccaaa taactactgg
7081 gggtggggcg gagaggacga cgacatctac aacagactgg tttttaaggg gatggggatt
7141 tcccgcccgg atgcagtaat aggcaagtgt cgtatgatac gccatagcag ggatagaaag
7201 aacgaaccca accctgagcg ctttgaccgg attgcacata caagagaaac tatgtcatct
7261 gatggactta actctctttc atatgaggtg ctgagaacag atcggttccc cctgtacact
7321 agaatcacag tagatatcgg ggcacctggg tcataagcct aaagtctagt atggggattg
7381 gtggcgacga ctcctggagc ccgtcagtat cggcggaatt cggtaccgga tccc
```

Fig. 9C

```
   1 cgaggaatat aaaaaaatta caggaggctt ataagcagcc cgaaagaaga gcgtaggcga
  61 gttcttgtat tccgtgtgat agctggttgg attggtaatt gatcggctgg cacgcggaat
 121 ataggaggtc gctgaatagt aaacttgtag acttggctac agcatagagt atcttctgta
 181 gctctgatga ctgctaggaa ataatgctac ggataatgtg gggagggcaa ggcttgcgaa
 241 tcgggttgta acgggcaagg cttgactgag gggacaatag catgtttagg cgaaaagcgg
 301 ggcttcggtt gtacgcggtt aggagtcccc tcaggatata gtagtttcgc ttttgcatag
 361 ggaggggac ggattggacg aaccactgaa ttccgcattg cagagatatt gtatttaagt
 421 gcctagctcg atacaataaa cgccatttga ccattcacca cattggtgtg cacctgggtt
 481 gatggccgga ccgttgattc cctgrcgact acgagcacat gcatgaagca gaaggcttca
 541 tttggtgacc ccgacgtgat cgttagggaa tacgcgctca ctggccgtcg ttttacaacg
 601 tcgtgactgg gaaaaccctg gcgttaccca acttaatcgc cttgcagcac atcccccttt
 661 cgccagctgg cgtaatagcg aagaggcccg caccgatcgc ccttcccaac agttgcgcag
 721 cctgaatggc gaatggaaat tgtaagcgtt aatattttgt taaaattcgc gttaaatttt
 781 tgttaaatca gctcattttt taaccaatag gccgaaatcg gcaaaatccc ttataaatca
 841 aaagaataga ccgagatagg gttgagtgtt gttccagttt ggaacaagag tccactatta
 901 aagaacgtgg actccaacgt caaagggcga aaaccgtct atcagggcga tggcccacta
 961 cgtgaaccat cacccctaatc aagtttttg gggtcgaggt gccgtaaagc actaaatcgg
1021 aaccctaaag ggagcccccg atttagagct tgacggggaa agccggcgaa cgtggcgaga
1081 aaggaaggga agaaagcgaa aggagcgggc gctagggcgc tggcaagtgt agcggtcacg
1141 ctgcgcgtaa ccaccacacc cgccgcgctt aatgcgccgc tacagggcgc gtcaggtggc
1201 acttttcggg gaaatgtgcg cggaaccccT atttgtttat ttttctaaat acattcaaat
1261 atgtatccgc tcatgagaca ataaccctga taaatgcttc aataatattg aaaaaggaag
1321 agtatgagta ttcaacattt ccgtgtcgcc cttattccct tttttgcggc attttgcctt
1381 cctgtttttg ctcacccaga aacgctggtg aaagtaaaag atgctgaaga tcagttgggt
1441 gcacgagtgg gttacatcga actggatctc aacagcggta agatccttga gagttttcgc
1501 cccgaagaac gttttccaat gatgagcact tttaaagttc tgctatgtgg cgcggtatta
1561 tcccgtattg acgccgggca agagcaactc ggtcgccgca tacactattc tcagaatgac
1621 ttggttgagt actcaccagt cacagaaaag catcttacgg atggcatgac agtaagagaa
1681 ttatgcagtg ctgccataac catgagtgat aacactgcgg ccaacttact tctgacaacg
1741 atcggaggac cgaaggagct aaccgctttt ttgcacaaca tgggggatca tgtaactcgc
1801 cttgatcgtt gggaaccgga gctgaatgaa gccataccaa acgacgagcg tgacaccacg
1861 atgcctgtag caatggcaac aacgttgcgc aaactattaa ctggcgaact acttactcta
1921 gcttcccggc aacaattaat agactggatg gaggcggata agttgcagg accacttctg
1981 cgctcggccc ttccggctgg ctggtttatt gctgataaat ctggagccgg tgagcgtggg
2041 tctcgcggta tcattgcagc actggggcca gatggtaagc cctcccgtat cgtagttatc
2101 tacacgacgg ggagtcaggc aactatggat gaacgaaata gacagatcgc tgagataggt
2161 gcctcactga ttaagcattg gtaactgtca gaccaagttt actcatatat actttagatt
2221 gatttaaaac ttcattttta atttaaaagg atctaggtga agatcctttt tgataatctc
2281 atgaccaaaa tcccttaacg tgagttttcg ttccactgag cgtcagaccc cgtagaaaag
2341 atcaaaggat cttcttgaga tcctttttt ctgcgcgtaa tctgctgctt gcaaacaaaa
2401 aaaccaccgc taccagcggt ggtttgtttg ccggatcaag agctaccaac tcttttttccg
2461 aaggtaactg gcttcagcag agcgcagata ccaaatactg tccttctagt gtagccgtag
2521 ttaggccacc acttcaagaa ctctgtagca ccgcctacat acctcgctct gctaatcctg
2581 ttaccagtgg ctgctgccag tggcgataag tcgtgtctta ccgggttgga ctcaagacga
2641 tagttaccgg ataaggcgca gcggtcgggc tgaacgggg gttcgtgcac acagcccagc
2701 ttggagcgaa cgacctacac cgaactgaga tacctacagc gtgagctatg agaaagcgcc
2761 acgcttcccg aagggagaaa ggcggacagg tatccggtaa cgccagggt cggaacagga
2821 gagcgcacga gggagcttcc agggggaaac gcctggtatc tttatagtcc tgtcgggttt
2881 cgccacctct gacttgagcg tcgatttttg tgatgctcgt caggggggcg gagcctatgg
2941 aaaaacgcca gcaacgcggc cttttacgg ttcctggcct tttgctggcc ttttgctcac
3001 atgttctttc ctgcgttatc ccctgattct gtggataacc gtattaccgc ctttgagtga
3061 gctgataccg ctcgccgcag ccgaacgacc gagcgcagcg agtcagtgag cgaggaagcg
3121 gaagagcgcc caatacgcaa accgcctctc cccgcgcgtt ggccgattca ttaatgcagc
3181 tggcacgaca ggtttcccga ctggaaagcg ggcagtgagc gcaacgcaat taatgtgagt
```

Fig. 10A

```
3241 tagctcactc attaggcacc ccaggctttta cactttatgc ttccggctcg tatgttgtgt
3301 ggaattgtga gcggataaca atttcacaca ggaaacagct atgaccatga ttacgccaag
3361 cgcgcattgg taattgatcg gctggcacgc ggaatatagg aggtcgctga atagtaaact
3421 tgtagacttg gctacagcat agagtatctt ctgtagctct gatgactgct aggaaataat
3481 gctacggata atgtggggag ggcaaggctt gcgaatcggg ttgtaacggg caaggcttga
3541 ctgaggggac aatagcatgt ttaggcgaaa agcggggctt cggttgtacg cggttaggag
3601 tccctcagg atatagtagt ttcgcttttg cataggagg gggaaatgta gtcttatgca
3661 atactcttgt agtcttgcaa catgcttatg taacgatgag ttagcaacat gccttataag
3721 gagagaaaaa gcaccgtgca tgccgattgg tgggagtaag gtggtatgat cgtggtatga
3781 tcgtgccttg ttaggaaggc aacagacggg tctaacacgg attggacgaa ccactgaatt
3841 ccgcattgca gagatattgt atttaagtgc ctagctcgat acaataaacg ccatttgacc
3901 attcaccaca ttggtgtgca cctgggttga tggccggacc gttgattccc tgrcgactac
3961 gagcacatgc atgaagcaga aggcttcatt tggtgaccc gacgtgatcg ttagggaata
4021 gtggtcggcc acaggcggcg tggcgatcct gtcctcatcc gtctcgctta ttcggggagc
4081 ggacgatgac cctagtagag ggggctgcgg cttaggaggg cagaagctga gtggcgtcgg
4141 agggagccct actgcagggg gccaacatac cctaccgaga actcagagag tcgttggaag
4201 acgggaagga agcccgacga ctgagcggtc caccccaggc gtgattccgg ttgctctgcg
4261 tgattccggt cgcccggtgg atcaagcatg gaagccgtca taaggtgat ttcgtccgcg
4321 tgtaagacct attgcgggaa aacctctcct tctaagaagg aaatagggc tatgttgtcc
4381 ctgttacaaa aggaagggtt gcttacgtcc ccctcagact tatattcccc atactggcca
4441 agtcctgccc agctgtcagc ctgctgaccc tctgcagttc aggaccatga aacgtggcac
4501 tgtaagacgt gtccctgcc tttgcttgcc cacagatctc tgcccttgtg ctgactcctg
4561 cacacaagag catttccctg tagccaaaca gcgattagcc ataagctgca cctgactttg
4621 aggattaaga gtttgcaatt aagtggattg cagcaggaga tcagtggcag ggttgcagat
4681 gaaatccttt tctaggggta gctaagggct gagcaacctg tcctacagca caagccaaac
4741 cagccaaggg ttttcctgtg ctgttcacag aggcagggcc agctggagct ggaggaggtt
4801 gtgctgggac ccttctccct gtgctgagaa tggagtgatt tctgggtgct gttcctgtgg
4861 cttgcactga gcagctcaag ggagatcggt gctcctcatg cagtgccaaa actcgtgttt
4921 gatgcagaaa gatggatgtg cacctccctc ctgctaatgc agccgtgagc ttatgaaggc
4981 aatgagccct cagtgcagca ggagctgtag tgcactcctg taggtgctag ggaaaatctc
5041 tggttcccag ggatgcattc ataagggcaa tatatcttga ggctgcgcca aatctttctg
5101 aaatattcat gcgtgttccc ttaatttata gaaacaaaca cagcagaata attattccaa
5161 tgcctcccct cgaaggaaac ccatatttcc atgtagaaat gtaacctata tacacacagc
5221 catgctgcat ccttcagaac gtgccagtgc tcatctccca tggcaaaata ctacaggtat
5281 tctcactatg ttggacctgt gaaaggaacc atggtaagaa acttcggtta aaggtatggc
5341 tgcaaaacta ctcataccaa aacagcagag ctccagacct cctcttagga aagagccact
5401 tggagaggga tggtgtgaag gctggaggtg agagacagag cctgtcccag ttttcctgtc
5461 tctattttct gaaacgtttg caggaggaaa ggacaactgt acttcaggc atagctggtg
5521 ccctcacgta aataagttcc ccgaacttct gtgtcatttg ttcttaagat gctttggcag
5581 aacactttga gtcaattcgc ttaactgtga ctaggtctgt aaataagtgc tccctgctga
5641 taaggttcaa gtgacatttt tagtggtatt tgacagcatt taccttgctt tcaagtcttc
5701 taccaagctc ttctatactt aagcagtgaa accgccaaga aacccttcct tttatcaagc
5761 tagtgctaaa taccattaac ttcataggtt agatacggtg ctgccagctt cacctggcag
5821 tggttggtca gttctgctgg tgacaaagcc tccctggcct gtgcttttac ctagaggtga
5881 atatccaaga atgcagaact gcatggaaag cagagctgca ggcacgatgg tgctgagcct
5941 tagctgcttc ctgctgggag atgtggatgc agagacgaat gaaggacctg tcccttactc
6001 ccctcagcat tctgtgctat ttagggttct accagagtcc ttaagaggtt tttttttttt
6061 ttggtccaaa agtctgtttg tttggttttg accactgaga gcatgtgaca cttgtctcaa
6121 gctattaacc aagtgtccag ccaaaatcaa ttgcctggga gacgcagacc attacctgga
6181 ggtcaggacc tcaataaaata ttaccagcct cattgtgccg ctgacagatt cagctggctg
6241 ctccgtgttc cagtccaaca gttcggacgc acgtttgta tatatttgca ggcagcctcg
6301 ggggaccat ctcaggagca gagcaccggc agccgcctgc agagccgggc agtacctcaa
6361 catgggtctt ttggttttca tgagaaatct gctgctggct ctgtgtctgt tcctggtcct
6421 gggatttctg tactactctg catggaagct ccacctgctg cgctgggagg atagctctaa
6481 atatggacgc ctgagccata gctcttttcc taagcaaaga ccaagtgctg attctgtggt
```

Fig. 10B

```
6541 cttgtcattt gactctgttg gacatactat tggctctgaa tatgacaaac tgggttttct
6601 gcttaacctt gattctaaac ttcccsctga attggcctca aaatatgcca acttctctga
6661 gggagtgtgc aagcctggtt atgcatctgc cctgatgact gtgattttcc ctaaattctc
6721 caaacctgcc cccatgttcc ttgatgactc cttccggcgc tgggcccgca ttagagactt
6781 tgtgcctcca tttggcatta aagggcagga caatctgata aaggcaatac tgtctgctac
6841 aaaagattac agactcacac cagcactgga cagcttgtca tgccgccgct gtatcattgt
6901 tgggaatggt ggtgttctgg ccaacaagag tttgggtctt aagattgatg actatgatgt
6961 ggtcgttcgc ctgaactctg cacctgtcaa aggctttgag aaagatgttg gtggaaagac
7021 aacactgcgg atcacttacc cagaggggc tattcagaag atggaacagt atgagaaaga
7081 ctccctgttt gtgctggcgg gatttaaatg gcaagacttt aagtggctga aatatattgt
7141 gtataaagaa aaggtctcag cttctgatgg cttctggaaa tcagtggcta cccgggtgcc
7201 tcggagcca catgaaattc gcatactgaa tccctatttc atccaagaag ctgcttttc
7261 attcattggc ctgccattca ataatggtct gatgggtcgg gggaatatcc ccaccctggg
7321 ttctgtggcc atcacaatgg ctctgcataa ttgtgatgag gtggctgttg ctggctttgg
7381 atatgacatg agttccccta atgctcccct gcattactat gagaacataa aaatgagtgc
7441 cattaaggag tcatggactc ataatataca acgggagaag gaatttcttc gcaagctggt
7501 taaagccaga gtgattacag atcttacatc tgggatatga ggatc
```

Fig. 10C

```
   1 cggatcsccg aggaatataa aaaaattaca ggaggcttat aagcagcccg aaagaagagc
  61 gtaggcgagt tcttgtattc cgtgtgatag ctggttggat tggtaattga tcggctggca
 121 cgcggaatat aggaggtcgc tgaatagtaa acttgtagac ttggctacag catagagtat
 181 cttctgtagc tctgatgact gctaggaaat aatgctacgg ataatgtggg gagggcaagg
 241 cttgcgaatc gggttgtaac gggcaaggct tgactgaggg gacaatagca tgtttaggcg
 301 aaaagcgggg cttcggttgt acgcggttag gagtcccctc aggatatagt agtttcgctt
 361 ttgcataggg aggggggacgg attggacgaa ccactgaatt ccgcattgca gagatattgt
 421 atttaagtgc ctagctcgat acaataaacg ccatttgacc attcaccaca ttggtgtgca
 481 cctgggttga tggccggacc gttgattccc tgrcgactac gagcacatgc atgaagcaga
 541 aggcttcatt tggtgacccc gacgtgatcg ttagggaata cgcgctcact ggccgtcgtt
 601 ttacaacgtc gtgactggga aaaccctggc gttacccaac ttaatcgcct tgcagcacat
 661 ccccctttcg ccagctggcg taatagcgaa gaggcccgca ccgatcgccc ttcccaacag
 721 ttgcgcagcc tgaatggcga atggaaattg taagcgttaa tattttgtta aaattcgcgt
 781 taaattttg ttaaatcagc tcattttta accaataggc cgaaatcggc aaaatccctt
 841 ataaatcaaa agaatagacc gagatagggt tgagtgttgt tccagtttgg aacaagagtc
 901 cactattaaa gaacgtggac tccaacgtca aagggcgaaa aaccgtctat cagggcgatg
 961 gcccactacg tgaaccatca ccctaatcaa gtttttggg gtcgaggtgc cgtaaagcac
1021 taaatcggaa ccctaaaggg agccccgat ttagagcttg acggggaaag ccggcaacg
1081 tggcgagaaa ggaagggaag aaagcgaaag gagcgggcgc tagggcgctg gcaagtgtag
1141 cggtcacgct gcgcgtaacc accacacccg ccgcgcttaa tgcgccgcta cagggcgcgt
1201 caggtggcac ttttcgggga aatgtgcgcg gaacccctat ttgtttattt ttctaaatac
1261 attcaaatat gtatccgctc atgagacaat aaccctgata aatgcttcaa taatattgaa
1321 aaaggaagag tatgagtatt caacatttcc gtgtcgccct tattcccttt tttgcggcat
1381 tttgccttcc tgttttgct cacccagaaa cgctggtgaa agtaaaagat gctgaagatc
1441 agttgggtgc acgagtgggt tacatcgaac tggatctcaa cagcggtaag atccttgaga
1501 gttttcgccc cgaagaacgt tttccaatga tgagcacttt taaagttctg ctatgtggcg
1561 cggtattatc ccgtattgac gccgggcaag agcaactcgg tcgccgcata cactattctc
1621 agaatgactt ggttgagtac tcaccagtca cagaaaagca tcttacggat ggcatgacag
1681 taagagaatt atgcagtgct gccataacca tgagtgataa cactgcggcc aacttacttc
1741 tgacaacgat cggaggaccg aaggagctaa ccgcttttt gcacaacatg gggatcatg
1801 taactcgcct tgatcgttgg gaaccggagc tgaatgaagc cataccaaac gacgagcgtg
1861 acaccacgat gcctgtagca atggcaacaa cgttgcgcaa actattaact ggcgaactac
1921 ttactctagc ttcccggcaa caattaatag actggatgga gcggataaa gttgcaggac
1981 cacttctgcg ctcggccctt ccggctggct ggtttattgc tgataaatct ggagccggtg
2041 agcgtgggtc tcgcggtatc attgcagcac tggggccaga tggtaagccc tcccgtatcg
2101 tagttatcta cacgacgggg agtcaggcaa ctatggatga acgaaataga cagatcgctg
2161 agataggtgc ctcactgatt aagcattggt aactgtcaga ccaagtttac tcatatatac
2221 tttagattga ttttaaactt catttttaat ttaaaaggat ctaggtgaag atcctttttg
2281 ataatctcat gaccaaaatc ccttaacgtg agttttcgtt ccactgagcg tcagaccccg
2341 tagaaaagat caaaggatct tcttgagatc ctttttttct gcgcgtaatc tgctgcttgc
2401 aaacaaaaaa accaccgcta ccagcggtgg tttgtttgcc ggatcaagag ctaccaactc
2461 tttttccgaa ggtaactggc ttcagcagag cgcagatacc aaatactgtc cttctagtgt
2521 agccgtagtt aggccaccac ttcaagaact ctgtagcacc gcctacatac ctcgctctgc
2581 taatcctgtt accagtggct gctgccagtg gcgataagtc gtgtcttacc gggttggact
2641 caagacgata gttaccggat aaggcgcagc ggtcgggctg aacggggggt tcgtgcacac
2701 agcccagctt ggagcgaacg acctacaccg aactgagata cctacagcgt gagctatgag
2761 aaagcgccac gcttcccgaa gggagaaagg cggacaggta tccggtaagc ggcagggtcg
2821 gaacaggaga gcgcacgagg gagcttccag ggggaaacgc ctggtatctt tatagtcctg
2881 tcgggtttcg ccacctctga cttgagcgtc gatttttgtg atgctcgtca gggggggcgga
2941 gcctatggaa aaacgccagc aacgcggcct ttttacggtt cctggccttt tgctggcctt
3001 ttgctcacat gttctttcct gcgttatccc ctgattctgt ggataaccgt attaccgcct
3061 ttgagtgagc tgataccgct cgccgcagcc gaacgaccga gcgcagcgag tcagtgagcg
3121 aggaagcgga gagcgcccca atacgcaaac cgcctctccc cgcgcgttgg ccgattcatt
3181 aatgcagctg gcacgacagg tttcccgact ggaaagcggg cagtgagcgc aacgcaatta
3241 atgtgagtta gctcactcat taggcacccc aggctttaca ctttatgctt ccggctcgta
```

Fig. 11A

```
3301 tgttgtgtgg aattgtgagc ggataacaat ttcacacagg aaacagctat gaccatgatt
3361 acgccaagcg cgcattggta attgatcggc tggcacgcgg aatataggag gtcgctgaat
3421 agtaaacttg tagacttggc tacagcatag agtatcttct gtagctctga tgactgctag
3481 gaaataatgc tacggataat gtggggaggg caaggcttgc gaatcgggtt gtaacgggca
3541 aggcttgact gaggggacaa tagcatgttt aggcgaaaag cggggcttcg gttgtacgcg
3601 gttaggagtc ccctcaggat atagtagttt cgcttttgca tagggagggg gaaatgtagt
3661 cttatgcaat actcttgtag tcttgcaaca tgcttatgta acgatgagtt agcaacatgc
3721 cttataagga gagaaaaagc accgtgcatg ccgattggtg ggagtaaggt ggtatgatcg
3781 tggtatgatc gtgccttgtt aggaaggcaa cagacgggtc taacacggat tggacgaacc
3841 actgaattcc gcattgcaga gatattgtat ttaagtgcct agctcgatac aataaacgcc
3901 atttgaccat tcaccacatt ggtgtgcacc tgggttgatg gccggaccgt tgattccctg
3961 rcgactacga gcacatgcat gaagcagaag gcttcatttg gtgaccccga cgtgatcgtt
4021 agggaatagt ggtcggccac aggcggcgtg gcgatcctgt cctcatccgt ctcgcttatt
4081 cggggagcgg acgatgaccc tagtagaggg ggctgcggct taggagggca gaagctgagt
4141 ggcgtcggag ggagccctac tgcaggggc caacataccc taccgagaac tcagagagtc
4201 gttggaagac gggaaggaag cccgacgact gagcggtcca ccccaggcgt gattccggtt
4261 gctctgcgtg attccggtcg cccggtggat caagcatgga agccgtcata aaggtgattt
4321 cgtccgcgtg taagacctat tgcgggaaaa cctctccttc taagaaggaa ataggggcta
4381 tgttgtccct gttacaaaag gaagggttgc ttacgtcccc ctcagactta tattccccgg
4441 ggtcctggga tctctgccct tgtgctgact cctgcacaca agagcatttc cctgtagcca
4501 aacagcgatt agccatgac tgcacctgac tttgaggatt aagagtttgc aattaagtgg
4561 attgcagcag gagatcagtg gcagggttgc agatgaaatc cttttctagg ggtagctaag
4621 ggctgagcaa cctgtcctac agcacaagcc aaaccagcca agggttttcc tgtgctgttc
4681 acagaggcag ggccagctgg agctggagga ggttgtgctg ggacccttct ccctgtgctg
4741 agaatggagt gatttctggg tgctgttcct gtggcttgca ctgagcagct caagggagat
4801 cggtgctcct catgcagtgc caaaactcgt gtttgatgca gaaagatgga tgtgcacctc
4861 cctcctgcta atgcagccgt gagcttatga aggcaatgag ccctcagtgc agcaggagct
4921 gtagtgcact cctgtaggtg ctagggaaaa tctctggttc cagggatgc attcataagg
4981 gcaatatatc ttgaggctgc gccaaatctt tctgaaatat tcatgcgtgt tcccttaatt
5041 tatagaaaca aacacagcag aataattatt ccaatgcctc ccctcgaagg aaacccatat
5101 ttccatgtag aaatgtaacc tatatacaca cagccatgct gcatccttca gaacgtgcca
5161 gtgctcatct cccatggcaa aatactacag gtattctcac tatgttggac ctgtgaaagg
5221 aaccatggta agaaacttcg gttaaaggta tggctgcaaa actactcata ccaaaacagc
5281 agagctccag acctcctctt aggaaagagc cacttggaga gggatggtgt gaaggctgga
5341 ggtgagagac agagcctgtc ccagttttcc tgtctctatt ttctgaaacg tttgcaggag
5401 gaaaggacaa ctgtactttc aggcatagct ggtgccctca cgtaaataag ttccccgaac
5461 ttctgtgtca tttgttctta agatgctttg cagaacact ttgagtcaat tcgcttaact
5521 gtgactaggt ctgtaaataa gtgctccctg ctgataaggt tcaagtgaca tttttagtgg
5581 tatttgacag catttacctt gctttcaagt cttctaccaa gctcttctat acttaagcag
5641 tgaaaccgcc aagaaaccct tcctttatc aagctagtgc taaataccat taacttcata
5701 ggttagatac ggtgctgcca gcttcacctg gcagtggttg gtcagttctg ctggtgacaa
5761 agcctccctg gcctgtgctt ttacctagag gtgaatatcc aagaatgcag aactgcatgg
5821 aaagcagagc tgcaggcacg atggtgctga gccttagctg cttcctgctg ggagatgtgg
5881 atgcagagac gaatgaagga cctgtccctt actccctca gcattctgtg ctatttaggg
5941 ttctaccaga gtccttaaga ggttttttt ttttttggtc caaaagtctg tttgtttggt
6001 tttgaccact gagagcatgt gacacttgtc tcaagctatt aaccaagtgt ccagccaaaa
6061 tcaattgcct gggagacgca gaccattacc tggaggtcag gacctcaata aatattacca
6121 gcctcattgt gccgctgaca gattcagctg gctgctccgt gttccagtcc aacagttcgg
6181 acgccacgtt tgtatatatt tgcaggcagc ctcgggggga ccatctcagg agcagagcac
6241 cggcagccgc ctgcagagcc gggcagtacc tcaacatgaa agaacctgca cttcctggta
6301 cttcactgca aagagcatgt agactgctgg tagcattttg cgccctgcac ctgagcgcaa
6361 ccctgctcta ctacctggct ggatccagcc tgactccacc ccgctctcca gaacctcccc
6421 ctcggaggcc gcctccagcc aacctctccc tgccaccctc ccggcctcct cctcccctg
6481 cggctcgccc ccgcccagga cctgtttctg cacaaccccg gaacctgcca gattctgcac
6541 catctggact gtgccccgat ccaagtccac tgctcgttgg tcctctgcgg gtggagttta
6601 gtcagccagt gaacctggag gaagtggctt ctaccaatcc ggaggtcagg gaaggaggga
```

Fig. 11B

```
6661 gattcgcccc aaaggactgc aaagcgctcc agaaggtggc tattattatc cccttcagga
6721 acagagagga gcacctgaag tattggctgt actacatgca cccgattctt cagagacagc
6781 aattggacta tggggtctat gtgattaatc aagacggcga tgaagaattt aacagagcta
6841 aactgcttaa tgtcggtttc actgaggcac tcaaggaata cgattatgat tgctttgtgt
6901 tttccgatgt ggatctgatt cctatggacg accgtaacac atataagtgc tatagtcaac
6961 cacgtcacct gagtgtgtca atggacaagt ttggctttag gctgccgtat aaccagtatt
7021 tcggaggagt ttcagcattg agtaaagaac agtttacaaa aatcaacggg ttcccaaata
7081 actactgggg gtggggcgga gaggacgacg acatctacaa cagactggtt tttaagggga
7141 tgggatttc ccgcccggat gcagtaatag gcaagtgtcg tatgatacgc catagcaggg
7201 atagaaagaa cgaacccaac cctgagcgct tgaccggat tgcacataca agagaaacta
7261 tgtcatctga tggacttaac tctctttcat atgaggtgct gagaacagat cggttccccc
7321 tgtacactag aatcacagta gatatcgggg cacctgggtc ataagcccgt tactggccga
7381 agccgcttgg aataaggccg gtgtgcgttt gtctatatgt tattttccac catattgccg
7441 tcttttggca atgtgagggc ccggaaacct ggccctgtct tcttgacgag cattcctagg
7501 ggtctttccc ctctcgccaa aggaatgcaa ggtctgttga atgtcgtgaa ggaagcagtt
7561 cctctggaag cttcttgaag acaaacaacg tctgtagcga ccctttgcag gcagcggaac
7621 cccccacctg gcgacaggtg cctctgcggc caaaagccac gtgtataaga tacacctgca
7681 aaggcggcac aaccccagtg ccacgttgtg agttggatag ttgtggaaag agtcaaatgg
7741 ctctcctcaa gcgtattcaa caggggctg aaggatgccc agaaggtacc ccattgtatg
7801 ggatctgatc tggggcctcg gtgcacatgc tttacgtgtg tttagtcgag gttaaaaaac
7861 gtctaggccc cccgaaccac ggggacgtgg ttttcctttg aaaaacacga tgataagctt
7921 gccacaacca tgggtctttt ggttttcatg agaaatctgc tgctggctct gtgtctgttc
7981 ctggtcctgg gatttctgta ctactctgca tggaagctcc acctgctgcg ctgggaggat
8041 agctctaaat atggacgcct gagccatagc tcttttccta agcaaagacc aagtgctgat
8101 tctgtggtct tgtcatttga ctctgttgga catactattg gctctgaata tgacaaactg
8161 ggttttctgc ttaaccttga ttctaaactt ccccctgaat tggcctcaaa atatgccaac
8221 ttctctgagg gagtgtgcaa gcctggttat gcatctgccc tgatgactgt gattttccct
8281 aaattctcca aacctgcccc catgttcctt gatgactcct tccggcgctg ggcccgcatt
8341 agagactttg tgcctccatt tggcattaaa gggcaggaca atctgataaa ggcaatactg
8401 tctgctacaa aagattacag actcacacca gcactggaca gcttgtcatg ccgccgctgt
8461 atcattgttg ggaatggtgg tgttctggcc aacaagagtt tgggtcttaa gattgatgac
8521 tatgatgtgg tcgttcgcct gaactctgca cctgtcaaag ctttgagaa agatgttggt
8581 ggaaagacaa cactgcggat cacttaccca gagggggcta ttcagaagat ggaacagtat
8641 gagaaagact ccctgtttgt gctggcggga tttaaatggc aagcttttaa gtggctgaaa
8701 tatattgtgt ataagaaaa ggtctcagct tctgatggct tctggaaatc agtggctacc
8761 cgggtgcctc gggagccaca tgaaattcgc atactgaatc cctatttcat ccaagaagct
8821 gctttttcat tcattggcct gccattcaat aatggtctga tgggtcgggg gaatatcccc
8881 accctgggtt ctgtggccat cacaatggct ctgcataatt gtgatgaggt ggctgttgct
8941 ggctttggat atgacatgag ttcccctaat gctccctgc attactatga aacataaaa
9001 atgagtgcca ttaaggagtc atggactcat aatatacaac gggagaagga atttcttcgc
9061 aagctggtta aagccagagt gattacagat cttacatctg ggatatgagg atccggtac
```

Fig. 11C

```
   1 gcatcccgtc cccggcggcg gcgcggggcg ggcggcggtc cccgtcagcg cggcggcatg
  61 aaggagccgg cgctgcccgg cacctcgctg cagcgggcct gccgcctcct cgtcgctttc
 121 tgcgcgctgc acctctcggc cacgctgctc tactacctgg cgggcagctc cctgacgccg
 181 ccgcgcagcc ccgagcctcc gccgcgccgc ccgcctcccg ccaacctctc gctgccgccc
 241 tcccgcccgc cgccgccgcc cgccgcccgg ccccgacccg gaccggtctc ggcacagccc
 301 cgcaacctcc cggactcggc gccgtcgggg ctgtgcccgg acccgtcccc gctgctcgtc
 361 ggaccgctgc gcgtggagtt ctcccagcct gtgaacctgg aggaggtggc gagcacaaac
 421 cctgaggtca ggagggagg tcgtttgct ccaaaggact gcaaggcgct gcagaaagta
 481 gcaatcatca tcccgttccg aaaccgagag gagcatctga agtactggct ctattacatg
 541 cacccaattc ttcaaaggca gcagctagat tatggagtgt atgtcatcaa ccaggatgga
 601 gacgaagaat ttaaccgtgc taaactgctg aatgtaggat tcacggaagc ttttgaaggag
 661 tatgactatg actgctttgt gtttagtgat gtagacctga tcccaatgga tgacaggaac
 721 acctacaagt gctacagcca accaaggcac ctttctgtct ccatggataa attcggattt
 781 cggttaccct acaatcagta ttttggaggt gtgtctgcct tgagcaaaga acaattcacg
 841 aagatcaatg ggtttccaaa caattactgg ggctggggag gcgaagatga tgacatctac
 901 aacaggctgg tgttcaaagg catgggcata tctcggccag atgctgtcat tgggaaatgc
 961 agaatgattc gccactcgcg tgatcggaag aacgagccca acccgagag gtttgaccgt
1021 attgctcaca ccagggagac gatgagctct gatggcttga actcgctctc ctacgaggtg
1081 ctaaggactg acaggttccc tctgtacacg aggatcacag tggatatcgg agcgcccggc
1141 agctgacacg gccggcacgg cggagacctc gggacggtgc cccgcacgct gggctggcag
1201 attctttgtg tcgtcgggtt ttataagggt tgtgatgaac aacacggagg tctctctgca
1261 tgtcagagcc tctccaaaag ggctggacga ctgcttttcc cgtcggttgt ttttgtaact
1321 ctgcctccag ctctccattg ttttgtaagt tcagaggctg tacgtaacag ttgtaaatac
1381 ttccttttg ccaggagatg ctgaatctga tccccgtgtt cggtcaccgc tggtcccggg
1441 ttagtttgac aactgcagcc gtggtgcacc agcagcgacc gcccatgata cggctttctt
1501 cttttttaat tgggtggacg aaaacattcc ttttaattca ttcctcgttt ttatctctat
1561 gaaggactgt aaaacgctgc taaaattgta tgagtttact catttcgtta gattgttttt
1621 tgtttttttt ttaagagagg caaaattacg tggggttttct tcttcttttt tttcttccta
1681 ctggtgacca aagcaaacaa tcttctccgc gtgcagagcg catgacgaat aaccaagtgt
1741 ggattcagca cacctcacta ttcctttcgg tctcaaaaga gacttccgag cgagctgagg
1801 cagatgtgcc ctcggagagc tctgtgcgtg ggctgggagc cgcagggatg tgcagcagag
1861 ctctccatga cccgcagcag ctgctggctc cccataacct gctgtcgggt gtggttttat
1921 tttattttat tttatctttt cttgcctggg cagagcaaga cacctggagga atctcttcgg
1981 tcggtcggtc agtttggttt gcttgtttgc tcttccccca aaagagcgga tggggtttaat
2041 tgcacaagga attgatagcc ttaaaattca cagacacttt taccagtggt aggaagttgc
2101 cacgctattt aaacatggtc tgaaggttct taagaacgac attctgcttg caaggtcatg
2161 tgtgaaactt gaactcactt attacttta ttgttgttgt aactttttga taactttaa
2221 aagtaatttg tatatcctaa gcggtatatt taataccaga ttaaagcagg gtgcagcat
```

Fig. 12A mkepalpgtslqracrllvafcalhlsatllyylagssltpprspeppprrpppanlslppsrpppppaarprpgpvsaq
prnlpdsapsglcpdpspllvgplrvefsqpvnleevastnpevreggrfapkdckalqkvaiiipfrnreehlkywlyy
mhpilqrqqldygvyvinqdgdeefnrakllnvgftealkeydydcfvfsdvdlipmddrntykcysqprhlsvsmdkfg
frlpynqyfggvsalskeqftkingfpnnywgwggedddiynrlvfkgmgisrpdavigkcrmirhsrdrknepnperfd
riahtretmssdglnslsyevlrtdrfplytritvdigapgs

Fig. 12B

```
   1 gtggcggtgg cccggccggc agggcccccg cagccccggc atgggcgccc gcggccggcg
  61 gccgggggaa gcggcggggg ccgctgacgc gccggggccg cgggaggagg tggtggcggc
 121 ggtggcggcg gcggggggacg gtgcggggcg gccgcggatc gggaccgtgg ctggagctgc
 181 ctgcctccct gtgcccagaa gatgaccagg ttgctcttgg gggtgaccct ggaaaggatt
 241 tgcaaggccg tgctgctgct ctgcctgctc cactttgtca tcatcatgat tctctacttt
 301 gacgtctacg cgcagcacct ggacttcttc agccgcttca atgccaggaa cacctcgcgc
 361 gtgcacccct ctccaactc ctctcggccc aacagcacgg cccccagcta cggcccacgt
 421 ggcgctgagc ccccctcccc cagcgccaag cccaacacca accgctccgt cacagagaag
 481 cccttgcagc cctgccagga gatgccctcc ggcttagtcg ggcgcctgct cattgagttc
 541 agctcccta tgagcatgga gcgggtgcaa cgggagaacc ctgacgtgag cctgggtggc
 601 aagtacaccc ccccagattg cctgccccgg cagaaggtgg ccatcctcat cccttccgg
 661 caccgcgagc accacctcaa atactggctg cactacctgc accccatcct gcgccggcag
 721 aaggtggctt atggcatcta catcatcaac cagtatggcg aggacacctt caaccgggcc
 781 aagctgctca atgtgggctt cctggaggcg ctgaaggatg acgaggagta cgactgcttc
 841 attttcagcg atgtggacct catccccatg gatgaccgca acctgtaccg ctgctatgag
 901 cagccacggc actttgctgt ggcatggac aagtttgggt tcaggttgcc ctatgcaggg
 961 tacttcggtg gtgtctctgg gctgagcaag tcccagttcc taaagatcaa cggctttccc
1021 aacgagtact ggggctgggg aggagaggac gacgacatct taaccggat ctccctgaat
1081 ggcatgaagg tgtcgaggcc cgacatccgc atgggaggt atcgcatgat caagcacgaa
1141 cgtgacaaac acaacgagcc caacccgcag agattcacca agatccagaa caccaaaatg
1201 accatgaagc gggatgggat cagctcactg cagtaccggc tggtggaggt gtcacgccag
1261 cccatgtaca ccaacatcac ggtggagatt ggcaggccgc cccacgcctt ggcccggggc
1321 tagtgcttgc cctgcaggca aagctgcatg aggctggcgc tctgtcgcag ggctggctgg
1381 acgctgtgga tgttgcccca gcccctgggc aaggactgaa cggggatgtt ttctgcctac
1441 tctgctgcct tttggagacg ctgtgcccca gcctacctgt tggtcctgag gatttctgca
1501 atctgttgtc cctccttttcc ccatccctac aagtgtgttt ccagaacccc catactatgc
1561 gtgttggctg aagcacccgt tcgccctgcg tgcagctccc agacagaggg aggggacagt
1621 cccagccctg gtgaggagcc ccttgcccac gtcacgtccc gcctgcaccc taggagggaa
1681 ggatgagccc caaggtcagc ctagccccca gtccccaccg gtgctgcgag aagcgggatg
1741 caggcttccc ccttcaccag cgctggagct gctactaccc tggctgaagg catgggaggt
1801 agcccaggcc cccacagcag gcaggatcgg acagacagat gtggctcact gtcttcctct
1861 gctttagtct ggtgctcagg gctgggtctc agctctgcta aacagcgacc tctggttagc
1921 aaacacccct tgctgtgcct cagtttcccc gggctggcag ccacgtcccc tttcccctct
1981 ctgaaggcag atgctgtgtg cgtgtccctg ttaacccaca catgcaccag ctctcccaac
2041 tttgggcagt agggtgacgt gaaacctcac agcccctctt ggccagggt ctgccccggg
2101 gaatctccac ccagatgctg tttgtaggca gtggggactg gctgctctgc ccttgctgct
2161 ctccagcttc ccctctctgc tctgggcag ggagaagagg aacagggcca tgcggcaggt
2221 gccccatctc tccccacttc ccctccttgg ggctggggca cagccacccc cctgcagcca
2281 gctagaagag ctgggcagca ggggcactgg caactttgt acatttgaat gtctgaccct
2341 tttttttgagc gtacgttgaa tgcagcattc ggtcatagag acctgggttt ttgtatttaa
2401 taaaaatttc aaaagttaac
```

Fig. 13A

```
mtrlllgvtlerickavlllcllhfviimilyfdvyaqhldffsrfnarntsrvhpfsnssrpnstapsygprgaeppsp
sakpntnrsvtekplqpcqempsglvgrlliefsspmsmervqrenpdvslggkytppdclprqkvailipfrhrehhlk
ywlhylhpilrrqkvaygiyiinqygedtfnrakllnvgflealkddeeydcfifsdvdlipmddrnlyrcyeqprhfav
gmdkfgfrlpyagyfggvsglsksqflkingfpneywgwggedddifnrislngmkvsrpdirmgryrmikherdkhnep
npqrftkiqntkmtmkrdgisslqyrlvevsrqpmytnitveigrppprlarg
```

Fig. 13B

```
   1 atgtccctgt cccgcgtgga gaacccctgc ttcctgctgt tcctgctcgt cttccaagcc
  61 gtgttcatcc tgatactgta ccgaggtgga gcctcgagcg tgttccgggg cttttggag
 121 tcgcagcgcg ttttggatta ctccaaaagc cacgacgtgt acacgaacct cagcctgctg
 181 gccccggctg gcggcgggc ggcgctgccc tactgctcgg agcgctcacc catcgccgtt
 241 ggtccattaa ccatcacttt tgacgtgctc cctagtgaaa gaacgatcat ccaaaaaaat
 301 ccttttgttc agtccggagg ccactacaga ccacctcact gcttggcccg ctacaagtca
 361 gccatccttg tagcatacag taaccaggag aaataccttc accatcttct ctactacatt
 421 catcctttct tgcagcgcca gcagctcagc tacagaatct acttgattca gcaggtgggg
 481 aatggtacgt ttaaccgagc aaagctgctt aatgttggtg tccgagaagc cctgaaggat
 541 gaagactggg actgcctcct cctgcacgat gtgaacctgg tacctgagaa tgattataat
 601 ctctatgtct gtgatgaata ctatcccaaa catatggcta gtgccatgga taaatttcag
 661 tacaaccttc cctacaagtc ctttttgga ggtgtatctg cattgactcc agagcactac
 721 atgaagatga tgggtttcc aaacacatac tggggcgacg gtggtgaaac agatgacatt
 781 gctgcaagga tccagttagc aggcatgaga attgtccgga ccccaccaca ccttggacgc
 841 tacaaagtga tggactacaa cagagagaca gaagagcctt ggagaaggcc tgcttcccac
 901 cacaacactg gaaaaacttg gaaggatgat gggatgaact ctttagagtt caagctcctt
 961 tccagaacaa agcatcctct ttataccaac gtcactgtgg acattggata tgttccccc
1021 ttttcttaag ataatgaaaa ctgaaacgtg gtgttggaat tcactgtggc agcacagtta
1081 tgggtactca gcctctacct ctggctgcgg tgcagtctgc agcacctgag actaatcctg
1141 gtgtctttca tacattgaac ttttcttcgg attataggag gctttgaaga aaaggcttca
1201 ggagtgagac atgatagcta caaacaggag ctggcttact gtagaagtcc tttaaagcac
1261 tgtaaaactg agccaaatct acatgtcatg cctcaggctg gatagagact gtctccttga
1321 cagtaagttg acccaagttt tctggaacct tgttccgta acgggatggc tctgccctgc
1381 tccttactca actggtaagt gggattcagg ctgtcctgtc agtcctctca aatgctgtat
1441 tttgagaaag atcttacttg gtgttgaagc ctattacagt tctgtaaata tctttgtga
1501 atttgtgtca agaaagttga ggtgtgtttg tttggattaa gattttccta gagtatttaa
1561 taagacttta ataaggaga agttgccct gaagttggtt gaaactagag cttaaaaatt
1621 cctggttgtc tggccacatt atgaatgagt gtgtgagttc ttactgtagc cataagtaat
1681 tcacatctaa agaggcctca gactgtcagc tatgctcagc agatggaaat taatctacca
1741 tttcagccat tgctcaaatg ttaattatct ctcaaggttg atctgtattc aattaaaaca
1801 cttctgagaa atgaaatact agaggaaaaa
```

Fig. 14A

```
mslsrvenpcfllfllvfqavfililyrggassvfrgflesqrvldyskshdvytnlsllapagggaalpycserspiav
gpltitfdvlpsertiiqknpfvqsgghyrpphclaryksailvaysnqekylhhllyyihpflqrqqlsyriyliqqvg
ngtfnraklllnvgvrealkdedwdclllhdvnlvpendynlyvcdeyypkhmasamdkfqynlpyksffggvsaltpehy
mkmmngfpntywgdggetddiaariqlagmrivrtpphlgrykvmdynreteepwrrpashhntgktwkddgmnslefkll
srtkhplytnvtvdigyvppfs
```

Fig. 14B

```
   1 ggggcaccgg cggcagagag gcccggggag gttaagtcat gttttctgac actcgaagaa
  61 cagtcagcgc tgcaattcca tgagtcacag aaccacaaga agtgcggctg ccctccctac
 121 atgcagcttc ccttctttac tgtaacgttc ttcttggcac ctctggcttc ttccctactg
 181 agtgcacagc gggggaccca cggtggcatc ggggggagcg atggccataa gcttgtatgt
 241 atttcacttc ttcaataagt tcaaagtgtt ccttcttgtc accttgtgtt tgatgatgct
 301 atgggctgcg ttcagttact ttgtggattc tggacagaca attcctaaac ttaagagtgt
 361 ggggagcat tttggaaaga taatcagctt ggagaagaaa gaggacagtc agaaggaaga
 421 aaagatgaag ataactgaag gagttcctgc aacaaagcca cctcagggtc cctgtccagc
 481 tctgtctccg tacctgcgag gtgccagcaa actgaccttc agtccatctc tcacgctaga
 541 agaagtggaa aaggagaacc ctcaggtggc caagggccga taccaccctg cagagtgttc
 601 agccttgcag cgtgtggcca tcctcatccc gcaccgcaac cgtgagaggc atctgctgta
 661 cctcctggag cacctgcacc cgttcctgca gaggcagcag ctggaatatg catctacgt
 721 tatccaccag gctggcagca ccaaatttaa tcgagctaaa ctgctgaacg tgggatactt
 781 agaggcccta aaagaagaga actgggactg tttcattttc catgacgtgg atctggtgcc
 841 agagaatgac ttcaatattt acatgtgtga cagacaaccc aagcaccttg tagttggccg
 901 gaacagtact ggatacaggt tacgttacca gggatatttt ggaggcgtaa cagctctaac
 961 aagagaccag ttttccatgg tgaatggatt tctcaacaac tattgggggtt gggcggaga
1021 agatgacgac cttcgaatca gggttgagat gcagaagatg cgagtgatga ggccatctgc
1081 tgatgtagcc agatacacaa tgatcttcca caaccgtgac catggcaatg aggagaacag
1141 agagaggatg aagcttctgc gtcaggtatc tagaacatgg aaaacagatg ggttgaattc
1201 ctgttcctat agactgctgt cagtggaaca taaccctta tacatcaaca tcacggtaga
1261 tttcagcatg cagccaaaga tctcataggg gtgagcaccg cacaggtttt aggaaatggc
1321 agcagatcct gtttgtggtt ggtggcacag cagatgactt gcagcgctct gcttgaaaga
1381 gtactttagc agcacagaag aatgttttc tgcatggcat ctaattagtc agcagagaag
1441 ctcatttct gaggactgga gaggcggact gacccctggg caggtcctgg tgttcttcta
1501 tgcactttct gctgagatgt tcgcaagttt ccttgtttgg gctggtccag tagaaggact
1561 tgaatcaagt ctccctgaaaa aaatatttct taaaactatt cctgaacttc cagtttgaag
1621 taggaaggtg acactgccaa ggcttcaaaa ggagcaggcc agtctttcc cctcaaaagc
1681 acaagaattt tttaccatct ataaacttgt tgagaaaagc ttgtttcttc tagcctgaag
1741 aaaaactgct tgtggggtgg aaacagcaat aatggtaata ggggagaaat gattaaaaaa
1801 atctctcaat aaaatataat ctgcttaatt caaaaa
```

Fig. 15A

```
maislyvfhffnkfkvfllvtlclmmlwaafsyfvdsgqtipklksvgehfgkiislekkedsqkeekmkitegvpatkp
pqgpcpalspylrgaskltfspsltleevekenpqvakgryhpaecsalqrvailiphrnrerhllyllehlhpflqrqq
leygiyvihqagstkfnraklnvgyleakeenwdcfifhdvdlvpendfniymcdrqpkhlvvgrnstgyrlryqgyf
ggvtaltrdqfsmvngfsnnywgwggedddlrirvemqkmrvmrpsadvarytmifhnrdhgneenrermkllrqvsrtw
ktdglnscsyrllsvehnplyinitvdfsmqpkis
```

Fig. 15B

```
   1 atgcccatgt gttcaaaggc tacctcagat tttctggagc catcactgtg tgtcccagaa
  61 caatgcctgg atatcctgag gccatccta tatgccccag gaccatgtcc aggcgtccta
 121 agactatcac cagttgtccc atggtcatca ctggtgcttg gatgccatca tcgtttgtcc
 181 cagaacccca ctaaggtgcc ccaaggccat tactgcctgc ctcaaggcca gctctggcat
 241 tctgaggcca ccgctcagcg tccccagcat cgtgcccggg tgtcgtgggg ctcccatcga
 301 ctgtcacagg gccacctctg tttccctggg gaagctattg gtgagaacag agcgaggggc
 361 gggcggcgca cgtcatcctt tgccgaagaa cactcccagc agcatgctct gcagcggggg
 421 ccggagtttg cagccggttc tcgctccgcc tcgccccgcc ccgccccgcc ccgcgtcgct
 481 gtggctcctt catgcggcgg cgttgggcgc gggcggtggc tcggagcggc tgcggtgcag
 541 cgcttcccgc cgggcctcgg cgcatgtgag cggcagggcg gcggcacatc ggccatgcgg
 601 tggccccgcg gcccccgcgg cgcctggcgg ctgttgcccc ggcgctcgct gctggccgtg
 661 ctcttcctct tctcgctctc ctcctccttc ctctacttcg tatatgtggc gccgggcatc
 721 gtgaacacct acctcttcat gatgcaagcc caaggcatca tgattcgtga aaacatgaga
 781 acaataggag ctcaggtgta tgaacaggtg gtccgcagtg cctatgccaa gaggaacagc
 841 agtgtgaatg actcagatta tcctcttgac ttgaatcaca atgaaacctt tctgcaagct
 901 acaactttc ttcctgaaga ttttacgtac ttccccaacc acacctgtcc tgagaggctc
 961 ccttctatga agggccccat tgatgtaaat atgagcgaga ttacgatgga ggacatccac
1021 cagttcttct ccagagaccc ttccatcaag ctgggaggcc actggaagcc gagcgactgc
1081 ctgcctcgct ggaaggtggc gatcctgatc ccattccgca atcgctatga acatcttcca
1141 gtccttttca ggcaccttat tccaatgctg cagcgtcagc gtttacagtt tgcatttat
1201 gttgtggaac aagctggtac tcagcccttc aaccgtgcca tgctcttcaa tgttggcttt
1261 cgggaagcga tgaaggactt ggactgggac tgtctcatct tccatgatgt ggaccacata
1321 ccagaaaatg accgcaacta ttatgggtgt ggacagatgc cgagacactt tgcggccaag
1381 ctggacaagt acatgtacct gttgccctat aatgaattct cggtggagt gagcggcctg
1441 actgttgagc agttctggaa gattaatggt ttcccaaatg ccttctgggg ctgggcggt
1501 gaggatgacg acttatggaa cagagtgcag tatgcaggct attcagtgac tcgaccagaa
1561 ggagacacag gaaaatacaa atcaattccc caccatcatc gaggagaagt gcagttccta
1621 ggaaggtatg ccttgctgag gaagtcaaaa gaaaggcaag ccctggatgg cctcaataat
1681 ttgaactact ttcctaatgt cacatatgac gccttgtata agaacatcac tgttaacctg
1741 acaccagagc tggctctggt aactgaatat taa
```

Fig. 16A mrwprgprgawrllpprrsllavlflfslsssflyfvyvapgivntylfmmqaqgimirenmrtigaqvyeqvvrsayakr
nssvndsdypldlnhnetflqattflpedftyfpnhtcperlpsmkgpidvnmseitmedihqffsrdpsiklgghwkps
dclprwkvailipfrnryehlpvlfrhlipmlqrqrlqfafyvveqagtqpfnramlfnvgfreamkdldwdclifhdvd
hipendrnyygcgqmprhfaakldkymyllpyneffggvsgltveqfwkingfpnafwgwggedddlwnrvqyagysvtr
pegdtgkyksiphhhrgevqflgryallrkskerqaldglnnlnyfpnvtydalyknitvnltpelalvtey

Fig. 16B

```
   1 gagagcgggc gcccagcggc gggagcggcc cccgagcccc gcggcagcgc tagggaccc
  61 ttcccgctca ggccgccgcc tcctcggctc tacgggcccc ccgccgggcg gtgggagcgg
 121 cgggagcgaa gcacagccct cgcccccgtc ccgccgccgc tccatgggag gagcccgccg
 181 ccgccctgcg ggaagcgcgg ccgccgcgcg ccgggattga ggggagcggg cagctctgag
 241 acggcgggag gatgcccctg ttccggaagg tgctgcgcgt ctccaatcgc tccatgctcg
 301 ccttcatctt cttcttctcc ttctcctcct cctgcctcta cttcatctac gtggcccccg
 361 gcatagcaaa tacatatctc ttcatggtgc aagcacgtgg tataatgttg agagaaaatg
 421 taaaaacaat aggacacatg atcagattgt atactaacaa aaatacaaca ctgaatggaa
 481 cagattatcc tgaaggaaac aattctagtg actgtgttgc tcaaacaaca atgtatcttc
 541 cagaaaactt cacttactct ccttaccagg cttgtccgga gaaactgcct tacatgagag
 601 gccttattga tgtaaatatg agtgaaatta gttttgatga aattcagcaa ctattttcaa
 661 aagacttgga cattaaacca ggaggacact ggaaacccaa agactgtaag ccacgatgga
 721 aggtggcgat catcattcct tttcgtaatc gtcacgagca tcttccaatt ttcttccggc
 781 atctgatacc gatgttgcag aagcagcggc tggaatttgc cttctatgtt gttgaacaga
 841 caggtacaca acctttaat cgtgcaatgc tttttaacgt tggcttcaag gaggccatga
 901 aggatgttgt ctgggactgc ataatatttc atgatgtgga tcacttacct gaaaatgacc
 961 gaaattatta cggatgtgga gaaatgccac gtcatttgc agcaaagttg gacaaataca
1021 tgtacattct tccatacaat gagttctttg gtggtgtaag tggactgaca gtggaacaat
1081 tcaagaagat taatggattt ccaaatgcct tctggggttg gggtggagaa gatgatgatc
1141 tttggaacag ggttcactat gctggataca acgtaacaag accagaggga gacttaggga
1201 aatacaaatc cattcctcat catcacagag gtgaagtcca gttttagga agatataaac
1261 ttctgaggta ttccagagaa cgtcagtata ttgatgggtt gaacaattta gtatatactc
1321 ctaaaatact tgtcagtaga ttgtataaaa atgtaactgt taatcttatg ccagaacttg
1381 ctcctattag agactattga tggaaatggt gtgacaagct atcctactgg agtaaacttt
1441 taatgcactg gaaggtatta atagacactg aagacgctgt aaaacaaaac aaaaaatcac
1501 aacaatcaac gtcttagaat tagggatctt tgtccatttg atgatgcata tttgggatga
1561 gaagtaaagt gattgtatgt gccgtgcatt ctgttcagaa agaaaagcca gcagctacca
1621 ctcagatgtt tacagcatga gactactgtt caagccttcg ttctccatgt tctctatctt
1681 aaccactcag ctaaataaac tgcagaaaac agacttgcta gcttcactgg aagtagaggc
1741 attcttcttc caggactttt tttatactaa attgctccca ctctgccctc ctgtatttaa
1801 atgaatgctt ttgttccttt ttaaaatgtg ttttgtaaat atgtgatgta aattaatgtg
1861 tgtacattgc ttttaaattg ctcaatattt tatgcttcag tatgtatttg ggtgtgttct
1921 tgtttgaatt ctataggaat gtttttatta gcatgaaaga acaagtataa gatgcaagta
1981 tccttaaaaa aggttatacc ttatgtgaga tgaaggaaat actaattgtt ggccagctat
2041 gactgtaaac tgttatacta gttttgagct ctaggcctcc tgcatatcta tatagaagaa
2101 tcaatttcat atatgaactt tctccaaaag aaagcttcta atttttattta ttgccagcaa
2161 aattatacaa taccctgcct gccatctaaa tcatatttat ataccattg catgtgtatt
2221 atggaaaatc ttgcagttgt tacatactat gatctacagg aactcttaaa tgtttccacg
2281 tgtgccacta gtgtcaatgt cagggatttt aatgctaaaa caatgtgtcc aggtgcgtac
2341 agtattttgg tattgtcttt tttttttaaa tactattgag aagcactttt attcctccaa
2401 aatcagaaga gccaaaaatg tgtcttcatt ggaagaatat taaagttaga ttttaagaa
2461 aataataaaa catagttcta atgcttgcag tgtggggttt tcagaaacat ggtgtgggtc
2521 aaactgttct acttacgatt gcataagtgg aactgaaatt aaactaagtg cttttaaaa
2581 ttccaactat aatatattaa tcaatatagc tattgaaggg cctattcgag tacagtgctg
2641 aatgctttta tgatgcacta agtatcctca agtctatgac ttcaaatgag attgaggttg
2701 cacagttcca ctaagaattg gtcctgtctg tttctctatt tttgtggtgt aaaatgtatg
2761 agtaactagc ctctctcctt ggcttagaat gaaaaacata tcttcttatt ttcctattat
2821 ctgtttgttt gtaatgttaa gctacttata agtaactcaa tgctaagaag tattttttcc
2881 tttttttttt tttacattct tgtttaaca ctaaggagaa ggactgaaac atttatttc
2941 tatgttaatg caaatatatt gactaaactc tcctgaactg ttttgtttgt cgcagttatt
3001 caactcttta ggaaccaaag actgacttct gcttctgtaa agaatggaaa gtatccgtag
3061 agtgttctgt aagaatgtag acaaaaaata ctaactcgtt actatgtgtt ggtttcctga
```

Fig. 17A

```
3121 attactgcca caaatagtgt ggtgctatgt atattttgtt tgccataaac acttttatt
3181 tccttgatga tcccagcagc aaattttgct cttagtcatt cttaggtaaa gttaggattt
3241 tacttgtaga catcccaaat attttgtaga aatgtaatga tttagttgta gtactcaaga
3301 gctaagggat aaaccttatg ggaattgccc taaaatctac cagtttatct aatatgcatt
3361 agcaatgatg tagtgcaatg aaaataatgc aaagtataaa gtgaacagaa catcttttca
3421 aaagttagat cccctcctga tatattttta taactgagtg tataggctat tctgaagcat
3481 atggataaag ggagataata tatgtatgat caacaacatc tttaaataaa attggtctta
3541 tttcataaca gactaataca attcttttaag aactgctgaa taaattttaa attgttgtaa
3601 ttttgatgtg atttctggtt ttcagtacaa agttcaacta caattcaaca cctatgatta
3661 ccaaacatcc tttggtactg tacgtctgta ctgttttctg aagcgtgctt ttgtgcccat
3721 ttggtaggca ttctgtgaaa tgtgcaattt tttaaccatt caaatgcata tttatgcata
3781 gatacatata tacataatat attacacact tgctgtggct gaactaatat aactttatag
3841 ctgtaagtga ttaatcatgt ttggtcttag gaaaaatatt attttaaacc aggatgtaaa
3901 tggattatga catatagcgg agttcttgaa aggtttgcat ttttggtgcc caaaagtgat
3961 ggacgttacc ttatgaaatg ttaaccaaca ctcctctcta ataactttg atcactttgt
4021 tgagaagttt tcaaaggtgc catcttaaat tacatccaaa taatgtttgt atgctatctg
4081 cttgagctca gtactattct gtactgaatt ttaacctaaa cagtgccttg aaacaaaata
4141 aatgcgatgc agaactaaga gttctgtaca ttccttttga tattttcat aattcttgta
4201 aaacatgggg agaggccaag cacattgttt tttgcattgg tgatgagcca aataaagaac
4261 atcttctctt tgaggagtta acttggaggg agaagaaagg aattattttt acgagattct
4321 gaagatcttg caattgagag taaaaatttt acagaaatat taacagtaga atctgcttca
4381 tatgctgaga tactcttaaa cccatttttcc gcaatataaa actaaataga agaatataaa
4441 atataaaatc catttcaaaa tagaaaatat attgaaaaat gtatgaaatt tccttttct
4501 tggatcttgc cagactattt ttctattacg tttactaatg actgtgttga agtggagttc
4561 tgatgagcca gttacttaaa aatattacaa gcacccactg catatcagca agaggaagtg
4621 tacttaagat tatttagttt gtagaggtat gtaagatagg ccttaatgaa aaatgcactg
4681 aaacatatgc tgggaatttc ttgtgtacta tcataacttt tgtttttttt gttgttgttg
4741 ttcatgagaa tgtttgtact tttttatcat tgtctttta gaaatataat gttctaaagc
4801 tggaaaaaaa aaaaaaaaa
```

Fig. 17B

```
mlafifffsfssssclyfiyvapgiantylfmvqargimlrenvktighmirlytnknttlngtdypegnnssdcvaqttm
ylpenftyspyqacpeklpymrglidvnmseisfdeiqqlfskdldikpgghwkpkdckprwkvaiiipfrnrhehlpif
frhlipmlqkqrlefafyvveqtgtqpfnramlfnvgfkeamkdvvwdciifhdvdhlpendrnyygcgemprhfaakld
kymyilpyneffggvsgltveqfkkingfpnafwgwggedddlwnrvhyagynvtrpegdlgkyksiphhhrgevqflgr
ykllrysrerqyidglnnlvytpkilvsrlyknvtvnlmpelapirdy
```

Fig. 17C

```
   1 ggaacggcgc ggctcggccc ggccagcgtg tcccggcggc ggggccgggg tccgccatgg
  61 ggccgggccg ccggagagcc gcgctgcgcc tgcggggcgg aggctccccg cagctcctgg
 121 gtctcctggc cggcaagttc tccatcttcc agctattctt cctcgcgctg ctgctgggct
 181 tcgcctcgct gctctggctg cagctcagct gctcgggcga agcgccctcc cccgggcgcg
 241 ggcccccccg gccgccctgc ccgcccgaac cccccgcccc gccggccgac gacccttcgt
 301 gggggccgca ccgcctggcc ctgctcgtgc ccttcgcgga gcgcttcgag gagctgctgg
 361 ccttcgtgcc ctacatgcac cgcttcctca gcaagaagag gatccgccac cacatcctgg
 421 tgctcaacca ggtggaccac ttcaggttta acagagcgtc gctgatcaac gtgggcttcc
 481 tggagagcgg caacgacacg gactacatcg ccatgcacga cgtcgacctg ctgcccctca
 541 acgagcagct ggactacggc ttccccgagg ccgggccctt ccacgtggcg tccccagagc
 601 tgcacccgct gtaccactac aaaacctacg tgggagggat cctgctgctc accaagcagc
 661 attatgagat gtgcaatggc atgtccaacc gcttctgggg ctggggacgg aggacgatg
 721 agttttatcg acgcatcaaa ggagctggcc tccaggttca tcgtccctct ggaatcacaa
 781 ctgggtatga gactttccag cacctgcatg acccagcctg gaggaagagg gaccagaagc
 841 gcattgctgc gcagaagcag gagcagttta aggtggatcg ggagggaggt ctgaacaacg
 901 tgagataccg gattgagtca cggactgctc tgagcgtggc aggggccccc tgcactgtcc
 961 ttaacatctt gttggactgc gacatgagtg agacaccgtg gtgcacgttt ggctgagctg
1021 tgtcccatgt gccagcatgc gctgcgctca tgccaaggcg ccagggctgc gccgagctgc
1081 ttggagcaag gcagagtttt gcagcaggcc agcacggtgc tgctggcagg acccagagga
1141 gcagaaaggg ctgagtgctt gaatttgctg ggatcagcag aagaggccaa gagcaggact
1201 ccatggcatt gctgtgagtg atgcggctgt ctcctagggc aggtgcagga ggcgtttttc
1261 ccatgctggg tatggccgag ctgccaccca gttcagagga caataaagaa ctatcaagg
```

Fig. 18A

```
mgpgrrraalrlrgggspqllgllagkfsifqlfflalllgfasllwlqlscsgeapspgrgaprppcppeppappaddp
swgphrlallvpfrerfeellafvpymhrflskkrirhhilvlnqvdhfrfnraslinvgflesgndtdyiamhdvdllp
lneqldygfpeagpfhvaspelhplyhyktyvggillltkqhyemcngmsnrfwgwgreddefyrrikgaglqvhrpsgi
ttgyetfqhlhdpawrkrdqkriaaqkqeqfkvdregglnnvryriesrtalsvagapctvlnilldcdmsetpwctfg
```

Fig. 18B

```
   1 cccatggaca gaggtactgc aggcagtagg tgcagcctag gccccaggtg gtgaccggcc
  61 ccaagaaggc cggcagcagc ctgtccttgt ggccttagct tcccccacg tcgtgctcca
 121 ccagcagcaa gatggtcacc gtcaggaaaa ggaacgtgaa ggtcttcaca ttcgccttcg
 181 tactcatcac ggtgacgtca ttcctgctga actacaagca ccaggtgacc atgaccactt
 241 gggatcctaa acatatcatc agtcagtttt ctgagcaagt ccgaaaactc atcaaatttc
 301 ctaggaggcc gtgcagctgt agcacctgta tttccgagct gggacattcc ctctggttcg
 361 accagaggtt taactcaact atgcaacctt tcctgacctc acaaaatgcc ttgatcccag
 421 aggacagcta caggtggtgg ctgaaactgc aaggagagaa atctccaaag aatattaatg
 481 atactctcaa ggaattgttt gggatcattc ctggggacag ggacccactg caggagcgag
 541 gcactttctc atgcagacgg tgtgccgtcg ttggcaactc cggcaacctt cgtcagtctc
 601 aatatggcca agatattgac tccatgact tgtgctcag aatgaaccgt gcacccacca
 661 ttggctacga atcagatgtt gggagcaaga ctacccacca ctttgtttat ccagagagct
 721 acaaagagct ggcagaaaat gtgagcatga tcgtgatccc cttcaaaacc ctggacctgc
 781 gctggattgt taccgctctc accacaggca ctatcaactt acatatgtt cctgttccac
 841 ggaaaatcaa agtcagaaaa gaaaaggtcc tgatttacaa tccatccttt atcaaatacg
 901 tctatgaaaa ctggcttcag aatcatggaa gatacccttc cacaggcctt ctttctgtga
 961 tatttgcact ccatgtatgc gatgaggtga atgtgtatgg ttttggagca gacagcaaag
1021 gacactggca tcactactgg gaaaataatg cttcagctgg ggctttccga cagacaggtg
1081 tccatgatgg agattttgag ttcaatgtaa ctttgactct tgcctccatt gaaaaaataa
1141 aattttcaa gggcagatga ccctagccac agggacaagc aggggctgca atttccaaca
1201 tgcagcagca caaagctcag tgaagatgat ctggatgaca gccaggtttg aaggtgtgaa
1261 tctggagtgg attcggagtg tcacactgct gcagtgctca ccacagggag ctcagctgag
1321 gaacagattc aatgctgcac ttgatttgct atctatagat agctgggaac taccgatcag
1381 ctgttggaat aaatgacatc ctgactcact ccttagtctc tacggattga ttcctgaatt
1441 actggtgaaa gatctacctg ttgcaattca gggaaaccta gacacaggaa ctgctgtttg
1501 tatgtccatt ctttccttga gtaaggcaag aaatccttga agaacatgga aaatgtcttc
1561 tgggatttga tacctactag agtagctctg aacatcatag taaggattac ctcaaagaaa
1621 ttaattcagt tctgctgtta atcttctttt tgaattctct tctgtttcct ctattacttc
1681 tggtttcatg cactataaat caaaaacgtg atgaagttgc cggagtagta actgtttcta
1741 ccattgccac attctgcatt gatggcatct agaaaataca gatcaattca cctgtgatca
1801 ttacttattt attattgctt cctatacagc catagtaa
```

Fig. 19A mvtvrkrnvkvftfafvlitvtsfllnykhqvtmttwdpkhiisqfseqvrklikfprrpcscstciselghslwfdqrf
nstmqpfltsqnalipedsyrwwlklqgekspkninndtlkelfgiipgdrdplqergtfscrrcavvgnsgnlrqsqygq
didshdfvlrmnraptigyesdvgsktthhfvypesykelaenvsmivipfktldlrwivtalttgtinftyvpvprkik
vrkekvliynpsfikyvyenwlqnhgrypstgllsvifalhvcdevnvygfgadskghwhhywennasagafrqtgvhdg
dfefnvtltlasiekikffkgr

Fig. 19B

```
   1 ggggcccgga ggctcccggc ggtggggccg ggccggagcg gagcgaggct gttgccaccg
  61 acgtgtccct ggcacaggac gatgagtgcc accgcggccc gggaccggct ggggacggct
 121 ccccgagccc acggggccac cgggacgcgg agctacggct gagcccggcg tgccgagccg
 181 cgccgagcca ggcggatgga aagctgcagc ccggcaggga gccccgcgcc caccccgcgc
 241 cccagcccta tgcccgggga gcggcgccga gcctgcccgc ccgcccacca tgaagtgctc
 301 gctgcgcgtc tgcttcctct cgaccgcctt cctcctcatc ttcgtcatgt cggtgctctt
 361 cacctactcc caccacagca tcgcctacct ggaccccggc gggctgggcg gcatccaccg
 421 ggtgaagctg gtgcccggtt acgccggcgt gcggcggctg agccacggcg tgccgtaccc
 481 caggggctgt gcgtgccgcc gctgccccga ggatgccgcc gccgccgccg ccgcctggtt
 541 tgacagccgc tatgacggcg gtgtgtctcc ggtgtggacc aaggagaaca tggagctgcc
 601 gcccgacgtg cagcggtggt ggatgatgct gcagccccag ttcaagtccc acaacacgca
 661 ggaggtgctg agcaagctct tccagatcgt gccaggggag aacccttacc gctggcgcga
 721 cccgcgtcac tgccggcgct gcgccgtggt cggcaactcg gcaacctgc gtggttccgg
 781 ctatggcac gagatcgatg ggcacgactt catcatgagg atgaaccagg cacccacggt
 841 gggcttcgag ggggacgtgg gcagccggac cacgcaccac ttcatgtacc ccgagagtgc
 901 caagaacctg cctgccaacg tcagcttttgt gctggtgccc ttcaaaacct tggacctgct
 961 ctggatcgcc agcgccctct ccactggcca gatcaggttc acctacgcgc ccgtgaagcc
1021 tttcctgcgg gtggacaaag agaaggtgca aatctacaac cctgccttct tcaagtacat
1081 ccacgaccgc tggacggagc accacgggcg ctacccctcc accggcatgc tggtgctctt
1141 cttcgccctc cacgtctgtg atgaggtgaa cgtcttcggg tttggcgccg acagccgggg
1201 caattggcac cactattggg agaacaaccg ctacgccggc gagttccgca agaccggggt
1261 gcacgacgcc gacttcgagg cgcacatcat cgacatgctg gccaaaacca gcaggattga
1321 gggtgtaccg gggcaataac tgagggccgg gcggccgcgc gtcctccagc tcctaacccc
1381 ggcactgcca gagctgcccc ggctgccgtt gggtgtcggc ggccgatggg ggttctgagt
1441 actcggcaga ctttgtgtgg ttggggggagt tctgacttga ccttgttagt attaaggaac
1501 ccgcttcagc caagtgagga ttttgtagac gccgcagcgc cccagccggc cggggggatgc
1561 gcccaactcg tatctgttac agtcaaacca aatggctgct cttttttaaa aaccagaaca
1621 agcaaaaaac cgtacaaaaa gcccccctaaa aa
```

Fig. 20A mkcslrvcflstaflllifvmsvlftyshhsiayldpgglggihrvklvpgyagvrrlshgvpyprgcacrrcpedaaaaa
aawfdsrydggvspvwtkenmelppdvqrwwmmlqpqfkshntqevlsklfqivpgenpyrwrdprhcrrcavvgnsgnl
rgsygheidghdfimrmnqaptvgfegdvgsrtthhfmypesaknlpanvsfvlvpfktldllwiasalstgqirftya
pvkpflrvdkekvqiynpaffkyihdrwtehhgrypstgmlvlffalhvcdevnvfgfgadsrgnwhhywennryagefr
ktgvhdadfeahiidmlaktsriegvpgq

Fig. 20B

```
   1 atgggactgc tggtgttcat gcgcaacctg ctgctcgccc tctgcctgtt cctggtgctg
  61 ggctttctgt actactccgc ctggaagctg cacctcctcc gctgggagga ctccagtaag
 121 tacgggcgcc tttcccattc ctcgttcccg aaacaaagac ccagtgctga ttcagtggtt
 181 ctttcctttg actccgttgg acatacaata ggctcagagt atgacaaact gggctttctc
 241 ctgaacctgg actcaaaatt gcctccagaa ttggcatcta agtatgcaaa tttctctgag
 301 ggagtgtgca agcctggtta tgcatcagca ctcatgactg tcatcttccc aaagttctcg
 361 aagccggcac caatgttctt agatgattcc ttcaggagat gggctcgtat cagggacttt
 421 gtacccccct ttggaattaa aggacaagat aatttgatca aagccatcct gtcagcaacc
 481 aaagattacc gtctaactcc agctcttgac agtctcagct gccgacgatg tattattgtg
 541 ggaaatggtg gagtacttgc caataagtca ttggggctaa agattgatga ctatgatgtt
 601 gttgtcaggc tgaactcggc tccggtgaag gggtttgaaa aagatgtggg tggcaaaaca
 661 actctccgca tcacatatcc tgaaggtgca atccagaaga tggagcagta tgaaggat
 721 tccctgtttg tcctggcggg attcaaatgg caggatttca agtggctgaa gtacattgtt
 781 tacaaggaga aagtgagcgc ctctgatggc ttttggaagt cagtggcaac ccgtgtcccc
 841 agagaacctc atgagatacg tatcctgaat ccctacttca tccaggaggc agctttcagc
 901 ttcattggac tgcctttcaa caacggcctg atgggcagag ggaacatccc caccttggga
 961 agcgtagcaa taaccatggc actccacaac tgtgatgagg tggcggtcgc tgggtttggc
1021 tatgacatga gttcacccaa tgcgccactg cactactatg agaacatcaa gatgtctgcc
1081 atcaaagagt cctggacgca caacatccaa cgggagaagg agttcctgcg gaagctggtg
1141 aaagcccgag tcatcacgga cctgaccagt gggatctgag tggctgcagc cctgcctca
1201 aagggaggag aggaagacat acgctgcggc tctgggagca ggcactggca gcccccaca
1261 agaatcccac ttccctggag acacacagag atgcccgggt gctctgggaa ggccctctcg
1321 catcgccggg ctgcaggaag gttgcatctg ctgcctccag tcctggagct ggcaggaggc
1381 gggcgagggg ctcagtgggc agttcttgaa ctctgcatca cagacggatc ttctgtgtcc
1441 agaattaaac aggaaagact caggagagag aagaaaggtt tgtgaataaa gcgatttgtg
1501 ccaaatggga ggtgacgctg ccccgaggca gcagtgcctg aatgtacaaa gtagtatttt
1561 ttaaagaaa ctctgctgga atcatcgtag aattaccaac gtgcaaagca agtctgcttg
1621 tgcacagccc tgcagaaagc tcggcctcac cacgtcccat ctgcattctc actgccctca
1681 gacctttccc caggaaaaca aatccgtcca aaccgtcagt gttgttggtg ctgctataat
1741 ttaaagggag gttggcttcc cctccttctc cacttggagc ttctcattgg agatgagcac
1801 gggtttgttt ttctgcactt ttcctccctt cctgcataga agcggcggcg gcagccactc
1861 acttggctgt gttttccata gctgtttgct ctgccctgac gctggaactg gtggctctct
1921 gcctgcagca ggcccaccgt gccgcctgtc acagcgctgc ggagcccacc tcgtcgtgct
1981 cagggctgtc aggtccgtgc ttgctgtgca gagccctcgt ggagtccgtg cagatcggtg
2041 tcaccacttc tggacagcat cctgctttgt ttttgtgggg gagatcagtg gtttgttttt
2101 tggaaggagg tccgatgctg cgtggggatc tgaagctttg catattgaag accaggccac
2161 cgaagatgtt ttatgttccg gactcgatca tgttccctat ttaagtgact tgtgacctca
2221 gcaatgatgg agcgtgctgg caagtgtggg ggcctgctgg aaccctcgc cttctgcttg
2281 gcccctgctc atttcatgtc caagctcctc ccgtgctgct cgagcgctgc tgctcctcct
2341 gctctcagga gcacgtccct tcctttgctg tcttggtccc gagatgcagt atttgcacat
2401 ttgatttgtg tacgtatttc agaggagctg gaataaactg agcgccgtgg ctgagtgcaa
2461 gg
```

Fig. 21A

```
mgllvfmrnlllalclflvlgflyysawklhllrwedsskygrlshssfpkqrpsadsvvlsfdsvghtigseydklgfl
lnldsklppelaskyanfsegvckpgyasalmtvifpkfskpapmflddsfrrwarirdfvppfgikgqdnlikailsat
kdyrltpaldslscrrciivgnggvlankslglkiddydvvvrlnsapvkgfekdvggkttlritypegaiqkmeqyekd
slfvlagfkwqdfkwlkyivykekvsasdgfwksvatrvprepheirilnpyfiqeaafsfiglpfnnglmgrgniptlg
svaitmalhncdevavagfgydmsspnaplhyyenikmsaikeswthniqrekeflrklvkarvitdltsgi
```

Fig. 21B

```
mgllvfmrnlllalclflvlgflyysawklhllrwedsnsvvlsfdsvghtigseydklgfllnldsklppe
laskyanfsegvckpgyasalmtvifpkfskpapmflddsfrrwarirdfvppfgikgqdnlikailsatkd
yrltpaldslscrrciivgnggvlankslglkiddydvvvrlnsapvkgfekdvggkttlritypegaiqkm
eqyekdslfvlagfkwqdfkwlkyivykekvsasdgfwksvatrvprepheirilnpyfiqeaafsfiglpf
nnglmgrgniptlgsvaitmalhncdevavagfgydmsspnaplhyyenikmsaikeswthniqrekeflrk
lvkarvitdltsgi
```

Fig. 21C

```
   1 agagagcaga agggggtgctg ctgtgcgcgg acacttttct ctgggaggaa ttggactttt
  61 tcttctccaa actgtgggga ggacatggaa attgggaagt ctggggacag cgaagggggc
 121 agagagcccc tgagcacatg gtgagcagtg ctgggccccg agatccccca gcctcacact
 181 gaggctctcc cttttttcct tcaccagaaga attgaggatg gccccatagc cccgcagccc
 241 ccggagctgc tgcccctct gctcgcacca cgtggaagaa ctgtgagcgg cagtggctgc
 301 gatgagagct ccggccctcg gctgatgcct gccctgctga taaagatgat caataagtcc
 361 cgagggaaga tactgggagt gctggcgctg tttctggtca tggtgtggta ctcgatatac
 421 cgggaggaca gctttttattt tcctgtgcaa gaaaacaaga ccgtatgtcc cattggggag
 481 gtggagagga aggcagcaca gctcatcggg aactacacga gggaccgccc gctcttcctg
 541 cagctgaagg attacttctg ggtgaggacg ccgtcgctct atgagctgcc ctacggcatc
 601 aaaggcagcg aggatgtcct cctgcgcctg ctgtcggtca ccagttactc actgcctgag
 661 agcatccaga gcctgaagtg tcggaggtgc gtggtggtgg gcaacgggca ccggctccgc
 721 aacagctcca tggggacac catcaacacc tacgacgtgg tgatcaggct gaacaacgcg
 781 ccggtgcacg gctatgagca ggacgtgggc tccaagacca ccatgcggct cttctacccc
 841 gagtcagccc attttgaccc ccaggcagag aacaatccga cacgctgct ggtgctggtg
 901 cccttcaagc ccgtggactt ccagtggatg gaggccatcc tcagcgacag gaagagggtt
 961 cgtaaagggt tttggaagca gccccactg atctgggatg ccaacccgga gcaagtgcgc
1021 atcctcaacc cgtactacat ggaagtaact gctgctaaac tgctcagcct cccatgaag
1081 cagccaagga aggtcaaaca gaaaccaacc acggggctgt tggccatcac cttggctctc
1141 cacttctgcg acctggtgca cattgcaggc tttgggtacc ctgactcggc caacaagaag
1201 caaaccatcc actactatga gcagatcaca ctcaagtcca tggctgcctc ggagcacaac
1261 atctcacatg aggcggtggc catcaagcgc atgctggagc tgggcctggt caagaacctc
1321 acctacttct gagggcaatg gggctgcgca gggacacgtc ccaccttgg agcccgcagt
1381 ggtcctggag gagccggtgt cactgagctc cccaccatgc tggtggcagt atgggggcca
1441 tgccagcttg ctgaccccgg gggtgcaggg agcccccttaa tggggacttt tcatatggaa
1501 acactgaaac tagtgaggac ctggagggga ttctggggag gatggagggg accttcccc
1561 agcaggtctg ggggggccacg gcagggtgca ctggagcccc tctcttccct tggatactct
1621 tg
```

Fig. 22A mpallikminksrgkilgvlalflvmvwysiyredsfyfpvqenktvcpigeverkaaqlignytrdrplflqlkdyfwv
rtpslyelpygikgsedvllrllsvtsyslpesiqslkcrrcvvvgnghrlrnssmgdtintydvvirlnnapvhgyeqd
vgskttmrlfypesahfdpqaennpntllvlpfkpvdfqwmeailsdrkrvrkgfwkqppliwdanpeqvrilnpyyme
vtaakllslpmkqprkvkqkpttgllaitlalhfcdlvhiagfgypdsankkqtihyyeqitlksmaasehnisheavai
krmlelglvknltyf

Fig. 22B

```
   1 gccccgatgc ggaggcgaag tgcccgggcc gagcccagcg cagcaatgct gagtgacgat
  61 aactctgtaa agctgaaaag tgattgtttg cctcctgtgc aatggtgtaa ggtagctgca
 121 catgaagatg agaagaccaa tctggttttt aaaaggtact cgcaaatttc ttgcactgtt
 181 tgtgattgga gggtgcttcc tttatatcct caaattacat ttttaccctg aagaatgtga
 241 cagaacaaaa acaccgtatg tggactttga tcgcgtaaag agagcacaac aatatgccag
 301 tgctgtgttg caggagcagt gccgaccttc gtatgtgaaa aaagcaatgg gaaagttatt
 361 tgcagagaaa tacagcatgg acatacctcc ctttgtagga aaaaatatag atgatgatga
 421 agctttattt aaatatggac ctccgtttgg attccacagg ttctttgata agcttaaaaa
 481 gcttctcgaa ctcttaccag agcacgattt gccagaggat ttgaagtcaa aacactgtaa
 541 gcgttgtgtt gttattggca gtggtggaat tctgtatgga tcagagctag gccacttact
 601 gaatcagtat gatattgtta taggttaaa tgatgcacca gttcaaggat acacggatca
 661 cgttggtaac aaaactacta aaggatgac ttacccagaa ggagctccac tttctgaaca
 721 cgagtatccc cctgctagtt tatttgtggc tgtcctcttt aaaagtgttg atttcaattg
 781 gcttcaagca atggtaaaaa atgaaacact gtctctgtgg atacgacttt tcttttggaa
 841 ggaagttgcc aagaaaattc cttttacatc aaaacaattt cggattctca atccagtcat
 901 cgttaaagag acagccttgg acatcctaga gttccccaaa cctcgatcaa tattctgggg
 961 ttgggataag aacgtaccca caattggggt catggcagtc gttctggcca cacatctatg
1021 tgatgaagta agcatagcag gatttggata cgacctcaac cagcccagca cacctttgca
1081 ctattacaac aacctctgca tggctgccat gaacagacaa acgatgcaca atgtgacagg
1141 tgaaacaaaa ttactgcaaa aactggtcaa agaaaaagtt gtgaaagacc tcactggtgg
1201 aatccattgt gaattctgca caaagacag ctagtaattg aagtgcagca cggcctggat
1261 ttgttaaatt cccagaagtt tgttggaac aaccctt
```

Fig. 23A

```
mrrpiwflkgtrkflalfviggcflyilklhfypeecdrtktpyvdfdrvkraqqyasavlqeqcrpsyvkkamgklfae
kysmdippfvgknidddealfkygppfgfhrffdklkkllellpehdlpedlkskhckrcvvigsggilygselghllnq
ydivirlndapvqgytdhvgnkttirmtypegaplseheyppaslfvavlfksvdfnwlqamvknetlslwirlffwkev
akkipftskqfrilnpvivketaldilefpkprsifwgwdknvptigvmavvlathlcdevsiagfgydlnqpstplhyy
nnlcmaamnrqtmhnvtgetkllqklvkekvvkdltggihcefcnkds
```

Fig. 23B

```
   1 tttttgcttt caaacaaggc gattttttgtt ttgtttctgt cctttgccgc cggcagagcc
  61 atcgagttgt gtgtcgatgc gagcgttggg gcgagcagag actttccagg aaccccccggc
 121 tgtctccggg ccggtaacgc cgggcgccac gggtgcagcc ctgtgccgtg cggctttct
 181 aggaccggtt cctcccccga tgccccgtgg gctttcgcgt gggtggcgat cgtcggaggc
 241 agcggcacgg agagggagac ccccgtgccc ctcagcttgc ctggcttttc gggttttttt
 301 gcttctcgag agggcgcccc gcctcccctc gctgcccggg aggggtcag ggctttccgc
 361 gggcgggcga gcagtcgctg taaccgcagc cgctgtggga ggacgcgcgg gggatggagc
 421 ggcgcggtgc cttccctcac acgaggctct cctcccctgg aaggcttcga tataagctga
 481 ggaggagctt cggcagacgc gagtcaaacg ccacctccat cctaacgcgc agcatgcttc
 541 cttccacgtt ttcttttgca gatggggttc agctgaacga agccccgctc ttcttcctca
 601 tcgttaccgt aagcgtgcgg aagtcgggct ggagctgctt gcggacggta cggcccctct
 661 aagaagctgc acgttaccct ctctctgcgg ttcgatctga tttgaagtcc cttccctgtt
 721 gacaactggt ctaccagtca tgaaacgaat tcttctgttt ttcatcctgg ctgctgctgt
 781 tatgtacggt atattgcatg gaaatctgtg gagaaataac ttctactgga ttagctttta
 841 tggacagact tcttctgtga ggggtccttc ttccagtgag gctagtggag ttacccagct
 901 gccacctacg gctgtggaga aaggaacgc cctaaacact tgcactctga accagcatt
 961 tgaatcttta ctggatgttg agaaaatata cccgttcctg tgtgccagtg attttatcag
1021 agtggcagag taccatggaa gtgataagtt cgagctacct tatggaataa agagagcaga
1081 acaatttttt cgttcagccc tttcaaaact gcaaaattgt ggactgtcca acaaagacga
1141 cagtgttgcc tgccgacggt gtgttgtggt cggtaatgga ggagtacttc gaaataagac
1201 gttaggaggg aaaattgact cctatgatgt gataataaga atgaataatg gccctgttat
1261 agggtacgaa gaggatgttg ggagaaggac gactttccgc cttttcctacc cagaatccat
1321 cttctcagat ccaatccact acgacctaa cactactgtt gttattatcg tcttcaaacc
1381 acgtgactta aagtggcttt gggagatttt aggtggtcag aaaataagtg ctaaaggctt
1441 ttggaagaaa ccagctctaa acatgatata taaatctaat caaatcagga ttcttgatcc
1501 cagcatcacc agaaaaacag cttatgattg gcttcatttc ccaacaagat ttcccaaaaa
1561 agagaaaccc aagcatccaa caacggggct aattgccatt acactagcat ttcacatttg
1621 tcatgaagtt cacctggcgg gcttcaaata tgacttcact gacaggaaca gttctttgca
1681 ctactatggc aacgaaacaa tgtctcagat gatgcagaat gaataccatg acatcagtgc
1741 tgagcagaaa ttcttgaaga agcttataga caagaacttt gtggtcaact tgacgtgaaa
1801 gctggatgga aaatctgaag aacagtcact actttcaaga tttcagaatc tttttatttt
1861 ttgtatgaca ttttttatttt ttaagtgcaa cgtaactgtt tactgttgaa aaacagcaag
1921 gaaacctcat aaggcagaag cttcttctaa gccagaggat aatggactat tctaagcaga
1981 gctaactgaa tttctgtgaa gctatttaat gggaaaaaca caaaactttc agctgaaagt
2041 atcagggatg tataaaaatg tgattcacat tacttattta tcagcaagaa ctttttttcca
2101 aacgattact tctctggaat accttctttt ctaacgtcct ccaaaaggat tacactgtta
2161 agggactgag acaactattt aagtagtgga tggatgtcaa tgcttgaatc tttcttgtaa
2221 tacaaaagtg gctttaaaag caatgccttg aagtcattac tatgcgtttg ggagaagggg
2281 aaacatgcgg aacatacaga ctttagtctg ctctcctcct gagcaggaga ctcatccatc
2341 catcttctgt ga
```

Fig. 24A mkrillffilaaavmygilhgnlwrnnfywisfygqtssvrgpssseasgvtqlpptaverrnalntctlkpafeslldv
ekiypflcasdfirvaeyhgsdkfelpygikraeqffrsalsklqncglsnkddsvacrrcvvvgnggvlrnktlggkid
sydviirmnngpvigyeedvgrrttfrlsypesifsdpihydpnttvviivfkprdlkwlweilggqkisakgfwkkpal
nmiyksnqirildpsitrktaydwlhfptrfpkkekpkhpttgliaitlafhichevhlagfkydftdrnsslhyygnet
msqmmqneyhdisaeqkflkklidknfvvnlt

Fig. 24B

```
   1 gagaagtgcc gcgctcggtg gccagcaagc tcgattagaa gtgagatgag ggcacgaaga
  61 gctgcttgca tggcacagat gtggcagtgg ctcatctgga tgtcacctgg ccaccccctt
 121 gtgactggaa gagtttgaca ggagctgctg aggacagcga aggatcctgg agatgaaggt
 181 gtttcttgaa ctcttcagcg cctcacgcgg ctgttgtgtt tggggatatc ctgccttaaa
 241 tcctggacaa aaatctgcca acagccaaaa atgacctgag tgggagagcc actgctttgt
 301 ccaacaggcc cagcttcctg ccccgtgctc actgtcccgt ttggatgcga cgtacactat
 361 ggttcacatc aatgtgctga aaaaattcat gtgtgttctt gtggtgatac tgatagctct
 421 gacggtttgc ctgtggaaag agacaagagg aagctactat gttcctttga agaacgatgg
 481 cacacaggtt cacagggctc tggacaaatg gaacctactt aaatcgcagg gcctcctcca
 541 tgaagctgct ggtgaaatgg gtcagatgcc taaagcattg cccaacaacc aaaacaaggt
 601 aaaaggcatc acctctggag cagtagagaa gtccaggaaa gcagcagagc acgtgaaggt
 661 atgggataag gacagctcgt ccagaaacct catacccagg ctgcagaagg tcaggaagaa
 721 ctacctgtcc atgaacaagt acaatgtgac ttacaatggg aagatgaatg ctgctaaact
 781 cagcccagag cagctgctgt gccggctgcg ggacagggtg aacgtgacca tgatacgggg
 841 atcggacggt ccatttaatt cctcagaatg cagcactac ctgccagaca aaagcctcaa
 901 tgagacggtg ggccgctgg gtcgtctgc tgttgtgtcc tcagcaggct ctctgaaatc
 961 atctcacttg ggaccagaga tagatagcca tgatgctgtc ttgcggttta atggggctcc
1021 tgtcaaagga tttcaagaag atgtggggca aaaaacgacg attcgtcttg tcaactccca
1081 gctggtcact gttgaggagc agcagttcct gaaagatgcg ctgtataaca ctggaatctt
1141 gattgtctgg gatccagcac cgtatcatgc agaaatccat gagtggtacc gaaaaccaga
1201 ctacaagttt tttgaagcct acaagtcgta tcgtattaga catccggagc agccctttta
1261 tatcctgaac ccaaagatgc agtggcaact ctgggatatt ctgcaggaga ttccctgga
1321 gcatattcag cctaacccac cgtcttcagg aatgctgggc attgtgatca tgatgacgct
1381 ctgtgatgag gtggatgtgt atgaatttct cccttctaag cggcagacgg acatttgcca
1441 ctactaccag aagtttcacg accatgcctg caccatggga gcttaccacc ctctcctgtt
1501 tgagaagaac ttggtgaagc atttaaacca aggcaccgat gaggacatct atactcacgg
1561 gaaggttact ttgcctggct ccgaaatgt acattgctag cgaatcggtt tttattgcat
1621 ttagactttt gccttgactg ttgaagcact ttgaaaatca gggttgtcat atttgttagg
1681 tctaagcact ggtgtgtttt gacggctctt ccgcgttgca ggactctgag gcaaagctcc
1741 tccgaactgg aaggcagtgc aatacgttgg ggtacatcca cgcagcgtct gcgtgagccc
1801 atgcaataaa tgtcctcctg gtggggctgg gctcgtgctg ctggtggata tctgtcttca
1861 gctcaactga tgatgccgtg tgggaatcgc gggagatgct ttctaagcag agactgcaca
1921 agtccgaatc gagtgctgat aaagttcagc ttgctccaaa ggggttctga cagccgaaag
1981 cctgatctgc tgagaacaag aagcattctt gaacacttgt tcttatcgtc cctggagctc
2041 tttggagcag tgattgaagg aatcactgtt aaagctgggt gctgataagc tcatctccta
2101 gtccaaaaat atttgatctt accattcaga taagcaaggc agcttccttt caaaaatata
2161 atgctttta aattcaaaaa aaaaaaaaa aa
```

Fig. 25A

```
mvhinvlkkfmcvlvviliailtvclwketrgsyyvplkndgtqvhraldkwnllksqgllheaagemgqmpkalpnnqnk
vkgitsgaveksrkaaehvkvwdkdsssrnliprlqkvrknylsmnkynvtyngkmnaaklspeqllcrlrdrvnvtmir
gsdgpfnssewqhylpdkslnetvgrlgrcavvssagslksshlgpeidshdavlrfngapvkgfqedvgqkttirlvns
qlvtveeqqflkdalyntgilivwdpapyhaeihewyrkpdykffeayksyrirhpeqpfyilnpkmqwqlwdilqensl
ehiqpnppssgmlgivimmtlcdevdvyeflpskrqtdichyyqkfhdhactmgayhpllfeknlvkhlnqgtdediyth
gkvtlpgfrnvhc
```

Fig. 25B

```
   1 atgaaaccta acttgaagca atggaaacaa ctcatgctgt ttggaatctt tgcatggggt
  61 ctgcttttc tagtgatctt catctatttc acagacagca acagtgctga gccagttccc
 121 agttcctttt cttacattga aacgaagagg ctcctgcccc tgcagggcaa gcagagagtc
 181 atcatgggag ccatacacga tccgtcattc tctgaagcca ttgatgggaa tgaggtactc
 241 cttaatgaag atcttttaga tacatttaaa tcagagactg gaagtattaa gaaatggact
 301 gatttggaag atgcctttag aagcgaagat gagttttttc catcccagat aggacgaaag
 361 tcaaaaagtg ctttctacca agtgaacgat gattatttat tcgctgctgg tcagcctatg
 421 tcacacaaca gcttccaaga gatagcaaaa ttcatctcag ccgatgagga taatccaaaa
 481 gaaagtattt tacagaacaa ctggagccgt cagaggagaa tgaggagaag gagcacaaag
 541 cacagaagaa gccagatgct tgatgaatct gatgactggg atggctgta ttctacaatg
 601 tcgaaatcct ttctatacaa gctctggaaa ggagatgtct cttccaagat gctgaaccct
 661 cgactgcaga aggcgatgaa agattatttg agcaccaata gcatgggt gcggttcaaa
 721 gggaaacgaa actcgaagct gacaggcgac cagcttttct gcgagctgaa agaaagggtg
 781 gatgtgaaaa caatagatgg caaggaagct cccttctcca ctcttggatg ggagaagcac
 841 gttcctcaaa ttccactggg caattgtat acacatggct tgggagctg tgccgtagtt
 901 atgtctgctg gtgcgatact gaactcctct ctaggggatg aaatagattc tcatgatgct
 961 gttctaagat ttaattctgc tccaacacgc ggctatgaaa aagatgttgg aaataaaaca
1021 acgatgcgaa tcattaactc tcagattctc accaacccaa accatcactt tgttgacagc
1081 tccttgtaca agatgttat cttagtagcc tgggatcctg ctccctactc tgcaaatctg
1141 aatgtgtggt ataagaagcc ggactacaat ctgttcactc cctatgtaca gcatcgcagg
1201 aagaatccaa accagccttt ttacattctc catccaaagt ttatattgga gctctgggac
1261 atcattcagg agaacacgaa agagaagata cagcccaacc ctccttcttc aggttttatt
1321 ggtatcctca tcatgatgtc catgtgtaac gaagtgcacg tgtacgaata catcccttca
1381 gtccgacaga ccgacctatg tcactatcat gaactctact acgatgcagc ttgtaccttta
1441 ggggcctatc acccgctgct ctatgagaag ctgttggtgc agaggatgaa caaaggtttg
1501 caggatgatc tgtatcggaa gggaaaggtc attttgccag ggttcaagtc tgtcaaatgc
1561 ccggaacgaa ataatttcc acccttgtag aagagagtct ttcacaaaca atgtgcaata
1621 aggtactact gtcgtactat aaacaaggag agaatacttg aaaaatgtat tagaccaacc
1681 cagtcttgag tctataaatt gtaattaagt agcaggcatg agaaatactt ctttcctgag
1741 cctgagtatt tattactgct ttgcaaatag ttaaagaaaa caaaaagctt agcttacaaa
1801 aggtgcagag gacatactta ggccgaaata taatgtattg ttgtgggtgt gaccgtcaga
1861 atttgtcagt ggtctcttgt gccacttatg ctagatggta acttttttt ttttttaaag
1921 gaatttattt aagtgttaaa tccagcattg tgaggcagcc tgtatcgctc atgtacagag
1981 ctgccagttg aacaatgcag cgtttctcat ggctccatgg gatttcaca ctctccagga
2041 atgaagtaat tgctactctg agctgaatat tcattaatta gaggagtctt tcagttcctg
2101 ttcatacact ggttcacttg caggcttcta actgtacagg aaaccttatg gtggctatga
2161 agtcagtgca gatgtaggaa gcagaacacg cagctaaacc aattaaacca ctggatgtac
2221 ccttggtgtc acatcccatt gctcacactg agcagggcag agggcaaaga gaaa
```

Fig. 26A mkpnlkqwkqlmlfgifawgllflvifiyftdsnsaepvpssfsyietkrllplqgkqrvimgaihdpsfseaidgnevl
lnedlldtfksetgsikkwtdledafrsedeffpsqigrksksafyqvnddylfaagqpmshnsfqeiakfisadednpk
esilqnnwsrqrrmrrrstkhrrsqmldesddwdglystmsksflyklwkgdvsskmlnprlqkamkdylstnkhgvrfk
gkrnskltgdqlfcelkervdvktidgkeapfstlgwekhvpqiplgklythgfgscavvmsagailnsslgdeidshda
vlrfnsaptrgyekdvgnkttmriinsqiltnpnhhfvdsslykdvilvawdpapysanlnvwykkpdynlftpyvqhrr
knpnqpfyilhpkfiwqlwdiiqentkekiqpnppssgfigilimmsmcnevhvyeyipsvrqtdlchyhelyydaactl
gayhpllyekllvqrmnkglqddlyrkgkvilpgfksvkcpernnfppl

Fig. 26B

```
   1 cgcgccccac gcctcctgtg accctcgtgc cccacggccg ccccagctcc gcgggataaa
  61 gatgctggtc cgcgtcttcg tcgtcctgct gtgcgcggcc gcgctctccg tgctctacgt
 121 gctgctgtgc cgcgaggccg ccgggcagag ggacggctcc gcgtacaccg cgcccgcggc
 181 gctcagcttg cagggctaca gccgcgtccc cgacgggaag ccgctgcgca gagctccgtg
 241 ccgccgctgc gccgtggtct ccagctcggg gcagatgctg ggatcgcacc tgggccggga
 301 gatcgacggg caggagtgcg tgctgcgcat gaaccacgcc cccaccgccg gcttcgagga
 361 ggacgtgggc acgcggagca ccgtccgcgt cgtgtcgcac accagcgtcc cgctgctgct
 421 caggaaccag ccctacttct tccagcagtc ccgggacacc atctacgtca tttggggtcc
 481 cagcaggaag atgagccgcg agaagggcgg cccgacgcac cgagcgctgc tcagggtgct
 541 ggagatgtac ccccgcctgc agctctacac gctgaccgag gagaagatgg cgtattgcga
 601 cgacgtcttc cagaacgaga caggcaagaa caggctgaaa tccggctcct cctgagcac
 661 ggggtggttc accatgatcc tggccatgga gctgtgcgag cacatctgcg tcttcggcat
 721 ggtcagcgac agctactgca gggagaagaa ccactcgagc gtgccttacc actacttcga
 781 gaaggggcgg ctggatgagt gcaggatgta cctggtgcac gagagggccc ccgcgccgg
 841 gcaccgcttc atcaccgaaa aagccatctt ctcccgctgg gccaagagga aggacatcat
 901 cttcagccac ccgtcgtggg caggggggta ggagaggcgg cagtgcggtt ggaagcccct
 961 cgatatgccc ggtattgggg gtctgcagcc actgggggg cagcagtgga gacccgttg
1021 cgttggagcg cataggacag gactggatcc accgagcccc ccagctgca ggccccgagc
1081 tggcttggac ccgtgcagtg tggatgttta atgtgggatt catcccggga cggaccccac
1141 gtatatgggg cacgtggagc ggggccggga ccccgtcc cacagacccc cgtgtgcccc
1201 ctgcccgcag ccctgagctg ccttgccaca agtgcccttg gattcagacc aaagccgact
1261 tgcccattaa aagcatttgt aagcccgaaa aa
```

Fig. 27A mlvrvfvvllcaaalsvlyvllcreaagqrdgsaytapaalslqgysrvpdgkplrrapcrrcavvsssgqmlgshlgre
idgqecvlrmnhaptagfeedvgtrstvrvvshtsvplllrnqpyffqqsrdtiyviwgpsrkmsrekggpthrallrvl
emyprlqlytlteekmaycddvfqnetgknrlksgsflstgwftmilamelcehicvfgmvsdsycreknhssvpyhyfe
kgrldecrmylvherapraghrfitekaifsrwakrkdiifshpswagg

Fig. 27B

```
   1 cctgcacggc ggcgcttccc cggccgagcc atggccgcgg ctcccccgcc atgccgagcc
  61 tagcggggag cgggcggagc ggcgcccggg aggcgcacaa aatgaagacc ctgatgcgcc
 121 acgggctggc cgtctgcttg gcgctcacca ccatgtgcac cagcttgttg ctcatgtacg
 181 gcggcatcgg aggcggcggc ggggccacc cggagcctcg gcggcggcag cagcagcagc
 241 agcaggtggc ggcggtgccc agccgccctc cgggacgcgg ccagcaccgc ccagcgctcc
 301 ccgtcggggc cggactcctg gagggctaca tcagcgtcct ggagcacaag cctttaaaaa
 361 tgcactgcaa gagctgtgca ttggtaacca gttctggaca ccttctggga agtaaacaag
 421 gtgacagaat cgacgagacg gagtgcgtaa tacgaatgaa tgatgcacct actcgaggtt
 481 atggacagga tgttgggaac aaaacaagcc ttcgagtcat tgcacactcc agcattcaga
 541 ggattttgcg aaatcgcaat gaactcttaa atatgagcca cggtgctgtg ttcatcttct
 601 ggggtcctag cagctacatg aggagagatg gtaaaggctt ggtgtacaac aacctgcagc
 661 tgatgaatca gatactgcct caattaaaag catacatgat ttctcgccac aagatgcttc
 721 aatttgatga cctttttaaa cgggaaactg ggaaagacag gaagatatcc aacacttggc
 781 ttagcacggg ctggttcaca atgactatcg ccttagagct gtgtgacagg ataaatgttt
 841 atggcatggt gccaccggat ttctgcaggg atcctaatca tctttcagta ccttatcatt
 901 attatgaacc tttgggacct gatgaatgca caatgtacat ttcacacgag cggggacgaa
 961 agggcagcca tcatcggttc atcacagaga acgagtgtt tgagaactgg gcgcggacat
1021 tcaacattca cttcttccaa ccagactgga accagaacc acttactgta aatcaccccg
1081 agatgaaagc agcggtctga gggatgaatg caaaagactg caaccgcaat caccgactgt
1141 atcagccatc aggggttgg accttctggg acagcaaggc aactgacagc aaaagggtaa
1201 cgggatttgc agctgataac tgcaacaagt caggaagttc cgatggaggg gtatatagag
1261 agcactttct gttgaactgt gtgttaatcc gctatatcgc ctttctggcc atctgacttc
1321 ctgtacgtgt gtgtgatttg tgaaaagcaa ctcggtatca ttacaggatg ggtaattcat
1381 tatggttttt taaagtacag caccactgac ttttcatagt gaaaactgat ggtatttatt
1441 taatggaggt ttttatgcaa cctaggccag tatttttcta attcacagtt ctgtggtcgt
1501 tgatctttca taatctttca aatcc
```

Fig. 28A

```
mpslagsgrsgareahkmktlmrhglavclalttmctslllmyggigggggghpeprrrqqqqqvaavpsrppgrgqhr
palpvgaglllegyisvlehkplkmhckscalvtssghllgskqgdridetecvirmndaptrgygqdvgnktslrviahs
siqrilrnrnellnmshgavfifwgpssymrrdgkglvynnlqlmnqilpqlkaymisrhkmlqfddlfkretgkdrkis
ntwlstgwftmtialelcdrinvygmvppdfcrdpnhlsvpyhyyeplgpdectmyishergrkgshhrfitekrvfenw
artfnihffqpdwkpepltvnhpemkaav
```

Fig. 28B

METHOD OF PRODUCING SIALYTRANSFERASE-MODIFIED PROTEINS

RELATED APPLICATION INFORMATION

This application claims the benefit of U.S. provisional application No. 61/010,207, filed Jan. 7, 2008, the disclosure of which is incorporated in its entirety herein by reference.

GOVERNMENT RIGHTS STATEMENT

This invention was made with Government support under SBIR Grant No. 1 R44 GM084539-01. The government has certain rights in this invention.

BACKGROUND

Certain proteins with potential commercial uses can require post-translational modifications that are efficiently produced by mammalian cells. However, mammalian cells, such as the industry standard Chinese Hamster Cells (CHO), can be difficult to grow under GMP conditions and require immense resources to propagate at the scale needed for commercial purposes. Animal based bioreactors systems are an attractive alternative to CHO and other mammalian cell based systems due to reasons which include low cost, low maintenance and ease of scalability. However, the post-translational modification of therapeutic proteins, in particular glycosylation, is executed differently in certain animals and plants as compared to mammalian cells such as CHO cells. Transgenic avians, in part because of their prolific egg laying and protein production abilities, have been successfully employed as therapeutic protein bioreactors. In some instances, sugar molecules (i.e., oligosaccharide or glycosylation structures) attached to proteins produced in the oviduct of avians such as chickens and deposited into eggs have been found to have basic structure similar to CHO and human proteins. However, there are some structural carbohydrate elements that are not present on certain proteins produced in the oviduct that can be important for bioactivity and bioavailability in human patients.

The egg white is formed around the yolk as it traverses the oviduct, the avian equivalent of the mammalian fallopian tube. The region of the oviduct in which egg white formation happens is called the magnum and is populated by cells called tubular gland cells (TGCs) which specialize in the synthesis and secretion of egg white proteins.

The two primary classes of glycosylation structures found on proteins, N- and O-linked oligosaccharides, are synthesized by different sets of enzymes. For O-linked oligosaccharides (also referred to as O-glycans) produced in the magnum of laying hens and deposited in the egg white, the enzymatic machinery for oligosaccharide production appears to be similar to that for human O-glycan production, since essentially the same sugars and linkages are present in oligosaccharide structures produced in both humans and in the avian oviduct.

Hen egg white N-linked oligosaccharides (also referred to as N-glycans) have a structure somewhat similar to those found in humans but are typically lacking the terminal galactose and sialic acid sugars. For certain therapeutic proteins, having the terminal galactose and sialic acid can be important for bioavailability and thus efficacy in patients.

Terminal sialic acid residues, which are rarely present or not present at all on N-glycan structures produced in the hen oviduct, shields the N-glycan from recognition by various lectins (receptors that recognize sugar molecules). Proteins with terminal Gal can be bound by lectins expressed in the liver and cleared from the blood circulation in patients (Ashwell and Morell. *Adv Enzymol Relat Areas Mol Biol* 41: 99-128, 1974). Proteins with the N-glycan having terminal N-acetylglucosamine (GlcNAc), as is typically the case in proteins produced in the hen oviduct, or mannose are bound by lectins expressed on macrophages, also leading to clearance (Schlesinger, et al. *Biochem J* 192: 597-606, 1980). These results can lead to proteins having a short half-life which often reduces efficacy.

Interestingly, N-glycans produced in other organs in the chicken such as those found in the blood are typically terminated with Gal and/or sialic acid (Ito, et al. *Rapid Commun Mass Spectrom* 20: 3557-65, 2006; Raju, et al. *Glycobiology* 10: 477-86, 2000). Thus it is apparent that the chicken genome contains genes that encode all of the enzymes needed to synthesize a fully sialylated N-glycan.

For chicken egg white derived N-glycans, a small percentage of the branches are occupied by Gal and a small percentage of those Gals are capped with sialic acid. For the egg white O-glycans, a high percentage of branches are capped by sialic acid. There is a substantial amount of galactose and sialic acid in egg white proteins, predominantly due to the abundance of O-glycan modified egg white proteins (Feeney, et al. *J Biol Chem* 235: 2633-7, 1960; Feeney, et al. *J Biol Chem* 235: 2307-11, 1960; Robinson and Monsey. *Biochem J* 147: 55-62, 1975). N- and O-glycan synthesis pathways share the same pools of Gal and sialic acid (Varki, et al., *Essentials of Glycobiology*. Plainview, N.Y., Cold Spring Harbor Laboratory Press, 1999). Thus the levels of Gal and sialic acid that are available for glycan synthesis in TGCs are high and should not be a limiting factor.

The structure of the egg white N-glycans in addition to what is known about the relevant enzymes in mammals gives clues as to the cellular mechanisms that give rise to the egg white N-glycan structures. In mammals, N-glycan synthesis begins in the endoplasmic reticulum with the synthesis of the dolichol oligosaccharide precursor which includes two GlcNAc residues and a number of mannose and glucose residues. This complex is attached to the asparagine of the target protein. The precursor is trimmed back to 3 mannose and 2 GlcNac residues by various glycosidases (termed the core pentasaccharide). GlcNac, Gal and sialic acid residues are then sequentially added by glycosyltransferases. It is at this stage that the diversity of N-glycan structures becomes prominent possibly due to the intracellular levels of the various glycosyltransferases and competition between the glycosyltransferases for free acceptor sites on the growing N-glycan branches (Varki, et al. *Essentials of Glycobiology*. Plainview, N.Y., Cold Spring Harbor Laboratory Press, 1999).

Starting with GlcNac, there are at least six N-acetylglucosaminyltransferases (GnTs) responsible for the addition of GlcNAc to the trimannosyl core of N-glycans. The high level of branching of egg white N-glycans indicates that all six GnTs may be expressed in oviduct cells of the hen to some extent.

The galactosyltransferases (e.g., (β1,4 galactosyltransferases), referred to as GalTs herein, are a family of at least 7 members which have distinct as well as overlapping roles in the formation of N- and O-glycans. Galactosyltransferase type 1 (GalT1) is thought to be primarily responsible for addition of Gal to the GlcNac residues of all linkages on the N-glycan (Lee, et al., *J Biol Chem* 276: 13924-34, 2001). The other members of the family, in particular types 2 and 3, are thought to be able to catalyze this transfer though their actual role in N-glycan synthesis appears to be minor. GalT1 is typically expressed in a ubiquitous manner in all cell types, though the levels can vary.

The sialyltransferase (SialT) family catalyzes addition of sialic acid to Gal or N-acetylgalactosamine (GalNac) (in the case of O-linked glycans) as well as other acceptors. With respect to N- and O-glycans, the sialic acid addition is produced by either an α2,3 or α2,6 linkage depending on the specific SialT involved. Human N-glycans can have either or both α2,3 and α2,6 linkages. CHO-produced N-glycans have only the α2,3 linkage, due to a lack of expression of the α2,6 SialTs (Lee, et al. *J Biol Chem* 264: 13848-55, 1989). Egg white N-glycans and O-glycans also appear to be linked only through the α2,3 linkage.

There are six members of the α2,3 SialT family. Types 1 and 2 may be involved in O-glycan synthesis as they use the Gal-GalNAc chain as an acceptor. Types 3, 4 and 6 apparently can add sialic acid to chains ending in Gal-GlcNac and may be involved in N-glycan and O-glycan synthesis. Type 5 appears to not be involved in O-glycan or N-glycan synthesis but rather may be involved in the addition of sialic acid to ceramide-containing compounds (Harduin-Lepers, et al. *Biochimie* 83: 727-37, 2001). Very little has been known about the avian α2,3 SialT family other than the expression analysis of type 1 (SialT1) in chick embryos (Kurosawa, et al. *Biochim Biophys Acta* 1244: 216-22, 1995).

It is currently estimated that the level for Gal at the last (i.e., terminal) or penultimate (i.e., second to last) position in egg white glycans is less than about 10% and the level for terminal sialic acid is less than about 2%. What is needed are birds which produce glycosylated proteins in oviduct tissue, such as magnum tissue, where a greater quantity of galactose and/or sialic acid is added to the N-linked oligosaccharides.

SUMMARY OF THE INVENTION

It has been discovered that the key enzyme involved in transfer of Gal to N-glycans is not expressed in TGCs. This is particularly significant since sialic acid is only attached to N-glycans through a Gal residue. It has also been discovered that the enzymes that transfer sialic acid to Gal on N-glycans are expressed but at levels that appear to preclude efficient sialylation. These discoveries in part have lead to the invention of transgenic birds that produce therapeutic proteins (e.g., human therapeutic proteins) having oligosaccharide structures (e.g., N-linked oligosaccharide structures) with a more complete complement of terminal sialic acid residues and Gal (e.g., penultimate Gal) residues. These birds are often referred to herein "transgene-augmented glycosylation" birds.

The invention includes transgenic avians (e.g., transgenic chickens) containing a transgene in their genome which contains a glycosyltransferase coding sequence which is expressed. The invention also includes methods of making the transgenic avians. The oviduct tissue, for example, magnum tissue (e.g., tubular gland cells) of the transgenic avian can produce protein (e.g., an exogenous protein, for example, a therapeutic protein) having an N-linked oligosaccharide with at least one saccharide that would not be present in the absence of the transgene. Also included in the invention are proteins having modified oligosaccharide patterns produced as disclosed herein.

In one embodiment, the glycosyltransferase is a N-acetylglucosaminyltransferase, for example, a N-acetylglucosaminyltransferase 3 and the sugar is N-acetylglucosamine.

In another embodiment, the glycosyltransferase is a galactosyltransferase (e.g., galactosyltransferase type 1) and the saccharide is galactose. In one embodiment, the exogenous protein (e.g., therapeutic protein) produced in the oviduct of transgene-augmented galactosyltransferase (e.g., galactosyltransferase type 1) birds can be used as a substrate for addition of sialic acid. For example, using well known in vitro methods, sialic acid is linked to Gal that has been added to the oligosaccharide structures by the recombinant or exogenous galactosyltransferase in the oviduct.

In another embodiment, the glycosyltransferase is a sialyltransferase (e.g., a sialyltransferase type 3) and the saccharide is sialic acid.

In one embodiment, cells of oviduct tissue of the transgenic avians of the invention secrete the protein in the presence of egg white.

In one embodiment, transgenes of the invention include at least one of an oviduct specific promoter and at least a portion of a retrovirus such as an LTR.

One aspect of the invention relates to isolating or purifying the protein having the altered oligosaccharide pattern.

In one particular embodiment, the invention is directed to methods of producing a protein in an avian wherein the protein is exogenous to the avian. The method can include producing a transgenic avian containing a transgene encoding a glycosyltransferase wherein oviduct tissue of the avian produces an exogenous protein encoded by a second transgene and having an N-linked oligosaccharide. The N-linked oligosaccharide will have at least one of a galactose and a sialic acid attached to it wherein the oligosaccharide would not have the galactose and/or sialic acid attached in the absence of the transgene encoding the glycosyltransferase.

The invention includes transgenic avians containing transgenes having coding sequences for enzyme(s) involved in the synthesis of oligosaccharide structures that are found to be present in relatively low quantities in the hen oviduct tissue such as the magnum (e.g., tubular gland cells). For example, the enzymes may be present in oviduct tissue in quantities less than that found in other tissue in the bird. For example, the enzymes may be present in oviduct tissue in an amount less than about 90% that found on average in other tissue in the avian such as liver and kidney tissue, or for example, the enzymes may be present in oviduct tissue in an amount less than about 80% that found on average in other tissue in the avian such as liver and kidney tissue, or for example, the enzymes may be present in oviduct tissue in an amount less than about 70% that found on average in other tissue in the avian such as liver and kidney tissue, or for example, the enzymes may be present in oviduct tissue in an amount less than about 60% that found on average in other tissue in the avian such as liver and kidney tissue, or for example, the enzymes may be present in oviduct tissue in an amount less than about 50% that found on average in other tissue in the avian such as liver and kidney tissue, or for example, the enzymes may be present in oviduct tissue in an amount less than about 30% that found on average in other tissue in the avian such as liver and kidney tissue, or for example, the enzymes may be present in oviduct tissue in an amount less than about 20% that found on average in other tissue in the avian such as liver and kidney tissue, or for example, the enzymes may be present in oviduct tissue in an amount less than about 10% that found on average in other tissue in the avian such as liver and kidney tissue.

The invention also includes vectors that contain transgenes of the invention. Vectors used in accordance with the invention are designed to integrate transgenes of the invention into the chicken genome and express enzyme(s) in the cells of the oviduct that make egg white proteins. Any useful vector may be employed to produce the avians of the invention such as the transgene-augmented glycosylation avians. Some useful vectors include viral vectors such as retroviral vectors and adenoviral vectors, plasmids and other nucleotide sequences that can become part of the avian genome (i.e., integrated into the genome).

Other useful vectors such as non-infective nucleic acid vectors are contemplated for use herein. For example, site directed DNA integration, integrase mediated integration and artificial chromosomes are also contemplated for use in accordance with the invention.

Examples of avian retroviruses which are contemplated for use in accordance with the invention include, without limitation, Avian Leukemia/Leukosis Viruses (ALV), for example, and without limitation, RAV-0, RAV-1, RAV-2; Avian Sarcoma Viruses (ASV); Avian Sarcoma/Acute Leukemia Viruses (ASLV) including, without limitation, Rous Sarcoma Virus (RSV); Fujinami Sarcoma Viruses (FSV); Avian Myeloblastosis Viruses (AMV); Avian Erythroblastosis Viruses (AEV); Avian Myelocytomatosis Viruses (MCV), for example, and without limitation, MC29; Reticuloendotheliosis Viruses (REV), for example, and without limitation, Spleen Necrosis Virus (SNV). The invention also contemplates the use of Murine Leukemia Viruses (MLV); Molony Murine Sarcoma Viruses (MMSV); Moloney Murine Leukemia Viruses (MMLV); and lentiviruses (e.g., human immunodeficiency virus (HIV), Equine Infectious Anemia Virus (EIAV), feline immunodeficiency virus (FIV), bovine immunodeficiency virus (BIV) and simian immunodeficiency virus (SIV), and replication deficient forms of these retroviruses. Typically, retroviral vectors used in accordance with the invention are replication-deficient.

Other methods may also be employed to produce transgene-augmented glycosylation avians where infective DNA is not required to produce germline transmission, such as those reported in de Lavoir et al, Jun. 8, 2006, Nature vol 441, p 766-769, the disclosure of which is incorporated in its entirety herein by reference.

In one embodiment, the invention is directed to transgene-augmented glycosylation birds that contain a GalT1, GalT2, GalT3, GalT4, GalT5, GalT6 and/or GalT7 encoding transgene in their genome and produce recombinant proteins, such as therapeutic proteins, in the oviduct tissue, e.g., magnum tissue (for example, in tubular gland cells), which carry N-glycans that are completely or substantially occupied by galactose at the terminal positions. For example, the exogenous proteins (e.g., therapeutic proteins) produced in accordance with the invention can have an N-glycan structure that is about 30% occupied by galactose at the terminal positions, or for example, the exogenous proteins can have an N-glycan structure that is about 40% occupied by galactose at the terminal positions, or for example, the exogenous proteins can have an N-glycan structure that is about 50% occupied by galactose at the terminal positions, or for example, the exogenous proteins can have an N-glycan structure that is about 60% occupied by galactose at the terminal positions, or for example, the exogenous proteins can have an N-glycan structure that is about 70% occupied by galactose at the terminal positions, or for example, the exogenous proteins can have an N-glycan structure that is about 80% occupied by galactose at the terminal positions, or for example, the exogenous proteins can have an N-glycan structure that is about 90% occupied by galactose at the terminal positions, or for example, the exogenous proteins can have an N-glycan structure that is about 95% occupied by galactose at the terminal positions, or for example, the exogenous proteins can have an N-glycan structure that is 100% occupied by galactose at the terminal positions.

In one embodiment, the invention is directed to transgene-augmented glycosylation birds that contain one or more GalT1, GalT2, GalT3, GalT4, GalT5, GalT6 and GalT7 encoding transgene(s) in their genome and produce recombinant proteins, such as therapeutic proteins, in the oviduct tissue, e.g., magnum tissue (for example, in tubular gland cells), which carry N-glycans that are completely or substantially occupied by galactose at the penultimate positions. For example, the exogenous proteins (e.g., therapeutic proteins) produced in accordance with the invention can have N-glycan structures that are about 30% occupied by galactose at the penultimate positions, or for example, the exogenous proteins can have N-glycan structures that are about 40% occupied by galactose at the penultimate positions, or for example, the exogenous proteins can have N-glycan structures that are about 50% occupied by galactose at the penultimate positions, or for example, the exogenous proteins can have N-glycan structures that are about 60% occupied by galactose at the penultimate positions, or for example, the exogenous proteins can have N-glycan structures that are about 70% occupied by galactose at the penultimate positions, or for example, the exogenous proteins can have N-glycan structures that are about 80% occupied by galactose at the penultimate positions, or for example, the exogenous proteins can have N-glycan structures that are about 90% occupied by galactose at the penultimate positions, or for example, the exogenous proteins can have N-glycan structures that are about 95% occupied by galactose at the penultimate positions, or for example, the exogenous proteins can have N-glycan structures that are 100% occupied by galactose at the penultimate positions.

In one embodiment, the invention is directed to transgene-augmented glycosylation birds that contain one or more GalT1, GalT2, GalT3, GalT4, GalT5, GalT6 and GalT7 encoding transgene(s) in their genome and produce recombinant proteins, such as therapeutic proteins, in the oviduct tissue, e.g., magnum tissue (for example, in tubular gland cells), which carry N-glycans that are completely or substantially occupied by sialic acid at the terminal positions. For example, the exogenous proteins can have an N-glycan structure that is about 30% occupied by sialic acid at the terminal positions, or for example, the exogenous proteins can have an N-glycan structure that is about 40% occupied by sialic acid at the terminal positions, or for example, the exogenous proteins can have an N-glycan structure that is about 50% occupied by sialic acid at the terminal positions, or for example, the exogenous proteins can have an N-glycan structure that is about 60% occupied by sialic acid at the terminal positions, or for example, the exogenous proteins can have an N-glycan structure that is about 70% occupied by sialic acid at the terminal positions, or for example, the exogenous proteins can have an N-glycan structure that is about 80% occupied by sialic acid at the terminal positions, or for example, the exogenous proteins can have an N-glycan structure that is about 90% occupied by sialic acid at the terminal positions, or for example, the exogenous proteins can have an N-glycan structure that is about 95% occupied by sialic acid at the terminal positions, or for example, the exogenous proteins can have an N-glycan structure that is about 100% occupied by sialic acid at the terminal positions.

In one embodiment, the invention is directed to transgene-augmented glycosylation birds that contain one or GalT1, GalT2, GalT3, GalT4, GalT5, GalT6 and GalT7 encoding transgene(s) in their genome and produce recombinant proteins, such as therapeutic proteins, in the oviduct tissue, e.g., magnum tissue (for example, in tubular gland cells) where one out of three GlcNac residues of the oligosaccharide has a galactose residue attached, or for example, where two out of three GlcNac residues of the oligosaccharide has a galactose residue attached, or for example, where three out of three GlcNac residues of the oligosaccharide has a galactose residue attached, or for example, where one out of four GlcNac residues of the oligosaccharide has a galactose residue attached, or for example, where two out of four GlcNac residues of the oligosaccharide has a galactose residue attached, or for example, where three out of four GlcNac residues of the oligosaccharide has a galactose residue attached, or for example, where four out of four GlcNac residues of the oligosaccharide has a galactose residue attached, or for example, where one out of five GlcNac residues of the oligosaccharide has a galactose residue attached, or for example, where two out of five GlcNac residues of the oligosaccharide has a galactose residue attached, or for example, where three out of five GlcNac residues of the oligosaccharide has a galactose residue attached, or for example, where four out of five GlcNac residues of the oligosaccharide has a galactose residue attached, or for example, where five out of five GlcNac residues of the oligosaccharide has a galactose residue attached.

In one embodiment, the invention is directed to transgene-augmented glycosylation birds that contain one or more SialT1, SialT2, SialT3, SialT4, SialT5 and SialT6 encoding transgene(s) in their genome and produce recombinant proteins, such as therapeutic proteins, in the oviduct tissue, e.g., magnum tissue (for example, in tubular gland cells) where one out of one galactose residues of the oligosaccharide has a terminal sialic acid residue attached, or for example, where one out of two galactose residues of the oligosaccharide has a terminal sialic acid residue attached, or for example, where two out of two galactose residues of the oligosaccharide has a terminal sialic acid residue attached, or for example, where one out of three galactose residues of the oligosaccharide has a terminal sialic acid residue attached, or for example, where two out of three galactose residues of the oligosaccharide has a terminal sialic acid residue attached, or for example, where three out of three galactose residues of the oligosaccharide has a terminal sialic acid residue attached, or for example, where one out of four galactose residues of the oligosaccharide has a terminal sialic acid residue attached, or for example, where two out of four galactose residues of the oligosaccharide has a terminal sialic acid residue attached, or for example, where three out of four galactose residues of the oligosaccharide has a terminal sialic acid residue attached, or for example, where four out of four galactose residues of the oligosaccharide has a terminal sialic acid residue attached, or for example, where one out of five galactose residues of the oligosaccharide has a terminal sialic acid residue attached, or for example, where two out of five galactose residues of the oligosaccharide has a terminal sialic acid residue attached, or for example, where three out of five galactose residues of the oligosaccharide has a terminal sialic acid residue attached, or for example, where four out of five galactose residues of the oligosaccharide has a terminal sialic acid residue attached, or for example, where five out of five galactose residues of the oligosaccharide has a terminal sialic acid residue attached, or for example, where one out of six galactose residues of the oligosaccharide has a terminal sialic acid residue attached, or for example, where two out of six galactose residues of the oligosaccharide has a terminal sialic acid residue attached, or for example, where three out of six galactose residues of the oligosaccharide has a terminal sialic acid residue attached, or for example, where four out of six galactose residues of the oligosaccharide has a terminal sialic acid residue attached, or for example, where five out of six galactose residues of the oligosaccharide has a terminal sialic acid residue attached, or for example, where six out of six galactose residues of the oligosaccharide has a terminal sialic acid residue attached.

In one embodiment, the invention provides for transgenic hens containing one or more SialT1, SialT2, SialT3, SialT4, SialT5 and SialT6 encoding transgene(s) in their genome which produce N-glycans in their oviduct tissue such as magnum tissue (for example, in tubular gland cells) with an increased percentage of branches ending with sialic acid relative to a non-transgenic bird. For example, the exogenous proteins can have an N-glycan structure that is 30% occupied by sialic acid at the terminal positions, or for example, the exogenous proteins can have an N-glycan structure that is 40% occupied by sialic acid at the terminal positions, or for example, the exogenous proteins can have an N-glycan structure that is 50% occupied by sialic acid at the terminal positions, or for example, the exogenous proteins can have an N-glycan structure that is 60% occupied by sialic acid at the terminal positions, or for example, the exogenous proteins can have an N-glycan structure that is 70% occupied by sialic acid at the terminal positions, or for example, the exogenous proteins can have an N-glycan structure that is 80% occupied by sialic acid at the terminal positions, or for example, the exogenous proteins can have an N-glycan structure that is 90% occupied by sialic acid at the terminal positions, or for example, the exogenous proteins can have an N-glycan structure that is 95% occupied by sialic acid at the terminal positions, or for example, the exogenous proteins can have an N-glycan structure that is 100% occupied by sialic acid at the terminal positions.

In one embodiment, the invention is directed to transgene-augmented glycosylation birds that contain one or more GalT1, GalT2, GalT3, GalT4, GalT5, GalT6, GalT7, SialT1, SialT2, SialT3, SialT4, SialT5 and SialT6 encoding transgenes, for example, GalT1 and SialT3 encoding transgene(s) in their genome and produce recombinant proteins, such as therapeutic proteins, in the oviduct tissue, e.g., magnum tissue (for example, in tubular gland cells) where one out of one galactose residues of the oligosaccharide has a terminal sialic acid residue attached, or for example, where one out of two galactose residues of the oligosaccharide has a terminal sialic acid residue attached, or for example, where two out of two galactose residues of the oligosaccharide has a terminal sialic acid residue attached, or for example, where one out of three galactose residues of the oligosaccharide has a terminal sialic acid residue attached, or for example, where two out of three galactose residues of the oligosaccharide has a terminal sialic acid residue attached, or for example, where three out of three galactose residues of the oligosaccharide has a terminal sialic acid residue attached, or for example, where one out of four galactose residues of the oligosaccharide has a terminal sialic acid residue attached, or for example, where two out of four galactose residues of the oligosaccharide has a terminal sialic acid residue attached, or for example, where three out of four galactose residues of the oligosaccharide has a terminal sialic acid residue attached, or for example, where four out of four galactose residues of the oligosaccharide has a terminal sialic acid residue attached, or for example, where one out of five galactose residues of the oligosaccharide has a terminal sialic acid residue attached, or for example, where two out of five galactose residues of the oligosaccharide has a terminal sialic acid residue attached, or for example, where three out of five galactose residues of the oligosaccharide has a terminal sialic acid residue attached, or for example, where four out of five galactose residues of the oligosaccharide has a terminal sialic acid residue attached, or for example, where five out of five galactose residues of the oligosaccharide has a terminal sialic acid residue attached, or for example, where one out of six galactose residues of the oligosaccharide has a terminal sialic acid residue attached, or for example, where two out of six galactose residues of the oligosaccharide has a terminal sialic acid residue attached, or for example, where three out of six galactose residues of the oligosaccharide has a terminal sialic acid residue attached, or for example, where four out of six galactose residues of the oligosaccharide has a terminal sialic acid residue attached, or for example, where five out of six galactose residues of the oligosaccharide has a terminal sialic acid residue attached, or for example, where six out of six galactose residues of the oligosaccharide has a terminal sialic acid residue attached.

In one embodiment, the invention provides for transgenic hens containing more than one of GalT1, GalT2, GalT3, GalT4, GalT5, GalT6, GalT7, SialT1, SialT2, SialT3, SialT4, SialT5 and SialT6 encoding transgenes, for example, GalT1 and SialT3 encoding transgenes, in their genome which produce exogenous protein in their oviduct tissue such as magnum tissue (for example, in tubular gland cells) with an increased percentage of branches ending with sialic acid relative to a non-transgenic bird. For example, the exogenous proteins can have an N-glycan structure that is 20% occupied by sialic acid at the terminal positions, or for example, the exogenous proteins can have an N-glycan structure that is 30% occupied by sialic acid at the terminal positions, or for example, the exogenous proteins can have an N-glycan structure that is 40% occupied by sialic acid at the terminal positions, or for example, the exogenous proteins can have an N-glycan structure that is 50% occupied by sialic acid at the terminal positions, or for example, the exogenous proteins can have an N-glycan structure that is 60% occupied by sialic acid at the terminal positions, or for example, the exogenous proteins can have an N-glycan structure that is 70% occupied by sialic acid at the terminal positions, or for example, the exogenous proteins can have an N-glycan structure that is 80% occupied by sialic acid at the terminal positions, or for example, the exogenous proteins can have an N-glycan structure that is 90% occupied by sialic acid at the terminal positions, or for example, the exogenous proteins can have an N-glycan structure that is 95% occupied by sialic acid at the terminal positions, or for example, the exogenous proteins can have an N-glycan structure that is 100% occupied by sialic acid at the terminal positions.

In one embodiment, proteins of the invention have oligosaccharides with between 1 and 5 sialic acids (e.g., between 1 and 4 sialic acids).

In one embodiment, proteins of the invention have oligosaccharides with between 1 and 5 galactoses (e.g., between 1 and 4 galactoses).

To produce transgene-augmented glycosylation birds that produce exogenous proteins the transgene-augmented glycosylation birds can be crossed with existing birds which are transgenic for therapeutic protein production in the oviduct where the efficacy of the therapeutic protein can be enhanced by having galactose and/or sialic acid at the oligosaccharide added to the therapeutic proteins. The transgene-augmented glycosylation birds can also be used to produce egg or embryo donors. Transgenes encoding proteins such as therapeutic proteins can be introduced into the embryos, for example, by methods known in the art, to produce lines of avians which will manufacture the transgene encoded proteins in the oviduct where the glycosylated transgene encoded proteins can have additional sugars such as galactose and sialic acid to the their oligosaccharide structures. In another embodiment, existing birds which are transgenic for therapeutic protein production are used to produce egg or embryo donors and a vector(s) encoding a glycosyltransferase(s) (e.g., GalT, SialT) transgene(s) is introduced into the donor egg or embryo.

In one embodiment, the invention is directed to producing hens such as chicken hens to make oligosaccharide structures in egg white-derived therapeutic proteins that more closely resemble the oligosaccharide structures naturally present on mammalian proteins, in particular human proteins.

First generation transgenic birds produced in accordance with the invention typically are referred to as the G0 generation and are usually hemizygous for each inserted transgene. The G0 generation may be bred to non-transgenic birds to give rise to fully transgenic G1 offspring which are also hemizygous for the transgene. The G1 hemizygous offspring may be bred to non-transgenic birds giving rise to G2 hemizygous offspring or may be bred together to give rise to G2 offspring homozygous for the transgene. Descendents of G0 birds which are hemizygous or homozygous for the transgene can be bred to descendents of G0 birds which are hemizygous or homozygous for another transgene to produce offspring hemizygous for both transgenes. The double hemizygous birds can be interbred to produce birds homozygous for one or both transgenes. These are merely examples of certain useful breeding schemes. The present invention contemplates the employment of any useful breeding scheme such as those known to individuals of ordinary skill in the art.

Any combination of features described herein is included within the scope of the present invention provided that the features included in any such combination are not mutually inconsistent. Such combinations will be apparent based on this specification and on the knowledge of one of ordinary skill in the art.

BRIEF DESCRIPTION OF THE FIGURES

FIG. 6A shows a 1.8 kb ovomucoid promoter operably linked to the chicken beta-1,4-galactosyltransferase type 1 coding sequence.

Figure 1A:
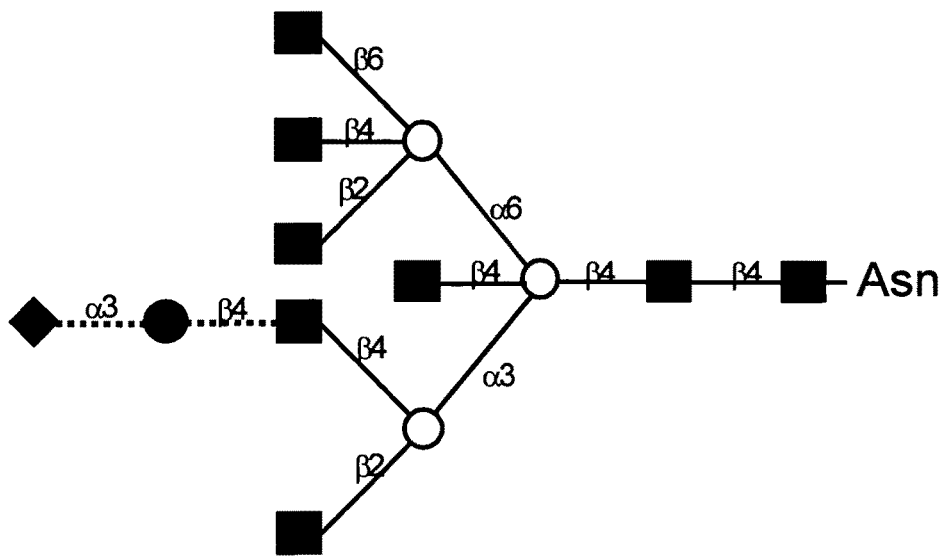
FIGS. 1 A and B show exemplary structures of an N-glycan which is attached to egg white proteins as occur naturally (1A) and in accordance with the invention (1B). Gal is occasionally found to occupy a terminal GlcNac residue and appears to be $\beta 1,4$-linked as shown in FIG. 1A. On naturally occurring egg white proteins, Gal has not been detected as being present on a bisecting GlcNac. In addition, it appears that when a Gal is present on an N-linked oligosaccharide it will sometimes, though rarely be sialated. With the addition of Gal to terminal GlcNac residues in accordance with the invention, more of the terminal GlcNac residues are sialated than would otherwise be sialated in the absence of the transgene-augmented glycosylation.
FIG. 1B shows an exemplary N-linked oligosaccharide structure present on a protein produced in the avian oviduct in accordance with the invention. In this exemplary diagrammatic and non-limiting structure all of the terminal GlcNac residues (except for the bisecting GlcNac) have an attached Gal which is sialated.
Figure 1B:
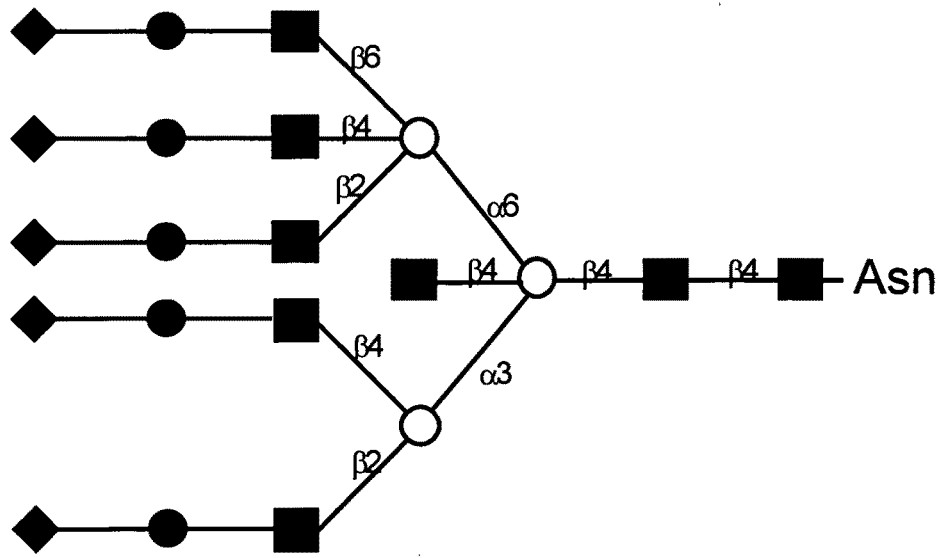

The invention includes proteins having an N-linked oligosaccharide, for example, human proteins including those disclosed in this application (e.g., human proteins) which can be expressed in the oviduct of transgene augmented glycosylation birds having novel oligosaccharide structures.

FIG. 9A-C (SEQ ID NO: 1) shows pSIN-OM-1.8-GalT1 which is 7434 bp in length. Some features of the sequence are as follows: LTR—nucleotides 370 . . . 542; LTR—3645 . . . 3990; CDS—268 . . . 7356; promoter 4441 . . . 6214.

FIG. 10A-C (SEQ ID NO: 2) shows pSIN-OM-1.8-SialT3 which is 7545 bp in length. Some features of the sequence are as follows: LTR—nucleotides 370 . . . 542; LTR—3645 . . . 3990; CDS—6362 . . . 7540 promoter 4431 . . . 6309.

FIG. 11A-C (SEQ ID NO: 3) shows pSIN-OM-1.8-GalT1-IRES-SialT3 9119 bp in length. Some features of the sequence are as follows: LTR—nucleotides 3653 . . . 3998; LTR—nucleotides 378 . . . 550; CDS—nucleotides 7930 . . . 9108; CDS—nucleotides 6276 . . . 7361; promoter nucleotides 4449 . . . 6222; IRES 7362 . . . 7929. It is contemplated that one or more of the following nucleotide substitutions will enhance the quantity of translated product produced by the IRES: nt 7920 T to G; nt 7918 C to A; nt 7917 G to T; nt 7836 G to A; nts 7366 to 7368 (CCC) replaced with

AATTCCCCCTCTCCCTCCCCCCCCCCTAAC. (SEQ ID NO: 39)

FIG. 12A (SEQ ID NO: 4) shows chicken beta-1,4-galactosyltransferase (CKI) mRNA type 1—ACCESSION NO. U19890. Some of the features are: 5'UTR—nucleotides 1 . . . 57; CDS—nucleotides 58 . . . 1146; 3'UTR—nucleotides 1147 . . . 2279; polyA_signal—nucleotides 2260 . . . 2265

FIG. 12B (SEQ ID NO: 5) shows the amino acid sequence for chicken beta-1,4-galactosyltransferase.

FIG. 13A (SEQ ID NO: 6) shows chicken beta-1,4-galactosyltransferase (CKII) mRNA type 2—ACCESSION U19889. The CDS is shown by nucleotides 202 . . . 1323.

FIG. 13B (SEQ ID NO: 7) shows the amino acid sequence for chicken beta-1,4-galactosyltransferase.

FIG. 14A (SEQ ID NO: 8) shows chicken beta-1,4-galactosyltransferase, type 3 mRNA—ACCESSION NO: XM_416564. The CDS is shown by nucleotides 1 . . . 1029.

FIG. 14B (SEQ ID NO: 9) shows the amino acid sequence for chicken beta-1,4-galactosyltransferase, type 3.

FIG. 15A (SEQ ID NO: 10) shows chicken beta-1,4-galactosyltransferase, type 4 mRNA—ACCESSION XM_416563. The CDS is shown by nucleotides 221 . . . 1288.

FIG. 15B (SEQ ID NO: 11) shows the amino acid sequence for chicken beta-1,4-galactosyltransferase, type 4.

FIG. 16A (SEQ ID NO: 12) shows chicken beta-1,4-galactosyltransferase, type 5 mRNA. The CDS is shown by nucleotides 1 . . . 1773.

FIG. 16B (SEQ ID NO: 13) shows the amino acid sequence for chicken beta-1,4-galactosyltransferase, type 5.

FIG. 17A-B (SEQ ID NO: 14) shows chicken beta-1,4-galactosyltransferase, type 6 mRNA. The CDS is shown by nucleotides 294 . . . 1400.

FIG. 17C (SEQ ID NO: 15) shows the amino acid sequence for chicken beta-1,4-galactosyltransferase, type 6.

FIG. 18A (SEQ ID NO: 16) shows chicken beta-1,4-galactosyltransferase, type 7 mRNA. The CDS is shown by nucleotides 57 . . . 1016.

FIG. 18B (SEQ ID NO: 17) shows the amino acid sequence for chicken beta-1,4-galactosyltransferase, type 7.

FIG. 19A (SEQ ID NO: 18) shows chicken alpha-2,3-sialyltransferase 1 mRNA. The CDS is shown by nucleotides 132 . . . 1160.

FIG. 19B (SEQ ID NO: 19) shows the amino acid sequence for chicken alpha-2,3-sialyltransferase 1.

FIG. 20A (SEQ ID NO: 20) shows chicken alpha-2,3-sialyltransferase 2 mRNA. The CDS is shown by nucleotides 290 . . . 1339.

FIG. 20B (SEQ ID NO: 21) shows the amino acid sequence for chicken alpha-2,3-sialyltransferase 2.

FIG. 21A (SEQ ID NO: 22) shows chicken alpha-2,3-sialyltransferase 3 mRNA. The CDS is shown by nucleotides 1 . . . 1179.

FIG. 21B (SEQ ID NO: 23) shows the amino acid sequence for chicken alpha-2,3-sialyltransferase 3.

FIG. 21C (SEQ ID NO: 24) shows an alternate isoform having an amino acid sequence segment deleted, i.e., the corresponding nucleotide sequence segment is deleted in the nucleotide sequence shown in FIG. 21a.

FIG. 22A (SEQ ID NO: 25) shows chicken alpha-2,3-sialyltransferase 4 mRNA. The CDS is shown by nucleotides 325 . . . 1332.

FIG. 22B (SEQ ID NO: 26) shows the amino acid sequence for chicken alpha-2,3-sialyltransferase 4.

FIG. 23A (SEQ ID NO: 27) shows chicken alpha-2,3-sialyltransferase 5 mRNA. The CDS is shown by nucleotides 128 . . . 1234.

FIG. 23B (SEQ ID NO: 28) shows the amino acid sequence for chicken alpha-2,3-sialyltransferase 5.

FIG. 24A (SEQ ID NO: 29) shows chicken alpha-2,3-sialyltransferase 6 mRNA. The CDS is shown by nucleotides 740 . . . 1798.

FIG. 24B (SEQ ID NO: 30) shows the amino acid sequence for chicken alpha-2,3-sialyltransferase 6.

FIG. 25A (SEQ ID NO: 31) shows chicken alpha-2,6-sialyltransferase 1 mRNA. The CDS is shown by nucleotides 359 . . . 1600.

FIG. 25B (SEQ ID NO: 32) shows the amino acid sequence for chicken alpha-2,6-sialyltransferase 1.

FIG. 26A (SEQ ID NO: 33) shows chicken alpha-2,6-sialyltransferase 2 mRNA. The CDS is shown by nucleotides 1 . . . 1590.

FIG. 26B (SEQ ID NO: 34) shows the amino acid sequence for chicken alpha-2,6-sialyltransferase 2.

FIG. 27A (SEQ ID NO: 35) shows chicken alpha-2,6-sialyltransferase 4 mRNA. The CDS is shown by nucleotides. The CDS is shown by nucleotides 62 . . . 931.

FIG. 27B (SEQ ID NO: 36) shows the amino acid sequence for chicken alpha-2,6-sialyltransferase 4.

FIG. 28A (SEQ ID NO: 37) shows chicken alpha-2,6-sialyltransferase 5 mRNA. The CDS is shown by nucleotides 51 . . . 1100.

FIG. 28B (SEQ ID NO: 38) shows the amino acid sequence for chicken alpha-2,6-sialyltransferase 5.

DETAILED DESCRIPTION

Some of the definitions and abbreviations used herein include the following: aa, amino acid(s); bp, base pair(s); CDS, coding sequence cDNA, DNA complementary to an RNA; GalNac, N-acetylgalactosamine; Gal, galactose; GlcNac, IRES, internal ribosome entry site; N-acetylglucosamine nt, nucleotide(s); kb, 1000 base pairs; µg, microgram; ml, milliliter; ng, nanogram; nt, nucleotide.

Certain definitions are set forth herein to illustrate and define the meaning and scope of the various terms used to describe the invention herein.

The term "avian" as used herein refers to any species, subspecies or strain of organism of the taxonomic class ava, such as, but not limited to, such organisms as chicken, turkey, duck, goose, quail, pheasants, parrots, finches, hawks, crows and ratites including ostrich, emu and cassowary. The term includes the various known strains of Gallus gallus, or chickens, (for example, White Leghorn, Brown Leghorn, Barred-Rock, Sussex, New Hampshire, Rhode Island, Ausstralorp, Minorca, Amrox, California Gray, Italian Partridge-colored), as well as strains of turkeys, pheasants, quails, duck, ostriches and other poultry commonly bred in commercial quantities.

The phrases "based on" and "derived from" typically mean obtained from, in whole or in part. For example, a retroviral vector being based on or derived from a particular retrovirus or based on a nucleotide sequence of a particular retrovirus mean that the genome of the retroviral vector contains a substantial portion of the nucleotide sequence of the genome of the particular retrovirus. The substantial portion may be a particular gene or nucleotide sequence such as the nucleotide sequence encoding the gag, pol and/or env proteins or other structural or functional nucleotide sequence of the virus genome such as sequences encoding the LTRs or may be substantially the complete retrovirus genome, for example, most (e.g., more than 60% or more than 70% or more than 80% or more than 90%) or all of the retrovirus genome, as will be apparent from the context in the specification as the knowledge of one skilled in the art. Examples of retroviral vectors that are based on or derived from a retrovirus are the NL retroviral vectors (e.g., NLB) which are based on the ALV retrovirus as disclosed in Cosset et al, Journal of Virology (1991) vol 65, p 3388-3394.

The term "coding sequence" and "coding region" as used herein refer to nucleotide sequences and nucleic acid sequences, including both RNA and DNA, that encode genetic information for the synthesis of an RNA, a protein, or any portion of an RNA or protein.

Nucleotide sequences that are not naturally part of a particular organism's genome or are introduced at a non-native site in the organisms genome are referred to as "foreign" nucleotide sequences, "heterologous" nucleotide sequences, "recombinant" nucleotide sequences or "exogenous" nucleotide sequences. In addition, a nucleotide sequence that has been isolated and then reintroduced into the same type (e.g., same species) of organism is not considered to be a naturally occurring part of a particular organism's genome and is therefore considered exogenous or heterologous. "Heterologous proteins" or "exogenous proteins" can be proteins encoded by foreign, heterologous or exogenous nucleotide sequences and therefore are often not naturally expressed in a cell of the organism.

As used herein, the terms "exogenous", "heterologous" and "foreign" with reference to nucleic acids, such as DNA and RNA, are used interchangeably and refer to nucleic acid that does not occur naturally as part of a chromosome, a genome or cell in which it is present or which is found in a location(s) and/or in amounts that differ from the location(s) and/or amounts in which it occurs in nature. It can be nucleic acid that is not endogenous to the genome, chromosome or cell and has been exogenously introduced into the genome, chromosome or cell. Examples of heterologous DNA include, but are not limited to, DNA that encodes a gene product or gene product(s) of interest, for example, for production of an encoded protein. Examples of heterologous DNA include, but are not limited to, DNA that encodes traceable marker proteins, DNA that encodes therapeutic proteins. The terms "heterologous" and "exogenous" can refer to a biomolecule such as a nucleic acid or a protein which is not normally found in a certain cell, tissue or substance produced by an organism or is not normally found in a certain cell, tissue or substance produced by an organism in an amount or location the same as that found to occur naturally. For example, a protein that is heterologous or exogenous to an egg is a protein that is not normally found in the egg.

The term "construct" as used herein refers to a linear or circular nucleotide sequence such as DNA that has been assembled from more than one segments of nucleotide sequence which have been isolated from a natural source or have been chemically synthesized, or combinations thereof.

The term "complementary" as used herein refers to two nucleic acid molecules that can form specific interactions with one another. In the specific interactions, an adenine base within one strand of a nucleic acid can form two hydrogen bonds with thymine within a second nucleic acid strand when the two nucleic acid strands are in opposing polarities. Also in the specific interactions, a guanine base within one strand of a nucleic acid can form three hydrogen bonds with cytosine within a second nucleic acid strand when the two nucleic acid strands are in opposing polarities. Complementary nucleic acids as referred to herein, may further comprise modified bases wherein a modified adenine may form hydrogen bonds with a thymine or modified thymine, and a modified cytosine may form hydrogen bonds with a guanine or a modified guanine.

The term "cytokine" as used herein refers to any secreted amino acid sequence that affects the functions of cells and is a molecule that modulates interactions between cells in the immune, inflammatory or hematopoietic responses. A cytokine includes, but is not limited to, monokines and lymphokines regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes. Lymphokines are generally referred to as being produced by lymphocyte cells. Examples of cytokines include, but are not limited to, interferon, erythropoietin, G-CSF, Interleukin-1 (IL-1), Interleukin-6 (IL-6), Interleukin-8 (IL-8), Tumor Necrosis Factor-alpha (TNF-alpha) and Tumor Necrosis Factor beta (TNF-beta).

The term "expressed" or "expression" as used herein refers to the transcription of a coding sequence to yield an RNA nucleic acid molecule at least complementary in part to a region of one of the two nucleic acid strands of the coding sequence. The term "expressed" or "expression" as used herein can also refer to the translation of RNA to produce a protein or peptide.

The term "expression vector" as used herein refers to a nucleic acid vector that comprises a gene expression controlling region, such as a promoter or promoter component, operably linked to a nucleotide sequence encoding at least one polypeptide.

The term "fragment" as used herein can refer to, for example, an at least about 10, 20, 50, 75, 100, 150, 200, 250, 300, 500, 1000, 2000, 5000, 6,000, 8,000, 10,000, 20,000, 30,000, 40,000, 50,000 or 60,000 nucleotide long portion of a nucleic acid that has been constructed artificially (e.g., by chemical synthesis) or by cleaving a natural product into multiple pieces, using restriction endonucleases or mechanical shearing, or enzymatically, for example, by PCR or any other polymerizing technique known in the art, or expressed in a host cell by recombinant nucleic acid technology known to one of skill in the art. The term "fragment" as used herein may also refer to, for example, an at least about 5, 10, 20, 30, 40, 50, 75, 100, 150, 200, 250, 300, 400, 500, 1000, 2000, 5000, 6,000, 8,000 or 10,000 amino acid portion of an amino acid sequence, which portion is cleaved from a naturally occurring amino acid sequence by proteolytic cleavage by at least one protease, or is a portion of the naturally occurring amino acid sequence synthesized by chemical methods or using recombinant DNA technology (e.g., expressed from a portion of the nucleotide sequence encoding the naturally occurring amino acid sequence) known to one of skill in the art. "Fragment" may also refer to a portion, for example, of about 5%, about 10%, about 20%, about 30%, about 40%, about 50%, about 60%, about 70%, about 80% about 90% about 95% or about 99% of a particular nucleotide sequence or amino acid sequence.

"Functional portion" and "functional fragment" can be used interchangeably and as used herein mean a portion or fragment of a whole capable of performing, in whole or in part, a function of the whole. For example, a biologically functional portion of a molecule means a portion of the molecule that performs a biological function of the whole or intact molecule. Functional portions may be of any useful size. For example, a functional fragment may range in size from about 20 bases in length to a length equal to the entire length of the specified sequence minus one nucleotide. In another example, a functional fragment may range in size from about 50 bases in length to a length equal to the entire length of the specified sequence minus one nucleotide. In another example, a functional fragment may range in size from about 50 bases in length to about 20 kb in length. In another example, a functional fragment may range in size from about 500 bases in length to about 20 kb in length. In another example, a functional fragment may range in size from about 1 kb in length to about 20 kb in length. In another example, a functional fragment may range in size from about 0.1 kb in length to about 10 kb in length. In another example, a functional fragment may range in size from about 20 bases kb in length to about 10 kb in length.

The term "fully transgenic" refers to an animal such as a bird that contains at least one copy of a transgene in essentially all of its somatic cells.

The term "gene expression controlling region" as used herein refers to nucleotide sequences that are associated with a coding sequence and which regulate, in whole or in part, expression of the coding sequence, for example, regulate, in whole or in part, the transcription of the coding sequence. Gene expression controlling regions may be isolated from a naturally occurring source or may be chemically synthesized and can be incorporated into a nucleic acid vector to enable regulated transcription in appropriate cells. The "gene expression controlling regions" may precede, but is not limited to preceding, the region of a nucleic acid sequence that is in the region 5' of the end of a coding sequence that may be transcribed into mRNA.

The term "isolated nucleic acid" as used herein covers, for example, (a) a DNA which has the sequence of part of a naturally occurring genomic molecule but is not flanked by at least one of the sequences that flank that part of the molecule in the genome of the species in which it naturally occurs; (b) a nucleic acid which has been incorporated into a vector or into the genomic DNA of a prokaryote or eukaryote in a manner such that the resulting vector or genomic DNA is not identical to naturally occurring DNA from which the nucleic acid was obtained; (c) a separate molecule such as a cDNA, a genomic fragment, a fragment produced by polymerase chain reaction (PCR), ligase chain reaction (LCR) or chemical synthesis, or a restriction fragment; (d) a recombinant nucleotide sequence that is part of a hybrid gene, i.e., a gene encoding a fusion protein, and (e) a recombinant nucleotide sequence that is part of a hybrid sequence that is not naturally occurring. Isolated nucleic acid molecules of the present invention can include, for example, natural allelic variants as well as nucleic acid molecules modified by nucleotide deletions, insertions, inversions, or substitutions.

The term "nucleic acid" as used herein refers to any linear or sequential array of nucleotides and nucleosides, for example cDNA, genomic DNA, mRNA, tRNA, oligonucleotides, oligonucleosides and derivatives thereof. For ease of discussion, non-naturally occurring nucleic acids may be referred to herein as constructs. Nucleic acids can include bacterial plasmid vectors including expression, cloning, cosmid and transformation vectors such as, animal viral vectors such as, but not limited to, modified adenovirus, influenza virus, polio virus, pox virus, retroviruses such as avian leukosis virus (ALV) retroviral vector, a murine leukemia virus (MLV) retroviral vector, and a lentivirus vector, and the like and fragments thereof. In addition, the nucleic acid can be an LTR of an avian leukosis virus (ALV) retroviral vector, a murine leukemia virus (MLV) retroviral vector, or a lentivirus vector and fragments thereof. Nucleic acids can also include NL vectors such as NLB, NLD and NLA and fragments thereof and synthetic oligonucleotides such as chemically synthesized DNA or RNA. Nucleic acids can include modified or derivatised nucleotides and nucleosides such as, but not limited to, halogenated nucleotides such as, but not only, 5-bromouracil, and derivatised nucleotides such as biotin-labeled nucleotides.

The term "vector" and "nucleic acid vector" as used herein refers to a natural or synthetic single or double stranded plasmid or viral nucleic acid molecule that can be transfected or transformed into cells and replicate independently of, or within, the host cell genome. A circular double stranded vector can be linearized by treatment with an appropriate restriction enzyme based on the nucleotide sequence of the vector. A nucleic acid can be inserted into a vector by cutting the vector with restriction enzymes and ligating the desired pieces together, as is understood in the art.

The term "operably linked" refers to an arrangement of elements wherein the components so described are configured so as to perform their usual function. Gene expression controlling regions or promoters (e.g., promoter components) operably linked to a coding sequence are capable of effecting the expression of the coding sequence. The controlling sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

The term "oviduct" or "oviduct tissue" refers to tissue of an avian oviduct, such as the magnum, e.g., tubular gland cells, where proteins are produced containing N-linked oligosaccharides that contain substantially reduced amounts of Gal and/or sialic acid relative to that of proteins produced in other tissue of the avian such as liver or kidney tissue.

The term "oviduct specific promoter" as used herein refers to promoters and promoter components which are functional, i.e., provide for transcription of a coding sequence, to a large extent, for example, primarily (i.e., more than 50% of the transcription product produced in the animal by a particular promoter type being produced in oviduct cells) or exclusively in oviduct cells of a bird. Examples of oviduct specific promoters include, ovalbumin promoter, ovomucoid promoter, ovoinhibitor promoter, lysozyme promoter and ovotransferrin promoter and functional portions of these promoters, e.g., promoter components. Glycosylation enzymes such as GalTs (e.g., GalT1) and SialTs (e.g., SialT3) are normally directed to the ER/Golgi organelles and participate in the N-glycan synthesis pathway. By limiting the expression of these enzymes to the magnum using oviduct specific promoters, deleterious physiological effects to the bird as result of expression of these enzymes in other tissues of the bird are minimized.

The terms "percent sequence identity", "percent identity", "% identity", "percent sequence homology", "percent homology", "% homology" and "percent sequence similarity" can each refer to the degree of sequence matching between two nucleic acid sequences or two amino acid sequences. Such sequence matching can be determined using the algorithm of Karlin & Attschul (1990) Proc. Natl. Acad. Sci. 87: 2264-2268, modified as in Karlin & Attschul (1993) Proc. Natl. Acad. Sci. 90: 5873-5877. Such an algorithm is incorporated into the NBLAST and XBLAST programs of Attschul et al. (1990) T. Mol. Biol. Q15: 403-410. BLAST nucleotide searches are performed with the NBLAST program, score=100, wordlength=12, to obtain nucleotide sequences homologous to a nucleic acid molecule of the invention. BLAST protein searches are performed with the XBLAST program, score=50, wordlength=3, to obtain amino acid sequences homologous to a reference amino acid sequence. To obtain gapped alignments for comparison purposes, Gapped BLAST is utilized as described in Attschul et al. (1997) Nucl. Acids Res. 25: 3389-3402. When utilizing BLAST and Gapped BLAST programs, the default parameters of the respective programs (e.g. XBLAST and NBLAST) are used. Other algorithms, programs and default settings may also be suitable such as, but not only, the GCG-Sequence Analysis Package of the U.K. Human Genome Mapping Project Resource Centre that includes programs for nucleotide or amino acid sequence comparisons.

The term "poultry derived" refers to a composition or substance produced by or obtained from poultry. "Poultry" refers to birds that can be kept as livestock, including but not limited to, chickens, duck, turkey, quail and ratites. For example, "poultry derived" may refer to chicken derived, turkey derived and/or quail derived. The term "avian derived" refers to a composition or substance produced by or obtained from an avian.

The terms "polynucleotide," "oligonucleotide", "nucleotide sequence" and "nucleic acid sequence" can be used interchangeably herein and include, but are not limited to, coding sequences, i.e., polynucleotide(s) or nucleic acid sequence(s) which are transcribed and translated into polypeptide in vitro or in vivo when placed under the control of appropriate regulatory or control sequences; controlling sequences, e.g., translational start and stop codons, promoter sequences, ribosome binding sites, polyadenylation signals, transcription factor binding sites, transcription termination sequences, upstream and downstream regulatory domains, enhancers, silencers, DNA sequences to which a transcription factor(s) binds and alters the activity of a gene's promoter either positively (induction) or negatively (repression) and the like. No limitation as to length or to synthetic origin are suggested by the terms described herein.

As used herein the terms "polypeptide" and "protein" refer to a polymer of amino acids, for example, three or more amino acids, in a serial array, linked through peptide bonds. The term "polypeptide" includes proteins, protein fragments, protein analogues, oligopeptides and the like. The term "polypeptides" includes polypeptides as defined above that are encoded by nucleic acids, produced through recombinant technology (e.g., isolated from a transgenic bird), or synthesized. The term "polypeptides" further contemplates polypeptides as defined above that include chemically modified amino acids or amino acids covalently or noncovalently linked to labeling ligands.

The term "promoter" as used herein refers to a DNA sequence useful to initiate transcription by an RNA polymerase in an avian cell. A "promoter component" is a DNA sequence that can, by itself or, in combination with other DNA sequences effect or facilitate transcription. Promoter components can be functional fragments of promoters. For example, an ovomucoid promoter component includes, without limitation, the about 1.8 kb, the about 3.9 kb and the about 10 kb ovomucoid promoters disclosed in U.S. application Ser. No. 11/649,543, published May 17, 2007, which is incorporated in its entirety herein by reference. "Promoter components" can also encompass rearranged gene expression controlling regions which function to initiate RNA transcription and hybrid DNA molecules composed of naturally occurring DNA sequences and/or synthetic DNA sequences which function to initiate RNA transcription.

The terms "recombinant nucleic acid" and "recombinant DNA" as used herein refer to combinations of at least two nucleic acid sequences that are not naturally found in a eukaryotic or prokaryotic cell. The nucleic acid sequences may include, but are not limited to, nucleic acid vectors, gene expression regulatory elements, origins of replication, suitable gene sequences that when expressed confer antibiotic resistance, protein-encoding sequences and the like. The term "recombinant polypeptide" is meant to include a polypeptide produced by recombinant DNA techniques such that it is distinct from a naturally occurring polypeptide either in its location, purity or structure. Generally, such a recombinant polypeptide will be present in a cell in an amount different from that normally observed in nature.

As used herein, the term "regulatory" sequences or elements include promoters, enhancers, terminators, stop codons, and other elements that can control gene expression.

A "retrovirus", "retroviral particle", "transducing particle", or "transduction particle" refers to a replication-defective or replication-competent virus capable of transducing non-viral DNA or RNA into a cell.

A "SIN vector" is a self-inactivating vector. In particular, a SIN vector is a retroviral vector having an altered genome such that upon integration into genomic DNA of the target cell (e.g., avian embryo cells) the 5' LTR of the integrated retroviral vector will not function as a promoter. For example, a portion or all of the nucleotide sequence of the retroviral vector that results in the U3 region of the 5' LTR of the retroviral vector once integrated may be deleted or altered in order to reduce or eliminate promoter activity of the 5' LTR. In certain examples, deletion of the CAAT box and/or the TAATA box from U3 of the 5' LTR can result in a SIN vector, as is understood in the art.

The term "sense strand" as used herein refers to a single stranded DNA molecule from a genomic DNA that can be transcribed into RNA and translated into the natural polypeptide product of the gene. The term "antisense strand" as used herein refers to the single strand DNA molecule of a genomic DNA that is complementary with the sense strand of the gene.

A "therapeutic protein" or "pharmaceutical protein" is a substance that, in whole or in part, makes up a drug. In particular, "therapeutic proteins" and "pharmaceutical proteins" include an amino acid sequence which in whole or in part makes up a drug.

The terms "transcription regulatory sequences" and "promoter components" as used herein refer to nucleotide which regulates the transcriptional expression of a coding sequence. Exemplary transcription regulatory sequences include enhancer elements, hormone response elements, steroid response elements, negative regulatory elements, and the like. The "transcription regulatory sequences" may be isolated and incorporated into a vector to enable regulated transcription in appropriate cells of portions of the vector DNA. The "transcription regulatory sequence" may precede, but is not limited to, the region of a nucleic acid sequence that is in the region 5' of the end of a protein coding sequence that is transcribed into mRNA. Transcriptional regulatory sequences may also be located within a protein coding region, for example, in regions of a gene that are identified as "intron" regions.

The terms "transformation" and "transfection" as used herein refer to the process of inserting a nucleic acid into a host. Many techniques are well known to those skilled in the art to facilitate transformation or transfection of a nucleic acid into a prokaryotic or eukaryotic organism. These methods involve a variety of techniques, such as treating the cells with certain concentrations of salt, for example, but without limitation, a calcium or magnesium salt, or exposing the cells to an electric field, detergent, or liposome material, to render the host cell competent for the uptake of the nucleic acid molecules.

As used herein, a "transgenic animal" is any non-human animal, such as an avian species, including the chicken, in which one or more of the cells of the animal contain heterologous nucleic acid introduced by way of human intervention, such as by transgenic techniques known in the art (see, for example, US patent publication No. 2007/0243165, published Oct. 18, 2007, the disclosure of which is incorporated in its entirety herein by reference) including those disclosed herein. The nucleic acid is introduced into an animal, directly or indirectly by introduction into a cell (e.g., egg or embryo cell) by way of deliberate genetic manipulation, such as by microinjection or by infection with a recombinant virus. The term genetic manipulation does not include classical crossbreeding, or in vitro fertilization, but rather is directed to the introduction of a recombinant DNA molecule. This molecule may be integrated within a chromosome, or it may be extrachromosomally replicating DNA. In the typical transgenic animal, the transgene can cause cells to express a recombinant form of the target protein or polypeptide. The terms "chimeric animal" or "mosaic animal" are used herein to refer to animals in which a transgene is found, or in which the recombinant nucleotide sequence is expressed, in some but not all cells of the animal. A germ-line chimeric animal contains a transgene in its germ cells and can give rise to an offspring transgenic animal in which most or all cells of the offspring will contain the transgene.

As used herein, the term "transgene" means a nucleic acid sequence (encoding, for example, a human protein) that is partly or entirely heterologous, i.e., foreign, to the animal or cell into which it is introduced, or, is partly or entirely homologous to an endogenous gene of the transgenic animal or cell into which it is introduced, but which is designed to be inserted, or is inserted, into the animal or cell genome in such a way as to alter the genome of the organism into which it is inserted (e.g., it is inserted at a location which differs from that of the natural gene or its insertion results in a knockout).

Techniques useful for isolating and characterizing the nucleic acids and proteins of the present invention are well known to those of skill in the art and standard molecular biology and biochemical manuals may be consulted to select suitable protocols for use without undue experimentation. See, for example, Sambrook et al, 1989, "Molecular Cloning: A Laboratory Manual", 2nd ed., Cold Spring Harbor, the content of which is herein incorporated by reference in its entirety.

Exogenous therapeutic proteins expressed and secreted in the oviduct and endogenous egg white proteins both have N-glycan structures that lack Gal and sialic acid. It has been discovered that this is a result of the glycosylation enzymatic pathway which is responsible for sugar modification of egg white proteins.

To date multiple proteins that are deposited in the egg white of transgenic hens have been produced including erythropoietin, interferon alpha and G-CSF. Avian derived G-CSF and avian derived interferon alpha are both proteins with only O-glycans and no N-glycans. Some O-glycan structures of these two proteins are similar to human O-glycans, with a high proportion of the structures synthesized to completion (Rapp, et al. *Transgenic Res* 12: 569-75, 2003). In addition, these proteins have been shown to have high stability as well as high efficacy and low immunological response in patients, all of which are expected of proteins having proper O-linked glycosylation (Patel, et al. *Int J Clin Pharmacol Ther* 45: 161-8, 2007).

Figure 8A:
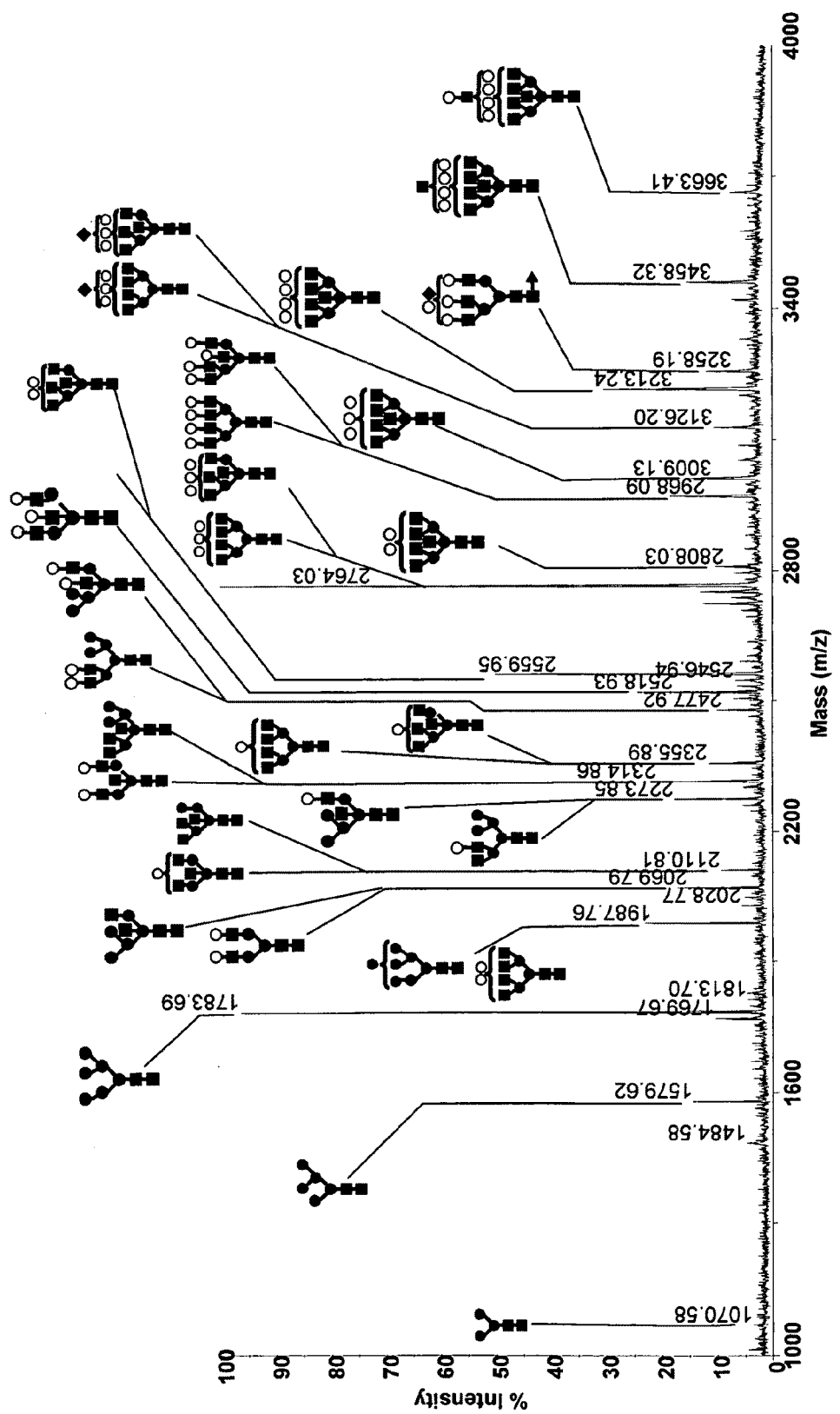
FIG. 8A shows a MALDI-MS analysis of oligosaccharide structures of egg white proteins produced in a transgene-augmented glycosylation chicken having the GalT1 transgene incorporated into its genome using the vector shown in FIG. 6A (FIG. 9). Thirteen separate analyses were performed and the figure shows exemplary results of one of the runs.

Glycosylation of proteins expressed in the hen oviduct that are modified with N-glycans such as human erythropoietin have been analyzed. See, for example, U.S. patent application Ser. No. 11/973,853, filed Oct. 10, 2007, the disclosure of which is incorporated in its entirety herein by reference. The basic N-linked structure has some similarities to that of human; however, there are also some differences. For example, in most cases of human N-glycans, a fucose is linked to the N-acetylglucosamine (GlcNac) residue that is linked to asparagine. In egg white proteins and recombinant proteins produced in the oviduct, this fucose is typically not present in large quantities. Human N-glycans are typically terminated in sialic acid at all or most terminal positions, being linked to galactose (Gal) which is linked to GlcNac. In the case of chicken egg white proteins and exogenous proteins produced in the oviduct, i.e., magnum (e.g., tubular gland cells), there is little or no sialic acid present in the N-glycans. In addition, there are typically few Gal residues at the terminal sugar in the N-glycan structures that have been characterized in transgenic avian derived exogenous protein (FIG. 8A). Thus, most of the terminal positions in N-glycans of egg white protein and exogenous protein produced and secreted by the chicken oviduct are occupied by GlcNac.

The inventor has also observed a bisecting GlcNac at the β1,4-linked mannose, a structure which is found in humans in certain tissues or cell types. Bisecting GlcNac is believed to increase the ADCC activity of antibodies. In one embodiment, transgenic avians of the invention have a transgene with a coding sequence for an acetylglucosaminyltransferase, such as N-acetylglucosaminyltransferase 3, linked to an oviduct specific promoter thereby imparting additional bisecting GlcNacs to N-linked oligosaccharide structures of protein produced in the oviduct (e.g., exogenous proteins such as antibodies).

The N-glycans that reside on exogenous and endogenous (e.g., ovalbumin, ovomucoid) proteins produced and secreted in the oviduct have a basic structure essentially that shown in FIG. 1A see (Yamashita, et al. *J Biol Chem* 257: 12809-14, 1982; Harvey, et al. *J Am Soc Mass Spectrom* 11: 564-71, 2000; Lattova, et al. *J Am Soc Mass Spectrom* 15: 725-35, 2004) and U.S. patent application Ser. No. 11/973,853, filed Oct. 10, 2007.

In one embodiment, the present invention is directed to correcting the glycosylation deficiency by introduction into the avian genome transgenes that will express glycosyltransferases whose expression is deficient in the magnum, e.g., TGCs (tubular gland cells). Endogenous egg white proteins having N-glycans, such as ovalbumin and ovomucoid, can be harvested from eggs of transgenic hens and assessed for the presence of terminal sialic acid and/or terminal Gal and/or penultimate Gal resulting in transgene-augmented glycosylation flocks.

The transgene-augmented glycosylation flocks will have multiple uses. For example, a flock can be crossed to an existing flock that produces a therapeutic protein the effectiveness of which can be enhanced by an increase in the number of sialylated N-glycan structures. In another use, the transgenic flock can be used to produce entirely new production flocks having transgenes containing coding sequences for exogenous proteins which are expressed in the oviduct, e.g., magnum tissue. That is, an exogenous (e.g., therapeutic) protein transgene is introduced into a transgene-augmented glycosylation flock.

Chicken beta 1,4 GalT types 1 and 2 were previously identified by screening of a chicken hepatoma cDNA library (Shaper, N. L., J. A. Meurer, et al. (1997) *J Biol Chem* 272 (50): 31389-99). Through analysis of the published chicken genome sequence the inventor has identified five additional GalTs (e.g., beta 1,4 GalT types 3 through seven) in the chicken genome that correspond to five members of the beta 1,4 GalT family which have been characterized in other species, including human, mouse, and hamster.

Figure 2:
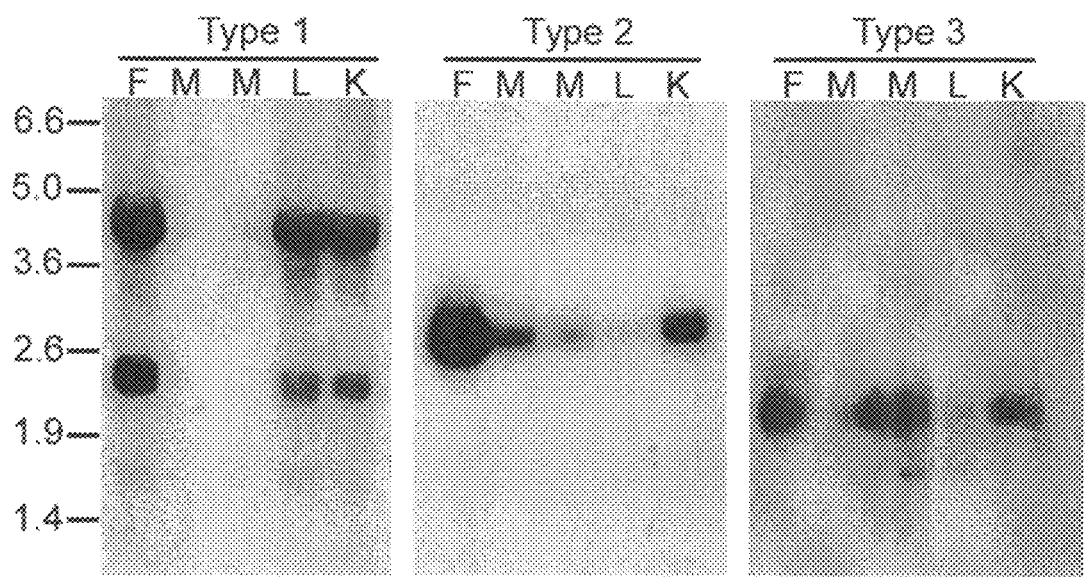
FIG. 2 shows an expression analysis of chicken galactosyltransferases. mRNA was isolated from cultured fibroblasts (F), magnum (M), liver (L) and kidney (K) tissues of a laying hen and analyzed by the Northern blot method. Blots were probed with sequences complementary to the chicken $\beta 1,4$ galactosyltransferases type 1, 2 and 3. The approximate positions of RNA molecular weight markers are shown to the left. The expected size for the type 1 mRNA is 2.2 kb. The about 4.3 kb band in the type 1 blot may represent a partially processed RNA. The data indicates an absence of type 1 production in the magnum.

The expression of the seven chicken GalTs in several tissues, including magnum tissue, has been analyzed by Northern analysis. The expression of GalT1 was found to be almost undetectable in the magnum while it was expressed at detectable levels in cultured chicken fibroblasts as well as liver and kidney tissues, as shown in FIG. 2. Expression of type 6 was also not detectable in magnum tissues. Types 2 through 5 and 7 were all found to be expressed in the magnum tissues.

The lack of expression of GalT1 is a surprising result as GalT1 is thought to be ubiquitously expressed in a variety of tissues (Hennet. *Cell Mol Life Sci* 59: 1081-95, 2002). In other studies GalT1 was shown to be expressed in a number of chicken tissues, though magnum tissue expression was not assessed in those studies (Shaper, Meurer, Joziasse, Chou, Smith, Schnaar and Shaper. *J Biol Chem* 272: 31389-99, 1997).

The inventor has found that the lack of GalT1 expression in the magnum is responsible for a lack of N-linked Gal. GalT6 expression is also absent in the hen magnum. However, GalT6 is believed to be primarily responsible for the addition of Gal to glucose-ceramide, a step in the synthesis of the glycolipid lactosylceramide (Guo, et al. *Glycobiology* 11: 813-20, 2001) but not typically involved in addition of Gal to other proteins produced in the hen.

Therefore, in view of these discoveries, it is an object of the invention to produce transgenic birds which contain a transgene having a coding sequence for GalT1 operably linked to a promoter which can function in the oviduct resulting in the addition of Gal to N-linked oligosaccharides of protein produced in oviduct tissue as disclosed in the Examples. In addition, as expected these GalT1 birds also result in the addition of some sialic acid to N-linked oligosaccharides of the protein.

The expression of GalT1 provides for the addition of Gal to N-linked oligosaccharides produced in the magnum which can serve as a point of attachment for sialic acid. As can be seen in FIG. 8, additional sialic acid is added to the N-linked oligosaccharide structure of proteins produced in the magnum of GalT1 birds compared to normal birds.

It is also contemplated in accordance with the present invention, that deficiencies in expression of members of SialT family can be compensated for to provide for transgene-augmented glycosylation birds which allow for more sialation of N-linked oligosaccharides than in GalT1 birds.

Figure 3:
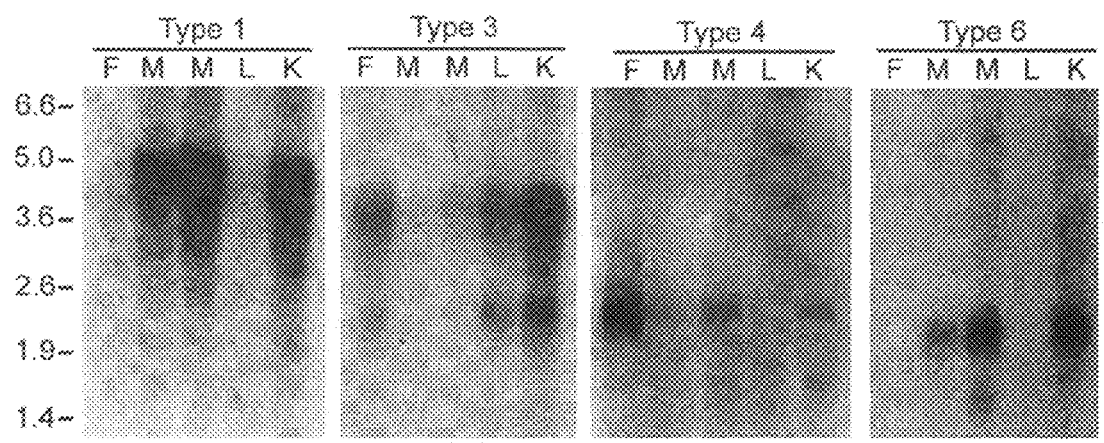
FIG. 3 shows the expression analysis of chicken sialyltransferases 1, 3, 4 and 6. mRNA was isolated from cultured fibroblasts (F), magnum (M), liver (L) and kidney (K) tissues of a laying hen and analyzed by the Northern blot method. Blots were probed with sequences complementary to the chicken 1, 3, 4 and 6 sialyltransferases. The approximate positions of RNA molecular weight markers are shown to the left. The data indicates low expression of type 3 and possibly low expression of type 4 in the magnum.
Figure 4:
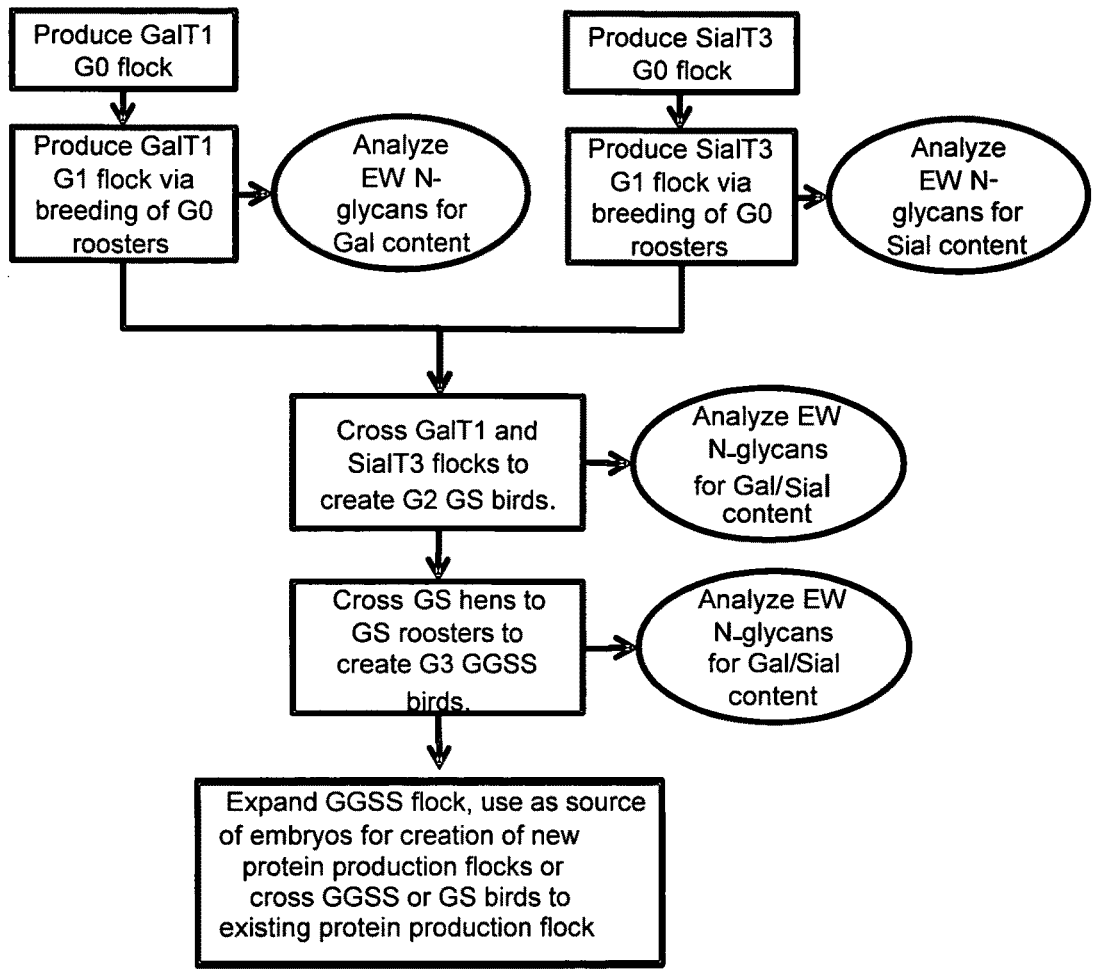
FIG. 4 shows a flow diagram of an exemplary two vector strategy. The GalT1 flock can be produced with the pALV-SIN-1.8-OM-GalT1 transgene shown in FIG. 6A. The SialT3 flock can be produced with the pALV-SIN-1.8-OM-SialT3 transgene shown in FIG. 6B. EW means egg white. Sial means sialic acid. Gal means galactose. GS birds are birds that contain transgenes for both GalT1 and SialT3. Gal/Sial means Gal and sialic acid. GGSS birds are birds homozygous for both GalT1 and SialT3 transgenes. A "protein production flock" is a flock that produces a protein with attached oligosaccharide structure(s) such as a therapeutic protein the effectiveness of which can be enhanced by the addition of Gal and/or sialic acid to the oligosaccharide structure(s).
Figure 5:
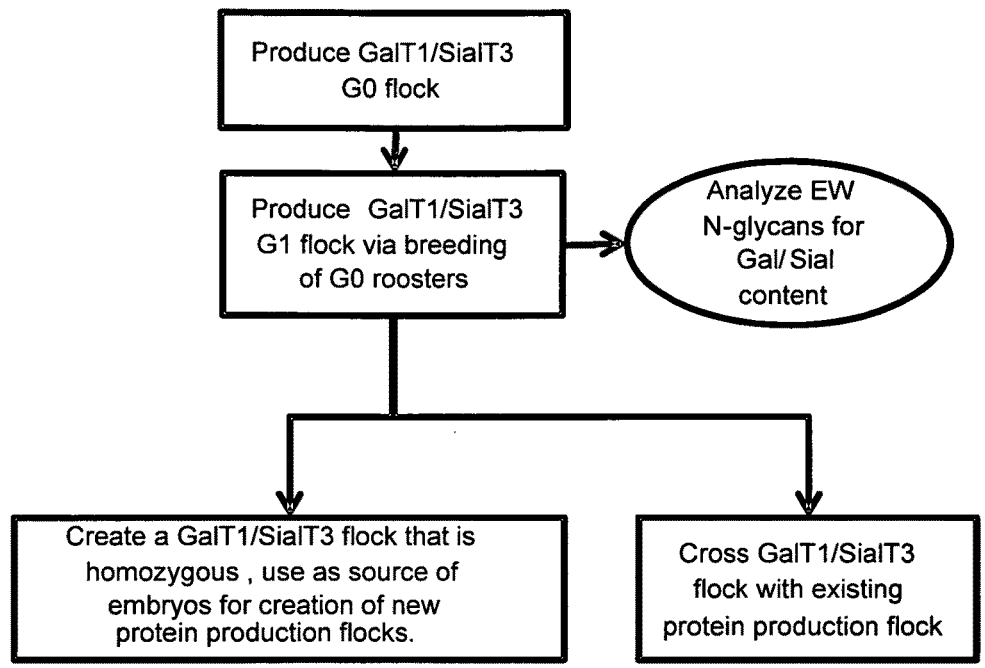
FIG. 5 shows a flow diagram of an exemplary one vector strategy. The flock is produced with the pALV-SIN-1.8-OM-GalT1-IRES-SialT3 vector shown in FIG. 6C. EW means egg white.

The inventor has analyzed the recently sequenced chicken genome finding that all six members of the α2,3 SialT family are present. Analysis of the expression of SialTs by the Northern blot method has also been performed. The expression of SialT1 in the magnum (FIG. 3) was very strong whereas the expression SialT2 was low, implicating SialT1 as having a major role in egg white O-glycan synthesis since the Galβ1, 3GalNAc chains in O-glycans found in egg white proteins are mostly sialylated (whereas the few Galβ1,4GlcNAc chains present on N-glycans have little or no attached sialic acid). The expression of SialT3 in the magnum is detectable but is quite low relative to that of chicken fibroblast, kidney and liver (FIG. 3). The fact that SialT3 synthesis is fairly abundant in the kidney and liver and the N-glycans that arise from these organs are sialylated to a high degree (Ito, Takegawa, Deguchi, Nagai, Nakagawa, Shinohara and Nishimura. *Rapid Commun Mass Spectrom* 20: 3557-65, 2006; Deguchi, et al. *Rapid Commun Mass Spectrom* 20: 741-6, 2006; Sasaki, et al. *J Biol Chem* 262: 12059-76, 1987) indicates SialT3 may have a significant role in the sialylation of N-glycans in the chicken. A faint signal was detected for SialT4 in chicken fibroblasts and an even fainter signal in magnum and kidney. The low expression of SialT4 in the tissues examined suggests that SialT4 may have a lessor role in the sialylation of chicken N-glycans. The expression of SialT6 in the magnum and kidney is relatively high and undetectable in chicken fibroblasts and liver.

Therefore, in accordance with the invention, transgenic avians are contemplated that express one or more recombinant or exogenous SialT coding sequence(s) in the oviduct tissue, e.g., magnum tissue. In one embodiment, a transgenic avian, e.g., transgenic chicken, is contemplated that expresses in the magnum tissue (e.g., in tubular gland cells) an exogenous SialT coding sequence, i.e., a recombinant avian, e.g., chicken, nucleotide sequence that encodes a SialT. In one embodiment, a transgenic avian is contemplated that expresses an exogenous SialT1 coding sequence. In one embodiment, a transgenic avian is contemplated that expresses an exogenous SialT2 coding sequence. In one embodiment, a transgenic avian is contemplated that expresses an exogenous SialT3 coding sequence. In one embodiment, a transgenic avian is contemplated that expresses an exogenous SialT4 coding sequence. In one embodiment, a transgenic avian is contemplated that expresses an exogenous SialT5 coding sequence. In one embodiment, a transgenic avian is contemplated that expresses an exogenous SialT6 coding sequence.

In one particularly useful embodiment, a transgenic avian such as a chicken is produced that expresses a SialT3 coding sequence in its magnum tissue (e.g., in its tubular gland cells).

In one embodiment, a transgene-augmented glycosylation avian is produced in accordance with the invention that contains one or more transgenes that provides for expression of one or more GalTs in the oviduct and one or more transgenes that provide for expression of one or more SialTs in the oviduct. In a particularly useful but non-limiting example, a transgenic avian is produced in accordance with the invention that contains a transgene that provides for expression of GalT1 in the oviduct and a transgene that provides for expression of SialT3 in the oviduct. In another non-limiting example, a transgenic avian is produced in accordance with the invention that contains a transgene that provides for expression of GalT1 in the oviduct and a transgene that provides for expression of SialT3 in the oviduct and a transgene that provides for expression of SialT4 in the oviduct. In another non-limiting example, a transgenic avian is produced in accordance with the invention that contains a transgene that provides for expression of GalT1 in the oviduct and a transgene that provides for expression of GalT6 in the oviduct and a transgene that provides for expression of SialT3 in the oviduct and a transgene that provides for expression of SialT4 in the oviduct.

Many methods which are useful to express more than one (for example, two, three or four or more) exogenous nucleotide sequence in an avian genome are apparent to practitioners of ordinary skill in the art. For example, one such method which employs a single transcript containing an internal ribosome entry site (IRES) is described in Example 6. In another example, a fully transgenic bird (i.e., a G1 transgenic or a descendent of a G1 transgenic) containing a first desired transgene can have a second transgene introduced into its genome using standard methods. That is, the transgene can be introduced into the fully transgenic bird in essentially the same manner as the first transgene. In another example, the fully transgenic bird can be crossed to a second fully transgenic bird containing a desired transgene, as is understood in the art. These processes can be repeated to introduce the desired number of transgenes into the genome.

Any useful IRES is contemplated for use in accordance with the invention including those IRESs disclosed herein as well as any other useful IRESs (e.g., Foot an Mouth disease virus IRES, see for example, Belsham and Brangwyn (1990) J of Virology, vol 64, p 5389-5395).

Any useful method can be used to introduce transgenes of the invention into an avian genome including, for example, those methods disclosed in US patent publication No. 2007/0180546, published Aug. 2, 2007; US patent publication No. 2007/0077650, published Apr. 5, 2007 and US patent publication No. 2008/0064862, published Mar. 13, 2008, the disclosures of each of these three patent applications are incorporated in their entireties herein by reference. One consideration is that the proteins produced in accordance with the methods disclosed in these cited documents were produced with a signal sequence so that the protein is secreted into the egg white whereas the glycosyltransferase produced in accordance with the present invention will not be secreted from the cell and therefore will typically not include a signal sequence.

Any gene expression controlling region (e.g., promoter) which can be made useful in accordance with the invention is contemplated for use in accordance with the invention. For example, constitutive promoters such as CMV and beta-actin which have been shown to function in the avian oviduct can be used. See, for example, US patent publication No. 2006/0015960, published Jan. 19, 2006 and 2006/0143725, published Jun. 29, 2006. The disclosure of each of these two patent applications is incorporated in its entirety herein by reference. In one particularly useful embodiment, the promoter is a promoter that primarily or exclusively is expressed in the oviduct such as ovomucoid promoters, ovalbumin promoters, and lysozyme promoters, conalbumin promoters, ovomucin promoters, ovotransferrin promoters. See, for example, US patent publication No. 2005/0176047, published, Aug. 11, 2005; U.S. Pat. No. 7,176,300, issued Feb. 13, 2007; US patent publication No. 2007/0124829, published May 31, 2007; and US patent publication No. 2006/0130170, published Jun. 15, 2006. The disclosure of each of these three patent applications and one issued patent is incorporated in its entirety herein by reference. Such promoters can be useful to avoid over expression of the glycosyltransferases in tissue aside from oviduct tissue of the avian, which could be problematic for the health or survival of the transgenic birds. Other promoters useful in accordance with the invention include, for example and without limitation, MDOT promoters and rous-sarcoma virus (RSV) promoters, murine leukemia virus (MLV) promoters, mouse mammary tumor virus (MMTV) promoters and SV40 promoters and functional portions of each of these promoters. Other promoters which may be useful in the present invention include, without limitation, Pol III promoters (for example, type 1, type 2 and type 3 Pol III promoters) such as H1 promoters, U6 promoters, tRNA promoters, RNase MPR promoters and functional portions of each of these promoters. Typically, functional terminator sequences are selected for use in the present invention in accordance with the promoter that is employed, as is understood in the art.

In one useful embodiment, a 1.8 kb ovomucoid promoter is employed which is disclosed essentially in US patent publication No. 2007/0113299, published May 17, 2007, the disclosure of which is incorporated in its entirety herein by reference. The 1.8 kb OM promoter has provided useful expression of GalT coding sequence in magnum cells as seen in Example 3. Other glycosylation enzymes are contemplated for production in the oviduct under the control of the 1.8 kb ovomucoid promoter.

Proteins which are contemplated for production in transgene-augmented glycosylation birds of the invention specifically include therapeutic proteins, including, but not limited to human proteins, which contain one or more N-linked oligosaccharide structures. Such proteins include, but are not limited to, the following proteins including where applicable their human protein equivalent: fusion proteins, growth hormones, cytokines, structural proteins and enzymes including human growth hormone, interferon, lysozyme, and β-casein, albumin, α-1 antitrypsin, antithrombin III, collagen, factors VIII, IX, X (and the like), fibrinogen, insulin, lactoferrin, protein C, erythropoietin (EPO), granulocyte colony-stimulating factor (G-CSF), granulocyte macrophage colony-stimulating factor (GM-CSF), tissue-type plasminogen activator (tPA), somatotropin, and chymotrypsin, glucocerebrosidase, lysosomal acid lipase, β-galactosidase and neuraminidase; galactosylceramidase (GALC); agalsidase alpha (Replagal), agalsidase beta (Fabrazyme) or alpha galactosidase A; alpha-glucosidase; acid sphingomyelinase (rhASM); galactosylceramidase (GALC); modified immunoglobulins and antibodies, including immunotoxins which may bind to surface antigens on human tumor cells, b-domain deleted factor VIII, factor VIIa, anticoagulants; hirudin, alteplase, tpa, reteplase, tpa, tpa—3 of 5 domains deleted, insulin, insulin lispro, insulin aspart, insulin glargine, long-acting insulin analogs, hgh, glucagons, tsh, follitropin-beta, fsh, gm-csf, pdgh, ifn alpha2, ifn alpha2a, ifn alpha2b, inf-apha, inf-beta 1b, ifn-beta 1a, ifn-gamma1b, il-2, il-11, hbsag, ospa, mab directed against t-lymphocyte antigen, mab directed against tag-72, tumor-associated glycoprotein, fab fragments derived from chimeric mab directed against platelet surface receptor gpII(b)/III(a), mab or mab fragment directed against tumor-associated antigen ca125, mab or mab fragment directed against human carcinoembryonic antigen, cea, mab or mab fragment directed against human cardiac myosin, mab or mab fragment directed against tumor surface antigen psma, mab fragments (fab/fab2 mix) directed against hmw-maa, mab or mab fragment (fab) directed against carcinoma-associated antigen, mab fragments (fab) directed against nca 90, a surface granulocyte nonspecific cross reacting antigen, chimeric mab directed against cd20 antigen found on surface of b lymphocytes, humanized mab directed against the alpha chain of the il2 receptor, chimeric mab directed against the alpha chain of the il2 receptor, chimeric mab directed against tnf-alpha, humanized mab directed against an epitope on the surface of respiratory synctial virus, humanized mab directed against her 2, human epidermal growth factor receptor 2, human mab directed against cytokeratin tumor-associated antigen anti-ctla4, chimeric mab directed against cd 20 surface antigen of b lymphocytes domase-alpha dnase, beta glucocerebrosidase, tnf-alpha, il-2-diptheria toxin fusion protein, tnfr-lgg fragment fusion protein laronidase, dnaases, mabs, alefacept, tositumomab, alemtuzumab, rasburicase, agalsidase beta, teriparatide, parathyroid hormone derivatives, adalimumab (lgg1), anakinra, biological modifier, nesiritide, human b-type natriuretic peptide (hbnp), colony stimulating factors, pegvisomant, human growth hormone receptor antagonist, recombinant activated protein c, omalizumab, immunoglobulin e (lge) blocker, lbritumomab tiuxetan, ACTH, glucagon, somatostatin, somatotropin, thymosin, parathyroid hormone, pigmentary hormones, somatomedin, erythropoietin, luteinizing hormone, chorionic gonadotropin, hypothalmic releasing factors, etanercept, antidiuretic hormones, prolactin, thyroid stimulating hormone, multimeric proteins including immunoglobulins, such as antibodies, and antigen binding fragments thereof, an immunoglobulin heavy chain polypeptide comprising a variable region or a variant thereof, which may comprise a D region, a J region, a C region, or a combination thereof; an immunoglobulin light chain polypeptide comprising a variable region or a variant thereof which may comprise a J region and a C region; an immunoglobulin polypeptide encoded by at least one expression vector comprises an immunoglobulin heavy chain variable region, an immunoglobulin light chain variable region, and a linker peptide thereby forming a single-chain antibody capable of selectively binding an antigen; HERCEPTIN™ (Trastuzumab) (Genentech, Calif.) which is a humanized anti-HER2 monoclonal antibody for the treatment of patients with metastatic breast cancer; REOPRO™ (abciximab) (Centocor) which is an anti-glycoprotein IIb/IIIa receptor on the platelets for the prevention of clot formation; ZENAPAX™ (daclizumab) (Roche Pharmaceuticals, Switzerland) which is an immunosuppressive, humanized anti-CD25 monoclonal antibody for the prevention of acute renal allograft rejection; PANOREX™ which is a anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-αVβ3 integrin antibody (Applied Molecular Evolution/MedImmune); Campath; Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); ICM3 is a humanized anti-ICAM3 antibody (ICOS Pharm); IDEC-114 is a primate anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); D2E7 is a humanized anti-TNF-α antibody (CATIBASF); CDP870 is a humanized anti-TNF-α Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CDP571 is a humanized anti-TNF-α IgG4 antibody (Celltech); LDP-02 is a humanized anti-α4β7 antibody (LeukoSite/Genentech); Ortho-Clone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); CAT-152, a human anti-TGF-β$_2$ antibody (Cambridge Ab Tech); Cetuximab (BMS) is a monoclonal anti-EGF receptor (EGFr) antibody; Bevacizuma (Genentech) is an anti-VEGF human monoclonal antibody; Infliximab (Centocore, JJ) is a chimeric (mouse and human) monoclonal antibody used to treat autoimmune disorders; Gemtuzumab ozogamicin (Wyeth) is a monoclonal antibody used for chemotherapy; Ranibizumab (Genentech) is a chimeric (mouse and human) monoclonal antibody used to treat macular degeneration, GM-CSF, interferon β, fusion protein, CTLA4-Fc fusion protein, growth hormones, cytokines, structural, interferon, lysozyme, β-casein, albumin, α-1 antitrypsin, antithrombin III, collagen, factors VIII, IX, X (and the like), fibrinogen, lactoferrin, protein C, tissue-type plasminogen activator (tPA), somatotropin, and chymotrypsin, immunoglobulins, antibodies, immunotoxins, factor VIII, b-domain deleted factor VIII, factor VIIa, factor IX, anticoagulants; hirudin, alteplase, tpa, reteplase, tpa, tpa—3 of 5 domains deleted, insulin, insulin lispro, insulin aspart, insulin glargine, long-acting insulin analogs, glucagons, tsh, follitropin-beta, fsh, pdgh, inf-beta, ifn-beta 1, ifn-beta 2, ifn-alpha, ifn-alpha 1, ifn-alpha 2, ifn-gamma, il-2, il-11, hbsag, ospa, domase-alpha dnase, beta glucocerebrosidase, tnf-alpha, il-2-diptheria toxin fusion protein, tnfr-lgg fragment fusion protein laronidase, dnaases, alefacept, tositumomab, murine mab, alemtuzumab, rasburicase, agalsidase beta, teriparatide, parathyroid hormone derivatives, adalimumab (lgg1), anakinra, biological modifier, nesiritide, human b-type natriuretic peptide (hbnp), colony stimulating factors, pegvisomant, human growth hormone receptor antagonist, recombinant activated protein c, omalizumab, immunoglobulin e (lge) blocker, lbritumomab tiuxetan, ACTH, glucagon, somatostatin, somatotropin, thymosin, parathyroid hormone, pigmentary hormones, somatomedin, luteinizing hormone, chorionic gonadotropin, hypothalmic releasing factors, etanercept, antidiuretic hormones, prolactin and thyroid stimulating hormone, an immunoglobulin polypeptide, immunoglobulin polypeptide D region, immunoglobulin polypeptide J region, immunoglobulin polypeptide C region, immunoglobulin light chain, immunoglobulin heavy chain, an immunoglobulin heavy chain variable region, an immunoglobulin light chain variable region and a linker peptide.

Proteins such as those disclosed herein not normally N-glycosylated can be engineered to contain a glycosylation site (i.e., an N-linked glycosyation site) which is glycosylated in the avian system, as is understood by a practitioner of skill in the art. In addition, proteins such as those disclosed herein can be engineered to contain one or more additional N-linked glycosylation sites. In one embodiment, the protein with an added glycosylation site has attached one or more N-linked oligosaccharide structures with terminal modifications produced as disclosed herein.

It is specifically contemplated that proteins produced as disclosed herein can be isolated or purified using methodologies well known to practitioners of ordinary skill in the art.

In one embodiment, eggs laid by avians produced in accordance with the invention contain an exogenous or heterologous protein (such as a therapeutic protein) having an altered glycosylation pattern produced in the oviduct as disclosed herein in an amount greater than about 0.01 μg per hard-shell egg. For example, the eggs may contain the heterologous protein in an amount in a range of between about 0.01 μg per hard-shell egg and about 2 grams per hard-shell egg. In one embodiment, the eggs contain between about 0.1 μg per hard-shell egg and about 1 gram per hard-shell egg. For example, the eggs may contain between about 1 μg per hard-shell egg and about 1 gram per hard-shell egg. In one embodiment, the eggs contain between about 10 μg per hard-shell egg and about 1 gram per hard-shell egg. For example, the eggs may contain between about 100 μg per hard-shell egg and about 1 gram per hard-shell egg (e.g., the eggs may contain between about 100 μg per hard-shell egg and about 100 mg per hard-shell egg).

Typically, the heterologous protein (e.g., therapeutic protein) having an altered glycosylation pattern as disclosed herein is present in the egg white of the eggs. In one embodiment, the heterologous protein is present in egg white in an amount greater than about 0.01 μg per ml of the egg. In another embodiment, the heterologous protein is present in egg white in an amount in a range of between about 0.01 μg per ml of the egg white and about 0.2 gram per ml of the egg white. For example, the heterologous protein may be present in egg white in an amount in a range of between about 0.1 μg per ml of the egg white and about 0.5 gram per ml of the egg white. In one embodiment, the heterologous protein is present in egg white in an amount in a range of between about 1 μg per ml of the egg white and about 0.2 gram per ml of the egg white. For example, the heterologous protein may be present in egg white in an amount in a range of between about 10 μg per ml of the egg white and about 0.1 gram per ml of the egg white (e.g., the heterologous protein may be present in egg white in an amount in a range of between about 10 μg per ml of the egg white and about 5 mg per ml of the egg white).

The invention also contemplates that pegylating proteins produced as disclosed herein may be advantageous as discussed, for example, in U.S. patent application Ser. No. 11/584,832, filed Oct. 23, 2006, the disclosure of which is incorporated it its entirety herein by reference.

While it is possible that therapeutic proteins produced in accordance with this invention may be administered in raw form, it is preferable to administer the therapeutic proteins as part of a pharmaceutical formulation.

The invention thus further provides pharmaceutical formulations comprising therapeutic proteins produced in accordance with the invention or a pharmaceutically acceptable derivative thereof together with one or more pharmaceutically acceptable carriers thereof and, optionally, other therapeutic and/or prophylactic ingredients and methods of administering such pharmaceutical formulations. The carrier(s) must be "acceptable" in the sense of being compatible with the other ingredients of the formulation and not deleterious to the recipient thereof. Methods of treating a patient (e.g., quantity of pharmaceutical protein administered, frequency of administration and duration of treatment period) using pharmaceutical compositions of the invention can be determined using standard methodologies known to physicians of skill in the art.

Pharmaceutical formulations include those suitable for oral, rectal, nasal, topical (including buccal and sub-lingual), vaginal administration. The pharmaceutical formulations include those suitable for administration by injection including intramuscular, sub-cutaneous and intravenous administration. The pharmaceutical formulations also include those for administration by inhalation or insufflation. The formulations may, where appropriate, be conveniently presented in discrete dosage units and may be prepared by any of the methods well known in the art of pharmacy. The methods of producing the pharmaceutical formulations typically include the step of bringing the therapeutic proteins into association with liquid carriers or finely divided solid carriers or both and then, if necessary, shaping the product into the desired formulation.

Pharmaceutical formulations suitable for oral administration may conveniently be presented as discrete units such as capsules, cachets or tablets each containing a predetermined amount of the active ingredient; as a powder or granules; as a solution; as a suspension; or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles, which may include edible oils, or preservatives.

Therapeutic proteins of the invention formulated for parenteral administration (e.g., by injection, for example bolus injection or continuous infusion) may be presented in unit dose form in ampoules, pre-filled syringes, small volume infusion or in multi-dose containers with an added preservative. The therapeutic proteins may be injected by, for example, subcutaneous injections, intramuscular injections, and intravenous infusions or injections.

The therapeutic proteins may take such forms as suspensions, solutions, or emulsions in oily or aqueous vehicles, and may contain formulatory agents such as suspending, stabilizing and/or dispersing agents. It is also contemplated that the therapeutic proteins may be in powder form, obtained by aseptic isolation of sterile solid or by lyophilization from solution, for constitution with a suitable vehicle, e.g., sterile, pyrogen-free water, before use.

For topical administration to the epidermis, the therapeutic proteins produced according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents or coloring agents.

Formulations suitable for topical administration in the mouth include lozenges comprising active ingredient in a flavored base, such as sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical formulations suitable for rectal administration wherein the carrier is a solid are most preferably represented as unit dose suppositories. Suitable carriers include cocoa butter and other materials commonly used in the art, and the suppositories may be conveniently formed by a mixture of the active compound with the softened or melted carrier(s) followed by chilling and shaping in molds.

Formulations suitable for vaginal administration may be presented as pessaries, tampons, creams, gels, pastes, foams or sprays containing in addition to the active ingredient, such carriers as are known in the art to be appropriate.

For intra-nasal administration the therapeutic proteins of the invention may be used as a liquid spray or dispersible powder or in the form of drops.

Drops may be formulated with an aqueous or non-aqueous base also comprising one or more dispersing agents, solubilizing agents or suspending agents. Liquid sprays are conveniently delivered from pressurized packs.

For administration by inhalation, therapeutic proteins according to the invention may be conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

For administration by inhalation or insufflation, the therapeutic proteins according to the invention may take the form of a dry powder composition, for example a powder mix of the compound and a suitable powder base such as lactose or starch. The powder composition may be presented in unit dosage form in, for example, capsules or cartridges or, e.g., gelatin or blister packs from which the powder may be administered with the aid of an inhalator or insufflator.

When desired, the above described formulations adapted to give sustained release of the active ingredient, may be employed.

The pharmaceutical compositions according to the invention may also contain other active ingredients such as antimicrobial agents, or preservatives. In addition, it is contemplated that the therapeutic proteins of the invention may be used in combination with other therapeutic agents.

Compositions or compounds of the invention can be used to treat a variety of conditions. For example, there are many conditions for which treatment therapies are known to practitioners of skill in the art in which therapeutic proteins obtained from cell culture (e.g., CHO cells) are employed. The present invention contemplates that the therapeutic proteins produced in accordance with the invention can be employed to treat such conditions. That is, the invention contemplates the treatment of conditions known to be treatable by conventionally produced therapeutic proteins by using therapeutic proteins produced in accordance with the invention. For example, erythropoietin produced in accordance with the invention can be used to treat human conditions such as anemia and kidney disease, e.g., chronic renal failure (or other conditions which may be treatable by administering EPO of the invention).

Generally, the dosage administered will vary depending upon known factors such as age, health and weight of the recipient, type of concurrent treatment, frequency of treatment, and the like. Usually, a dosage of active ingredient can be between about 0.0001 and about 10 milligrams per kilogram of body weight. Precise dosage, frequency of administration and time span of treatment can be determined by a physician skilled in the art of administration of the respective therapeutic protein.

Figure 6:
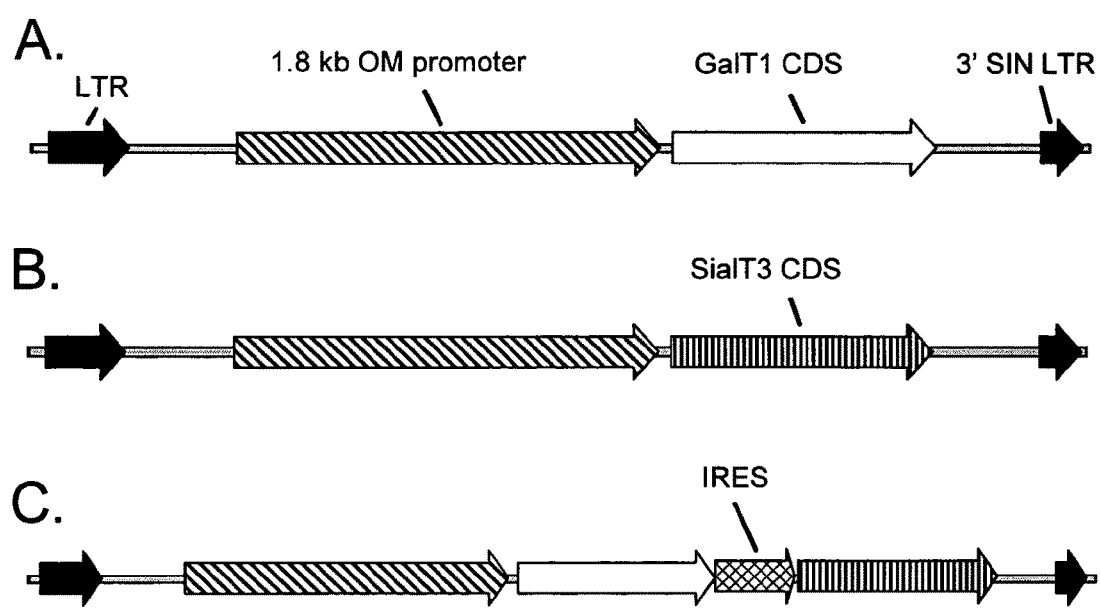
FIGS. 6A, B and C show maps of pALV-SIN-1.8-OM-GalT1, pALV-SIN-1.8-OM-SialT3 and pALV-SIN-1.8-OM-GalT1-IRES-SialT3 vectors respectively. The retroviral transgene portion of each vector is shown. The vector backbones are not shown for simplicity. Upon integration of the vector in the chick embryo cells, the 3' SIN LTR is copied over to the 5' LTR such that the transgene is flanked by inactivated LTRs.
FIG. 6B shows a 1.8 kb ovomucoid promoter operably linked to the chicken alpha-2,3-sialyltransferase type 3.
FIG. 6C shows a 1.8 kb ovomucoid promoter operably linked to the chicken beta-1,4-galactosyltransferase type 1 coding sequence and chicken alpha-2,3-sialyltransferase 3 coding sequence with an IRES between the two coding sequences such as the translational enhancer disclosed in U.S. Pat. No. 4,937,190, issued Jun. 26, 1990, the disclosure of which is incorporated in its entirety herein by reference.
Figure 7:
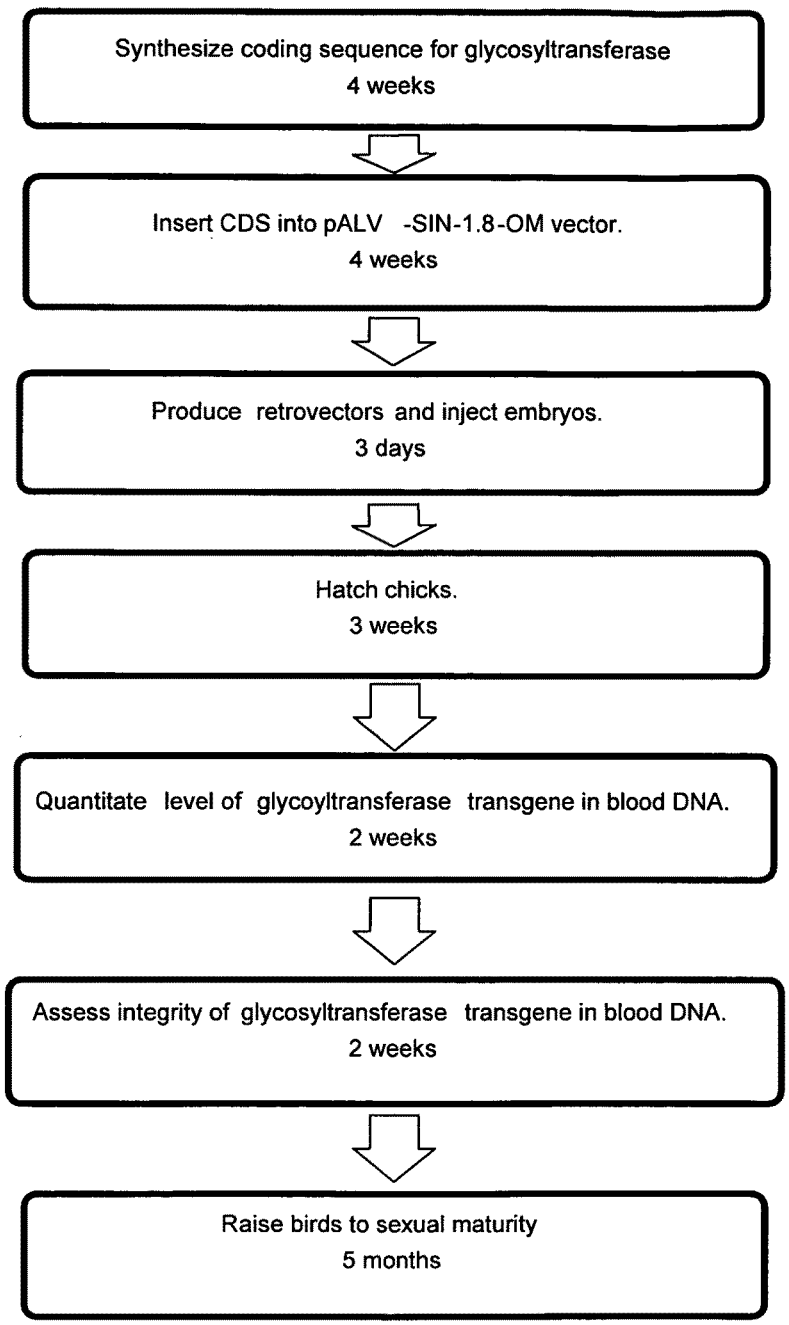
FIG. 7 show a general method and timeline for producing transgene-augmented glycosylation birds.

Nucleotide sequences of vectors shown at least in part in FIG. 6 are disclosed herein, for example, in FIGS. 9 to 11. Also shown are exemplary glycosyltransferase amino acid sequences and nucleotide sequences that encode glycosyltransferases, which are examples of those contemplated for use in accordance with the invention. Amino acid sequences which are 80%, 85%, 90%, 91%, 92%, 93%, 94%, 95%, 96%, 97%, 98% and 99% identical or homologous to each of the amino acid sequences disclosed herein including those disclosed in FIGS. 12 to 28 are also contemplated for use in accordance with the invention. Nucleotide sequences which are 80%, 85%, 90%, 91%, 92%, 93%, 94%, 95%, 96%, 97%, 98% and 99% identical or homologous to each of the nucleotide sequences disclosed herein, including those disclosed in FIGS. 9 to 28 are also contemplated for use in accordance with the invention.

Coding sequences are indicated for the glycosyltransferases disclosed herein and a practitioner of skill in the art can determine amino acid sequences from these specified coding sequences. Accordingly, the invention includes nucleotide sequences which will code for amino acid sequences which function as glycosyltransferases that are 80%, 85%, 90%, 91%, 92%, 93%, 94%, 95%, 96%, 97%, 98% and 99% identical to the amino acid sequence encoded by each of the glycosyltransferase coding sequences disclosed herein.

Also included within the scope of the invention is the use in accordance with the invention of functional fragments of each of the nucleotide and amino acid sequences disclosed herein.

The concepts and methods disclosed herein for adding sugars (e.g., sialic acid, galactose) to N-linked oligosaccharide structures of proteins are also contemplated for use in other animals and other organisms such as plants.

The present invention is further illustrated by the following examples, which are provided by way of illustration and should not be construed as limiting. The contents of all references, published patent applications and patents cited throughout the present application are hereby incorporated by reference in their entireties.

Example 1

Vector Design and Construction for Expression of GalT1 in the Avian Oviduct

The GalT1 coding sequence was synthesized by Integrated DNA Technologies (Coralville, Iowa) with codon usage optimized for expression in the hen magnum and is shown below (SEQ ID NO: 40):

```
ATGAAAGAACCTGCACTTCCTGGTACTTCACTGCAAAGAGCATGTAGACT
GCTGGTAGCATTTTGCGCCCTGCACCTGAGCGCAACCCTGCTCTACTACC
TGGCTGGATCCAGCCTGACTCCACCCCGCTCTCCAGAACCTCCCCCTCGG
AGGCCGCCTCCAGCCAACCTCTCCCTGCCACCCTCCCGGCCTCCTCCTCC
CCCTGCGGCTCGCCCCCGCCCAGGACCTGTTTCTGCACAACCCCGGAACC
TGCCAGATTCTGCACCATCTGGACTGTGCCCCGATCCAAGTCCACTGCTC
GTTGGTCCTCTGCGGGTGGAGTTTAGTCAGCCAGTGAACCTGGAGGAAGT
GGCTTCTACCAATCCGGAGGTCAGGGAAGGAGGGAGATTCGCCCCAAAGG
ACTGCAAAGCGCTCCAGAAGGTGGCTATTATTATCCCCTTCAGGAACAGA
GAGGAGCACCTGAAGTATTGGCTGTACTACATGCACCCGATTCTTCAGAG
ACAGCAATTGGACTATGGGGTCTATGTGATTAATCAAGACGGCGATGAAG
AATTTAACAGAGCTAAACTGCTTAATGTCGGTTTCACTGAGGCACTCAAG
GAATACGATTATGATTGCTTTGTGTTTTCCGATGTGGATCTGATTCCTAT
GGACGACCGTAACACATATAAGTGCTATAGTCAACCACGTCACCTGAGTG
TGTCAATGGACAAGTTTGGCTTTAGGCTGCCGTATAACCAGTATTTCGGA
GGAGTTTCAGCATTGAGTAAAGAACAGTTTACAAAAATCAACGGGTTCCC
AAATAACTACTGGGGGTGGGCGGAGAGGACGACGACATCTACAACAGAC
TGGTTTTTAAGGGGATGGGGATTTCCCGCCCGGATGCAGTAATAGGCAAG
TGTCGTATGATACGCCATAGCAGGGATAGAAAGAACGAACCCAACCCTGA
GCGCTTTGACCGGATTGCACATACAAGAGAAACTATGTCATCTGATGGAC
TTAACTCTCTTTCATATGAGGTGCTGAGAACAGATCGGTTCCCCCTGTAC
ACTAGAATCACAGTAGATATCGGGGCACCTGGGTCATAA
```

The synthetic coding sequence was inserted into an ALV vector (gag, pol and env genes deleted) downstream of an ovomucoid (OM) promoter as shown in FIG. 6A (sequence shown in FIG. 9).

The LTRs of the ALV vector are self-inactivating (SIN) thus the vector is called pALV-SIN and is disclosed in US patent publication No. 2008/0064862, published Mar. 13, 2008, the disclosure of which is incorporated in its entirety herein by reference. The vector used is also an SC-negative vector as disclosed in US patent publication No. 2008/0064862. That is, elements associated with genes used for titering (i.e., the neomycin resistance gene) have been removed from pALV-SIN.

The pALV-SIN vector shown in FIG. 6A (FIG. 9) employs a 1.8 kb ovomucoid (OM) promoter which is used to drive magnum-specific expression of the galactosyltransferase coding sequence. The OM protein is one of the major egg white proteins and expression of the OM gene is essentially limited to the magnum. The vector is referred to as pALV-SIN-GalT1.

Example 2

Production of GalT1 Transgene Augmented Birds

The pALV-SIN-GalT1 vector produced as described in Example 1 was packaged into viral particles by the transient transfection method as disclosed in US patent publication No. 2007/0077650, published Apr. 5, 2007.

Virus-containing media was collected 48 hr post-transfection and concentrated by centrifugation and immediately injected into stage X embryos of windowed eggs (stage X is an approximately 50,000 cell embryo, typically found in a freshly laid egg).

Approximately 150 embryos were injected. The eggs were sealed with a hot glue plug and incubated (Andacht, et al. *Mol Reprod Dev* 69: 31-4, 2004). 42 chicks hatched about 21 days later and the blood DNA was assessed for the presence of the transgene one week later. The hatched chicks are designated G0 for generation zero.

To assess the success of the transgenesis procedure, a Taqman® quantitative PCR system was used to determine transgene content in the blood DNA of hatched G0 chicks (Harvey, et al. *Poultry Science* 81: 202-12, 2002). Primers and a probe tagged with fluorescent labels were designed based on the sequence of the glycosyltransferase CDS. Blood DNA was purified, quantitated by the Picogreen® kit and analyzed with Taqman assay. About 80% of the chicks had detectable levels of the transgene in their blood DNA.

Further analysis was performed to confirm that the transgene integrated intact. PCR primers were used to amplify various parts of the transgene (the OM promoter, the CDS and 3' untranslated region) from the blood DNA of positive chicks and the sizes of the PCR products were determined by agarose gel electrophoresis. All GalT1 positive G0 birds that were tested were found to contain intact copies of the transgene.

Example 3

Production of Fully Transgenic GalT1 Birds And Assessment of Transgene-Augmented Glycosylation Semen was collected from G0 roosters of Example 2 and sperm DNA was analyzed by the Taqman assay for transgene content (Harvey, Speksnijder, Baugh, Morris and Ivarie. *Poultry Science* 81: 202-12, 2002). Roosters with the highest transgene content were bred to wild-type hens and offspring were analyzed by Taqman to identify fully transgenic G1s.

Figure 8B:
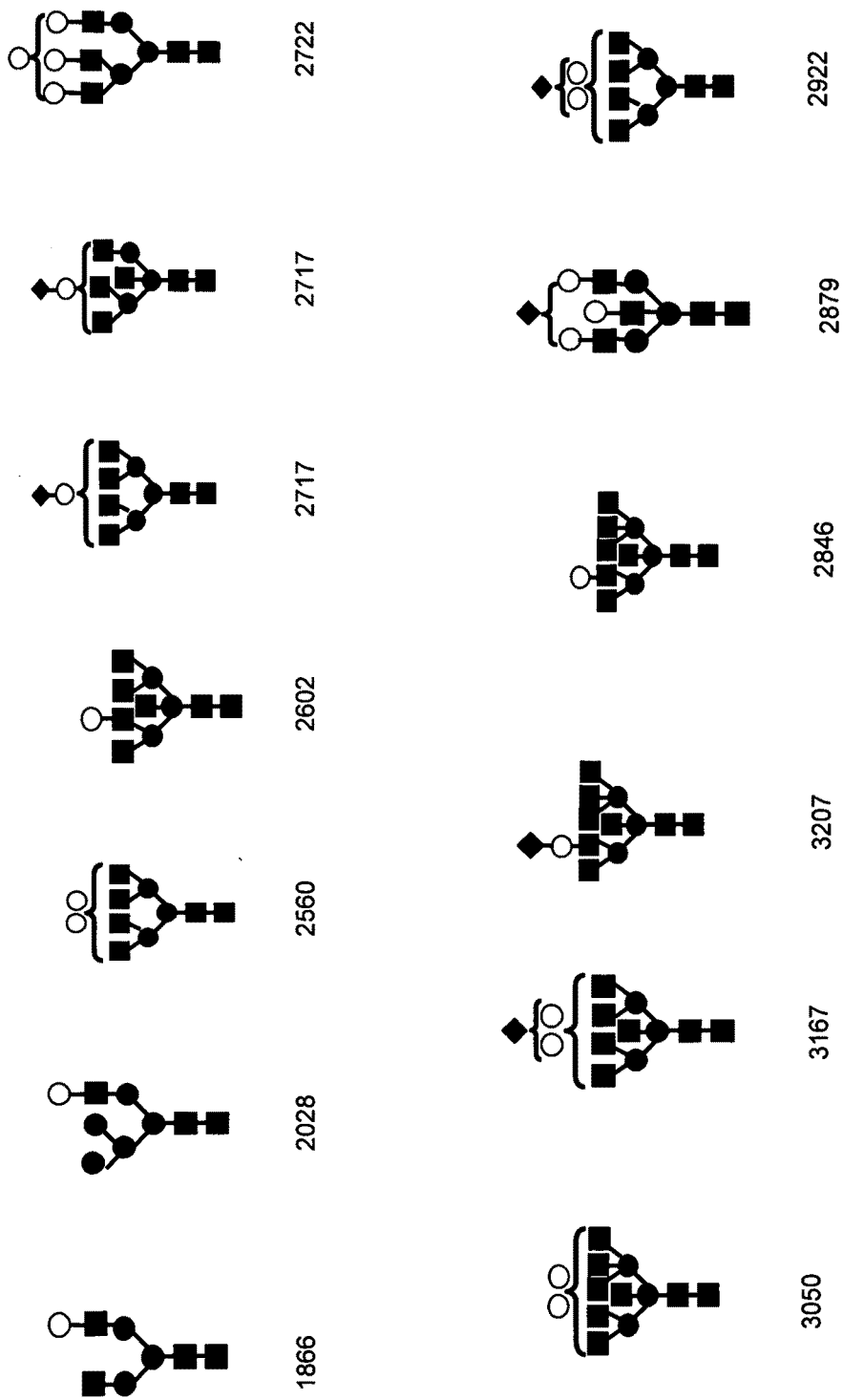
FIG. 8B-8C shows additional oligosaccharide structures that have Gal and/or sialic acid added that were also identified in one or more of the other twelve analyses (mass/mz is specified for each).
Figure 8C:
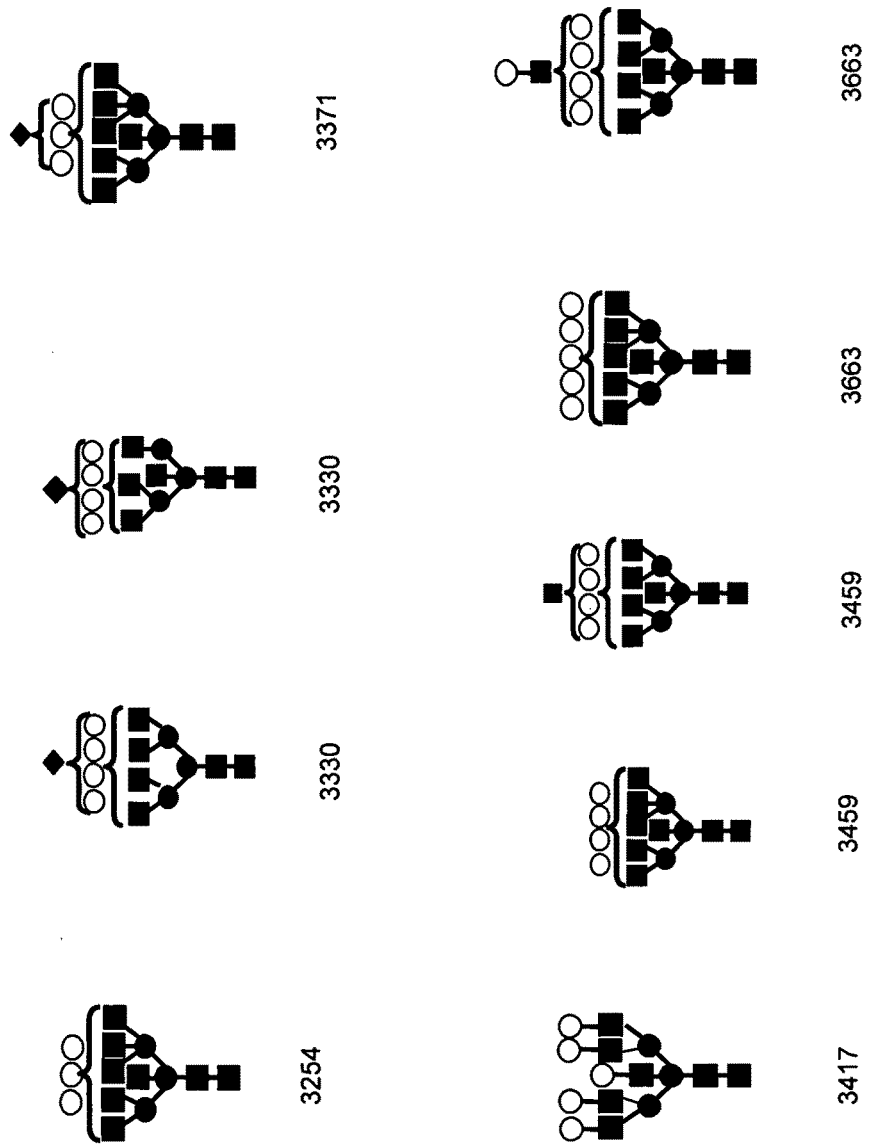
Figure 8D:
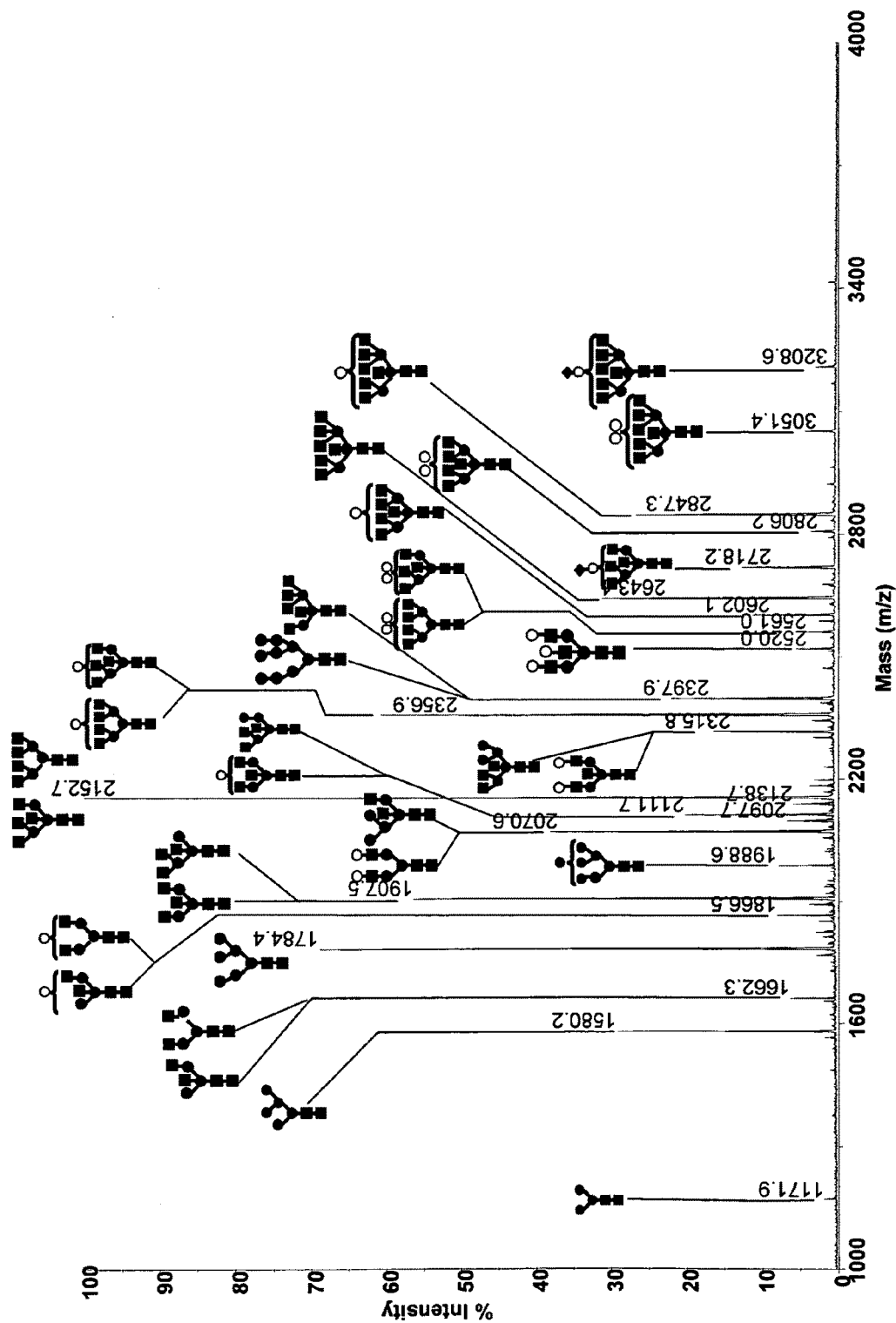
FIG. 8D is a control sample. The data demonstrates that Gal and some Sialic Acid were added to oligosaccharide structures present on egg white protein as a result of transgene-augmented glycosylation. Legend: ●=mannose; ▲=fucose; o=galactose; ■=N-acetylglucosamine; ♦=sialic acid.

Eggs were collected from 13 G1 hens. Egg white proteins were treated with PNGase which specifically releases N-linked oligosaccharides (N-glycans) from proteins. The N-glycans were purified and structures were determined by MALDI-MS analysis, the results of which are shown in FIG. 8. As can be seen, the results demonstrate the effectiveness of the invention with a substantial amount of galactose being added to many of the oligosaccharide structures. In addition, FIGS. 8A-8C shows that more sialic acid has been added to the oligosaccharide structures of the protein of the GalT1 birds relative to the oligosaccharide structures of the protein from the wild type (FIG. 8D) hen.

Example 4

Vector Design and Construction for Expression of SialT3 Transgene Augmented Birds The SialT3 coding sequence has been synthesized with codon usage optimized for expression for Synthetic Chicken α-2,3-Sialyltransferase Type 3 in the hen magnum and is shown below (SEQ ID NO: 41):

```
ATGGGTCTTTTGGTTTTCATGAGAAATCTGCTGCTGGCTCTGTGTCTGTT
CCTGGTCCTGGGATTTCTGTACTACTCTGCATGGAAGCTCCACCTGCTGC
GCTGGGAGGATAGCTCTAAATATGGACGCCTGAGCCATAGCTCTTTTCCT
AAGCAAAGACCAAGTGCTGATTCTGTGGTCTTGTCATTTGACTCTGTTGG
ACATACTATTGGCTCTGAATATGACAAACTGGGTTTTCTGCTTAACCTTG
ATTCTAAACTTCCCCCTGAATTGGCCTCAAAATATGCCAACTTCTCTGAG
GGAGTGTGCAAGCCTGGTTATGCATCTGCCCTGATGACTGTGATTTTCCC
TAAATTCTCCAAACCTGCCCCCATGTTCCTTGATGACTCCTTCCGGCGCT
GGGCCCGCATTAGAGACTTTGTGCCTCCATTTGGCATTAAAGGGCAGGAC
AATCTGATAAAGGCAATACTGTCTGCTACAAAAGATTACAGACTCACACC
AGCACTGGACAGCTTGTCATGCCGCCGCTGTATCATTGTTGGGAATGGTG
GTGTTCTGGCCAACAAGAGTTTGGGTCTTAAGATTGATGACTATGATGTG
GTCGTTCGCCTGAACTCTGCACCTGTCAAAGGCTTTGAGAAAGATGTTGG
TGGAAAGACAACACTGCGGATCACTTACCCAGAGGGGCTATTCAGAAGA
TGGAACAGTATGAGAAAGACTCCCTGTTTGTGCTGGCGGATTTAAATGG
CAAGACTTTAAGTGGCTGAAATATATTGTGTATAAAGAAAAGGTCTCAGC
TTCTGATGGCTTCTGGAAATCAGTGGCTACCCGGGTGCCTCGGGAGCCAC
ATGAAATTCGCATACTGAATCCCTATTTCATCCAAGAAGCTGCTTTTTCA
TTCATTGGCCTGCCATTCAATAATGGTCTGATGGGTCGGGGAATATCCC
CACCCTGGGTTCTGTGGCCATCACAATGGCTCTGCATAATTGTGATGAGG
TGGCTGTTGCTGGCTTTGGATATGACATGAGTTCCCCTAATGCTCCCCTG
CATTACTATGAGAACATAAAAATGAGTGCCATTAAGGAGTCATGGACTCA
TAATATACAACGGGAGAAGGAATTTCTTCGCAAGCTGGTTAAAGCCAGAG
TGATTACAGATCTTACATCTGGGATATGA
```

The synthetic coding sequence was inserted into a pALV-SIN vector downstream of an ovomucoid (OM) promoter as shown in FIG. 6B to produce pALV-SIN-SialT3, sequence shown in FIG. 10. The construct is assembled and G0 birds are then produced and analyzed essentially as described for the GalT1 G0 birds in Examples 1 and 2 and G1 birds produced essentially as described for the GalT1 birds in Example 3.

Example 5

Production of SialT3/GalT1 Transgene Augmented Birds by Crossing SialT3 Positive Birds and GalT1 Positive Birds One or more of the GalT1 G1 birds of Example 3 (or a homozygous G2 GalT1 bird obtained from crossing two GalT1 G1 birds) is crossed with a SialT3 G1 bird of Example 4 (or crossed with a homozygous G2 SialT3 bird obtained from crossing two SialT3 G1 birds) such that the resulting offspring birds carry both the GalT1 and SialT3 transgenes, as is understood in the art. These birds can be crossed to each other a second time to produce birds that are homozygous for both transgenes, as is understood in the art.

Example 6

Vector Design and Construction for Production of SialT3 and GalT1 Transgene Augmented Birds Using a Single Expression Vector The GalT1 and SialT3 coding sequences are synthesized with codon usage optimized for expression in the hen magnum as in Example 1 and Example 4. The coding sequences are inserted into a single retroviral vector downstream of a single 1.8 kb ovomucoid promoter. A sequence (e.g., an IRES) which provides for translation of the second or downstream CDS is inserted between the GalT1 and SialT3 CDSs, thus producing a vector having a bicistronic message as shown in FIG. 6C and in FIG. 11.

Translation of GalT1 is initiated by the upstream translation initiation site and SialT3 translation is initiated by the internal ribosome entry site (IRES) and accordingly both the GalT1 and SialT3 CDSs are expressed from the same mRNA. The IRES in FIG. 6C is from the encephalomyocarditis virus (EMCV) (Jang, et al. *J Virol* 62: 2636-43, 1988; Ghattas, et al. *Mol Cell Biol* 11: 5848-59, 1991).

The vector is inserted into avian (e.g., chicken, quail, turkey) embryos and G0s G1s are obtained essentially as described in the Examples above for pALV-SIN-GalT1. Homozygotes can be obtained as is understood in the art.

All references cited herein are incorporated by reference herein in their entirety and for all purposes to the same extent as if each individual publication, patent or patent application is specifically and individually indicated to be incorporated by reference in its entirety for all purposes.

The citation of any publication is for its disclosure prior to the filing date and should not be construed as an admission that the present invention is not entitled to antedate such publication by virtue of prior invention.

While this invention has been described with respect to various specific examples and embodiments, it is to be understood that the invention is not limited thereto and that it can be variously practiced with the scope of the following claims.

What is claimed is:

1. A method of producing an isolated protein modified by sialyltransferase using a transgenic chicken, the method comprising:

a) producing a transgenic chicken containing a transgene encoding sialyltransferase operably linked to an oviduct-specific promoter, wherein the sialyltransferase is expressed in oviduct tissue of the chicken, and wherein the sialyltransferase adds terminal sialic acid on oligosaccharides of proteins in oviduct tissue of the chicken; and b) isolating protein with additional terminal sialic acid on oligosaccharides from egg white of the transgenic chicken.

2. The method of claim 1 wherein the sialyltransferase is sialyltransferase type 1, 2, 3, 4, 5 or 6.

3. The method of claim 1 wherein the protein is produced in tubular gland cells.

4. The method of claim 1 wherein the oligosaccharide comprises 1 to 5 sialic acids.

5. The method of claim 1 wherein the oviduct specific promoter is an ovalbumin promoter.

6. The method of claim 1 wherein the oviduct specific promoter is an ovomucoid promoter.

7. The method of claim 2 wherein the sialyltransferase is sialyltransferase type 2.

8. The method of claim 2 wherein the sialyltransferase is sialyltransferase type 3.

9. The method of claim 2 wherein the sialyltransferase is sialyltransferase type 6.

* * * * *

SEQUENCE LISTING

```
<160> NUMBER OF SEQ ID NOS: 41

<210> SEQ ID NO 1
<211> LENGTH: 7434
<212> TYPE: DNA
<213> ORGANISM: Artificial Sequence
<220> FEATURE:
<223> OTHER INFORMATION: pSIN-OM-1.8-GalT1

<400> SEQUENCE: 1
cgaggaatat aaaaaaatta caggaggctt ataagcagcc cgaaagaaga gcgtaggcga      60
gttcttgtat tccgtgtgat agctggttgg attggtaatt gatcggctgg cacgcggaat     120
ataggaggtc gctgaatagt aaacttgtag acttggctac agcatagagt atcttctgta     180
gctctgatga ctgctaggaa ataatgctac ggataatgtg gggagggcaa ggcttgcgaa     240 tcggttgta acgggcaagg cttgactgag gggacaatag catgtttagg cgaaaagcgg      300
ggcttcggtt gtacgcggtt aggagtcccc tcaggatata gtagtttcgc ttttgcatag     360 ggaggggggac ggattggacg aaccactgaa ttccgcattg cagagatatt gtatttaagt    420
gcctagctcg atacaataaa cgccatttga ccattcacca cattggtgtg cacctggtt      480 gatggccgga ccgttgattc cctgrcgact acgagcacat gcatgaagca gaaggcttca     540
tttggtgacc ccgacgtgat cgttagggaa tacgcgctca ctggccgtcg ttttacaacg    600
tcgtgactgg gaaaaccctg gcgttaccca acttaatcgc cttgcagcac atcccccttt    660
cgccagctgg cgtaatagcg aagaggcccg caccgatcgc ccttcccaac agttgcgcag    720
cctgaatggc gaatggaaat tgtaagcgtt aatattttgt taaaattcgc gttaaatttt     780
tgttaaatca gctcatttt taaccaatag gccgaaatcg gcaaaatccc ttataaatca     840
aaagaataga ccgagatagg gttgagtgtt gttccagttt ggaacaagag tccactatta    900
aagaacgtgg actccaacgt caaagggcga aaaccgtct atcagggcga tggcccacta    960
cgtgaaccat caccctaatc aagttttttg gggtcgaggt gccgtaaagc actaaatcgg   1020
aaccctaaag ggagcccccg atttagagct tgacggggaa agccggcgaa cgtggcgaga   1080
aaggaaggga agaaagcgaa aggagcgggc gctagggcgc tggcaagtgt agcggtcacg   1140
ctgcgcgtaa ccaccacacc cgccgcgctt aatgcgccgc tacagggcgc gtcaggtggc   1200
acttttcggg gaaatgtgcg cggaacccct atttgtttat ttttctaaat acattcaaat   1260
atgtatccgc tcatgagaca ataaccctga taaatgcttc aataatattg aaaaaggaag   1320
agtatgagta ttcaacattt ccgtgtcgcc cttattccct ttttgcggc attttgcctt    1380 cctgttttg ctcacccaga aacgctggtg aaagtaaaag atgctgaaga tcagttgggt   1440
gcacgagtgg gttacatcga actggatctc aacagcggta agatccttga gagttttcgc   1500
cccgaagaac gttttccaat gatgagcact tttaaagttc tgctatgtgg cgcggtatta   1560
tcccgtattg acgccgggca agagcaactc ggtcgccgca tacactattc tcagaatgac   1620
ttggttgagt actcaccagt cacagaaaag catcttacgg atggcatgac agtaagagaa   1680
ttatgcagtg ctgccataac catgagtgat aacactgcgg ccaacttact tctgacaacg   1740
atcggaggac cgaaggagct aaccgctttt ttgcacaaca tgggggatca tgtaactcgc   1800
```

```
cttgatcgtt gggaaccgga gctgaatgaa gccataccaa acgacgagcg tgacaccacg   1860
atgcctgtag caatggcaac aacgttgcgc aaactattaa ctggcgaact acttactcta   1920
gcttcccggc aacaattaat agactggatg gaggcggata agttgcagg accacttctg    1980 cgctcggccc ttccggctgg ctggtttatt gctgataaat ctggagccgg tgagcgtggg   2040
tctcgcggta tcattgcagc actggggcca gatggtaagc cctcccgtat cgtagttatc   2100
tacacgacgg ggagtcaggc aactatggat gaacgaaata gacagatcgc tgagataggt   2160
gcctcactga ttaagcattg gtaactgtca gaccaagttt actcatatat actttagatt   2220
gatttaaaac ttcatttta atttaaaagg atctaggtga agatcctttt tgataatctc    2280
atgaccaaaa tcccttaacg tgagttttcg ttccactgag cgtcagaccc cgtagaaaag   2340
atcaaaggat cttcttgaga tccttttttt ctgcgcgtaa tctgctgctt gcaaacaaaa   2400
aaaccaccgc taccagcggt ggtttgtttg ccggatcaag agctaccaac tcttttttccg   2460 aaggtaactg gcttcagcag agcgcagata ccaaatactg tccttctagt gtagccgtag   2520
ttaggccacc acttcaagaa ctctgtagca ccgcctacat acctcgctct gctaatcctg   2580
ttaccagtgg ctgctgccag tggcgataag tcgtgtctta ccgggttgga ctcaagacga   2640
tagttaccgg ataaggcgca gcggtcgggc tgaacggggg gttcgtgcac acagcccagc   2700
ttggagcgaa cgacctacac cgaactgaga tacctacagc gtgagctatg agaaagcgcc   2760
acgcttcccg aagggagaaa ggcggacagg tatccggtaa gcggcagggt cggaacagga   2820
gagcgcacga gggagcttcc agggggaaac gcctggtatc tttatagtcc tgtcgggttt   2880
cgccacctct gacttgagcg tcgatttttg tgatgctcgt caggggggcg agcctatgg    2940 aaaaacgcca gcaacgcggc cttttacgg ttcctggcct tttgctggcc ttttgctcac    3000
atgttctttc ctgcgttatc ccctgattct gtggataacc gtattaccgc ctttgagtga   3060
gctgataccg ctcgccgcag ccgaacgacc gagcgcagcg agtcagtgag cgaggaagcg   3120
gaagagcgcc caatacgcaa accgcctctc cccgcgcgtt ggccgattca ttaatgcagc   3180
tggcacgaca gtttcccga ctggaaagcg ggcagtgagc gcaacgcaat taatgtgagt    3240
tagctcactc attaggcacc ccaggcttta cactttatgc ttccggctcg tatgttgtgt   3300
ggaattgtga gcggataaca atttcacaca ggaaacagct atgaccatga ttacgccaag   3360
cgcgcattgg taattgatcg gctggcacgc ggaatatagg aggtcgctga atagtaaact   3420
tgtagacttg gctacagcat agagtatctt ctgtagctct gatgactgct aggaaataat   3480
gctacggata atgtggggag gcaaggcctt gcgaatcggg ttgtaacggg caaggcttga   3540 ctgagggac aatagcatgt ttaggcgaaa agcggggctt cggttgtacg cggttaggag    3600 tccccctcagg atatagtagt ttcgcttttg catagggagg gggaaatgta gtcttatgca   3660
atactcttgt agtcttgcaa catgcttatg taacgatgag ttagcaacat gccttataag   3720
gagagaaaaa gcaccgtgca tgccgattgg tgggagtaag gtggtatgat cgtggtatga   3780
tcgtgccttg ttaggaaggc aacagacggg tctaacacgg attggacgaa ccactgaatt   3840
ccgcattgca gagatattgt atttaagtgc ctagctcgat acaataaacg ccatttgacc   3900
attcaccaca ttggtgtgca cctgggttga tggccggacc gttgattccc tgrcgactac   3960
gagcacatgc atgaagcaga aggcttcatt tggtgacccc gacgtgatcg ttagggaata   4020
gtggtcggcc acaggcggcg tggcgatcct gtcctcatcc gtctcgctta tcggggagc    4080 ggacgatgac cctagtagag ggggctgcgg cttaggaggg cagaagctga gtggcgtcgg   4140
agggagccct actgcagggg gccaacatac cctaccgaga actcagagag tcgttggaag   4200
```

```
acgggaagga agcccgacga ctgagcggtc cacccaggc gtgattccgg ttgctctgcg      4260
tgattccggt cgcccggtgg atcaagcatg gaagccgtca taaaggtgat ttcgtccgcg      4320
tgtaagacct attgcgggaa aacctctcct tctaagaagg aaatagggc tatgttgtcc      4380
ctgttacaaa aggaagggtt gcttacgtcc ccctcagact tatattcccc ggggtcctgg      4440
gatctctgcc cttgtgctga ctcctgcaca aagagcatt tccctgtagc caaacagcga      4500
ttagccataa gctgcacctg actttgagga ttaagagttt gcaattaagt ggattgcagc      4560
aggagatcag tggcagggtt gcagatgaaa tcctttctta ggggtagcta agggctgagc      4620
aacctgtcct acagcacaag ccaaaccagc caagggtttt cctgtgctgt tcacagaggc      4680
agggccagct ggagctggag gaggttgtgc tgggaccctt ctccctgtgc tgagaatgga      4740
gtgatttctg ggtgctgttc ctgtggcttg cactgagcag ctcaagggag atcggtgctc      4800
ctcatgcagt gccaaaactc gtgtttgatg cagaaagatg gatgtgcacc tccctcctgc      4860
taatgcagcc gtgagcttat gaaggcaatg agccctcagt gcagcaggag ctgtagtgca      4920
ctcctgtagg tgctagggaa aatctctggt tcccagggat gcattcataa gggcaatata      4980
tcttgaggct gcgccaaatc tttctgaaat attcatgcgt gttcccttaa tttatagaaa      5040
caaacacagc agaataatta ttccaatgcc tcccctcgaa ggaaacccat atttccatgt      5100
agaaatgtaa cctatataca cacagccatg ctgcatcctt cagaacgtgc cagtgctcat      5160
ctcccatggc aaaatactac aggtattctc actatgttgg acctgtgaaa ggaaccatgg      5220
taagaaactt cggttaaagg tatggctgca aaactactca taccaaaaca gcagagctcc      5280
agacctcctc ttaggaaaga gccacttgga gagggatggt gtgaaggctg gaggtgagag      5340
acagagcctg tcccagtttt cctgtctcta ttttctgaaa cgtttgcagg aggaaaggac      5400
aactgtactt tcaggcatag ctggtgccct cacgtaaata agttccccga acttctgtgt      5460
catttgttct taagatgctt tggcagaaca ctttgagtca attcgcttaa ctgtgactag      5520
gtctgtaaat aagtgctccc tgctgataag gttcaagtga cattttttagt ggtatttgac      5580
agcatttacc ttgctttcaa gtcttctacc aagctcttct atacttaagc agtgaaaccg      5640
ccaagaaacc cttcctttta tcaagctagt gctaaatacc attaacttca taggttagat      5700
acggtgctgc cagcttcacc tggcagtggt tggtcagttc tgctggtgac aaagcctccc      5760
tggcctgtgc ttttacctag aggtgaatat ccaagaatgc agaactgcat ggaaagcaga      5820
gctgcaggca cgatggtgct gagccttagc tgcttcctgc tgggagatgt ggatgcagag      5880
acgaatgaag gacctgtccc ttactcccct cagcattctg tgctatttag ggttctacca      5940
gagtccttaa gaggtttttt tttttttttgg tccaaaagtc tgtttgtttg gttttgacca      6000
ctgagagcat gtgacacttg tctcaagcta ttaaccaagt gtccagccaa atcaattgc      6060
ctgggagacg cagaccatta cctggaggtc aggacctcaa taaatattac cagcctcatt      6120
gtgccgctga cagattcagc tggctgctcc gtgttccagt ccaacagttc ggacgccacg      6180
tttgtatata tttgcaggca gcctcggggg gaccatctca ggagcagagc accggcagcc      6240
gcctgcagag ccgggcagta cctcaacatg aaagaacctg cacttcctgg tacttcactg      6300
caaagagcat gtagactgct ggtagcattt tgcgccctgc acctgagcgc aaccctgctc      6360
tactacctgg ctggatccag cctgactcca cccgctctc cagaacctcc cctcggagg      6420
ccgcctccag ccaacctctc cctgccaccc tcccggcctc ctcctccccc tgcggctcgc      6480
ccccgcccag gacctgtttc tgcacaaccc cggaacctgc cagattctgc accatctgga      6540
ctgtgccccg atccaagtcc actgctcgtt ggtcctctgc gggtggagtt tagtcagcca      6600
```

```
gtgaacctgg aggaagtggc ttctaccaat ccggaggtca gggaaggagg gagattcgcc      6660
ccaaaggact gcaaagcgct ccagaaggtg gctattatta tccccttcag gaacagagag      6720
gagcacctga agtattggct gtactacatg caccgattc ttcagagaca gcaattggac       6780 tatgggtct atgtgattaa tcaagacggc gatgaagaat ttaacagagc taaactgctt       6840
aatgtcggtt tcactgaggc actcaaggaa tacgattatg attgctttgt gttttccgat      6900
gtggatctga ttcctatgga cgaccgtaac acatataagt gctatagtca accacgtcac      6960
ctgagtgtgt caatggacaa gtttggcttt aggctgccgt ataaccagta tttcggagga      7020
gtttcagcat tgagtaaaga acagtttaca aaaatcaacg ggttcccaaa taactactgg      7080
gggtggggcg agaggacga cgacatctac aacagactgg ttttttaaggg gatggggatt      7140 tcccgcccgg atgcagtaat aggcaagtgt cgtatgatac gccatagcag ggatagaaag      7200
aacgaaccca accctgagcg cttttgaccgg attgcacata caagagaaac tatgtcatct      7260 gatgggactta actctctttc atatgaggtg ctgagaacag atcggttccc cctgtacact     7320
agaatcacag tagatatcgg ggcacctggg tcataagcct aaagtctagt atggggattg      7380
gtggcgacga ctcctggagc ccgtcagtat cggcggaatt cggtaccgga tccc             7434
```

<210> SEQ ID NO 2
<211> LENGTH: 7545
<212> TYPE: DNA
<213> ORGANISM: Artificial Sequence
<220> FEATURE:
<223> OTHER INFORMATION: pSIN-OM-1.8-SialT3

<400> SEQUENCE: 2

```
cgaggaatat aaaaaaatta caggaggctt ataagcagcc cgaaagaaga gcgtaggcga      60
gttcttgtat tccgtgtgat agctggttgg attggtaatt gatcggctgg cacgcggaat      120
ataggaggtc gctgaatagt aaacttgtag acttggctac agcatagagt atcttctgta      180
gctctgatga ctgctaggaa ataatgctac ggataatgtg gggagggcaa ggcttgcgaa      240
tcgggttgta acgggcaagg cttgactgag gggacaatag catgtttagg cgaaaagcgg      300
ggcttcggtt gtacgcggtt aggagtcccc tcaggatata gtagtttcgc ttttgcatag      360 ggaggggac ggattggacg aaccactgaa ttccgcattg cagagatatt gtatttaagt       420
gcctagctcg atacaataaa cgccatttga ccattcacca cattggtgtg cacctggggtt     480 gatggccgga ccgttgattc cctgrcgact acgagcacat gcatgaagca gaaggcttca     540
tttggtgacc ccgacgtgat cgttagggaa tacgcgctca ctggccgtcg ttttacaacg     600
tcgtgactgg gaaaaccctg gcgttaccca acttaatcgc cttgcagcac atccccctttt    660 cgccagctgg cgtaatagcg aagaggcccg caccgatcgc ccttcccaac agttgcgcag     720
cctgaatggc gaatggaaat tgtaagcgtt aatattttgt taaaattcgc gttaaatttt     780
tgttaaatca gctcattttt taaccaatag gccgaaatcg gcaaaatccc ttataaatca     840
aaagaataga ccgagatagg gttgagtgtt gttccagttt ggaacaagag tccactatta     900
aagaacgtgg actccaacgt caaagggcga aaaccgtct atcagggcga tggcccacta      960
cgtgaaccat cacccctaatc aagttttttg gggtcgaggt gccgtaaagc actaaatcgg     1020
aaccctaaag ggagccccg atttagagct tgacggggaa agccggcgaa cgtggcgaga      1080
aaggaaggga gaaagcgaa aggagcgggc gctagggcgc tggcaagtgt agcggtcacg     1140
ctgcgcgtaa ccaccacacc cgccgcgctt aatgcgccgc tacagggcgc gtcaggtggc      1200
acttttcggg gaaatgtgcg cggaacccct atttgtttat ttttctaaat acattcaaat     1260
```

```
atgtatccgc tcatgagaca ataaccctga taaatgcttc aataatattg aaaaaggaag    1320
agtatgagta ttcaacattt ccgtgtcgcc cttattccct tttttgcggc attttgcctt    1380
cctgtttttg ctcacccaga aacgctggtg aaagtaaaag atgctgaaga tcagttgggt    1440
gcacgagtgg gttacatcga actggatctc aacagcggta agatccttga gagttttcgc    1500
cccgaagaac gttttccaat gatgagcact tttaaagttc tgctatgtgg cgcggtatta    1560
tcccgtattg acgccgggca agagcaactc ggtcgccgca tacactattc tcagaatgac    1620
ttggttgagt actcaccagt cacagaaaag catcttacgg atggcatgac agtaagagaa    1680
ttatgcagtg ctgccataac catgagtgat aacactgcgg ccaacttact tctgacaacg    1740
atcggaggac cgaaggagct aaccgctttt ttgcacaaca tgggggatca tgtaactcgc    1800
cttgatcgtt gggaaccgga gctgaatgaa gccataccaa acgacgagcg tgacaccacg    1860
atgcctgtag caatggcaac aacgttgcgc aaactattaa ctggcgaact acttactcta    1920
gcttcccggc aacaattaat agactggatg gaggcggata agttgcagg accacttctg    1980 cgctcggccc ttccggctgg ctggtttatt gctgataaat ctggagccgg tgagcgtggg    2040
tctcgcggta tcattgcagc actggggcca gatggtaagc cctcccgtat cgtagttatc    2100
tacacgacgg ggagtcaggc aactatggat gaacgaaata gacagatcgc tgagataggt    2160
gcctcactga ttaagcattg gtaactgtca gaccaagttt actcatatat actttagatt    2220
gatttaaaac ttcattttta atttaaaagg atctaggtga agatccttt tgataatctc    2280 atgaccaaaa tcccttaacg tgagttttcg ttccactgag cgtcagaccc cgtagaaaag    2340
atcaaaggat cttcttgaga tcctttttt ctgcgcgtaa tctgctgctt gcaaacaaaa    2400
aaaccaccgc taccagcggt ggtttgtttg ccggatcaag agctaccaac tcttttccg    2460 aaggtaactg gcttcagcag agcgcagata ccaaatactg tccttctagt gtagccgtag    2520
ttaggccacc acttcaagaa ctctgtagca ccgcctacat acctcgctct gctaatcctg    2580
ttaccagtgg ctgctgccag tggcgataag tcgtgtctta ccgggttgga ctcaagacga    2640
tagttaccgg ataaggcgca gcggtcgggc tgaacggggg gttcgtgcac acagcccagc    2700
ttggagcgaa cgacctacac cgaactgaga tacctacagc gtgagctatg agaaagcgcc    2760
acgcttcccg aagggagaaa ggcggacagg tatccggtaa gcggcagggt cggaacagga    2820
gagcgcacga gggagcttcc aggggggaaac gcctggtatc tttatagtcc tgtcgggttt    2880
cgccacctct gacttgagcg tcgatttttg tgatgctcgt caggggggcg agcctatgg    2940 aaaaacgcca gcaacgcggc ctttttacgg ttcctggcct tttgctggcc ttttgctcac    3000
atgttctttc ctgcgttatc ccctgattct gtggataacc gtattaccgc ctttgagtga    3060
gctgataccg ctcgccgcag ccgaacgacc gagcgcagcg agtcagtgag cgaggaagcg    3120
gaagagcgcc caatacgcaa accgcctctc cccgcgcgtt ggccgattca ttaatgcagc    3180
tggcacgaca ggtttcccga ctggaaagcg ggcagtgagc gcaacgcaat taatgtgagt    3240
tagctcactc attaggcacc ccaggcttta cactttatgc ttccggctcg tatgttgtgt    3300
ggaattgtga gcggataaca atttcacaca ggaaacagct atgaccatga ttacgccaag    3360
cgcgcattgg taattgatcg gctggcacgc ggaatatagg aggtcgctga atagtaaact    3420
tgtagacttg gctacagcat agagtatctt ctgtagctct gatgactgct aggaaataat    3480
gctacggata atgtggggag ggcaaggctt gcgaatcggg ttgtaacggg caaggcttga    3540
ctgaggggac aatagcatgt ttaggcgaaa agcggggctt cggttgtacg cggttaggag    3600 tccccctcagg atatagtagt ttcgcttttg catagggagg gggaaatgta gtcttatgca    3660
```

-continued

```
atactcttgt agtcttgcaa catgcttatg taacgatgag ttagcaacat gccttataag    3720
gagagaaaaa gcaccgtgca tgccgattgg tgggagtaag gtggtatgat cgtggtatga    3780
tcgtgccttg ttaggaaggc aacagacggg tctaacacgg attggacgaa ccactgaatt    3840
ccgcattgca gagatattgt atttaagtgc ctagctcgat acaataaacg ccatttgacc    3900
attcaccaca ttggtgtgca cctgggttga tggccggacc gttgattccc tgrcgactac    3960
gagcacatgc atgaagcaga aggcttcatt tggtgacccc gacgtgatcg ttagggaata    4020
gtggtcggcc acaggcggcg tggcgatcct gtcctcatcc gtctcgctta ttcggggagc    4080
ggacgatgac cctagtagag ggggctgcgg cttaggaggg cagaagctga gtggcgtcgg    4140
agggagccct actgcagggg gccaacatac cctaccgaga actcagagag tcgttggaag    4200
acggaaggaa agcccgacga ctgagcggtc cacccaggc gtgattccgg ttgctctgcg     4260
tgattccggt cgccggtgg atcaagcatg gaagccgtca taaggtgat ttcgtccgcg      4320
tgtaagacct attgcgggaa aacctctcct tctaagaagg aaatagggc tatgttgtcc     4380
ctgttacaaa aggaagggtt gcttacgtcc ccctcagact tatattcccc atactggcca    4440
agtcctgccc agctgtcagc ctgctgaccc tctgcagttc aggaccatga acgtggcac     4500
tgtaagacgt gtccctgcc tttgcttgcc cacagatctc tgcccttgtg ctgactcctg     4560
cacacaagag catttccctg tagccaaaca gcgattagcc ataagctgca cctgactttg    4620
aggattaaga gtttgcaatt aagtggattg cagcaggaga tcagtggcag ggttgcagat    4680
gaaatccttt tctaggggta gctaagggct gagcaacctg tcctacagca caagccaaac    4740
cagccaaggg ttttcctgtg ctgttcacag aggcagggcc agctggagct ggaggaggtt    4800
gtgctgggac ccttctccct gtgctgagaa tggagtgatt tctgggtgct gttcctgtgg    4860
cttgcactga gcagctcaag ggagatcggt gctcctcatg cagtgccaaa actcgtgttt    4920
gatgcagaaa gatggatgtg cacctccctc ctgctaatgc agccgtgagc ttatgaaggc    4980
aatgagccct cagtgcagca ggagctgtag tgcactcctg taggtgctag ggaaaatctc    5040
tggttcccag ggatgcattc ataagggcaa tatatcttga ggctgcgcca aatcttttctg   5100
aaatattcat gcgtgttccc ttaatttata gaaacaaaca cagcagaata attattccaa    5160
tgcctcccct cgaaggaaac ccatatttcc atgtagaaat gtaacctata tacacacagc    5220
catgctgcat ccttcagaac gtgccagtgc tcatctccca tggcaaaata ctacaggtat    5280
tctcactatg ttggacctgt gaaaggaacc atggtaagaa acttcggtta aaggtatggc    5340
tgcaaaacta ctcataccaa aacagcagag ctccagacct cctcttagga aagagccact    5400
tggagaggga tggtgtgaag gctggaggtg agagacagag cctgtcccag ttttcctgtc    5460
tctattttct gaaacgtttg caggaggaaa ggacaactgt actttcaggc atagctggtg    5520
ccctcacgta aataagttcc ccgaacttct gtgtcatttg ttcttaagat gctttggcag    5580
aacactttga gtcaattcgc ttaactgtga ctaggtctgt aaataagtgc tccctgctga    5640
taaggttcaa gtgacatttt tagtggtatt tgacagcatt taccttgctt tcaagtcttc    5700
taccaagctc ttctatactt aagcagtgaa accgccaaga aacccttcct tttatcaagc    5760
tagtgctaaa taccattaac ttcataggtt agatacggtg ctgccagctt cacctggcag    5820
tggttggtca gttctgctgg tgacaaagcc tccctggcct gtgcttttac ctagaggtga    5880
atatccaaga atgcagaact gcatggaaag cagagctgca ggcacgatgg tgctgagcct    5940
tagctgcttc ctgctgggag atgtggatgc agagacgaat gaaggacctg tcccttactc    6000
ccctcagcat tctgtgctat ttagggttct accagagtcc ttaagaggtt tttttttttt    6060
```

```
ttggtccaaa agtctgtttg tttggttttg accactgaga gcatgtgaca cttgtctcaa      6120
gctattaacc aagtgtccag ccaaaatcaa ttgcctggga cacgcagacc attacctgga      6180
ggtcaggacc tcaataaata ttaccagcct cattgtgccg ctgacagatt cagctggctg      6240
ctccgtgttc cagtccaaca gttcggacgc cacgtttgta tatatttgca ggcagcctcg      6300
gggggaccat ctcaggagca gagcaccggc agccgcctgc agagccgggc agtacctcaa      6360
catgggtctt ttggttttca tgagaaatct gctgctggct ctgtgtctgt tcctggtcct      6420
gggatttctg tactactctg catggaagct ccacctgctg cgctgggagg atagctctaa      6480
atatggacgc ctgagccata gctctttttcc taagcaaaga ccaagtgctg attctgtggt      6540
cttgtcattt gactctgttg gacatactat tggctctgaa tatgacaaac tgggttttct      6600
gcttaacctt gattctaaac ttccccctga attggcctca aaatatgcca acttctctga      6660
gggagtgtgc aagcctggtt atgcatctgc cctgatgact gtgatttttcc ctaaattctc      6720 caaacctgcc cccatgttcc ttgatgactc cttccggcgc tgggcccgca ttagagactt      6780
tgtgcctcca tttggcatta aagggcagga caatctgata aaggcaatac tgtctgctac      6840
aaaagattac agactcacac cagcactgga cagcttgtca tgccgccgct gtatcattgt      6900
tgggaatggt ggtgttctgg ccaacaagag tttgggtctt aagattgatg actatgatgt      6960
ggtcgttcgc ctgaactctg cacctgtcaa aggctttgag aaagatgttg gtggaaagac      7020
aacactgcgg atcacttacc cagaggggggc tattcagaag atggaacagt atgagaaaga      7080
ctccctgttt gtgctggcgg gatttaaatg gcaagacttt aagtggctga atatattgt       7140 gtataaagaa aaggtctcag cttctgatgg cttctggaaa tcagtggcta cccgggtgcc      7200
tcggagccca catgaaattc gcatactgaa tccctatttc atccaagaag ctgcttttttc      7260 attcattggc ctgccattca ataatggtct gatgggtcgg gggaatatcc ccaccctggg      7320
ttctgtggcc atcacaatgg ctctgcataa ttgtgatgag gtggctgttg ctggcttttgg      7380 atatgacatg agttccccta atgctcccct gcattactat gagaacataa aaatgagtgc      7440
cattaaggag tcatggactc ataatataca acgggagaag gaatttcttc gcaagctggt      7500
taaagccaga gtgattacag atcttacatc tgggatatga ggatc                     7545
```

<210> SEQ ID NO 3
<211> LENGTH: 9119
<212> TYPE: DNA
<213> ORGANISM: Artificial Sequence
<220> FEATURE:
<223> OTHER INFORMATION: pSIN-OM-1.8-GalT1-IRES-SialT3

<400> SEQUENCE: 3

```
cggatccccg aggaatataa aaaaattaca ggaggcttat aagcagcccg aaagaagagc       60
gtaggcgagt tcttgtattc cgtgtgatag ctggttggat tggtaattga tcggctggca      120
cgcggaatat aggaggtcgc tgaatagtaa acttgtagac ttggctacag catagagtat      180
cttctgtagc tctgatgact gctaggaaat aatgctacgg ataatgtggg gagggcaagg      240
cttgcgaatc gggttgtaac gggcaaggct tgactgaggg acaatagca tgtttaggcg       300 aaaagcgggg cttcggttgt acgcggttag gagtcccctc aggatatagt agtttcgctt      360
ttgcataggg aggggggacgg attggacgaa ccactgaatt ccgcattgca gagatattgt      420
atttaagtgc ctagctcgat acaataaacg ccatttgacc attcaccaca ttggtgtgca      480
cctgggttga tggccggacc gttgattccc tgrcgactac gagcacatgc atgaagcaga      540
aggcttcatt tggtgacccc gacgtgatcg ttagggaata cgcgctcact ggccgtcgtt      600
```

```
ttacaacgtc gtgactggga aaccctggc gttacccaac ttaatcgcct tgcagcacat    660
cccccttcg ccagctggcg taatagcgaa gaggcccgca ccgatcgccc ttcccaacag    720
ttgcgcagcc tgaatggcga atggaaattg taagcgttaa tattttgtta aaattcgcgt    780
taaattttg ttaaatcagc tcattttta accaataggc cgaaatcggc aaaatccctt     840
ataaatcaaa agaatagacc gagatagggt tgagtgttgt tccagtttgg aacaagagtc    900
cactattaaa gaacgtggac tccaacgtca aagggcgaaa aaccgtctat cagggcgatg    960
gcccactacg tgaaccatca ccctaatcaa gttttttggg gtcgaggtgc cgtaaagcac   1020
taaatcggaa ccctaaaggg agccccgat ttagagcttg acggggaaag ccggcgaacg   1080
tggcgagaaa ggaagggaag aaagcgaaag gagcgggcgc tagggcgctg gcaagtgtag   1140
cggtcacgct gcgcgtaacc accacacccg ccgcgcttaa tgcgccgcta cagggcgcgt   1200
caggtggcac ttttcgggga aatgtgcgcg gaacccctat ttgtttattt ttctaaatac   1260
attcaaatat gtatccgctc atgagacaat aaccctgata aatgcttcaa taatattgaa   1320
aaaggaagag tatgagtatt caacatttcc gtgtcgccct tattcccttt tttgcggcat   1380
tttgccttcc tgttttgct cacccagaaa cgctggtgaa agtaaaagat gctgaagatc   1440
agttgggtgc acgagtgggt tacatcgaac tggatctcaa cagcggtaag atccttgaga   1500
gttttcgccc cgaagaacgt tttccaatga tgagcacttt taaagttctg ctatgtggcg   1560
cggtattatc ccgtattgac gccgggcaag agcaactcgg tcgccgcata cactattctc   1620
agaatgactt ggttgagtac tcaccagtca cagaaaagca tcttacggat ggcatgacag   1680
taagagaatt atgcagtgct gccataacca tgagtgataa cactgcggcc aacttacttc   1740
tgacaacgat cggaggaccg aaggagctaa ccgcttttt gcacaacatg ggggatcatg   1800
taactcgcct tgatcgttgg gaaccggagc tgaatgaagc cataccaaac gacgagcgtg   1860
acaccacgat gcctgtagca atggcaacaa cgttgcgcaa actattaact ggcgaactac   1920
ttactctagc ttcccggcaa caattaatag actggatgga ggcggataaa gttgcaggac   1980
cacttctgcg ctcggccctt ccggctggct ggtttattgc tgataaatct ggagccggtg   2040
agcgtgggtc tcgcggtatc attgcagcac tggggccaga tggtaagccc tcccgtatcg   2100
tagttatcta cacgacgggg agtcaggcaa ctatggatga acgaaataga cagatcgctg   2160
agataggtgc ctcactgatt aagcattggt aactgtcaga ccaagtttac tcatatatac   2220
tttagattga tttaaaactt catttttaat ttaaaaggat ctaggtgaag atcctttttg   2280
ataatctcat gaccaaaatc ccttaacgtg agttttcgtt ccactgagcg tcagaccccg   2340
tagaaaagat caaaggatct tcttgagatc ctttttttct gcgcgtaatc tgctgcttgc   2400
aaacaaaaaa accaccgcta ccagcggtgg tttgtttgcc ggatcaagag ctaccaactc   2460
tttttccgaa ggtaactggc ttcagcagag cgcagatacc aaatactgtc cttctagtgt   2520
agccgtagtt aggccaccac ttcaagaact ctgtagcacc gcctacatac ctcgctctgc   2580
taatcctgtt accagtggct gctgccagtg gcgataagtc gtgtcttacc gggttggact   2640
caagacgata gttaccggat aaggcgcagc ggtcgggctg aacggggggt tcgtgcacac   2700
agcccagctt ggagcgaacg acctacaccg aactgagata cctacagcgt gagctatgag   2760
aaagcgccac gcttcccgaa gggagaaagg cggacaggta tccggtaagc ggcagggtcg   2820
gaacaggaga gcgcacgagg gagcttccag ggggaaacgc ctggtatctt tatagtcctg   2880
tcgggtttcg ccacctctga cttgagcgtc gatttttgtg atgctcgtca gggggggcgga   2940
gcctatggaa aaacgccagc aacgcggcct ttttacggtt cctggccttt tgctggcctt   3000
```

```
ttgctcacat gttctttcct gcgttatccc ctgattctgt ggataaccgt attaccgcct    3060
ttgagtgagc tgataccgct cgccgcagcc gaacgaccga gcgcagcgag tcagtgagcg    3120
aggaagcgga agagcgccca atacgcaaac cgcctctccc cgcgcgttgg ccgattcatt    3180
aatgcagctg gcacgacagg tttcccgact ggaaagcggg cagtgagcgc aacgcaatta    3240
atgtgagtta gctcactcat taggcacccc aggctttaca ctttatgctt ccggctcgta    3300
tgttgtgtgg aattgtgagc ggataacaat ttcacacagg aaacagctat gaccatgatt    3360
acgccaagcg cgcattggta attgatcggc tggcacgcgg aatataggag gtcgctgaat    3420
agtaaacttg tagacttggc tacagcatag agtatcttct gtagctctga tgactgctag    3480
gaaataatgc tacggataat gtggggaggg caaggcttgc gaatcgggtt gtaacgggca    3540
aggcttgact gaggggacaa tagcatgttt aggcgaaaag cggggcttcg gttgtacgcg    3600
gttaggagtc ccctcaggat atagtagttt cgcttttgca tagggagggg gaaatgtagt    3660
cttatgcaat actcttgtag tcttgcaaca tgcttatgta acgatgagtt agcaacatgc    3720
cttataagga gagaaaaagc accgtgcatg ccgattggtg ggagtaaggt ggtatgatcg    3780
tggtatgatc gtgccttgtt aggaaggcaa cagacgggtc taacacggat tggacgaacc    3840
actgaattcc gcattgcaga gatattgtat ttaagtgcct agctcgatac aataaacgcc    3900
atttgaccat tcaccacatt ggtgtgcacc tgggttgatg gccggaccgt tgattccctg    3960
rcgactacga gcacatgcat gaagcagaag gcttcatttg gtgacccega cgtgatcgtt    4020 agggaatagt ggtcggccac aggcggcgtg gcgatcctgt cctcatccgt ctcgcttatt    4080
cggggagcgg acgatgaccc tagtagaggg ggctgcggct taggagggca gaagctgagt    4140
ggcgtcggag ggagccctac tgcagggggc caacataccc taccgagaac tcagagagtc    4200
gttggaagac gggaaggaag cccgacgact gagcggtcca ccccaggcgt gattccggtt    4260
gctctgcgtg attccggtcg cccggtggat caagcatgga agccgtcata aggtgatttt    4320
cgtccgcgtg taagacctat tgcgggaaaa cctctccttc taagaaggaa ataggggcta    4380
tgttgtccct gttacaaaag gaagggttgc ttacgtcccc ctcagactta tattccccgg    4440
ggtcctggga tctctgccct tgtgctgact cctgcacaca agagcatttc cctgtagcca    4500
aacagcgatt agccataagc tgcacctgac tttgaggatt aagagtttgc aattaagtgg    4560
attgcagcag gagatcagtg gcagggttgc agatgaaatc cttttctagg ggtagctaag    4620
ggctgagcaa cctgtcctac agcacaagcc aaaccagcca agggttttcc tgtgctgttc    4680
acagaggcag ggccagctgg agctggagga ggttgtgctg ggacccttct ccctgtgctg    4740
agaatggagt gatttctggg tgctgttcct gtggcttgca ctgagcagct caagggagat    4800
cggtgctcct catgcagtgc caaaactcgt gtttgatgca gaaagatgga tgtgcacctc    4860
cctcctgcta atgcagccgt gagcttatga aggcaatgag ccctcagtgc agcaggagct    4920
gtagtgcact cctgtaggtg ctagggaaaa tctctggttc ccaggatgc attcataagg     4980 gcaatatatc ttgaggctgc gccaaatctt tctgaaatat tcatgcgtgt tcccttaatt    5040
tatagaaaca acacagcag aataattatt ccaatgcctc ccctcgaagg aaacccatat     5100
ttccatgtag aaatgtaacc tatatacaca cagccatgct gcatccttca gaacgtgcca    5160
gtgctcatct cccatggcaa aatactacag gtattctcac tatgttggac ctgtgaaagg    5220
aaccatggta agaaacttcg gttaaaggta tggctgcaaa actactcata ccaaaacagc    5280
agagctccag acctcctctt aggaaagagc cacttggaga gggatggtgt gaaggctgga    5340
ggtgagagac agagcctgtc ccagttttcc tgtctctatt ttctgaaacg tttgcaggag    5400
```

-continued

| | |
|---|---|
| gaaaggacaa ctgtactttc aggcatagct ggtgccctca cgtaaataag ttccccgaac | 5460 |
| ttctgtgtca tttgttctta agatgctttg cagaacact ttgagtcaat tcgcttaact | 5520 |
| gtgactaggt ctgtaaataa gtgctccctg ctgataaggt tcaagtgaca tttttagtgg | 5580 |
| tatttgacag catttacctt gctttcaagt cttctaccaa gctcttctat acttaagcag | 5640 |
| tgaaaccgcc aagaaaccct tccttttatc aagctagtgc taaataccat taacttcata | 5700 |
| ggttagatac ggtgctgcca gcttcacctg gcagtggttg gtcagttctg ctggtgacaa | 5760 |
| agcctccctg gcctgtgctt ttacctagag gtgaatatcc aagaatgcag aactgcatgg | 5820 |
| aaagcagagc tgcaggcacg atggtgctga gccttagctg cttcctgctg ggagatgtgg | 5880 |
| atgcagagac gaatgaagga cctgtccctt actcccctca gcattctgtg ctatttaggg | 5940 |
| ttctaccaga gtccttaaga ggttttttttt tttttggtc aaaagtctg tttgtttggt | 6000 |
| tttgaccact gagagcatgt gacacttgtc tcaagctatt aaccaagtgt ccagccaaaa | 6060 |
| tcaattgcct gggagacgca gaccattacc tggaggtcag gacctcaata aatattacca | 6120 |
| gcctcattgt gccgctgaca gattcagctg gctgctccgt gttccagtcc aacagttcgg | 6180 |
| acgccacgtt tgtatatatt tgcaggcagc ctcgggggga ccatctcagg agcagagcac | 6240 |
| cggcagccgc ctgcagagcc gggcagtacc tcaacatgaa agaacctgca cttcctggta | 6300 |
| cttcactgca aagagcatgt agactgctgg tagcatttg cgccctgcac ctgagcgcaa | 6360 |
| ccctgctcta ctacctggct ggatccagcc tgactccacc ccgctctcca gaacctcccc | 6420 |
| ctcggaggcc gcctccagcc aacctctccc tgccaccctc ccggcctcct cctcccctg | 6480 |
| cggctcgccc ccgcccagga cctgtttctg cacaaccccg gaacctgcca gattctgcac | 6540 |
| catctggact gtgccccgat ccaagtccac tgctcgttgg tcctctgcgg gtggagttta | 6600 |
| gtcagccagt gaacctggag gaagtggctt ctaccaatcc ggaggtcagg gaaggaggga | 6660 |
| gattcgcccc aaaggactgc aaagcgctcc agaaggtggc tattattatc cccttcagga | 6720 |
| acagagagga gcacctgaag tattggctgt actacatgca cccgattctt cagagacagc | 6780 |
| aattggacta tggggtctat gtgattaatc aagacggcga tgaagaattt aacagagcta | 6840 |
| aactgcttaa tgtcggtttc actgaggcac tcaaggaata cgattatgat tgctttgtgt | 6900 |
| tttccgatgt ggatctgatt cctatggacg accgtaacac atataagtgc tatagtcaac | 6960 |
| cacgtcacct gagtgtgtca atggacaagt ttggctttag gctgccgtat aaccagtatt | 7020 |
| tcggaggagt ttcagcattg agtaaagaac agtttacaaa aatcaacggg ttcccaaata | 7080 |
| actactgggg gtgggcgga gaggacgacg acatctacaa cagactggtt tttaagggga | 7140 |
| tggggatttc ccgcccggat gcagtaatag gcaagtgtcg tatgatacgc catagcaggg | 7200 |
| atagaaagaa cgaacccaac cctgagcgct ttgaccggat tgcacataca agagaaacta | 7260 |
| tgtcatctga tggacttaac tctctttcat atgaggtgct gagaacagat cggttccccc | 7320 |
| tgtacactag aatcacagta gatatcgggg cacctgggtc ataagccgt tactggccga | 7380 |
| agccgcttgg aataaggccg gtgtgcgttt gtctatatgt tattttccac catattgccg | 7440 |
| tcttttggca atgtgagggc ccggaaacct ggccctgtct tcttgacgag cattcctagg | 7500 |
| ggtctttccc ctctcgccaa aggaatgcaa ggtctgttga atgtcgtgaa ggaagcagtt | 7560 |
| cctctggaag cttcttgaag acaaacaacg tctgtagcga ccctttgcag gcagcggaac | 7620 |
| cccccacctg gcgacaggtg cctctgcggc caaaagccac gtgtataaga tacacctgca | 7680 |
| aaggcggcac aaccccagtg ccacgttgtg agttggatag ttgtggaaag agtcaaatgg | 7740 |
| ctctcctcaa gcgtattcaa caaggggctg aaggatgccc agaaggtacc ccattgtatg | 7800 |

-continued

```
ggatctgatc tggggcctcg gtgcacatgc tttacgtgtg tttagtcgag gttaaaaaac      7860
gtctaggccc cccgaaccac ggggacgtgg ttttcctttg aaaaacacga tgataagctt      7920
gccacaacca tgggtctttt ggttttcatg agaaatctgc tgctggctct gtgtctgttc      7980
ctggtcctgg gatttctgta ctactctgca tggaagctcc acctgctgcg ctgggaggat      8040
agctctaaat atggacgcct gagccatagc tcttttccta agcaaagacc aagtgctgat      8100
tctgtggtct tgtcatttga ctctgttgga catactattg gctctgaata tgacaaactg      8160
ggttttctgc ttaaccttga ttctaaactt cccctgaat tggcctcaaa atatgccaac       8220
ttctctgagg gagtgtgcaa gcctggttat gcatctgccc tgatgactgt gattttccct      8280
aaattctcca acctgccccc catgttcctt gatgactcct tccggcgctg ggcccgcatt      8340
agagactttg tgcctccatt tggcattaaa gggcaggaca atctgataaa ggcaatactg      8400
tctgctacaa agattacag actcacacca gcactggaca gcttgtcatg ccgccgctgt       8460
atcattgttg gaatggtgg tgttctggcc aacaagagtt tgggtcttaa gattgatgac       8520
tatgatgtgg tcgttcgcct gaactctgca cctgtcaaag ctttgagaa agatgttggt       8580
ggaaagacaa cactgcggat cacttaccca gaggggcta ttcagaagat ggaacagtat       8640
gagaaagact ccctgtttgt gctggcggga tttaaatggc aagactttaa gtggctgaaa      8700
tatattgtgt ataagaaaa ggtctcagct tctgatggct tctggaaatc agtggctacc       8760
cgggtgcctc gggagccaca tgaaattcgc atactgaatc cctatttcat ccaagaagct      8820
gctttttcat tcattggcct gccattcaat aatggtctga tgggtcgggg gaatatcccc      8880
accctgggtt ctgtggccat cacaatggct ctgcataatt gtgatgaggt ggctgttgct      8940
ggctttggat atgacatgag ttcccctaat gctcccctgc attactatga gaacataaaa      9000
atgagtgcca ttaaggagtc atggactcat aatatacaac gggagaagga atttcttcgc      9060
aagctggtta agccagagt gattacagat cttacatctg ggatatgagg atccggtac       9119
```

<210> SEQ ID NO 4
<211> LENGTH: 2279
<212> TYPE: DNA
<213> ORGANISM: Gallus gallus

<400> SEQUENCE: 4

```
gcatcccgtc cccggcggcg gcgcggggcg ggcggcggtc cccgtcagcg cggcggcatg       60
aaggagccgg cgctgcccgg cacctcgctg cagcgggcct gccgcctcct cgtcgctttc      120
tgcgcgctgc acctctcggc cacgctgctc tactacctgg cgggcagctc cctgacgccg      180
ccgcgcagcc ccgagcctcc gccgcgccgc ccgcctcccg ccaacctctc gctgccgccc      240
tcccgcccgc cgccgccgcc cgccgccggc cccgacccg accggtctc ggcacagccc        300
cgcaacctcc cggactcggc gccgtcgggg ctgtgcccgg accgtccc gctgctcgtc         360
ggaccgctgc gcgtggagtt ctcccagcct gtgaacctgg aggaggtggc gagcacaaac      420
cctgaggtca gggagggagg tcgttttgct ccaaaggact gcaaggcgct gcagaaagta      480
gcaatcatca tcccgttccg aaaccgagag gagcatctga gtactggct ctattacatg       540
cacccaattc ttcaaaggca gcagctagat tatggagtgt atgtcatcaa ccaggatgga      600
gacgaagaat taaccgtgc taaactgctg aatgtaggat tcacggaagc tttgaaggag      660
tatgactatg actgctttgt gtttagtgat gtagacctga tcccaatgga tgacaggaac       720
acctacaagt gctacagcca accaaggcac ctttctgtct ccatggataa attcggattt        780
cggttacccct acaatcagta ttttggaggt gtgtctgcct tgagcaaaga acaattcacg        840
```

```
aagatcaatg ggtttccaaa caattactgg ggctggggag gcgaagatga tgacatctac    900
aacaggctgg tgttcaaagg catgggcata tctcggccag atgctgtcat ggggaaatgc    960
agaatgattc gccactcgcg tgatcggaag aacgagccca acccggagag gtttgaccgt   1020
attgctcaca ccagggagac gatgagctct gatggcttga actcgctctc ctacgaggtg   1080
ctaaggactg acaggttccc tctgtacacg aggatcacag tggatatcgg agcgcccggc   1140
agctgacacg gccggcacgg cggagacctc gggacggtgc cccgcacgct gggctggcag   1200
attctttgtg tcgtcgggtt ttataagggt tgtgatgaac aacacggagg tctctctgca   1260
tgtcagagcc tctccaaaag ggctggacga ctgcttttcc cgtcggttgt ttttgtaact   1320
ctgcctccag ctctccattg ttttgtaagt tcagaggctg tacgtaacag ttgtaaatac   1380
ttccttttg ccaggagatg ctgaatctga tccccgtgtt cggtcaccgc tggtcccggg    1440
ttagtttgcc aactgcagcc gtggtgcacc agcagcgacc gcccatgata cggctttctt   1500
cttttttaat tgggtggacg aaaacattcc ttttaattca ttcctcgttt ttatctctat   1560
gaaggactgt aaaacgctgc taaaattgta tgagtttact catttcgtta gattgttttt   1620
tgttttttt ttaagagagg caaaattacg tggggtttct tcttctttt tttcttccta    1680
ctggtgacca aagcaaacaa tcttctccgc gtgcagagcg catgacgaat aaccaagtgt   1740
ggattcagca cacctcacta ttcctttcgg tctcaaaaga gacttccgag cgagctgagg   1800
cagatgtgcc ctcggagagc tctgtgcgtg ggctgggagc cgcagggatg tgcagcagag   1860
ctctccatga cccgcagcag ctgctggctc cccataacct gctgtcgggt gtggtttat    1920
tttatttat tttatcttt cttgcctggg cagagcaaga cacctgggag atctcttcgg    1980
tcggtcggtc agtttggttt gcttgtttgc tcttccccca aaagagcgga tgggtttaat   2040
tgcacaagga attgatagcc ttaaaattca cagacacttt taccagtggt aggaagttgc   2100
cacgctattt aaacatggtc tgaaggttct taagaacgac attctgcttg caaggtcatg   2160
tgtgaaactt gaactcactt attactttta ttgttgttgt aacttttga taacttttaa     2220
aagtaatttg tatatcctaa gcggtatatt taataccaga ttaaagcagg gtgcagcat    2279
```

<210> SEQ ID NO 5
<211> LENGTH: 362
<212> TYPE: PRT
<213> ORGANISM: Gallus gallus

<400> SEQUENCE: 5

```
Met Lys Glu Pro Ala Leu Pro Gly Thr Ser Leu Gln Arg Ala Cys Arg
1               5                   10                  15

Leu Leu Val Ala Phe Cys Ala Leu His Leu Ser Ala Thr Leu Leu Tyr
            20                  25                  30

Tyr Leu Ala Gly Ser Ser Leu Thr Pro Pro Arg Ser Pro Glu Pro Pro
        35                  40                  45

Pro Arg Arg Pro Pro Ala Asn Leu Ser Leu Pro Pro Ser Arg Pro
    50                  55                  60

Pro Pro Pro Pro Ala Ala Arg Pro Arg Pro Gly Pro Val Ser Ala Gln
65                  70                  75                  80

Pro Arg Asn Leu Pro Asp Ser Ala Pro Ser Gly Leu Cys Pro Asp Pro
                85                  90                  95

Ser Pro Leu Leu Val Gly Pro Leu Arg Val Glu Phe Ser Gln Pro Val
            100                 105                 110

Asn Leu Glu Glu Val Ala Ser Thr Asn Pro Glu Val Arg Glu Gly Gly
        115                 120                 125
```

```
Arg Phe Ala Pro Lys Asp Cys Lys Ala Leu Gln Lys Val Ala Ile Ile
        130                 135                 140

Ile Pro Phe Arg Asn Arg Glu Glu His Leu Lys Tyr Trp Leu Tyr Tyr
145                 150                 155                 160

Met His Pro Ile Leu Gln Arg Gln Gln Leu Asp Tyr Gly Val Tyr Val
                165                 170                 175

Ile Asn Gln Asp Gly Asp Glu Glu Phe Asn Arg Ala Lys Leu Leu Asn
            180                 185                 190

Val Gly Phe Thr Glu Ala Leu Lys Glu Tyr Asp Tyr Asp Cys Phe Val
        195                 200                 205

Phe Ser Asp Val Asp Leu Ile Pro Met Asp Asp Arg Asn Thr Tyr Lys
    210                 215                 220

Cys Tyr Ser Gln Pro Arg His Leu Ser Val Ser Met Asp Lys Phe Gly
225                 230                 235                 240

Phe Arg Leu Pro Tyr Asn Gln Tyr Phe Gly Gly Val Ser Ala Leu Ser
                245                 250                 255

Lys Glu Gln Phe Thr Lys Ile Asn Gly Phe Pro Asn Asn Tyr Trp Gly
            260                 265                 270

Trp Gly Gly Glu Asp Asp Asp Ile Tyr Asn Arg Leu Val Phe Lys Gly
        275                 280                 285

Met Gly Ile Ser Arg Pro Asp Ala Val Ile Gly Lys Cys Arg Met Ile
    290                 295                 300

Arg His Ser Arg Asp Arg Lys Asn Glu Pro Asn Pro Glu Arg Phe Asp
305                 310                 315                 320

Arg Ile Ala His Thr Arg Glu Thr Met Ser Ser Asp Gly Leu Asn Ser
                325                 330                 335

Leu Ser Tyr Glu Val Leu Arg Thr Asp Arg Phe Pro Leu Tyr Thr Arg
            340                 345                 350

Ile Thr Val Asp Ile Gly Ala Pro Gly Ser
        355                 360

<210> SEQ ID NO 6
<211> LENGTH: 2420
<212> TYPE: DNA
<213> ORGANISM: Gallus gallus

<400> SEQUENCE: 6
gtggcggtgg cccggccggc agggcccccg cagccccggc atgggcgccc gcggccggcg      60
gccgggggaa gcggcggggg ccgctgacgc gccggggccg cgggaggagg tggtggcggc     120
ggtggcggcg gcggggacg tgcggggcg ccgcggatc gggaccgtgg ctggagctgc       180
ctgcctccct gtgcccagaa gatgaccagg ttgctcttgg gggtgaccct ggaaaggatt     240
tgcaaggccg tgctgctgct ctgcctgctc cactttgtca tcatcatgat tctctacttt     300
gacgtctacg cgcagcacct ggacttcttc agccgcttca tgccaggaa cacctcgcgc     360 gtgcacccct tctccaactc ctctcggccc aacagcacgg cccccagcta cggcccacgt     420
ggcgctgagc cccctccccc cagcgccaag cccaacacca accgctccgt cacagagaag     480
cccttgcagc cctgccagga gatgccctcc ggcttagtcg gcgcctgct cattgagttc     540 agctccccta tgagcatgga gcgggtgcaa cgggagaacc ctgacgtgag cctgggtggc     600
aagtacaccc cccagattg cctgcccggg cagaaggtgg ccatcctcat ccccttccgg     660
caccgcgagc accacctcaa atactggctg cactacctgc accccatcct gcgccggcag     720
aaggtggctt atgcatcta catcatcaac cagtatggcg aggacacctt caaccgggcc     780
aagctgctca atgtgggctt cctggagcg ctgaaggatg acgaggagta cgactgcttc     840
```

```
attttcagcg atgtggacct catccccatg gatgaccgca acctgtaccg ctgctatgag    900
cagccacggc actttgctgt tggcatggac aagtttgggt tcaggttgcc ctatgcaggg    960
tacttcggtg gtgtctctgg gctgagcaag tcccagttcc taaagatcaa cggcttcccc   1020
aacgagtact ggggctgggg aggagaggac gacgacatct taaccggat ctccctgaat    1080 ggcatgaagg tgtcgaggcc cgacatccgc atggggaggt atcgcatgat caagcacgaa   1140
cgtgacaaac acaacgagcc caaccccag agattcacca gatccagaa caccaaaatg     1200 accatgaagc gggatgggat cagctcactg cagtaccggc tggtggaggt gtcacgccag   1260
cccatgtaca ccaacatcac ggtggagatt ggcaggccgc ccccacgctt ggcccggggc   1320
tagtgcttgc cctgcaggca aagctgcatg aggctggcgc tctgtcgcag ggctggctgg   1380
acgctgtgga tgttgcccca gcccctgggc aaggactgaa cggggatgtt ttctgcctac   1440
tctgctgcct tttggagacg ctgtgcccca gcctacctgt tggtcctgag gatttctgca   1500
atctgttgtc cctcctttcc ccatccctac aagtgtgttt ccagaacccc catactatgc   1560
gtgttggctg aagcacccgt tcgccctgcg tgcagctccc agacagaggg aggggacagt   1620
cccagccctg gtgaggagcc ccttgccac gtcacgtccc gcctgcaccc taggagggaa    1680
ggatgagccc caaggtcagc ctagccccca gtccccaccg gtgctgcgag aagcgggatg   1740
caggcttccc ccttcaccag cgctggagct gctactaccc tggctgaagg catgggaggt   1800
agcccaggcc cccacagcag gcaggatcgg acagacagat gtggctcact gtcttcctct   1860
gctttagtct ggtgctcagg gctgggtctc agctctgcta acagcgacc tctggttagc    1920 aaacacccct tgctgtgcct cagtttcccc gggctggcag ccacgtcccc tttcccctct   1980
ctgaaggcag atgctgtgtg cgtgtccctg ttaacccaca catgcaccag ctctcccaac   2040
tttgggcagt agggtgacgt gaaacctcac agcccctctt ggccagggt ctgccccggg    2100 gaatctccac ccagatgctg tttgtaggca gtggggactg gctgctctgc ccttgctgct   2160
ctccagcttc ccctctctgc tctggggcag ggagaagagg aacagggcca tgcggcaggt   2220
gccccatctc tccccacttc ccctccttgg ggctggggca cagccacccc cctgcagcca   2280
gctagaagag ctgggcagca ggggcactgg caacttttgt acatttgaat gtctgaccct   2340
ttttttgagc gtacgttgaa tgcagcattc ggtcatagag acctgggttt ttgtatttaa   2400
taaaaatttc aaaagttaac                                               2420
```

<210> SEQ ID NO 7
<211> LENGTH: 373
<212> TYPE: PRT
<213> ORGANISM: Gallus gallus

<400> SEQUENCE: 7

```
Met Thr Arg Leu Leu Leu Gly Val Thr Leu Glu Arg Ile Cys Lys Ala
1               5                   10                  15

Val Leu Leu Leu Cys Leu Leu His Phe Val Ile Met Ile Leu Tyr
            20                  25                  30

Phe Asp Val Tyr Ala Gln His Leu Asp Phe Phe Ser Arg Phe Asn Ala
            35                  40                  45

Arg Asn Thr Ser Arg Val His Pro Phe Ser Asn Ser Ser Arg Pro Asn
        50                  55                  60

Ser Thr Ala Pro Ser Tyr Gly Pro Arg Gly Ala Glu Pro Pro Ser Pro
65                  70                  75                  80

Ser Ala Lys Pro Asn Thr Asn Arg Ser Val Thr Glu Lys Pro Leu Gln
                85                  90                  95
```

Pro Cys Gln Glu Met Pro Ser Gly Leu Val Gly Arg Leu Leu Ile Glu
            100                 105                 110

Phe Ser Ser Pro Met Ser Met Glu Arg Val Gln Arg Glu Asn Pro Asp
            115                 120                 125

Val Ser Leu Gly Gly Lys Tyr Thr Pro Pro Asp Cys Leu Pro Arg Gln
130                 135                 140

Lys Val Ala Ile Leu Ile Pro Phe Arg His Arg Glu His His Leu Lys
145                 150                 155                 160

Tyr Trp Leu His Tyr Leu His Pro Ile Leu Arg Arg Gln Lys Val Ala
                165                 170                 175

Tyr Gly Ile Tyr Ile Ile Asn Gln Tyr Gly Glu Asp Thr Phe Asn Arg
            180                 185                 190

Ala Lys Leu Leu Asn Val Gly Phe Leu Glu Ala Leu Lys Asp Asp Glu
            195                 200                 205

Glu Tyr Asp Cys Phe Ile Phe Ser Asp Val Asp Leu Ile Pro Met Asp
210                 215                 220

Asp Arg Asn Leu Tyr Arg Cys Tyr Glu Gln Pro Arg His Phe Ala Val
225                 230                 235                 240

Gly Met Asp Lys Phe Gly Phe Arg Leu Pro Tyr Ala Gly Tyr Phe Gly
                245                 250                 255

Gly Val Ser Gly Leu Ser Lys Ser Gln Phe Leu Lys Ile Asn Gly Phe
            260                 265                 270

Pro Asn Glu Tyr Trp Gly Trp Gly Gly Glu Asp Asp Asp Ile Phe Asn
            275                 280                 285

Arg Ile Ser Leu Asn Gly Met Lys Val Ser Arg Pro Asp Ile Arg Met
290                 295                 300

Gly Arg Tyr Arg Met Ile Lys His Glu Arg Asp Lys His Asn Glu Pro
305                 310                 315                 320

Asn Pro Gln Arg Phe Thr Lys Ile Gln Asn Thr Lys Met Thr Met Lys
                325                 330                 335

Arg Asp Gly Ile Ser Ser Leu Gln Tyr Arg Leu Val Glu Val Ser Arg
            340                 345                 350

Gln Pro Met Tyr Thr Asn Ile Thr Val Glu Ile Gly Arg Pro Pro
            355                 360                 365

Arg Leu Ala Arg Gly
            370

<210> SEQ ID NO 8
<211> LENGTH: 1830
<212> TYPE: DNA
<213> ORGANISM: Gallus gallus

<400> SEQUENCE: 8
atgtccctgt cccgcgtgga gaacccctgc ttcctgctgt tcctgctcgt cttccaagcc    60
gtgttcatcc tgatactgta ccgaggtgga gcctcgagcg tgttccgggg cttttggag   120 tcgcagcgcg tttggatta ctccaaaagc acgacgtgt acacgaacct cagcctgctg   180
gccccggctg gcggcggggc ggcgctgccc tactgctcgg agcgctcacc catcgccgtt   240
ggtccattaa ccatcacttt tgacgtgctc cctagtgaaa gaacgatcat ccaaaaaaat   300
ccttttgttc agtccggagg ccactacaga ccacctcact gcttggcccg ctacaagtca   360
gccatccttg tagcatacag taaccaggag aaataccttc accatcttct ctactacatt   420
catcctttct tgcagcgcca gcagctcagc tacagaatct acttgattca gcaggtgggg   480
aatggtacgt ttaaccgagc aaagctgctt aatgttggtg tccgagaagc cctgaaggat   540

```
gaagactggg actgcctcct cctgcacgat gtgaacctgg tacctgagaa tgattataat    600
ctctatgtct gtgatgaata ctatcccaaa catatggcta gtgccatgga taaatttcag    660
tacaaccttc cctacaagtc cttttttgga ggtgtatctg cattgactcc agagcactac    720
atgaagatga atgggtttcc aaacacatac tggggcgacg gtggtgaaac agatgacatt    780
gctgcaagga tccagttagc aggcatgaga attgtccgga ccccaccaca ccttggacgc    840
tacaaagtga tggactacaa cagagagaca gaagagcctt ggagaaggcc tgcttcccac    900
cacaacactg gaaaaacttg gaaggatgat gggatgaact ctttagagtt caagctcctt    960
tccagaacaa agcatcctct ttataccaac gtcactgtgg acattggata tgttcccccc   1020 tttctcttaag ataatgaaaa ctgaaacgtg tgttggaat tcactgtggc agcacagtta   1080
tgggtactca gcctctacct ctggctgcgg tgcagtctgc agcacctgag actaatcctg   1140
gtgtctttca tacattgaac tttcttcgg attataggag ctttgaagaa aaaggcttca   1200
ggagtgagac atgatagcta caaacaggag ctggcttact gtagaagtcc tttaaagcac   1260
tgtaaaactg agccaaatct acatgtcatg cctcaggctg gatagagact gtctccttga   1320
cagtaagttg acccaagttt tctggaacct ttgttccgta acgggatggc tctgccctgc   1380
tccttactca actggtaagt gggattcagg ctgtcctgtc agtcctctca aatgctgtat   1440
tttgagaaag atcttacttg tgttgaagc ctattacagt tctgtaaata ctctttgtga   1500
atttgtgtca agaaagttga ggtgtgtttg tttggattaa gattttccta gagtatttaa   1560
taagacttta ataaggaga aagttgccct gaagttggtt gaaactagag cttaaaaatt   1620
cctggttgtc tggccacatt atgaatgagt gtgtgagttc ttactgtagc cataagtaat   1680
tcacatctaa agaggcctca gactgtcagc tatgctcagc agatggaaat taatctacca   1740
tttcagccat tgctcaaatg ttaattatct ctcaaggttg atctgtattc aattaaaaca   1800
cttctgagaa atgaaatact agaggaaaaa                                    1830
```

<210> SEQ ID NO 9
<211> LENGTH: 342
<212> TYPE: PRT
<213> ORGANISM: Gallus gallus

<400> SEQUENCE: 9

```
Met Ser Leu Ser Arg Val Glu Asn Pro Cys Phe Leu Leu Phe Leu Leu
1               5                   10                  15

Val Phe Gln Ala Val Phe Ile Leu Ile Leu Tyr Arg Gly Gly Ala Ser
            20                  25                  30

Ser Val Phe Arg Gly Phe Leu Glu Ser Gln Arg Val Leu Asp Tyr Ser
        35                  40                  45

Lys Ser His Asp Val Tyr Thr Asn Leu Ser Leu Leu Ala Pro Ala Gly
    50                  55                  60

Gly Gly Ala Ala Leu Pro Tyr Cys Ser Glu Arg Ser Pro Ile Ala Val
65                  70                  75                  80

Gly Pro Leu Thr Ile Thr Phe Asp Val Leu Pro Ser Glu Arg Thr Ile
                85                  90                  95

Ile Gln Lys Asn Pro Phe Val Gln Ser Gly Gly His Tyr Arg Pro Pro
            100                 105                 110

His Cys Leu Ala Arg Tyr Lys Ser Ala Ile Leu Val Ala Tyr Ser Asn
        115                 120                 125

Gln Glu Lys Tyr Leu His Leu Leu Tyr Tyr Ile His Pro Phe Leu
    130                 135                 140
```

-continued

```
Gln Arg Gln Gln Leu Ser Tyr Arg Ile Tyr Leu Ile Gln Gln Val Gly
145                 150                 155                 160

Asn Gly Thr Phe Asn Arg Ala Lys Leu Leu Asn Val Gly Val Arg Glu
            165                 170                 175

Ala Leu Lys Asp Glu Asp Trp Asp Cys Leu Leu Leu His Asp Val Asn
        180                 185                 190

Leu Val Pro Glu Asn Asp Tyr Asn Leu Tyr Val Cys Asp Glu Tyr Tyr
    195                 200                 205

Pro Lys His Met Ala Ser Ala Met Asp Lys Phe Gln Tyr Asn Leu Pro
210                 215                 220

Tyr Lys Ser Phe Phe Gly Gly Val Ser Ala Leu Thr Pro Glu His Tyr
225                 230                 235                 240

Met Lys Met Asn Gly Phe Pro Asn Thr Tyr Trp Gly Asp Gly Gly Glu
            245                 250                 255

Thr Asp Asp Ile Ala Ala Arg Ile Gln Leu Ala Gly Met Arg Ile Val
        260                 265                 270

Arg Thr Pro Pro His Leu Gly Arg Tyr Lys Val Met Asp Tyr Asn Arg
    275                 280                 285

Glu Thr Glu Pro Trp Arg Arg Pro Ala Ser His His Asn Thr Gly
290                 295                 300

Lys Thr Trp Lys Asp Asp Gly Met Asn Ser Leu Glu Phe Lys Leu Leu
305                 310                 315                 320

Ser Arg Thr Lys His Pro Leu Tyr Thr Asn Val Thr Val Asp Ile Gly
            325                 330                 335

Tyr Val Pro Pro Phe Ser
        340

<210> SEQ ID NO 10
<211> LENGTH: 1836
<212> TYPE: DNA
<213> ORGANISM: Gallus gallus

<400> SEQUENCE: 10
ggggcaccgg cggcagagag gcccggggag gttaagtcat gttttctgac actcgaagaa      60
cagtcagcgc tgcaattcca tgagtcacag aaccacaaga agtgcggctg ccctccctac     120
atgcagcttc ccttctttac tgtaacgttc ttcttggcac ctctggcttc ttccctactg     180
agtgcacagc gggggaccca cggtggcatc ggggggagcg atggccataa gcttgtatgt     240
atttcacttc ttcaataagt tcaaagtgtt ccttcttgtc accttgtgtt tgatgatgct     300
atgggctgcg ttcagttact ttgtggattc tggacagaca attcctaaac ttaagagtgt     360
gggggagcat tttggaaaga taatcagctt ggagaagaaa gaggacagtc agaaggaaga     420
aaagatgaag ataactgaag gagttcctgc aacaaagcca cctcagggtc cctgtccagc     480
tctgtctccg tacctgcgag gtgccagcaa actgaccttc agtccatctc tcacgctaga     540
agaagtggaa aaggagaacc ctcaggtggc caagggccga taccaccctg cagagtgttc     600
agccttgcag cgtgtggcca tcctcatccc gcaccgcaac cgtgagaggc atctgctgta     660
cctcctggag cacctgcacc cgttcctgca gaggcagcag ctggaatatg catctacgt     720 tatccaccag gctggcagca ccaaatttaa tcgagctaaa ctgctgaacg tgggatactt     780
agaggcccta aaagaagaga actgggactg tttcattttc catgacgtgg atctggtgcc     840
agagaatgac ttcaatattt acatgtgtga cagacaaccc aagcaccttg tagttggccg     900
gaacagtact ggatacaggt tacgttacca gggatatttt ggaggcgtaa cagctctaac     960
aagagaccag tttttccatgg tgaatggatt ctctaacaac tattggggtt ggggcggaga    1020
```

```
agatgacgac cttcgaatca gggttgagat gcagaagatg cgagtgatga ggccatctgc   1080
tgatgtagcc agatacacaa tgatcttcca caaccgtgac catggcaatg aggagaacag   1140
agagaggatg aagcttctgc gtcaggtatc tagaacatgg aaaacagatg ggttgaattc   1200
ctgttcctat agactgctgt cagtggaaca taacccttta tacatcaaca tcacggtaga   1260
tttcagcatg cagccaaaga tctcataggg gtgagcaccg cacaggtttt aggaaatggc   1320
agcagatcct gtttgtggtt ggtggcacag cagatgactt gcagcgctct gcttgaaaga   1380
gtactttagc agcacagaag aatgtttttc tgcatggcat ctaattagtc agcagagaag   1440
ctcattttct gaggactgga gaggcggact gaccccctggg caggtcctgg tgttcttcta   1500
tgcactttct gctgagatgt tcgcaagttt ccttgtttgg gctggtccag tagaaggact   1560
tgaatcaagt ctcctgaaag aaatatttct taaaactatt cctgaacttc cagtttgaag   1620
taggaaggtg acactgccaa ggcttcaaaa ggagcaggcc agtcttttcc cctcaaaagc   1680
acaagaattt tttaccatct ataaacttgt tgagaaaagc ttgtttcttc tagcctgaag   1740
aaaaactgct tgtggggtgg aacagcaat aatggtaata ggggagaaat gattaaaaaa   1800
atctctcaat aaaatataat ctgcttaatt caaaaa                             1836

<210> SEQ ID NO 11
<211> LENGTH: 355
<212> TYPE: PRT
<213> ORGANISM: Gallus gallus

<400> SEQUENCE: 11

Met Ala Ile Ser Leu Tyr Val Phe His Phe Asn Lys Phe Lys Val
1               5                   10                  15

Phe Leu Leu Val Thr Leu Cys Leu Met Met Leu Trp Ala Ala Phe Ser
            20                  25                  30

Tyr Phe Val Asp Ser Gly Gln Thr Ile Pro Lys Leu Lys Ser Val Gly
        35                  40                  45

Glu His Phe Gly Lys Ile Ile Ser Leu Glu Lys Lys Glu Asp Ser Gln
    50                  55                  60

Lys Glu Glu Lys Met Lys Ile Thr Glu Gly Val Pro Ala Thr Lys Pro
65                  70                  75                  80

Pro Gln Gly Pro Cys Pro Ala Leu Ser Pro Tyr Leu Arg Gly Ala Ser
                85                  90                  95

Lys Leu Thr Phe Ser Pro Ser Leu Thr Leu Glu Glu Val Glu Lys Glu
            100                 105                 110

Asn Pro Gln Val Ala Lys Gly Arg Tyr His Pro Ala Glu Cys Ser Ala
        115                 120                 125

Leu Gln Arg Val Ala Ile Leu Ile Pro His Arg Asn Arg Glu Arg His
    130                 135                 140

Leu Leu Tyr Leu Leu Glu His Leu His Pro Phe Leu Gln Arg Gln Gln
145                 150                 155                 160

Leu Glu Tyr Gly Ile Tyr Val Ile His Gln Ala Gly Ser Thr Lys Phe
                165                 170                 175

Asn Arg Ala Lys Leu Leu Asn Val Gly Tyr Leu Glu Ala Leu Lys Glu
            180                 185                 190

Glu Asn Trp Asp Cys Phe Ile Phe His Asp Val Asp Leu Val Pro Glu
        195                 200                 205

Asn Asp Phe Asn Ile Tyr Met Cys Asp Arg Gln Pro Lys His Leu Val
    210                 215                 220

Val Gly Arg Asn Ser Thr Gly Tyr Arg Leu Arg Tyr Gln Gly Tyr Phe
```

```
                225                 230                 235                 240
Gly Gly Val Thr Ala Leu Thr Arg Asp Gln Phe Ser Met Val Asn Gly
                    245                 250                 255

Phe Ser Asn Asn Tyr Trp Gly Trp Gly Gly Glu Asp Asp Asp Leu Arg
                260                 265                 270

Ile Arg Val Glu Met Gln Lys Met Arg Val Met Arg Pro Ser Ala Asp
            275                 280                 285

Val Ala Arg Tyr Thr Met Ile Phe His Asn Arg Asp His Gly Asn Glu
        290                 295                 300

Glu Asn Arg Glu Arg Met Lys Leu Leu Arg Gln Val Ser Arg Thr Trp
305                 310                 315                 320

Lys Thr Asp Gly Leu Asn Ser Cys Ser Tyr Arg Leu Leu Ser Val Glu
                325                 330                 335

His Asn Pro Leu Tyr Ile Asn Ile Thr Val Asp Phe Ser Met Gln Pro
                340                 345                 350

Lys Ile Ser
        355

<210> SEQ ID NO 12
<211> LENGTH: 1773
<212> TYPE: DNA
<213> ORGANISM: Gallus gallus

<400> SEQUENCE: 12
atgcccatgt gttcaaaggc tacctcagat tttctggagc catcactgtg tgtcccagaa      60
caatgcctgg atatcctgag ccatccctat atgccccag gaccatgtcc aggcgtccta     120
agactatcac cagttgtccc atggtcatca ctggtgcttg gatgccatca tcgtttgtcc     180
cagaaccccca ctaaggtgcc ccaaggccat tactgcctgc tcaaggcca gctctggcat     240
tctgaggcca ccgctcagcg tccccagcat cgtgcccggg tgtcgtgggg ctcccatcga     300
ctgtcacagg gccacctctg tttccctggg gaagctattg tgagaacag agcgaggggc     360
gggcggcgca cgtcatcctt tgccgaagaa cactcccagc agcatgctct gcagcgggg      420
ccggagtttg cagccggttc tcgctccgcc tcgccccgcc cgccccgcc cgcgtcgct      480
gtggctcctt catgcggcgg cgttgggcgc gggcggtggc tcggagcggc tgcggtgcag     540
cgcttcccgc cgggcctcgg cgcatgtgag cggcagggcg gcggcacatc ggccatgcgg     600
tggcccccgcg gccccccgcgg cgcctggcgg ctgttgcccc ggcgctcgct gctggccgtg     660
ctcttcctct tctcgctctc ctcctccttc tctacttcg tatatgtggc gccgggcatc     720
gtgaacacct acctcttcat gatgcaagcc caaggcatca tgattcgtga aaacatgaga     780
acaataggag ctcaggtgta tgaacaggtg gtccgcagtg cctatgccaa aggaacagc     840
agtgtgaatg actcagatta tcctcttgac ttgaatcaca atgaaacctt tctgcaagct     900
acaactttc ttcctgaaga ttttacgtac ttccccaacc acacctgtcc tgagaggctc     960
ccttctatga agggccccat tgatgtaaat atgagcgaga ttacgatgga ggacatccac    1020
cagttcttct ccagagaccc ttccatcaag ctgggaggcc actggaagcc gagcgactgc    1080
ctgcctcgct ggaaggtggc gatcctgatc ccattccgca atcgctatga acatcttcca    1140
gtccttttca ggcaccttat tccaatgctg cagcgtcagc gtttacagtt tgcattttat    1200
gttgtggaac aagctggtac tcagcccttc aaccgtgcca tgctcttcaa tgttggcttt    1260
cgggaagcga tgaaggactt ggactgggac tgtctcatct ccatgatgt ggaccacata    1320
ccagaaaatg accgcaacta ttatgggtgt ggacagatgc cgagacactt tgcggccaag    1380
```

```
ctggacaagt acatgtacct gttgccctat aatgaattct tcggtggagt gagcggcctg   1440
actgttgagc agttctggaa gattaatggt ttcccaaatg ccttctgggg ctggggcggt   1500
gaggatgacg acttatggaa cagagtgcag tatgcaggct attcagtgac tcgaccagaa   1560
ggagacacag gaaaatacaa atcaattccc caccatcatc gaggagaagt gcagttccta   1620
ggaaggtatg ccttgctgag gaagtcaaaa gaaaggcaag ccctggatgg cctcaataat   1680
ttgaactact ttcctaatgt cacatatgac gccttgtata agaacatcac tgttaacctg   1740
acaccagagc tggctctggt aactgaatat taa                                1773

<210> SEQ ID NO 13
<211> LENGTH: 392
<212> TYPE: PRT
<213> ORGANISM: Gallus gallus

<400> SEQUENCE: 13

Met Arg Trp Pro Arg Gly Pro Arg Gly Ala Trp Arg Leu Leu Pro Arg
1               5                   10                  15

Arg Ser Leu Leu Ala Val Leu Phe Leu Phe Ser Leu Ser Ser Ser Phe
            20                  25                  30

Leu Tyr Phe Val Tyr Val Ala Pro Gly Ile Val Asn Thr Tyr Leu Phe
        35                  40                  45

Met Met Gln Ala Gln Gly Ile Met Ile Arg Glu Asn Met Arg Thr Ile
    50                  55                  60

Gly Ala Gln Val Tyr Glu Gln Val Arg Ser Ala Tyr Ala Lys Arg
65                  70                  75                  80

Asn Ser Ser Val Asn Asp Ser Asp Tyr Pro Leu Asp Leu Asn His Asn
                85                  90                  95

Glu Thr Phe Leu Gln Ala Thr Thr Phe Leu Pro Glu Asp Phe Thr Tyr
            100                 105                 110

Phe Pro Asn His Thr Cys Pro Glu Arg Leu Pro Ser Met Lys Gly Pro
        115                 120                 125

Ile Asp Val Asn Met Ser Glu Ile Thr Met Glu Asp Ile His Gln Phe
    130                 135                 140

Phe Ser Arg Asp Pro Ser Ile Lys Leu Gly Gly His Trp Lys Pro Ser
145                 150                 155                 160

Asp Cys Leu Pro Arg Trp Lys Val Ala Ile Leu Ile Pro Phe Arg Asn
                165                 170                 175

Arg Tyr Glu His Leu Pro Val Leu Phe Arg His Leu Ile Pro Met Leu
            180                 185                 190

Gln Arg Gln Arg Leu Gln Phe Ala Phe Tyr Val Val Glu Gln Ala Gly
        195                 200                 205

Thr Gln Pro Phe Asn Arg Ala Met Leu Phe Asn Val Gly Phe Arg Glu
    210                 215                 220

Ala Met Lys Asp Leu Asp Trp Asp Cys Leu Ile Phe His Asp Val Asp
225                 230                 235                 240

His Ile Pro Glu Asn Asp Arg Asn Tyr Tyr Gly Cys Gly Gln Met Pro
                245                 250                 255

Arg His Phe Ala Ala Lys Leu Asp Lys Tyr Met Tyr Leu Leu Pro Tyr
            260                 265                 270

Asn Glu Phe Phe Gly Gly Val Ser Gly Leu Thr Val Glu Gln Phe Trp
        275                 280                 285

Lys Ile Asn Gly Phe Pro Asn Ala Phe Trp Gly Trp Gly Gly Glu Asp
    290                 295                 300

Asp Asp Leu Trp Asn Arg Val Gln Tyr Ala Gly Tyr Ser Val Thr Arg
```

```
                305                 310                 315                 320
        Pro Glu Gly Asp Thr Gly Lys Tyr Lys Ser Ile Pro His His His Arg
                        325                 330                 335
        Gly Glu Val Gln Phe Leu Gly Arg Tyr Ala Leu Leu Arg Lys Ser Lys
                        340                 345                 350
        Glu Arg Gln Ala Leu Asp Gly Leu Asn Asn Leu Asn Tyr Phe Pro Asn
                        355                 360                 365
        Val Thr Tyr Asp Ala Leu Tyr Lys Asn Ile Thr Val Asn Leu Thr Pro
                        370                 375                 380
        Glu Leu Ala Leu Val Thr Glu Tyr
        385                 390

<210> SEQ ID NO 14
<211> LENGTH: 4819
<212> TYPE: DNA
<213> ORGANISM: Gallus gallus

<400> SEQUENCE: 14
```

| | | | | | |
|---|---|---|---|---|---|
| gagagcgggc | gcccagcggc | gggagcggcc | cccgagcccc | gcggcagcgc | taggggaccc | 60 |
| ttcccgctca | ggccgccgcc | tcctcggctc | tacgggccct | ccgccgggcg | gtgggagcgg | 120 |
| cgggagcgaa | gcacagccct | cgccccgtc | ccgccgccgc | tccatgggag | gagcccgccg | 180 |
| ccgccctgcg | ggaagcgcgg | ccgccgcgcg | ccgggattga | gggagcggg | cagctctgag | 240 |
| acggcgggag | gatgcccctg | ttccggaagg | tgctgcgcgt | ctccaatcgc | tccatgctcg | 300 |
| ccttcatctt | cttcttctcc | ttctcctcct | cctgcctcta | cttcatctac | gtggcccccg | 360 |
| gcatagcaaa | tacatatctc | ttcatggtgc | aagcacgtgg | tataatgttg | agagaaaatg | 420 |
| taaaaacaat | aggacacatg | atcagattgt | atactaacaa | aaatacaaca | ctgaatggaa | 480 |
| cagattatcc | tgaaggaaac | aattctagtg | actgtgttgc | tcaaacaaca | atgtatcttc | 540 |
| cagaaaactt | cacttactct | ccttaccagg | cttgtccgga | gaaactgcct | acatgagag | 600 |
| gccttattga | tgtaaatatg | agtgaaatta | gttttgatga | aattcagcaa | ctattttcaa | 660 |
| aagacttgga | cattaaacca | ggaggacact | ggaaacccaa | agactgtaag | ccacgatgga | 720 |
| aggtggcgat | catcattcct | tttcgtaatc | gtcacgagca | tcttccaatt | ttcttccggc | 780 |
| atctgatacc | gatgttgcag | aagcagcggc | tggaatttgc | cttctatgtt | gttgaacaga | 840 |
| caggtacaca | acctttaat | cgtgcaatgc | tttttaacgt | tggcttcaag | gaggccatga | 900 |
| aggatgttgt | ctgggactgc | ataatatttc | atgatgtgga | tcacttacct | gaaaatgacc | 960 |
| gaaattatta | cggatgtgga | gaaatgccac | gtcattttgc | agcaaagttg | gacaaataca | 1020 |
| tgtacattct | tccatacaat | gagttctttg | tggtgtaag | tggactgaca | gtggaacaat | 1080 |
| tcaagaagat | taatggattt | ccaaatgcct | tctggggttg | gggtggagaa | gatgatgatc | 1140 |
| tttggaacag | ggttcactat | gctggataca | acgtaacaag | accagaggga | gacttaggga | 1200 |
| aatacaaatc | cattcctcat | catcacagag | gtgaagtcca | gttttagga | agatataaac | 1260 |
| ttctgaggta | ttccagagaa | cgtcagtata | ttgatgggtt | gaacaattta | gtatatactc | 1320 |
| ctaaaatact | tgtcagtaga | ttgtataaaa | atgtaactgt | taatcttatg | ccagaacttg | 1380 |
| ctcctattag | agactattga | tggaaatggt | gtgacaagct | atcctactgg | agtaaacttt | 1440 |
| taatgcactg | gaaggtatta | atagacactg | aagacgctgt | aaaacaaaac | aaaaaatcac | 1500 |
| aacaatcaac | gtcttagaat | tagggatctt | tgtccatttg | atgatgcata | tttgggatga | 1560 |
| gaagtaaagt | gattgtatgt | gccgtgcatt | ctgttcagaa | agaaaagcca | gcagctacca | 1620 |
| ctcagatgtt | tacagcatga | gactactgtt | caagccttcg | ttctccatgt | tctctatctt | 1680 |

```
aaccactcag ctaaataaac tgcagaaaac agacttgcta gcttcactgg aagtagaggc   1740
attcttcttc caggactttt tttatactaa attgctccca ctctgccctc ctgtatttaa   1800
atgaatgctt ttgttccttt ttaaaatgtg ttttgtaaat atgtgatgta aattaatgtg   1860
tgtacattgc ttttaaattg ctcaatattt tatgcttcag tatgtatttg ggtgtgttct   1920
tgtttgaatt ctataggaat gttttttatta gcatgaaaga acaagtataa gatgcaagta   1980
tccttaaaaa aggttatacc ttatgtgaga tgaaggaaat actaattgtt ggccagctat   2040
gactgtaaac tgttatacta gttttgagct ctaggcctcc tgcatatcta tatagaagaa   2100
tcaatttcat atatgaactt tctccaaaag aaagcttcta attttattta ttgccagcaa   2160
aattatacaa tacccctgcct gccatctaaa tcatatttat atacctattg catgtgtatt   2220
atggaaaatc ttgcagttgt tacatactat gatctacagg aactcttaaa tgtttccacg   2280
tgtgccacta gtgtcaatgt cagggatttt aatgctaaaa caatgtgtcc aggtgcgtac   2340
agtattttgg tattgtcttt ttttttttaaa tactattgag aagcactttt attcctccaa   2400
aatcagaaga gccaaaaatg tgtcttcatt ggaagaatat taaagttaga tttttaagaa   2460
aataataaaa catagttcta atgcttgcag tgtggggttt tcagaaacat ggtgtgggtc   2520
aaactgttct acttacgatt gcataagtgg aactgaaatt aaactaagtg ctttttaaaa   2580
ttccaactat aatatattaa tcaatatagc tattgaaggg cctattcgag tacagtgctg   2640
aatgctttta tgatgcacta agtatcctca agtctatgac ttcaaatgag attgaggttg   2700
cacagttcca ctaagaattg gtcctgtctg tttctctatt tttgtggtgt aaaatgtatg   2760
agtaactagc ctctctcctt ggcttagaat gaaaaacata tcttcttatt ttcctattat   2820
ctgtttgttt gtaatgttaa gctacttata agtaactcaa tgctaagaag tattttttcc   2880 ttttttttt tttacattct ttgtttaaca ctaaggagaa ggactgaaac atttatttc   2940 tatgttaatg caaatatatt gactaaactc tcctgaactg ttttgtttgt cgcagttatt   3000 caactctta ggaaccaaag actgacttct gcttctgtaa agaatggaaa gtatccgtag   3060
agtgttctgt aagaatgtag acaaaaaata ctaactcgtt actatgtgtt ggtttcctga   3120
attactgcca caaatagtgt ggtgctatgt atattttgtt tgccataaac acttttattt   3180
tccttgatga tcccagcagc aaatttttgct cttagtcatt cttaggtaaa gttaggatt   3240 tacttgtaga catcccaaat attttgtaga aatgtaatga tttagttgta gtactcaaga   3300
gctaagggat aaaccttatg ggaattgccc taaaatctac cagtttatct aatatgcatt   3360
agcaatgatg tagtgcaatg aaaataatgc aaagtataaa gtgaacagaa catctttca   3420 aaagttagat cccctcctga tatattttta taactgagtg tataggctat tctgaagcat   3480
atggataaag ggagataata tatgtatgat caacaacatc tttaaataaa attggtctta   3540
tttcataaca gactaataca attcttaag aactgctgaa taaattttaa attgttgtaa   3600
ttttgatgtg atttctggtt ttcagtacaa agttcaacta caattcaaca cctatgatta   3660
ccaaacatcc tttggtactg tacgtctgta ctgttttctg aagcgtgctt ttgtgcccat   3720
ttggtaggca ttctgtgaaa tgtgcaattt tttaaccatt caaatgcata tttatgcata   3780
gatacatata tacataatat attacacact tgctgtggct gaactaatat aactttatag   3840
ctgtaagtga ttaatcatgt ttggtcttag gaaaatatt attttaaacc aggatgtaaa   3900
tggattatga catatagcgg agttcttgaa aggtttgcat ttttggtgcc caaaagtgat   3960
ggacgttacc ttatgaaatg ttaaccaaca ctcctctcta aataactttg atcactttgt   4020
tgagaagttt tcaaaggtgc catcttaaat tacatccaaa taatgtttgt atgctatctg   4080
```

```
cttgagctca gtactattct gtactgaatt ttaacctaaa cagtgccttg aaacaaaata    4140
aatgcgatgc agaactaaga gttctgtaca ttccttttga tattttttcat aattcttgta   4200 aaacatgggg agaggccaag cacattgttt tttgcattgg tgatgaggca aataaagaac    4260
atcttctctt tgaggagtta acttggaggg agaagaaagg aattattttt acgagattct    4320
gaagatcttg caattgagag taaaaatttt acagaaatat taacagtaga atctgcttca   4380
tatgctgaga tactcttaaa cccatttttcc gcaatataaa actaaataga agaatataaa  4440
atataaaatc catttcaaaa tagaaaatat attgaaaaat gtatgaaatt tccttttct    4500 tggatcttgc cagactattt ttctattacg tttactaatg actgtgttga agtggagttc    4560
tgatgagcca gttacttaaa aatattacaa gcacccactg catatcagca agaggaagtg   4620
tacttaagat tatttagttt gtagaggtat gtaagatagg ccttaatgaa aaatgcactg   4680
aaacatatgc tgggaatttc ttgtgtacta tcataacttt tgtttttttt gttgttgttg   4740
ttcatgagaa tgtttgtact tttttatcat tgtcttttat gaaatataat gttctaaagc   4800
tggaaaaaaa aaaaaaaaa                                                4819
```

<210> SEQ ID NO 15
<211> LENGTH: 368
<212> TYPE: PRT
<213> ORGANISM: Gallus gallus
<400> SEQUENCE: 15

```
Met Leu Ala Phe Ile Phe Phe Ser Phe Ser Ser Cys Leu Tyr
1               5                   10                  15

Phe Ile Tyr Val Ala Pro Gly Ile Ala Asn Thr Tyr Leu Phe Met Val
            20                  25                  30

Gln Ala Arg Gly Ile Met Leu Arg Glu Asn Val Lys Thr Ile Gly His
        35                  40                  45

Met Ile Arg Leu Tyr Thr Asn Lys Asn Thr Thr Leu Asn Gly Thr Asp
    50                  55                  60

Tyr Pro Glu Gly Asn Asn Ser Ser Asp Cys Val Ala Gln Thr Thr Met
65                  70                  75                  80

Tyr Leu Pro Glu Asn Phe Thr Tyr Ser Pro Tyr Gln Ala Cys Pro Glu
                85                  90                  95

Lys Leu Pro Tyr Met Arg Gly Leu Ile Asp Val Asn Met Ser Glu Ile
            100                 105                 110

Ser Phe Asp Glu Ile Gln Gln Leu Phe Ser Lys Asp Leu Asp Ile Lys
        115                 120                 125

Pro Gly Gly His Trp Lys Pro Lys Asp Cys Lys Pro Arg Trp Lys Val
    130                 135                 140

Ala Ile Ile Ile Pro Phe Arg Asn Arg His Glu His Leu Pro Ile Phe
145                 150                 155                 160

Phe Arg His Leu Ile Pro Met Leu Gln Lys Arg Leu Glu Phe Ala
                165                 170                 175

Phe Tyr Val Val Glu Gln Thr Gly Thr Gln Pro Phe Asn Arg Ala Met
            180                 185                 190

Leu Phe Asn Val Gly Phe Lys Glu Ala Met Lys Asp Val Val Trp Asp
        195                 200                 205

Cys Ile Ile Phe His Asp Val Asp His Leu Pro Glu Asn Asp Arg Asn
    210                 215                 220

Tyr Tyr Gly Cys Gly Glu Met Pro Arg His Phe Ala Ala Lys Leu Asp
225                 230                 235                 240
```

Lys Tyr Met Tyr Ile Leu Pro Tyr Asn Glu Phe Phe Gly Gly Val Ser
            245                 250                 255

Gly Leu Thr Val Glu Gln Phe Lys Lys Ile Asn Gly Phe Pro Asn Ala
        260                 265                 270

Phe Trp Gly Trp Gly Gly Glu Asp Asp Asp Leu Trp Asn Arg Val His
    275                 280                 285

Tyr Ala Gly Tyr Asn Val Thr Arg Pro Glu Gly Asp Leu Gly Lys Tyr
290                 295                 300

Lys Ser Ile Pro His His His Arg Gly Glu Val Gln Phe Leu Gly Arg
305                 310                 315                 320

Tyr Lys Leu Leu Arg Tyr Ser Arg Glu Arg Gln Tyr Ile Asp Gly Leu
                325                 330                 335

Asn Asn Leu Val Tyr Thr Pro Lys Ile Leu Val Ser Arg Leu Tyr Lys
            340                 345                 350

Asn Val Thr Val Asn Leu Met Pro Glu Leu Ala Pro Ile Arg Asp Tyr
        355                 360                 365

<210> SEQ ID NO 16
<211> LENGTH: 1319
<212> TYPE: DNA
<213> ORGANISM: Gallus gallus

<400> SEQUENCE: 16

| | |
|---|---:|
| ggaacggcgc ggctcggccc ggccagcgtg tcccggcggc ggggccgggg tccgccatgg | 60 |
| ggccgggccg ccggagagcc gcgctgcgcc tgcggggcgg aggctccccg cagctcctgg | 120 |
| gtctcctggc cggcaagttc tccatcttcc agctattctt cctcgcgctg ctgctgggct | 180 |
| tcgcctcgct gctctggctg cagctcagct gctcgggcga agcgccctcc cccgggcgcg | 240 |
| ggcccccccg gccgccctgc ccgcccgaac ccccgccc gccggccgac gaccccttcgt | 300 |
| ggggccgca ccgcctggcc ctgctcgtgc ccttccgcga cgcttcgag gagctgctgg | 360 |
| ccttcgtgcc ctacatgcac cgcttcctca gcaagaagag gatccgccac acatcctgg | 420 |
| tgctcaacca ggtggaccac ttcaggttta acagagcgtc gctgatcaac gtgggcttcc | 480 |
| tggagagcgg caacgacacg gactacatcg ccatgcacga cgtcgacctg ctgccctca | 540 |
| acgagcagct ggactacggc ttccccgagg ccgggccctt ccacgtggcg tccccagagc | 600 |
| tgcacccgct gtaccactac aaaacctacg tgggagggat cctgctgctc accaagcagc | 660 |
| attatgagat gtgcaatggc atgtccaacc gcttctgggg ctggggacgg gaggacgatg | 720 |
| agttttatcg acgcatcaaa ggagctggcc tccaggttca tcgtccctct ggaatcacaa | 780 |
| ctgggtatga gactttccag cacctgcatg acccagcctg aggaagagg gaccagaagc | 840 |
| gcattgctgc gcagaagcag gagcagttta aggtggatcg ggaggaggt ctgaacaacg | 900 |
| tgagataccg gattgagtca cggactgctc tgagcgtggc agggggccccc tgcactgtcc | 960 |
| ttaacatctt gttggactgc gacatgagtg agacaccgtg tgcacgtttt ggctgagctg | 1020 |
| tgtcccatgt gccagcatgc gctgcgctca tgccaaggcg ccagggctgc gccgagctgc | 1080 |
| ttggagcaag gcagagtttt gcagcaggcc agcacggtgc tgctggcagg acccagagga | 1140 |
| gcagaaaggg ctgagtgctt gaatttgctg ggatcagcag aagaggccaa gagcaggact | 1200 |
| ccatggcatt gctgtgagtg atgcggctgt tccctagggc aggtgcagga ggcgttttc | 1260 |
| ccatgctggg tatggccgag ctgccaccca gttcagagga caataaagaa ctatcaagg | 1319 |

<210> SEQ ID NO 17
<211> LENGTH: 319
<212> TYPE: PRT

<213> ORGANISM: Gallus gallus

<400> SEQUENCE: 17

```
Met Gly Pro Gly Arg Arg Ala Ala Leu Arg Leu Arg Gly Gly
1               5                   10                  15
Ser Pro Gln Leu Leu Gly Leu Leu Ala Gly Lys Phe Ser Ile Phe Gln
            20                  25                  30
Leu Phe Phe Leu Ala Leu Leu Leu Gly Phe Ala Ser Leu Leu Trp Leu
        35                  40                  45
Gln Leu Ser Cys Ser Gly Glu Ala Pro Ser Pro Gly Arg Gly Ala Pro
    50                  55                  60
Arg Pro Pro Cys Pro Pro Glu Pro Pro Ala Pro Pro Ala Asp Asp Pro
65                  70                  75                  80
Ser Trp Gly Pro His Arg Leu Ala Leu Leu Val Pro Phe Arg Glu Arg
                85                  90                  95
Phe Glu Glu Leu Leu Ala Phe Val Pro Tyr Met His Arg Phe Leu Ser
            100                 105                 110
Lys Lys Arg Ile Arg His His Ile Leu Val Leu Asn Gln Val Asp His
        115                 120                 125
Phe Arg Phe Asn Arg Ala Ser Leu Ile Asn Val Gly Phe Leu Glu Ser
    130                 135                 140
Gly Asn Asp Thr Asp Tyr Ile Ala Met His Asp Val Asp Leu Leu Pro
145                 150                 155                 160
Leu Asn Glu Gln Leu Asp Tyr Gly Phe Pro Glu Ala Gly Pro Phe His
                165                 170                 175
Val Ala Ser Pro Glu Leu His Pro Leu Tyr His Tyr Lys Thr Tyr Val
            180                 185                 190
Gly Gly Ile Leu Leu Leu Thr Lys Gln His Tyr Glu Met Cys Asn Gly
        195                 200                 205
Met Ser Asn Arg Phe Trp Gly Trp Gly Arg Glu Asp Asp Glu Phe Tyr
    210                 215                 220
Arg Arg Ile Lys Gly Ala Gly Leu Gln Val His Arg Pro Ser Gly Ile
225                 230                 235                 240
Thr Thr Gly Tyr Glu Thr Phe Gln His Leu His Asp Pro Ala Trp Arg
                245                 250                 255
Lys Arg Asp Gln Lys Arg Ile Ala Ala Gln Lys Gln Glu Gln Phe Lys
            260                 265                 270
Val Asp Arg Glu Gly Gly Leu Asn Asn Val Arg Tyr Arg Ile Glu Ser
        275                 280                 285
Arg Thr Ala Leu Ser Val Ala Gly Ala Pro Cys Thr Val Leu Asn Ile
    290                 295                 300
Leu Leu Asp Cys Asp Met Ser Glu Thr Pro Trp Cys Thr Phe Gly
305                 310                 315
```

<210> SEQ ID NO 18
<211> LENGTH: 1838
<212> TYPE: DNA
<213> ORGANISM: Gallus gallus

<400> SEQUENCE: 18

```
cccatggaca gaggtactgc aggcagtagg tgcagcctag gccccaggtg gtgaccggcc    60
ccaagaaggc cggcagcagc ctgtccttgt ggccttagct tccccccacg tcgtgctcca   120
ccagcagcaa gatggtcacc gtcaggaaaa ggaacgtgaa ggtcttcaca ttcgccttcg   180
tactcatcac ggtgacgtca ttcctgctga actacaagca ccaggtgacc atgaccactt   240
```

```
gggatcctaa acatatcatc agtcagtttt ctgagcaagt ccgaaaactc atcaaatttc     300
ctaggaggcc gtgcagctgt agcacctgta tttccgagct gggacattcc ctctggttcg     360
accagaggtt taactcaact atgcaacctt cctgacctc acaaaatgcc ttgatcccag      420
aggacagcta caggtggtgg ctgaaaactgc aaggagagaa atctccaaag aatattaatg    480
atactctcaa ggaattgttt gggatcattc ctggggacag ggacccactg caggagcgag    540
gcactttctc atgcagacgg tgtgccgtcg ttggcaactc cggcaacctt cgtcagtctc    600
aatatggcca agatattgac tcccatgact ttgtgctcag aatgaaccgt gcacccacca    660
ttggctacga atcagatgtt gggagcaaga ctacccacca ctttgtttat ccagagagct    720
acaaagagct ggcagaaaat gtgagcatga tcgtgatccc cttcaaaacc ctggacctgc    780
gctggattgt taccgctctc accacaggca ctatcaactt cacatatgtt cctgttccac    840
ggaaaatcaa agtcagaaaa gaaaaggtcc tgatttacaa tccatccttt atcaaatacg    900
tctatgaaaa ctggcttcag aatcatgaaa gataccttc cacaggcctt ctttctgtga     960
tatttgcact ccatgtatgc gatgaggtga atgtgtatgg ttttggagca gacagcaaag    1020
gacactggca tcactactgg gaaaataatg cttcagctgg ggctttccga cagacaggtg    1080
tccatgatgg agattttgag ttcaatgtaa ctttgactct tgcctccatt gaaaaaataa    1140 aattttttcaa gggcagatga ccctagccac agggacaagc aggggctgca atttccaaca   1200
tgcagcagca caaagctcag tgaagatgat ctggatgaca gccaggtttg aaggtgtgaa    1260
tctggagtgg attcggagtg tcacactgct gcagtgctca ccacagggag ctcagctgag    1320
gaacagattc aatgctgcac ttgatttgct atctatagat agctgggaac taccgatcag    1380
ctgttggaat aaatgacatc ctgactcact ccttagtctc tacggattga ttcctgaatt    1440
actggtgaaa gatctacctg ttgcaattca gggaaaccta gacacaggaa ctgctgtttg    1500
tatgtccatt ctttccttga gtaaggcaag aaatccttga agaacatgga aaatgtcttc    1560
tgggatttga tacctactag agtagctctg aacatcatag taaggattac ctcaaagaaa    1620
ttaattcagt tctgctgtta atcttctttt tgaattctct tctgtttcct ctattacttc    1680
tggtttcatg cactataaat caaaaacgtg atgaagttgc cggagtagta actgtttcta    1740
ccattgccac attctgcatt gatggcatct agaaaataca gatcaattca cctgtgatca    1800
ttacttattt attattgctt cctatacagc catagtaa                             1838

<210> SEQ ID NO 19
<211> LENGTH: 342
<212> TYPE: PRT
<213> ORGANISM: Gallus gallus

<400> SEQUENCE: 19

Met Val Thr Val Arg Lys Arg Asn Val Lys Val Phe Thr Phe Ala Phe
1               5                   10                  15

Val Leu Ile Thr Val Thr Ser Phe Leu Leu Asn Tyr Lys His Gln Val
            20                  25                  30

Thr Met Thr Thr Trp Asp Pro Lys His Ile Ile Ser Gln Phe Ser Glu
        35                  40                  45

Gln Val Arg Lys Leu Ile Lys Phe Pro Arg Arg Pro Cys Ser Cys Ser
    50                  55                  60

Thr Cys Ile Ser Glu Leu Gly His Ser Leu Trp Phe Asp Gln Arg Phe
65                  70                  75                  80

Asn Ser Thr Met Gln Pro Phe Leu Thr Ser Gln Asn Ala Leu Ile Pro
                85                  90                  95
```

```
Glu Asp Ser Tyr Arg Trp Trp Leu Lys Leu Gln Gly Glu Lys Ser Pro
                100                 105                 110

Lys Asn Ile Asn Asp Thr Leu Lys Glu Leu Phe Gly Ile Ile Pro Gly
            115                 120                 125

Asp Arg Asp Pro Leu Gln Glu Arg Gly Thr Phe Ser Cys Arg Arg Cys
130                 135                 140

Ala Val Val Gly Asn Ser Gly Asn Leu Arg Gln Ser Gln Tyr Gly Gln
145                 150                 155                 160

Asp Ile Asp Ser His Asp Phe Val Leu Arg Met Asn Arg Ala Pro Thr
                165                 170                 175

Ile Gly Tyr Glu Ser Asp Val Gly Ser Lys Thr Thr His Phe Val
            180                 185                 190

Tyr Pro Glu Ser Tyr Lys Glu Leu Ala Glu Asn Val Ser Met Ile Val
        195                 200                 205

Ile Pro Phe Lys Thr Leu Asp Leu Arg Trp Ile Val Thr Ala Leu Thr
    210                 215                 220

Thr Gly Thr Ile Asn Phe Thr Tyr Val Pro Val Pro Arg Lys Ile Lys
225                 230                 235                 240

Val Arg Lys Glu Lys Val Leu Ile Tyr Asn Pro Ser Phe Ile Lys Tyr
                245                 250                 255

Val Tyr Glu Asn Trp Leu Gln Asn His Gly Arg Tyr Pro Ser Thr Gly
            260                 265                 270

Leu Leu Ser Val Ile Phe Ala Leu His Val Cys Asp Glu Val Asn Val
        275                 280                 285

Tyr Gly Phe Gly Ala Asp Ser Lys Gly His Trp His His Tyr Trp Glu
    290                 295                 300

Asn Asn Ala Ser Ala Gly Ala Phe Arg Gln Thr Gly Val His Asp Gly
305                 310                 315                 320

Asp Phe Glu Phe Asn Val Thr Leu Thr Leu Ala Ser Ile Glu Lys Ile
                325                 330                 335

Lys Phe Phe Lys Gly Arg
            340

<210> SEQ ID NO 20
<211> LENGTH: 1652
<212> TYPE: DNA
<213> ORGANISM: Gallus gallus

<400> SEQUENCE: 20
ggggcccgga ggctcccggc ggtggggccg ggccggagcg agcgaggct gttgccaccg       60 acgtgtccct ggcacaggac gatgagtgcc accgcggccc gggaccggct ggggacggct      120
ccccgagccc acggggccac cgggacgcgg agctacggct gagcccggcg tgccgagccg      180
cgccgagcca ggcggatgga aagctgcagc ccggcaggga gccccgcgcc caccccgcgc      240
cccagcccta tgcccgggga gcggcgccga ggctgcccgc cgcccaccca tgaagtgctc      300
gctgcgcgtc tgcttcctct cgaccgcctt cctcctcatc ttcgtcatgt cggtgctctt      360
cacctactcc caccacagca tcgcctacct ggacccggcc gggctgggcg gcatccaccg      420
ggtgaagctg gtgcccggtt acgccggcgt gcggcggctg agccacggcg tgccgtaccc      480
caggggctgt gcgtgccgcc gctgcccga ggatgccgcc gcgccgccg ccgcctggtt       540 tgacagccgc tatgacggcg tgtgtctcc ggtgtggacc aaggagaaca tggagctgcc       600
gcccgacgtg cagcggtggt ggatgatgct cagccccag ttcaagtccc acaacacgca       660
ggaggtgctg agcaagctct tccagatcgt gccaggggag aacccttacc gctggcgcga      720
```

-continued

```
cccgcgtcac tgccggcgct gcgccgtggt cggcaactcg ggcaacctgc gtggttccgg      780
ctatgggcac gagatcgatg ggcacgactt catcatgagg atgaaccagg cacccacggt      840
gggcttcgag ggggacgtgg gcagccggac cacgcaccac ttcatgtacc ccgagagtgc      900
caagaacctg cctgccaacg tcagctttgt gctggtgccc ttcaaaacct tggacctgct      960
ctggatcgcc agcgccctct ccactggcca gatcaggttc acctacgcgc ccgtgaagcc     1020
tttcctgcgg gtggacaaag agaaggtgca aatctacaac cctgccttct tcaagtacat     1080
ccacgaccgc tggacggagc accacgggcg ctacccctcc accggcatgc tggtgctctt     1140
cttcgccctc cacgtctgtg atgaggtgaa cgtcttcggg tttggcgccg acagccgggg     1200
caattggcac cactattggg agaacaaccg ctacgccggc gagttccgca agaccggggt     1260
gcacgacgcc gacttcgagg cgcacatcat cgacatgctg gccaaaacca gcaggattga     1320
gggtgtaccg gggcaataac tgagggccgg gcggccgcgc gtcctccagc tcctaacccc     1380
ggcactgcca gagctgcccc ggctgccgtt gggtgtcggc ggccgatggg ggttctgagt     1440
actcggcaga ctttgtgtgg ttgggggagt tctgacttga ccttgttagt attaaggaac     1500
ccgcttcagc caagtgagga ttttgtagac gccgcagcgc cccagccggc cggggggatgc     1560 gcccaactcg tatctgttac agtcaaacca aatggctgct ctttttttaaa aaccagaaca     1620 agcaaaaaac cgtacaaaaa gcccctaaa aa     1652
```

<210> SEQ ID NO 21
<211> LENGTH: 349
<212> TYPE: PRT
<213> ORGANISM: Gallus gallus

<400> SEQUENCE: 21

```
Met Lys Cys Ser Leu Arg Val Cys Phe Leu Ser Thr Ala Phe Leu Leu
1               5                   10                  15

Ile Phe Val Met Ser Val Leu Phe Thr Tyr Ser His His Ser Ile Ala
                20                  25                  30

Tyr Leu Asp Pro Gly Gly Leu Gly Gly Ile His Arg Val Lys Leu Val
            35                  40                  45

Pro Gly Tyr Ala Gly Val Arg Arg Leu Ser His Gly Val Pro Tyr Pro
        50                  55                  60

Arg Gly Cys Ala Cys Arg Arg Cys Pro Glu Asp Ala Ala Ala Ala
65                  70                  75                  80

Ala Ala Trp Phe Asp Ser Arg Tyr Asp Gly Gly Val Ser Pro Val Trp
                85                  90                  95

Thr Lys Glu Asn Met Glu Leu Pro Pro Asp Val Gln Arg Trp Trp Met
                100                 105                 110

Met Leu Gln Pro Gln Phe Lys Ser His Asn Thr Gln Glu Val Leu Ser
            115                 120                 125

Lys Leu Phe Gln Ile Val Pro Gly Glu Asn Pro Tyr Arg Trp Arg Asp
        130                 135                 140

Pro Arg His Cys Arg Arg Cys Ala Val Val Gly Asn Ser Gly Asn Leu
145                 150                 155                 160

Arg Gly Ser Gly Tyr Gly His Glu Ile Asp Gly His Asp Phe Ile Met
                165                 170                 175

Arg Met Asn Gln Ala Pro Thr Val Gly Phe Glu Gly Asp Val Gly Ser
            180                 185                 190

Arg Thr Thr His His Phe Met Tyr Pro Glu Ser Ala Lys Asn Leu Pro
        195                 200                 205

Ala Asn Val Ser Phe Val Leu Val Pro Phe Lys Thr Leu Asp Leu Leu
```

```
                  210                 215                 220
Trp Ile Ala Ser Ala Leu Ser Thr Gly Gln Ile Arg Phe Thr Tyr Ala
225                 230                 235                 240

Pro Val Lys Pro Phe Leu Arg Val Asp Lys Glu Lys Val Gln Ile Tyr
                245                 250                 255

Asn Pro Ala Phe Phe Lys Tyr Ile His Asp Arg Trp Thr Glu His His
                260                 265                 270

Gly Arg Tyr Pro Ser Thr Gly Met Leu Val Leu Phe Phe Ala Leu His
                275                 280                 285

Val Cys Asp Glu Val Asn Val Phe Gly Phe Gly Ala Asp Ser Arg Gly
                290                 295                 300

Asn Trp His His Tyr Trp Glu Asn Asn Arg Tyr Ala Gly Glu Phe Arg
305                 310                 315                 320

Lys Thr Gly Val His Asp Ala Asp Phe Glu Ala His Ile Ile Asp Met
                325                 330                 335

Leu Ala Lys Thr Ser Arg Ile Glu Gly Val Pro Gly Gln
                340                 345
```

<210> SEQ ID NO 22
<211> LENGTH: 2462
<212> TYPE: DNA
<213> ORGANISM: Gallus gallus

<400> SEQUENCE: 22

```
atgggactgc tggtgttcat gcgcaacctg ctgctcgccc tctgcctgtt cctggtgctg      60
ggctttctgt actactccgc ctggaagctg cacctcctcc gctgggagga ctccagtaag     120
tacgggcgcc tttcccattc ctcgttcccg aaacaaagac ccagtgctga ttcagtggtt     180
ctttcctttg actccgttgg acatacaata ggctcagagt atgacaaact gggctttctc     240
ctgaacctgg actcaaaatt gcctccagaa ttggcatcta gtatgcaaat tttctctgag     300
ggagtgtgca agcctggtta tgcatcagca ctcatgactg tcatcttccc aaagttctcg     360
aagccggcac caatgttctt agatgattcc ttcaggagat gggctcgtat cagggacttt     420 gtaccccccct ttggaattaa aggacaagat aatttgatca agccatcct gtcagcaacc     480 aaagattacc gtctaactcc agctcttgac agtctcagct gccgacgatg tattattgtg     540
ggaaatggtg gagtacttgc caataagtca ttggggctaa agattgatga ctatgatgtt     600
gttgtcaggc tgaactcggc tccggtgaag gggtttgaaa agatgtgggt ggcaaaaca      660 actctccgca tcacatatcc tgaaggtgca atccagaaga tggagcagta tgagaaggat     720
tccctgtttg tcctggcggg attcaaatgg caggatttca gtggctgaa gtacattgtt      780 tacaaggaga agtgagcgc ctctgatggc ttttggaagt cagtggcaac ccgtgtcccc      840
agagaacctc atgagatacg tatcctgaat ccctacttca tccaggaggc agctttcagc     900
ttcattggac tgccttttcaa caacggcctg atgggcagag gaacatccc caccttggga     960 agcgtagcaa taaccatggc actccacaac tgtgatgagg tggcggtcgc tgggtttggc     1020
tatgacatga gttcacccaa tgcgccactg cactactatg agaacatcaa gatgtctgcc     1080
atcaaagagt cctggacgca caacatccaa cgggagaagg agttcctgcg gaagctggtg    1140
aaagcccgag tcatcacgga cctgaccagt gggatctgag tggctgcagc ccctgcctca    1200
aagggaggag aggaagacat acgctgcggc tctggagca ggcactggca gcccccaca     1260 agaatcccac ttccctggag acacacagag atgcccgggt gctctgggaa ggccctctcg    1320
catcgccggg ctgcaggaag gttgcatctg ctgcctccag tcctggagct ggcaggaggc    1380
```

-continued

```
gggcgagggg ctcagtgggc agttcttgaa ctctgcatca cagacggatc ttctgtgtcc   1440
agaattaaac aggaaagact caggagagag aagaaaggtt tgtgaataaa gcgatttgtg   1500
ccaaatggga ggtgacgctg ccccgaggca gcagtgcctg aatgtacaaa gtagtatttt   1560
ttaaaagaaa ctctgctgga atcatcgtag aattaccaac gtgcaaagca agtctgcttg   1620
tgcacagccc tgcagaaagc tcggcctcac cacgtcccat ctgcattctc actgccctca   1680
gacctttccc caggaaaaca aatccgtcca accgtcagt gttgttggtg ctgctataat    1740
ttaaagggag gttggcttcc cctccttctc cacttggagc ttctcattgg agatgagcac   1800
gggtttgttt ttctgcactt ttcctccctt cctgcataga agcggcggcg gcagccactc   1860
acttggctgt gttttccata gctgtttgct ctgccctgac gctggaactg gtggctctct   1920
gcctgcagca ggcccaccgt gccgcctgtc acagcgctgc ggagcccacc tcgtcgtgct   1980
cagggctgtc aggtccgtgc ttgctgtgca gagccctcgt ggagtccgtg cagatcggtg   2040
tcaccacttc tggacagcat cctgctttgt ttttgtgggg gagatcagtg gtttgttttt   2100
tggaaggagg tccgatgctg cgtggggatc tgaagctttg catattgaag accaggccac   2160
cgaagatgtt ttatgttccg gactcgatca tgttccctat ttaagtgact tgtgacctca   2220
gcaatgatgg agcgtgctgg caagtgtggg ggcctgctgg gaaccctcgc cttctgcttg   2280
gccctgctc atttcatgtc caagctcctc ccgtgctgct cgagcgctgc tgctcctcct    2340
gctctcagga gcacgtccct tcctttgctg tcttggtccc gagatgcagt atttgcacat   2400
ttgatttgtg tacgtatttc agaggagctg gaataaactg agcgccgtgg ctgagtgcaa   2460
gg                                                                  2462
```

<210> SEQ ID NO 23
<211> LENGTH: 392
<212> TYPE: PRT
<213> ORGANISM: Gallus gallus

<400> SEQUENCE: 23

```
Met Gly Leu Leu Val Phe Met Arg Asn Leu Leu Ala Leu Cys Leu
1               5                   10                  15

Phe Leu Val Leu Gly Phe Leu Tyr Tyr Ser Ala Trp Lys Leu His Leu
            20                  25                  30

Leu Arg Trp Glu Asp Ser Ser Lys Tyr Gly Arg Leu Ser His Ser Ser
        35                  40                  45

Phe Pro Lys Gln Arg Pro Ser Ala Asp Ser Val Val Leu Ser Phe Asp
    50                  55                  60

Ser Val Gly His Thr Ile Gly Ser Glu Tyr Asp Lys Leu Gly Phe Leu
65                  70                  75                  80

Leu Asn Leu Asp Ser Lys Leu Pro Pro Glu Leu Ala Ser Lys Tyr Ala
                85                  90                  95

Asn Phe Ser Glu Gly Val Cys Lys Pro Gly Tyr Ala Ser Ala Leu Met
            100                 105                 110

Thr Val Ile Phe Pro Lys Phe Ser Lys Pro Ala Pro Met Phe Leu Asp
        115                 120                 125

Asp Ser Phe Arg Arg Trp Ala Arg Ile Arg Asp Phe Val Pro Pro Phe
    130                 135                 140

Gly Ile Lys Gly Gln Asp Asn Leu Ile Lys Ala Ile Leu Ser Ala Thr
145                 150                 155                 160

Lys Asp Tyr Arg Leu Thr Pro Ala Leu Asp Ser Leu Ser Cys Arg Arg
                165                 170                 175

Cys Ile Ile Val Gly Asn Gly Gly Val Leu Ala Asn Lys Ser Leu Gly
```

```
                    180                 185                 190
Leu Lys Ile Asp Asp Tyr Asp Val Val Arg Leu Asn Ser Ala Pro
            195                 200                 205

Val Lys Gly Phe Glu Lys Asp Val Gly Gly Lys Thr Thr Leu Arg Ile
210                 215                 220

Thr Tyr Pro Glu Gly Ala Ile Gln Lys Met Glu Gln Tyr Glu Lys Asp
225                 230                 235                 240

Ser Leu Phe Val Leu Ala Gly Phe Lys Trp Gln Asp Phe Lys Trp Leu
                    245                 250                 255

Lys Tyr Ile Val Tyr Lys Glu Lys Val Ser Ala Ser Asp Gly Phe Trp
            260                 265                 270

Lys Ser Val Ala Thr Arg Val Pro Arg Glu Pro His Glu Ile Arg Ile
        275                 280                 285

Leu Asn Pro Tyr Phe Ile Gln Glu Ala Ala Phe Ser Phe Ile Gly Leu
    290                 295                 300

Pro Phe Asn Asn Gly Leu Met Gly Arg Gly Asn Ile Pro Thr Leu Gly
305                 310                 315                 320

Ser Val Ala Ile Thr Met Ala Leu His Asn Cys Asp Glu Val Ala Val
                    325                 330                 335

Ala Gly Phe Gly Tyr Asp Met Ser Ser Pro Asn Ala Pro Leu His Tyr
            340                 345                 350

Tyr Glu Asn Ile Lys Met Ser Ala Ile Lys Glu Ser Trp Thr His Asn
        355                 360                 365

Ile Gln Arg Glu Lys Glu Phe Leu Arg Lys Leu Val Lys Ala Arg Val
    370                 375                 380

Ile Thr Asp Leu Thr Ser Gly Ile
385                 390

<210> SEQ ID NO 24
<211> LENGTH: 374
<212> TYPE: PRT
<213> ORGANISM: Gallus gallus

<400> SEQUENCE: 24

Met Gly Leu Leu Val Phe Met Arg Asn Leu Leu Ala Leu Cys Leu
1               5                   10                  15

Phe Leu Val Leu Gly Phe Leu Tyr Tyr Ser Ala Trp Lys Leu His Leu
                20                  25                  30

Leu Arg Trp Glu Asp Ser Asn Ser Val Val Leu Ser Phe Asp Ser Val
            35                  40                  45

Gly His Thr Ile Gly Ser Glu Tyr Asp Lys Leu Gly Phe Leu Leu Asn
        50                  55                  60

Leu Asp Ser Lys Leu Pro Pro Glu Leu Ala Ser Lys Tyr Ala Asn Phe
65                  70                  75                  80

Ser Glu Gly Val Cys Lys Pro Gly Tyr Ala Ser Ala Leu Met Thr Val
                85                  90                  95

Ile Phe Pro Lys Phe Ser Lys Pro Ala Pro Met Phe Leu Asp Asp Ser
            100                 105                 110

Phe Arg Arg Trp Ala Arg Ile Arg Asp Phe Val Pro Pro Phe Gly Ile
        115                 120                 125

Lys Gly Gln Asp Asn Leu Ile Lys Ala Ile Leu Ser Ala Thr Lys Asp
    130                 135                 140

Tyr Arg Leu Thr Pro Ala Leu Asp Ser Leu Ser Cys Arg Arg Cys Ile
145                 150                 155                 160

Ile Val Gly Asn Gly Gly Val Leu Ala Asn Lys Ser Leu Gly Leu Lys
```

|  | 165 |  | 170 |  |  | 175 |  |
|--|--|--|--|--|--|--|--|

Ile Asp Asp Tyr Asp Val Val Arg Leu Asn Ser Ala Pro Val Lys
            180                 185                 190

Gly Phe Glu Lys Asp Val Gly Gly Lys Thr Thr Leu Arg Ile Thr Tyr
        195                 200                 205

Pro Glu Gly Ala Ile Gln Lys Met Glu Gln Tyr Lys Asp Ser Leu
    210                 215                 220

Phe Val Leu Ala Gly Phe Lys Trp Gln Asp Phe Lys Trp Leu Lys Tyr
225                 230                 235                 240

Ile Val Tyr Lys Glu Lys Val Ser Ala Ser Asp Gly Phe Trp Lys Ser
                245                 250                 255

Val Ala Thr Arg Val Pro Arg Glu Pro His Glu Ile Arg Ile Leu Asn
                260                 265                 270

Pro Tyr Phe Ile Gln Glu Ala Ala Phe Ser Phe Ile Gly Leu Pro Phe
            275                 280                 285

Asn Asn Gly Leu Met Gly Arg Gly Asn Ile Pro Thr Leu Gly Ser Val
        290                 295                 300

Ala Ile Thr Met Ala Leu His Asn Cys Asp Glu Val Ala Val Ala Gly
305                 310                 315                 320

Phe Gly Tyr Asp Met Ser Ser Pro Asn Ala Pro Leu His Tyr Tyr Glu
                325                 330                 335

Asn Ile Lys Met Ser Ala Ile Lys Glu Ser Trp Thr His Asn Ile Gln
                340                 345                 350

Arg Glu Lys Glu Phe Leu Arg Lys Leu Val Lys Ala Arg Val Ile Thr
            355                 360                 365

Asp Leu Thr Ser Gly Ile
    370

<210> SEQ ID NO 25
<211> LENGTH: 1622
<212> TYPE: DNA
<213> ORGANISM: Gallus gallus

<400> SEQUENCE: 25

```
agagagcaga aggggtgctg ctgtgcgcgg acacttttct ctgggaggaa ttggactttt      60
tcttctccaa actgtgggga ggacatggaa attgggaagt ctggggacag cgaaggggggc   120
agagagcccc tgagcacatg gtgagcagtg ctgggccccg agatccccca gcctcacact    180
gaggctctcc cttttcctt caccagaaga attgaggatg ccccatagc cccgcagccc      240
ccggagctgc tgccccctct gctcgcacca cgtggaagaa ctgtgagcgg cagtggctgc    300
gatgagagct ccggccctcg gctgatgcct gccctgctga taaagatgat caataagtcc    360
cgagggaaga tactgggagt gctggcgctg tttctggtca tggtgtggta ctcgatatac    420
cgggaggaca gcttttattt tcctgtgcaa gaaaacaaga ccgtatgtcc cattggggag    480
gtggagagga aggcagcaca gctcatcggg aactacacga gggaccgccc gctcttcctg    540
cagctgaagg attacttctg ggtgaggacg ccgtcgctct atgagctgcc ctacggcatc    600
aaaggcagcg aggatgtcct cctgcgcctg ctgtcggtca ccagttactc actgcctgag    660
agcatccaga gcctgaagtg tcggaggtgc gtggtggtgg gcaacgggca ccggctccgc    720
aacagctcca tggggacac catcaacacc tacgacgtgg tgatcaggct gaacaacgcg    780
ccggtgcacg gctatgagca ggacgtgggc tccaagacca ccatgcggct cttctacccc    840
gagtcagccc attttgaccc ccaggcagag aacaatccga acacgctgct ggtgctggtg    900
cccttcaagc ccgtggactt ccagtggatg gaggccatcc tcagcgacag gaagagggtt    960
```

```
cgtaaagggt tttggaagca gcccccactg atctgggatg ccaacccgga gcaagtgcgc    1020
atcctcaacc cgtactacat ggaagtaact gctgctaaac tgctcagcct ccccatgaag    1080
cagccaagga aggtcaaaca gaaaccaacc acggggctgt tggccatcac cttggctctc    1140
cacttctgcg acctggtgca cattgcaggc tttgggtacc ctgactcggc caacaagaag    1200
caaaccatcc actactatga gcagatcaca ctcaagtcca tggctgcctc ggagcacaac    1260
atctcacatg aggcggtggc catcaagcgc atgctggagc tgggcctggt caagaacctc    1320
acctacttct gagggcaatg gggctgcgca gggacacgtc cccaccttgg agcccgcagt    1380
ggtcctggag gagccggtgt cactgagctc cccaccatgc tggtggcagt atgggggcca    1440
tgccagcttg ctgaccccgg gggtgcaggg agccccttaa tggggacttt tcatatggaa    1500
acactgaaac tagtgaggac ctgggaggga ttctggggag gatggagggg accttccccc    1560
agcaggtctg gggggccacg gcaggtgcag ctggagcccc tctcttccct tggatactct    1620
tg                                                                    1622
```

<210> SEQ ID NO 26
<211> LENGTH: 335
<212> TYPE: PRT
<213> ORGANISM: Gallus gallus

<400> SEQUENCE: 26

```
Met Pro Ala Leu Leu Ile Lys Met Ile Asn Lys Ser Arg Gly Lys Ile
1               5                   10                  15

Leu Gly Val Leu Ala Leu Phe Leu Val Met Val Trp Tyr Ser Ile Tyr
            20                  25                  30

Arg Glu Asp Ser Phe Tyr Phe Pro Val Gln Glu Asn Lys Thr Val Cys
        35                  40                  45

Pro Ile Gly Glu Val Glu Arg Lys Ala Ala Gln Leu Ile Gly Asn Tyr
    50                  55                  60

Thr Arg Asp Arg Pro Leu Phe Leu Gln Leu Lys Asp Tyr Phe Trp Val
65                  70                  75                  80

Arg Thr Pro Ser Leu Tyr Glu Leu Pro Tyr Gly Ile Lys Gly Ser Glu
                85                  90                  95

Asp Val Leu Leu Arg Leu Leu Ser Val Thr Ser Tyr Ser Leu Pro Glu
            100                 105                 110

Ser Ile Gln Ser Leu Lys Cys Arg Arg Cys Val Val Val Gly Asn Gly
        115                 120                 125

His Arg Leu Arg Asn Ser Ser Met Gly Asp Thr Ile Asn Thr Tyr Asp
    130                 135                 140

Val Val Ile Arg Leu Asn Asn Ala Pro Val His Gly Tyr Glu Gln Asp
145                 150                 155                 160

Val Gly Ser Lys Thr Thr Met Arg Leu Phe Tyr Pro Glu Ser Ala His
                165                 170                 175

Phe Asp Pro Gln Ala Glu Asn Asn Pro Asn Thr Leu Leu Val Leu Val
            180                 185                 190

Pro Phe Lys Pro Val Asp Phe Gln Trp Met Glu Ala Ile Leu Ser Asp
        195                 200                 205

Arg Lys Arg Val Arg Lys Gly Phe Trp Lys Gln Pro Pro Leu Ile Trp
    210                 215                 220

Asp Ala Asn Pro Glu Gln Val Arg Ile Leu Asn Pro Tyr Tyr Met Glu
225                 230                 235                 240

Val Thr Ala Ala Lys Leu Leu Ser Leu Pro Met Lys Gln Pro Arg Lys
                245                 250                 255
```

```
Val Lys Gln Lys Pro Thr Thr Gly Leu Leu Ala Ile Thr Leu Ala Leu
        260                 265                 270

His Phe Cys Asp Leu Val His Ile Ala Gly Phe Gly Tyr Pro Asp Ser
        275                 280                 285

Ala Asn Lys Lys Gln Thr Ile His Tyr Tyr Glu Gln Ile Thr Leu Lys
        290                 295                 300

Ser Met Ala Ala Ser Glu His Asn Ile Ser His Glu Ala Val Ala Ile
305                 310                 315                 320

Lys Arg Met Leu Glu Leu Gly Leu Val Lys Asn Leu Thr Tyr Phe
                325                 330                 335

<210> SEQ ID NO 27
<211> LENGTH: 1296
<212> TYPE: DNA
<213> ORGANISM: Gallus gallus

<400> SEQUENCE: 27
gccccgatgc ggaggcgaag tgcccgggcc gagcccagcg cagcaatgct gagtgacgat      60
aactctgtaa agctgaaaag tgattgtttg cctcctgtgc aatggtgtaa ggtagctgca     120
catgaagatg agaagaccaa tctggttttt aaaaggtact cgcaaatttc ttgcactgtt     180
tgtgattgga gggtgcttcc tttatatcct caaattacat ttttaccctg aagaatgtga     240
cagaacaaaa acaccgtatg tggactttga tcgcgtaaag agagcacaac aatatgccag     300
tgctgtgttg caggagcagt gccgaccttc gtatgtgaaa aaagcaatgg aaagttatt      360
tgcagagaaa tacagcatgg acatacctcc ctttgtagga aaaaatatag atgatgatga     420
agctttattt aaatatggac ctccgtttgg attccacagg ttctttgata agcttaaaaa     480
gcttctcgaa ctcttaccag agcacgattt gccagaggat ttgaagtcaa acactgtaa      540
gcgttgtgtt gttattggca gtggtggaat tctgtatgga tcagagctag gccacttact     600
gaatcagtat gatattgtta taaggttaaa tgatgcacca gttcaaggat acacggatca     660
cgttggtaac aaaactacta taaggatgac ttacccagaa ggagctccac tttctgaaca     720
cgagtatccc cctgctagtt tatttgtggc tgtcctcttt aaaagtgttg atttcaattg     780
gcttcaagca atggtaaaaa atgaaacact gtctctgtgg atacgacttt tcttttggaa     840
ggaagttgcc aagaaaattc cttttacatc aaaacaattt cggattctca atccagtcat     900
cgttaaagag acagccttgg acatcctaga gttccccaaa cctcgatcaa tattctgggg     960
ttgggataag aacgtaccca caattggggt catggcagtc gttctggcca cacatctatg    1020
tgatgaagta agcatagcag gatttggata cgacctcaac cagcccagca cctttgca      1080
ctattacaac aacctctgca tggctgccat gaacagacaa acgatgcaca atgtgacagg    1140
tgaaacaaaa ttactgcaaa aactggtcaa agaaaagtt gtgaaagacc tcactggtgg    1200
aatccattgt gaattctgca acaaagacag ctagtaattg aagtgcagca cggcctggat    1260
ttgttaaatt cccagaagtt ttgttggaac aacctt                              1296

<210> SEQ ID NO 28
<211> LENGTH: 368
<212> TYPE: PRT
<213> ORGANISM: Gallus gallus

<400> SEQUENCE: 28

Met Arg Arg Pro Ile Trp Phe Leu Lys Gly Thr Arg Lys Phe Leu Ala
1               5                   10                  15

Leu Phe Val Ile Gly Gly Cys Phe Leu Tyr Ile Leu Lys Leu His Phe
```

```
                        20                  25                  30
Tyr Pro Glu Glu Cys Asp Arg Thr Lys Thr Pro Tyr Val Asp Phe Asp
                35                  40                  45

Arg Val Lys Arg Ala Gln Gln Tyr Ala Ser Ala Val Leu Gln Glu Gln
            50                  55                  60

Cys Arg Pro Ser Tyr Val Lys Ala Met Gly Lys Leu Phe Ala Glu
65                  70                  75                  80

Lys Tyr Ser Met Asp Ile Pro Pro Phe Val Gly Lys Asn Ile Asp Asp
                    85                  90                  95

Asp Glu Ala Leu Phe Lys Tyr Gly Pro Pro Phe Gly Phe His Arg Phe
                100                 105                 110

Phe Asp Lys Leu Lys Lys Leu Leu Glu Leu Leu Pro Glu His Asp Leu
                115                 120                 125

Pro Glu Asp Leu Lys Ser Lys His Cys Lys Arg Cys Val Val Ile Gly
            130                 135                 140

Ser Gly Gly Ile Leu Tyr Gly Ser Glu Leu Gly His Leu Leu Asn Gln
145                 150                 155                 160

Tyr Asp Ile Val Ile Arg Leu Asn Asp Ala Pro Val Gln Gly Tyr Thr
                165                 170                 175

Asp His Val Gly Asn Lys Thr Thr Ile Arg Met Thr Tyr Pro Glu Gly
                180                 185                 190

Ala Pro Leu Ser Glu His Glu Tyr Pro Pro Ala Ser Leu Phe Val Ala
                195                 200                 205

Val Leu Phe Lys Ser Val Asp Phe Asn Trp Leu Gln Ala Met Val Lys
            210                 215                 220

Asn Glu Thr Leu Ser Leu Trp Ile Arg Leu Phe Phe Trp Lys Glu Val
225                 230                 235                 240

Ala Lys Lys Ile Pro Phe Thr Ser Lys Gln Phe Arg Ile Leu Asn Pro
                245                 250                 255

Val Ile Val Lys Glu Thr Ala Leu Asp Ile Leu Glu Phe Pro Lys Pro
                260                 265                 270

Arg Ser Ile Phe Trp Gly Trp Asp Lys Asn Val Pro Thr Ile Gly Val
            275                 280                 285

Met Ala Val Val Leu Ala Thr His Leu Cys Asp Glu Val Ser Ile Ala
290                 295                 300

Gly Phe Gly Tyr Asp Leu Asn Gln Pro Ser Thr Pro Leu His Tyr Tyr
305                 310                 315                 320

Asn Asn Leu Cys Met Ala Ala Met Asn Arg Gln Thr Met His Asn Val
                325                 330                 335

Thr Gly Glu Thr Lys Leu Leu Gln Lys Leu Val Lys Glu Lys Val Val
                340                 345                 350

Lys Asp Leu Thr Gly Gly Ile His Cys Glu Phe Cys Asn Lys Asp Ser
            355                 360                 365

<210> SEQ ID NO 29
<211> LENGTH: 2352
<212> TYPE: DNA
<213> ORGANISM: Gallus gallus

<400> SEQUENCE: 29
tttttgcttt caaacaaggc gattttttgtt ttgtttctgt cctttgccgc cggcagagcc      60
atcgagttgt gtgtcgatgc gagcgttggg gcgagcagag actttccagg aaccccggc     120 tgtctccggg ccggtaacgc cgggcgccac gggtgcagcc ctgtgccgtg gcggcttttct    180 aggaccggtt cctcccccga tgccccgtgg gctttcgcgt gggtggcgat cgtcggaggc     240
```

```
agcggcacgg agagggagac ccccgtgccc ctcagcttgc ctggcttttc gggttttttt    300
gcttctcgag agggcgcccc gcctcccctc gctgcccggg aggggtcag  ggctttccgc    360
gggcgggcga gcagtcgctg taaccgcagc cgctgtggga ggacgcgcgg gggatggagc    420
ggcgcggtgc cttccctcac acgaggctct cctcccctgg aaggcttcga tataagctga    480
ggaggagctt cggcagacgc gagtcaaacg ccacctccat cctaacgcgc agcatgcttc    540
cttccacgtt ttcttttgca gatggggttc agctgaacga agccccgctc ttcttcctca    600
tcgttaccgt aagcgtgcgg aagtcgggct ggagctgctt gcggacggta cggcccctct    660
aagaagctgc acgttacctt ctctctgcgg ttcgatctga tttgaagtcc cttccctgtt    720
gacaactggt ctaccagtca tgaaacgaat tcttctgttt ttcatcctgg ctgctgctgt    780
tatgtacggt atattgcatg gaaatctgtg gagaaataac ttctactgga ttagctttta    840
tggacagact tcttctgtga ggggtccttc ttccagtgag gctagtggag ttacccagct    900
gccacctacg gctgtggaga gaaggaacgc cctaaacact tgcactctga aaccagcatt    960
tgaatcttta ctggatgttg agaaaatata cccgttcctg tgtgccagtg attttatcag   1020
agtggcagag taccatggaa gtgataagtt cgagctacct tatggaataa agagagcaga   1080
acaatttttt cgttcagccc tttcaaaact gcaaaattgt ggactgtcca acaaagacga   1140
cagtgttgcc tgccgacggt gtgttgtggt cggtaatgga ggagtacttc gaaataagac   1200
gttaggaggg aaaattgact cctatgatgt gataataaga atgaataatg gccctgttat   1260
agggtacgaa gaggatgttg ggagaaggac gactttccgc cttcctacc  cagaatccat   1320
cttctcagat ccaatccact acgaccctaa cactactgtt gttattatcg tcttcaaacc   1380
acgtgactta aagtggcttt gggagatttt aggtggtcag aaaataagtg ctaaaggctt   1440
ttggaagaaa ccagctctaa acatgatata taaatctaat caaatcagga ttcttgatcc   1500
cagcatcacc agaaaaacag cttatgattg gcttcatttc ccaacaagat tcccaaaaa   1560
agagaaaccc aagcatccaa caacggggct aattgccatt acactagcat tcacatttg    1620
tcatgaagtt cacctggcgg gcttcaaata tgacttcact gacaggaaca gttctttgca   1680
ctactatggc aacgaaacaa tgtctcagat gatgcagaat gaataccatg acatcagtgc   1740
tgagcagaaa ttcttgaaga agcttataga caagaacttt gtggtcaact tgacgtgaaa   1800
gctggatgga aaatctgaag aacagtcact actttcaaga tttcagaatc ttttatttt    1860
ttgtatgaca tttttatttt ttaagtgcaa cgtaactgtt tactgttgaa aaacagcaag   1920
gaaacctcat aaggcagaag cttcttctaa gccagaggat aatggactat tctaagcaga   1980
gctaactgaa tttctgtgaa gctatttaat gggaaaaaca caaaactttc agctgaaagt   2040
atcagggatg tataaaaatg tgattcacat tacttattta tcagcaagaa cttttttcca   2100
aacgattact tctctggaat accttctttt ctaacgtcct ccaaaaggat tacactgtta   2160
agggactgag acaactattt aagtagtgga tggatgtcaa tgcttgaatc tttcttgtaa   2220
tacaaaagtg gctttaaaag caatgccttg aagtcattac tatgcgtttg ggagaagggg   2280
aaacatgcgg aacatacaga ctttagtctg ctctcctcct gagcagagga ctcatccatc   2340
catcttctgt ga                                                       2352
```

<210> SEQ ID NO 30
<211> LENGTH: 352
<212> TYPE: PRT
<213> ORGANISM: Gallus gallus

<400> SEQUENCE: 30

```
Met Lys Arg Ile Leu Leu Phe Phe Ile Leu Ala Ala Val Met Tyr
1               5                   10                  15

Gly Ile Leu His Gly Asn Leu Trp Arg Asn Asn Phe Tyr Trp Ile Ser
            20                  25                  30

Phe Tyr Gly Gln Thr Ser Ser Val Arg Gly Pro Ser Ser Glu Ala
            35                  40                  45

Ser Gly Val Thr Gln Leu Pro Pro Thr Ala Val Glu Arg Arg Asn Ala
50                      55                  60

Leu Asn Thr Cys Thr Leu Lys Pro Ala Phe Glu Ser Leu Leu Asp Val
65                  70                  75                  80

Glu Lys Ile Tyr Pro Phe Leu Cys Ala Ser Asp Phe Ile Arg Val Ala
                85                  90                  95

Glu Tyr His Gly Ser Asp Lys Phe Glu Leu Pro Tyr Gly Ile Lys Arg
                100                 105                 110

Ala Glu Gln Phe Phe Arg Ser Ala Leu Ser Lys Leu Gln Asn Cys Gly
            115                 120                 125

Leu Ser Asn Lys Asp Asp Ser Val Ala Cys Arg Arg Cys Val Val Val
130                 135                 140

Gly Asn Gly Gly Val Leu Arg Asn Lys Thr Leu Gly Gly Lys Ile Asp
145                 150                 155                 160

Ser Tyr Asp Val Ile Ile Arg Met Asn Asn Gly Pro Val Ile Gly Tyr
                165                 170                 175

Glu Glu Asp Val Gly Arg Arg Thr Thr Phe Arg Leu Ser Tyr Pro Glu
                180                 185                 190

Ser Ile Phe Ser Asp Pro Ile His Tyr Asp Pro Asn Thr Thr Val Val
            195                 200                 205

Ile Ile Val Phe Lys Pro Arg Asp Leu Lys Trp Leu Trp Glu Ile Leu
            210                 215                 220

Gly Gly Gln Lys Ile Ser Ala Lys Gly Phe Trp Lys Lys Pro Ala Leu
225                 230                 235                 240

Asn Met Ile Tyr Lys Ser Asn Gln Ile Arg Ile Leu Asp Pro Ser Ile
                245                 250                 255

Thr Arg Lys Thr Ala Tyr Asp Trp Leu His Phe Pro Thr Arg Phe Pro
                260                 265                 270

Lys Lys Glu Lys Pro Lys His Pro Thr Thr Gly Leu Ile Ala Ile Thr
            275                 280                 285

Leu Ala Phe His Ile Cys His Glu Val His Leu Ala Gly Phe Lys Tyr
            290                 295                 300

Asp Phe Thr Asp Arg Asn Ser Ser Leu His Tyr Tyr Gly Asn Glu Thr
305                 310                 315                 320

Met Ser Gln Met Met Gln Asn Glu Tyr His Asp Ile Ser Ala Glu Gln
                325                 330                 335

Lys Phe Leu Lys Lys Leu Ile Asp Lys Asn Phe Val Val Asn Leu Thr
            340                 345                 350

<210> SEQ ID NO 31
<211> LENGTH: 2192
<212> TYPE: DNA
<213> ORGANISM: Gallus gallus

<400> SEQUENCE: 31
gagaagtgcc gcgctcggtg gccagcaagc tcgattagaa gtgagatgag ggcacgaaga    60
gctgcttgca tggcacagat gtggcagtgg ctcatctgga tgtcacctgg ccacccccctt   120 gtgactggaa gagtttgaca ggagctgctg aggacagcga aggatcctgg agatgaaggt    180
```

```
gtttcttgaa ctcttcagcg cctcacgcgg ctgttgtgtt tggggatatc ctgccttaaa    240
tcctggacaa aaatctgcca acagccaaaa atgacctgag tgggagagcc actgctttgt    300
ccaacaggcc cagcttcctg ccccgtgctc actgtcccgt ttggatgcga cgtacactat    360
ggttcacatc aatgtgctga aaaaattcat gtgtgttctt gtggtgatac tgatagctct    420
gacggtttgc ctgtggaaag agacaagagg aagctactat gttcctttga agaacgatgg    480
cacacaggtt cacagggctc tggacaaatg gaacctactt aaatcgcagg gcctcctcca    540
tgaagctgct ggtgaaatgg gtcagatgcc taaagcattg cccaacaacc aaaacaaggt    600
aaaaggcatc acctctggag cagtagagaa gtccaggaaa gcagcagagc acgtgaaggt    660
atgggataag gacagctcgt ccagaaacct catacccagg ctgcagaagg tcaggaagaa    720
ctacctgtcc atgaacaagt acaatgtgac ttacaatggg aagatgaatg ctgctaaact    780
cagcccagag cagctgctgt gccggctgcg ggacagggtg aacgtgacca tgatacgggg    840
atcggacggt ccatttaatt cctcagaatg gcagcactac ctgccagaca aaagcctcaa    900
tgagacggtg ggccgcctgg gtcgctgtgc tgttgtgtcc tcagcaggct ctctgaaatc    960
atctcacttg ggaccagaga tagatagcca tgatgctgtc ttgcggttta tggggctcc    1020 tgtcaaagga tttcaagaag atgtggggca aaaacgacg attcgtcttg tcaactccca    1080
gctggtcact gttgaggagc agcagttcct gaaagatgcg ctgtataaca ctggaatctt    1140
gattgtctgg gatccagcac cgtatcatgc agaaatccat gagtggtacc gaaaaccaga    1200
ctacaagttt tttgaagcct acaagtcgta tcgtattaga catccggagc agccctttta    1260
tatcctgaac ccaaagatgc agtggcaact ctgggatatt ctgcaggaga attccctgga    1320
gcatattcag cctaacccac cgtcttcagg aatgctgggc attgtgatca tgatgacgct    1380
ctgtgatgag gtggatgtgt atgaatttct cccttctaag cggcagacgg acatttgcca    1440
ctactaccag aagtttcacg accatgcctg caccatggga gcttaccacc ctctcctgtt    1500
tgagaagaac ttggtgaagc atttaaacca aggcaccgat gaggacatct atactcacgg    1560
gaaggttact ttgcctggct ccgaaatgt acattgctag cgaatcggtt tttattgcat    1620
ttagactttt gccttgactg ttgaagcact ttgaaaatca gggttgtcat atttgttagg    1680
tctaagcact ggtgtgtttt gacggctctt ccgcgttgca ggactctgag gcaaagctcc    1740
tccgaactgg aaggcagtgc aatacgttgg ggtacatcca cgcagcgtct gcgtgagccc    1800
atgcaataaa tgtcctcctg gtggggctgg gctcgtgctg ctggtggata tctgtcttca    1860
gctcaactga tgatgccgtg tgggaatcgc gggagatgct ttctaagcag agactgcaca    1920
agtccgaatc gagtgctgat aaagttcagc ttgctccaaa ggggttctga cagccgaaag    1980
cctgatctgc tgagaacaag aagcattctt gaacacttgt tcttatcgtc cctggagctc    2040
tttggagcag tgattgaagg aatcactgtt aaagctgggt gctgataagc tcatctccta    2100
gtccaaaaat atttgatctt accattcaga taagcaaggc agcttccttt caaaaatata    2160
atgcttttta aattcaaaaa aaaaaaaaaa aa                                  2192
```

<210> SEQ ID NO 32
<211> LENGTH: 413
<212> TYPE: PRT
<213> ORGANISM: Gallus gallus

<400> SEQUENCE: 32

```
Met Val His Ile Asn Val Leu Lys Lys Phe Met Cys Val Leu Val Val
1               5                   10                  15
```

```
Ile Leu Ile Ala Leu Thr Val Cys Leu Trp Lys Glu Thr Arg Gly Ser
            20              25                  30

Tyr Tyr Val Pro Leu Lys Asn Asp Gly Thr Gln Val His Arg Ala Leu
        35                  40                  45

Asp Lys Trp Asn Leu Leu Lys Ser Gln Gly Leu Leu His Glu Ala Ala
50                  55                  60

Gly Glu Met Gly Gln Met Pro Lys Ala Leu Pro Asn Asn Gln Asn Lys
65                  70                  75                  80

Val Lys Gly Ile Thr Ser Gly Ala Val Glu Lys Ser Arg Lys Ala Ala
                85                  90                  95

Glu His Val Lys Val Trp Asp Lys Asp Ser Ser Arg Asn Leu Ile
            100                 105                 110

Pro Arg Leu Gln Lys Val Arg Lys Asn Tyr Leu Ser Met Asn Lys Tyr
            115                 120                 125

Asn Val Thr Tyr Asn Gly Lys Met Asn Ala Ala Lys Leu Ser Pro Glu
            130                 135                 140

Gln Leu Leu Cys Arg Leu Arg Asp Arg Val Asn Val Thr Met Ile Arg
145                 150                 155                 160

Gly Ser Asp Gly Pro Phe Asn Ser Ser Glu Trp Gln His Tyr Leu Pro
                165                 170                 175

Asp Lys Ser Leu Asn Glu Thr Val Gly Arg Leu Gly Arg Cys Ala Val
            180                 185                 190

Val Ser Ser Ala Gly Ser Leu Lys Ser Ser His Leu Gly Pro Glu Ile
            195                 200                 205

Asp Ser His Asp Ala Val Leu Arg Phe Asn Gly Ala Pro Val Lys Gly
            210                 215                 220

Phe Gln Glu Asp Val Gly Gln Lys Thr Thr Ile Arg Leu Val Asn Ser
225                 230                 235                 240

Gln Leu Val Thr Val Glu Glu Gln Phe Leu Lys Asp Ala Leu Tyr
            245                 250                 255

Asn Thr Gly Ile Leu Ile Val Trp Asp Pro Ala Pro Tyr His Ala Glu
            260                 265                 270

Ile His Glu Trp Tyr Arg Lys Pro Asp Tyr Lys Phe Phe Glu Ala Tyr
            275                 280                 285

Lys Ser Tyr Arg Ile Arg His Pro Glu Gln Pro Phe Tyr Ile Leu Asn
            290                 295                 300

Pro Lys Met Gln Trp Gln Leu Trp Asp Ile Leu Gln Glu Asn Ser Leu
305                 310                 315                 320

Glu His Ile Gln Pro Asn Pro Ser Ser Gly Met Leu Gly Ile Val
            325                 330                 335

Ile Met Thr Leu Cys Asp Glu Val Asp Val Tyr Glu Phe Leu Pro
            340                 345                 350

Ser Lys Arg Gln Thr Asp Ile Cys His Tyr Tyr Gln Lys Phe His Asp
            355                 360                 365

His Ala Cys Thr Met Gly Ala Tyr His Pro Leu Leu Phe Glu Lys Asn
            370                 375                 380

Leu Val Lys His Leu Asn Gln Gly Thr Asp Glu Asp Ile Tyr Thr His
385                 390                 395                 400

Gly Lys Val Thr Leu Pro Gly Phe Arg Asn Val His Cys
                405                 410

<210> SEQ ID NO 33
<211> LENGTH: 2274
<212> TYPE: DNA
<213> ORGANISM: Gallus gallus
```

<400> SEQUENCE: 33

```
atgaaaccta acttgaagca atggaaacaa ctcatgctgt ttggaatctt tgcatggggt      60
ctgcttttc tagtgatctt catctatttc acagacagca acagtgctga gccagttccc     120
agttcctttt cttacattga aacgaagagg ctcctgcccc tgcagggcaa gcagagagtc     180
atcatgggag ccatacacga tccgtcattc tctgaagcca ttgatgggaa tgaggtactc     240
cttaatgaag atcttttaga tacatttaaa tcagagactg gaagtattaa gaaatggact     300
gatttggaag atgcctttag aagcgaagat gagtttttc catcccagat aggacgaaag     360
tcaaaaagtg ctttctacca agtgaacgat gattatttat tcgctgctgg tcagcctatg     420
tcacacaaca gcttccaaga gatagcaaaa ttcatctcag ccgatgagga taatccaaaa     480
gaaagtattt tacagaacaa ctggagccgt cagaggagaa tgaggagaag gagcacaaag     540
cacagaagaa gccagatgct tgatgaatct gatgactggg atgggctgta ttctacaatg     600
tcgaaatcct ttctatacaa gctctggaaa ggagatgtct cttccaagat gctgaaccct     660
cgactgcaga aggcgatgaa agattatttg agcaccaata gcatggggt gcggttcaaa     720
gggaaacgaa actcgaagct gacaggcgac cagcttttct gcgagctgaa agaaagggtg     780
gatgtgaaaa caatagatgg caaggaagct cccttctcca ctcttggatg ggagaagcac     840
gttcctcaaa ttccactggg caaattgtat acacatggct tgggagctg tgccgtagtt     900
atgtctgctg gtgcgatact gaactcctct ctaggggatg aaatagattc tcatgatgct     960
gttctaagat ttaattctgc tccaacacgc ggctatgaaa aagatgttgg aaataaaaca    1020
acgatgcgaa tcattaactc tcagattctc accaacccaa accatcactt tgttgacagc    1080
tccttgtaca aagatgttat cttagtagcc tgggatcctg ctccctactc tgcaaatctg    1140
aatgtgtggt ataagaagcc ggactacaat ctgttcactc cctatgtaca gcatcgcagg    1200
aagaatccaa accagccttt ttacattctc catccaaagt ttatatggca gctctgggac    1260
atcattcagg agaacacgaa agagaagata cagcccaacc ctccttcttc aggttttatt    1320
ggtatcctca tcatgatgtc catgtgtaac gaagtgcacg tgtacgaata catcccttca    1380
gtccgacaga ccgacctatg tcactatcat gaactctact acgatgcagc ttgtacctta    1440
ggggcctatc acccgctgct ctatgagaag ctgttggtgc agaggatgaa caaaggtttg    1500
caggatgatc tgtatcggaa gggaaaggtc attttgccag ggttcaagtc tgtcaaatgc    1560
ccggaacgaa ataatttttcc acccttgtag aagagagtct ttcacaaaca atgtgcaata    1620
aggtactact gtcgtactat aaacaaggag agaatacttg aaaaatgtat tagaccaacc    1680
cagtcttgag tctataaatt gtaattaagt agcaggcatg agaaatactt ctttcctgag    1740
cctgagtatt tattactgct ttgcaaatag ttaaagaaaa caaaaagctt agcttacaaa    1800
aggtgcagag gacatactta ggccgaaata taatgtattg ttgtgggtgt gaccgtcaga    1860
atttgtcagt ggtctcttgt gccacttatg ctagatggta actttttttt tttttttaaag    1920
gaatttattt aagtgttaaa tccagcattg tgaggcagcc tgtatcgctc atgtacagag    1980
ctgccagttg aacaatgcag cgtttctcat ggctccatgg gattttcaca ctctccagga    2040
atgaagtaat tgctactctg agctgaatat tcattaatta gaggagtctt tcagttcctg    2100
ttcatacact ggttcacttg caggcttcta actgtacagg aaaccttatg gtggctatga    2160
agtcagtgca gatgtaggaa gcagaacacg cagctaaacc aattaaacca ctggatgtac    2220
ccttggtgtc acatcccatt gctcacactg agcagggcag agggcaaaga gaaa           2274
```

<210> SEQ ID NO 34
<211> LENGTH: 529
<212> TYPE: PRT
<213> ORGANISM: Gallus gallus

<400> SEQUENCE: 34

Met Lys Pro Asn Leu Lys Gln Trp Lys Gln Leu Met Leu Phe Gly Ile
1               5                   10                  15

Phe Ala Trp Gly Leu Leu Phe Leu Val Ile Phe Ile Tyr Phe Thr Asp
            20                  25                  30

Ser Asn Ser Ala Glu Pro Val Pro Ser Ser Phe Ser Tyr Ile Glu Thr
        35                  40                  45

Lys Arg Leu Leu Pro Leu Gln Gly Lys Gln Arg Val Ile Met Gly Ala
    50                  55                  60

Ile His Asp Pro Ser Phe Ser Glu Ala Ile Asp Gly Asn Glu Val Leu
65                  70                  75                  80

Leu Asn Glu Asp Leu Leu Asp Thr Phe Lys Ser Glu Thr Gly Ser Ile
                85                  90                  95

Lys Lys Trp Thr Asp Leu Glu Asp Ala Phe Arg Ser Glu Asp Glu Phe
            100                 105                 110

Phe Pro Ser Gln Ile Gly Arg Lys Ser Lys Ser Ala Phe Tyr Gln Val
        115                 120                 125

Asn Asp Asp Tyr Leu Phe Ala Ala Gly Gln Pro Met Ser His Asn Ser
130                 135                 140

Phe Gln Glu Ile Ala Lys Phe Ile Ser Ala Asp Glu Asp Asn Pro Lys
145                 150                 155                 160

Glu Ser Ile Leu Gln Asn Asn Trp Ser Arg Gln Arg Met Arg Arg
                165                 170                 175

Arg Ser Thr Lys His Arg Arg Ser Gln Met Leu Asp Glu Ser Asp Asp
            180                 185                 190

Trp Asp Gly Leu Tyr Ser Thr Met Ser Lys Ser Phe Leu Tyr Lys Leu
        195                 200                 205

Trp Lys Gly Asp Val Ser Ser Lys Met Leu Asn Pro Arg Leu Gln Lys
    210                 215                 220

Ala Met Lys Asp Tyr Leu Ser Thr Asn Lys His Gly Val Arg Phe Lys
225                 230                 235                 240

Gly Lys Arg Asn Ser Lys Leu Thr Gly Asp Gln Leu Phe Cys Glu Leu
                245                 250                 255

Lys Glu Arg Val Asp Val Lys Thr Ile Asp Gly Lys Glu Ala Pro Phe
            260                 265                 270

Ser Thr Leu Gly Trp Glu Lys His Val Pro Gln Ile Pro Leu Gly Lys
        275                 280                 285

Leu Tyr Thr His Gly Phe Gly Ser Cys Ala Val Val Met Ser Ala Gly
    290                 295                 300

Ala Ile Leu Asn Ser Ser Leu Gly Asp Glu Ile Asp Ser His Asp Ala
305                 310                 315                 320

Val Leu Arg Phe Asn Ser Ala Pro Thr Arg Gly Tyr Glu Lys Asp Val
                325                 330                 335

Gly Asn Lys Thr Thr Met Arg Ile Ile Asn Ser Gln Ile Leu Thr Asn
            340                 345                 350

Pro Asn His His Phe Val Asp Ser Ser Leu Tyr Lys Asp Val Ile Leu
        355                 360                 365

Val Ala Trp Asp Pro Ala Pro Tyr Ser Ala Asn Leu Asn Val Trp Tyr
    370                 375                 380

Lys Lys Pro Asp Tyr Asn Leu Phe Thr Pro Tyr Val Gln His Arg Arg

```
                385                 390                 395                 400
Lys Asn Pro Asn Gln Pro Phe Tyr Ile Leu His Pro Lys Phe Ile Trp
                    405                 410                 415

Gln Leu Trp Asp Ile Ile Gln Glu Asn Thr Lys Glu Lys Ile Gln Pro
                420                 425                 430

Asn Pro Pro Ser Ser Gly Phe Ile Gly Ile Leu Ile Met Met Ser Met
            435                 440                 445

Cys Asn Glu Val His Val Tyr Glu Tyr Ile Pro Ser Val Arg Gln Thr
        450                 455                 460

Asp Leu Cys His Tyr His Glu Leu Tyr Tyr Asp Ala Ala Cys Thr Leu
465                 470                 475                 480

Gly Ala Tyr His Pro Leu Leu Tyr Glu Lys Leu Leu Val Gln Arg Met
                485                 490                 495

Asn Lys Gly Leu Gln Asp Asp Leu Tyr Arg Lys Gly Lys Val Ile Leu
            500                 505                 510

Pro Gly Phe Lys Ser Val Lys Cys Pro Glu Arg Asn Asn Phe Pro Pro
        515                 520                 525

Leu

<210> SEQ ID NO 35
<211> LENGTH: 1292
<212> TYPE: DNA
<213> ORGANISM: Gallus gallus

<400> SEQUENCE: 35
cgcgccccac gcctcctgtg accctcgtgc cccacggccg ccccagctcc gcgggataaa      60
gatgctggtc cgcgtcttcg tcgtcctgct gtgcgcggcc gcgctctccg tgctctacgt     120
gctgctgtgc cgcgaggccg ccgggcagag ggacggctcc gcgtacaccg cgcccgcggc     180
gctcagcttg cagggctaca gccgcgtccc cgacgggaag ccgctgcgca gagctccgtg     240
ccgccgctgc gccgtggtct ccagctcggg gcagatgctg ggatcgcacc tgggccggga     300
gatcgacggg caggagtgcg tgctgcgcat gaaccacgcc cccacgccg gcttcgagga     360 ggacgtgggc acgcggagca ccgtccgcgt cgtgtcgcac accagcgtcc cgctgctgct     420
caggaaccag ccctacttct tccagcagtc ccggacacc atctacgtca tttggggtcc     480
cagcaggaag atgagccgcg agaagggcgg cccgacgcac cgagcgctgc tcagggtgct     540
ggagatgtac ccccgcctgc agctctacac gctgaccgag gagaagatgg cgtattgcga     600
cgacgtcttc cagaacgaga caggcaagaa caggctgaaa tccggctcct tcctgagcac     660
ggggtggttc accatgatcc tggccatgga gctgtgcgag cacatctgcg tcttcggcat     720
ggtcagcgac agctactgca gggagaagaa ccactcgagc gtgccttacc actacttcga     780
gaagggggcg ctggatgagt gcaggatgta cctggtgcac gagagggccc ccgcgccgg     840 gcaccgcttc atcaccgaaa aagccatctt ctcccgctgg gccaagagga aggacatcat     900
cttcagccac ccgtcgtggg caggggggta ggagaggcgg cagtgcggtt ggaagcccct     960
cgatatgccc ggtattgggg gtctgcagcc actgggggg cagcagtgga ccccgttg     1020 cgttggagcg cataggacag gactggatcc accgagcccc cccagctgca ggccccgagc    1080
tggcttggac ccgtgcagtg tggatgttta atgtgggatt catcccggga cggaccccac    1140
gtatatgggg cacgtggagc ggggccggga ccccgtcc cacagacccc cgtgtgcccc      1200
ctgcccgcag ccctgagctg ccttgccaca agtgccttg gattcagacc aaagccgact     1260
tgcccattaa aagcatttgt aagcccgaaa aa                                    1292
```

<210> SEQ ID NO 36
<211> LENGTH: 289
<212> TYPE: PRT
<213> ORGANISM: Gallus gallus

<400> SEQUENCE: 36

```
Met Leu Val Arg Val Phe Val Val Leu Leu Cys Ala Ala Ala Leu Ser
1               5                   10                  15

Val Leu Tyr Val Leu Leu Cys Arg Glu Ala Ala Gly Gln Arg Asp Gly
            20                  25                  30

Ser Ala Tyr Thr Ala Pro Ala Ala Leu Ser Leu Gln Gly Tyr Ser Arg
        35                  40                  45

Val Pro Asp Gly Lys Pro Leu Arg Arg Ala Pro Cys Arg Arg Cys Ala
50                  55                  60

Val Val Ser Ser Ser Gly Gln Met Leu Gly Ser His Leu Gly Arg Glu
65                  70                  75                  80

Ile Asp Gly Gln Glu Cys Val Leu Arg Met Asn His Ala Pro Thr Ala
                85                  90                  95

Gly Phe Glu Glu Asp Val Gly Thr Arg Ser Thr Val Arg Val Val Ser
            100                 105                 110

His Thr Ser Val Pro Leu Leu Leu Arg Asn Gln Pro Tyr Phe Phe Gln
        115                 120                 125

Gln Ser Arg Asp Thr Ile Tyr Val Ile Trp Gly Pro Ser Arg Lys Met
130                 135                 140

Ser Arg Glu Lys Gly Gly Pro Thr His Arg Ala Leu Leu Arg Val Leu
145                 150                 155                 160

Glu Met Tyr Pro Arg Leu Gln Leu Tyr Thr Leu Thr Glu Glu Lys Met
                165                 170                 175

Ala Tyr Cys Asp Asp Val Phe Gln Asn Glu Thr Gly Lys Asn Arg Leu
            180                 185                 190

Lys Ser Gly Ser Phe Leu Ser Thr Gly Trp Phe Thr Met Ile Leu Ala
        195                 200                 205

Met Glu Leu Cys Glu His Ile Cys Val Phe Gly Met Val Ser Asp Ser
210                 215                 220

Tyr Cys Arg Glu Lys Asn His Ser Ser Val Pro Tyr His Tyr Phe Glu
225                 230                 235                 240

Lys Gly Arg Leu Asp Glu Cys Arg Met Tyr Leu Val His Glu Arg Ala
                245                 250                 255

Pro Arg Ala Gly His Arg Phe Ile Thr Glu Lys Ala Ile Phe Ser Arg
            260                 265                 270

Trp Ala Lys Arg Lys Asp Ile Ile Phe Ser His Pro Ser Trp Ala Gly
        275                 280                 285

Gly
```

<210> SEQ ID NO 37
<211> LENGTH: 1525
<212> TYPE: DNA
<213> ORGANISM: Gallus gallus

<400> SEQUENCE: 37

```
cctgcacggc ggcgcttccc cggccgagcc atggccgcgg ctcccccgcc atgccgagcc      60
tagcggggag cgggcggagc ggcgcccggg aggcgcacaa aatgaagacc ctgatgcgcc     120
acgggctggc cgtctgcttg gcgctcacca ccatgtgcac cagcttgttg ctcatgtacg     180
gcggcatcgg aggcggcggc gggggccacc cggagcctcg gcggcggcag cagcagcagc     240
```

-continued

```
agcaggtggc ggcggtgccc agccgccctc cgggacgcgg ccagcaccgc ccagcgctcc    300
ccgtcgggc cggactcctg gagggctaca tcagcgtcct ggagcacaag cctttaaaaa    360
tgcactgcaa gagctgtgca ttggtaacca gttctggaca ccttctggga agtaaacaag    420
gtgacagaat cgacgagacg gagtgcgtaa tacgaatgaa tgatgcacct actcgaggtt    480
atggacagga tgttgggaac aaaacaagcc ttcgagtcat tgcacactcc agcattcaga    540
ggattttgcg aaatcgcaat gaactcttaa atatgagcca cggtgctgtg ttcatcttct    600
ggggtcctag cagctacatg aggagagatg gtaaaggctt ggtgtacaac aacctgcagc    660
tgatgaatca gatactgcct caattaaaag catacatgat ttctcgccac aagatgcttc    720
aatttgatga cctttttaaa cgggaaactg ggaaagacag gaagatatcc aacacttggc    780
ttagcacggg ctggttcaca atgactatcg cctagagct gtgtgacagg ataaatgttt    840
atggcatggt gccaccggat ttctgcaggg atcctaatca tctttcagta ccttatcatt    900
attatgaacc tttgggacct gatgaatgca caatgtacat ttcacacgag cggggacgaa    960
agggcagcca tcatcggttc atcacagaga aacgagtgtt tgagaactgg gcgcggacat   1020
tcaacattca cttcttccaa ccagactgga accagaacc acttactgta aatcaccccg   1080
agatgaaagc agcggtctga gggatgaatg caaaagactg caaccgcaat caccgactgt   1140
atcagccatc agggggttgg accttctggg acagcaaggc aactgacagc aaaagggtaa   1200
cgggatttgc agctgataac tgcaacaagt caggaagttc cgatggaggg gtatatagag   1260
agcactttct gttgaactgt gtgttaatcc gctatatcgc ctttctggcc atctgacttc   1320
ctgtacgtgt gtgtgatttg tgaaaagcaa ctcggtatca ttacaggatg ggtaattcat   1380
tatggttttt taaagtacag caccactgac ttttcatagt gaaaactgat ggtatttatt   1440
taatggaggt ttttatgcaa cctaggccag tattttctta attcacagtt ctgtggtcgt   1500
tgatctttca taatctttca aatcc                                        1525
```

```
<210> SEQ ID NO 38
<211> LENGTH: 349
<212> TYPE: PRT
<213> ORGANISM: Gallus gallus

<400> SEQUENCE: 38
```

Met Pro Ser Leu Ala Gly Ser Gly Arg Ser Gly Ala Arg Glu Ala His
1               5                   10                  15

Lys Met Lys Thr Leu Met Arg His Gly Leu Ala Val Cys Leu Ala Leu
            20                  25                  30

Thr Thr Met Cys Thr Ser Leu Leu Leu Met Tyr Gly Gly Ile Gly Gly
        35                  40                  45

Gly Gly Gly Gly His Pro Glu Pro Arg Arg Gln Gln Gln Gln Gln Gln
    50                  55                  60

Gln Val Ala Ala Val Pro Ser Arg Pro Pro Gly Arg Gly Gln His Arg
65                  70                  75                  80

Pro Ala Leu Pro Val Gly Ala Gly Leu Leu Glu Gly Tyr Ile Ser Val
                85                  90                  95

Leu Glu His Lys Pro Leu Lys Met His Cys Lys Ser Cys Ala Leu Val
            100                 105                 110

Thr Ser Ser Gly His Leu Leu Gly Ser Lys Gln Gly Asp Arg Ile Asp
        115                 120                 125

Glu Thr Glu Cys Val Ile Arg Met Asn Asp Ala Pro Thr Arg Gly Tyr
    130                 135                 140

Gly Gln Asp Val Gly Asn Lys Thr Ser Leu Arg Val Ile Ala His Ser

```
                145                 150                 155                 160
Ser Ile Gln Arg Ile Leu Arg Asn Arg Asn Glu Leu Leu Asn Met Ser
                    165                 170                 175

His Gly Ala Val Phe Ile Phe Trp Gly Pro Ser Ser Tyr Met Arg Arg
                180                 185                 190

Asp Gly Lys Gly Leu Val Tyr Asn Asn Leu Gln Leu Met Asn Gln Ile
            195                 200                 205

Leu Pro Gln Leu Lys Ala Tyr Met Ile Ser Arg His Lys Met Leu Gln
        210                 215                 220

Phe Asp Asp Leu Phe Lys Arg Glu Thr Gly Lys Asp Arg Lys Ile Ser
225                 230                 235                 240

Asn Thr Trp Leu Ser Thr Gly Trp Phe Thr Met Thr Ile Ala Leu Glu
                245                 250                 255

Leu Cys Asp Arg Ile Asn Val Tyr Gly Met Val Pro Pro Asp Phe Cys
                260                 265                 270

Arg Asp Pro Asn His Leu Ser Val Pro Tyr His Tyr Tyr Glu Pro Leu
            275                 280                 285

Gly Pro Asp Glu Cys Thr Met Tyr Ile Ser His Glu Arg Gly Arg Lys
        290                 295                 300

Gly Ser His His Arg Phe Ile Thr Glu Lys Arg Val Phe Glu Asn Trp
305                 310                 315                 320

Ala Arg Thr Phe Asn Ile His Phe Phe Gln Pro Asp Trp Lys Pro Glu
                325                 330                 335

Pro Leu Thr Val Asn His Pro Glu Met Lys Ala Ala Val
            340                 345
```

<210> SEQ ID NO 39
<211> LENGTH: 30
<212> TYPE: DNA
<213> ORGANISM: Artificial Sequence
<220> FEATURE:
<223> OTHER INFORMATION: IRES insert

<400> SEQUENCE: 39
aattccccct ctccctcccc cccccctaac                                    30

<210> SEQ ID NO 40
<211> LENGTH: 1089
<212> TYPE: DNA
<213> ORGANISM: Artificial Sequence
<220> FEATURE:
<223> OTHER INFORMATION: chicken beta 1,4- galactosyltransferase Type 1
      codon optimized DNA sequence

<400> SEQUENCE: 40
atgaaagaac ctgcacttcc tggtacttca ctgcaaagag catgtagact gctggtagca    60
ttttgcgccc tgcacctgag cgcaaccctg ctctactacc tggctggatc cagcctgact   120
ccaccccgct ctcagaaacc tcccctcgg aggccgcctc cagccaacct ctccctgcca    180
ccctcccggc ctcctcctcc ccctgcggct cgccccgcc caggacctgt ttctgcacaa    240
ccccggaacc tgccagattc tgcaccatct ggactgtgcc ccgatccaag tccactgctc   300
gttggtcctc tgcgggtgga gtttagtcag ccagtgaacc tggaggaagt ggcttctacc   360
aatccggagg tcagggaagg agggagattc gcccaaagg actgcaaagc gctccagaag    420
gtggctatta ttatcccctt caggaacaga gaggagcacc tgaagtattg gctgtactac   480
atgcacccga ttcttcagag acagcaattg gactatgggg tctatgtgat taatcaagac   540
ggcgatgaag aatttaacag agctaaactg cttaatgtcg gtttcactga ggcactcaag    600

```
gaatacgatt atgattgctt tgtgttttcc gatgtggatc tgattcctat ggacgaccgt    660
aacacatata agtgctatag tcaaccacgt cacctgagtg tgtcaatgga caagtttggc    720
tttaggctgc cgtataacca gtatttcgga ggagtttcag cattgagtaa agaacagttt    780
acaaaaatca acgggttccc aaataactac tgggggtggg gcggagagga cgacgacatc    840
tacaacagac tggtttttaa ggggatgggg atttcccgcc cggatgcagt aataggcaag    900
tgtcgtatga tacgccatag cagggataga aagaacgaac ccaaccctga gcgctttgac    960
cggattgcac atacaagaga aactatgtca tctgatggac ttaactctct ttcatatgag   1020
gtgctgagaa cagatcggtt ccccctgtac actagaatca cagtagatat cggggcacct   1080
gggtcataa                                                           1089

<210> SEQ ID NO 41
<211> LENGTH: 1179
<212> TYPE: DNA
<213> ORGANISM: Artificial Sequence
<220> FEATURE:
<223> OTHER INFORMATION: chicken alpha-2,3-sialyltransferase Type 3
      codon optimized DNA sequence

<400> SEQUENCE: 41
atgggtcttt tggttttcat gagaaatctg ctgctggctc tgtgtctgtt cctggtcctg     60
ggatttctgt actactctgc atggaagctc cacctgctgc gctgggagga tagctctaaa    120 tatgacgcc tgagccatag ctcttttcct aagcaaagac caagtgctga ttctgtggtc    180
ttgtcatttg actctgttgg acatactatt ggctctgaat atgacaaact gggttttctg    240
cttaaccttg attctaaact tccccctgaa ttggcctcaa aatatgccaa cttctctgag    300
ggagtgtgca agcctggtta tgcatctgcc ctgatgactg tgattttccc taaattctcc    360
aaacctgccc ccatgttcct tgatgactcc ttccggcgct gggcccgcat tagagacttt    420
gtgcctccat ttggcattaa agggcaggac aatctgataa aggcaatact gtctgctaca    480
aaagattaca gactcacacc agcactggac agcttgtcat gccgccgctg tatcattgtt    540
gggaatggtg gtgttctggc caacaagagt ttgggtctta agattgatga ctatgatgtg    600
gtcgttcgcc tgaactctgc acctgtcaaa ggctttgaga agatgttgg tggaaagaca    660 acactgcgga tcacttaccc agagggggct attcagaaga tggaacagta tgagaaagac    720
tccctgtttg tgctggcggg atttaaatgg caagactta agtggctgaa atatattgtg    780
tataaagaaa aggtctcagc ttctgatggc ttctggaaat cagtggctac ccgggtgcct    840
cgggagccac atgaaattcg catactgaat ccctatttca tccaagaagc tgcttttttca    900 ttcattggcc tgccattcaa taatggtctg atgggtcggg ggaatatccc caccctgggt    960
tctgtggcca tcacaatggc tctgcataat tgtgatgagg tggctgttgc tggctttgga   1020
tatgacatga gttcccctaa tgctcccctg cattactatg agaacataaa aatgagtgcc   1080
attaaggagt catggactca taatatacaa cgggagaagg aatttcttcg caagctggtt   1140
aaagccagag tgattacaga tcttacatct gggatatga                          1179
```